United States Patent
Donner et al.

(10) Patent No.: US 10,603,055 B2
(45) Date of Patent: Mar. 31, 2020

(54) SYSTEMS FOR AND METHODS OF PREPARING AND FUSING A SACROILIAC JOINT

(71) Applicant: JCBD, LLC, Fort Collins, CO (US)

(72) Inventors: Edward Jeffrey Donner, Fort Collins, CO (US); Christopher Thomas Donner, Fort Collins, CO (US); Taylor Davis, Atlanta, GA (US); Brian VanHiel, Atlanta, GA (US); Hai Trieu, Cordova, TN (US)

(73) Assignee: JCBD, LLC, Fort Collins, CO (US)

( * ) Notice: Subject to any disclaimer, the term of this patent is extended or adjusted under 35 U.S.C. 154(b) by 4 days.

(21) Appl. No.: 16/133,605

(22) Filed: Sep. 17, 2018

(65) Prior Publication Data

US 2019/0083271 A1 Mar. 21, 2019

Related U.S. Application Data

(60) Provisional application No. 62/559,386, filed on Sep. 15, 2017, provisional application No. 62/608,476, (Continued)

(51) Int. Cl.
*A61F 2/30* (2006.01)
*A61F 2/46* (2006.01)
(Continued)

(52) U.S. Cl.
CPC ...... *A61B 17/1757* (2013.01); *A61B 17/1659* (2013.01); *A61B 17/1662* (2013.01);
(Continued)

(58) Field of Classification Search
CPC .................. A61B 17/1757; A61F 2/30988
See application file for complete search history.

(56) References Cited

U.S. PATENT DOCUMENTS

| 3,426,364 A | 2/1969 | Lumb |
| 4,488,542 A | 12/1984 | Helland |

(Continued)

FOREIGN PATENT DOCUMENTS

| AU | 1753200 | 8/2000 |
| CN | 2265765 | 10/1997 |

(Continued)

OTHER PUBLICATIONS

Arman et al. The Human Sacrum and Safe Approaches for Screw Placement. *Journal of Clinical Neuroscience* 2008 Elsevier Inc.;16(2009):1046-1049.
(Continued)

*Primary Examiner* — Christian A Sevilla
(74) *Attorney, Agent, or Firm* — Polsinelli PC; Joshua J. Pranckun; Samuel Wade Johnson

(57) ABSTRACT

A system for performing a fusion procedure on a sacroiliac joint defined between a sacrum and an ilium. The system may include a working cannula including a proximal end, a distal end, a tubular body extending between the proximal and distal ends, a cannula passageway defined within the tubular body and having a cannula axis extending there through, a pair of prongs coupled to the tubular body and extending distally there from, an anchor arm engagement structure coupled to the tubular body, and a pin guide coupled to the tubular body and defining a pin passageway having a guidance axis there through that is generally parallel with the cannula axis.

31 Claims, 117 Drawing Sheets

Related U.S. Application Data filed on Dec. 20, 2017, provisional application No. 62/609,095, filed on Dec. 21, 2017, provisional application No. 62/632,635, filed on Feb. 20, 2018, provisional application No. 62/640,026, filed on Mar. 8, 2018.

(51) Int. Cl.

| | | |
|---|---|---|
| *A61B 17/16* | (2006.01) | |
| *A61B 17/17* | (2006.01) | |
| *A61B 17/70* | (2006.01) | |
| *A61B 17/86* | (2006.01) | |
| *A61B 17/02* | (2006.01) | |
| *A61B 90/00* | (2016.01) | |

(52) U.S. Cl.
CPC ...... *A61B 17/1671* (2013.01); *A61B 17/1739* (2013.01); *A61B 17/7055* (2013.01); *A61B 17/7076* (2013.01); *A61B 17/8625* (2013.01); *A61F 2/30749* (2013.01); *A61F 2/30988* (2013.01); *A61F 2/4603* (2013.01); *A61B 2017/0256* (2013.01); *A61B 2017/0275* (2013.01); *A61B 2090/062* (2016.02); *A61F 2002/30179* (2013.01); *A61F 2002/30271* (2013.01); *A61F 2002/30622* (2013.01); *A61F 2002/30769* (2013.01); *A61F 2002/30858* (2013.01); *A61F 2002/30995* (2013.01)

(56) References Cited

U.S. PATENT DOCUMENTS

| | | | |
|---|---|---|---|
| 4,569,338 | A | 2/1986 | Edwards |
| 4,590,928 | A | 5/1986 | Hunt et al. |
| 4,622,959 | A | 11/1986 | Marcus |
| 4,714,469 | A | 12/1987 | Kenna |
| 4,773,402 | A | 9/1988 | Asher et al. |
| 4,794,918 | A | 1/1989 | Wolter |
| 4,805,602 | A | 2/1989 | Puno |
| 4,863,476 | A | 9/1989 | Shepperd |
| 4,881,535 | A | 11/1989 | Sohngen |
| 4,911,153 | A | 3/1990 | Border |
| 4,920,958 | A | 5/1990 | Walt et al. |
| 4,950,270 | A | 8/1990 | Bowman et al. |
| 5,026,373 | A | 6/1991 | Ray et al. |
| 5,052,375 | A | 10/1991 | Stark et al. |
| 5,108,397 | A | 4/1992 | White |
| 5,112,337 | A | 5/1992 | Paulos et al. |
| 5,176,681 | A | 1/1993 | Lawes et al. |
| 5,192,327 | A | 3/1993 | Brantigan |
| 5,242,444 | A | 9/1993 | MacMillan |
| 5,282,861 | A | 2/1994 | Kaplan |
| 5,334,192 | A | 8/1994 | Behrens |
| 5,334,205 | A | 8/1994 | Cain |
| 5,336,225 | A | 8/1994 | Zang |
| 5,368,546 | A | 11/1994 | Stark et al. |
| 5,368,593 | A | 11/1994 | Stark |
| 5,437,674 | A | 8/1995 | Worcel et al. |
| 5,443,509 | A | 8/1995 | Boucher et al. |
| 5,456,267 | A | 10/1995 | Stark |
| 5,480,402 | A | 1/1996 | Kim |
| 5,484,389 | A | 1/1996 | Stark et al. |
| 5,591,165 | A | 1/1997 | Jackson |
| 5,591,235 | A | 1/1997 | Kuslich |
| 5,593,407 | A | 1/1997 | Reis |
| 5,607,424 | A | 3/1997 | Tropiano |
| 5,609,635 | A | 3/1997 | Michelson |
| 5,609,636 | A | 3/1997 | Kohrs et al. |
| 5,626,434 | A | 5/1997 | Cook |
| 5,658,337 | A | 8/1997 | Kohrs et al. |
| 5,662,652 | A | 9/1997 | Schafer |
| 5,669,909 | A | 9/1997 | Zdeblick et al. |
| 5,683,391 | A | 11/1997 | Boyd |
| 5,688,284 | A | 11/1997 | Chervitz et al. |
| 5,743,914 | A | 4/1998 | Skiba |
| 5,772,594 | A | 6/1998 | Barrick |
| 5,823,975 | A | 10/1998 | Stark et al. |
| 5,888,224 | A | 3/1999 | Beckers et al. |
| 5,891,150 | A | 4/1999 | Chan |
| 5,919,193 | A | 7/1999 | Slavitt |
| 5,928,239 | A | 7/1999 | Mirza |
| 5,929,782 | A | 7/1999 | Stark et al. |
| 5,993,463 | A | 11/1999 | Truwit |
| 6,053,916 | A | 4/2000 | Moore |
| 6,056,749 | A | 5/2000 | Kuslich |
| 6,063,442 | A | 5/2000 | Cohen et al. |
| 6,175,758 | B1 | 1/2001 | Kambin |
| 6,184,797 | B1 | 2/2001 | Stark et al. |
| 6,236,891 | B1 | 5/2001 | Ingle et al. |
| 6,241,771 | B1 | 6/2001 | Gresser et al. |
| 6,290,724 | B1 | 9/2001 | Marino |
| 6,296,595 | B1 | 10/2001 | Stark et al. |
| 6,302,885 | B1 | 10/2001 | Essiger |
| 6,322,562 | B1 | 11/2001 | Wolter |
| 6,325,827 | B1 | 12/2001 | Lin |
| 6,371,123 | B1 | 4/2002 | Stark et al. |
| 6,413,278 | B1 | 7/2002 | Marchosky |
| 6,432,107 | B1 | 8/2002 | Ferree |
| 6,432,140 | B1 | 8/2002 | Lin |
| 6,515,593 | B1 | 2/2003 | Stark et al. |
| 6,520,990 | B1 | 2/2003 | Ray |
| 6,540,707 | B1 | 4/2003 | Stark et al. |
| 6,547,795 | B2 | 4/2003 | Schneiderman |
| 6,547,823 | B2 | 4/2003 | Scarborough et al. |
| 6,558,423 | B1 | 5/2003 | Michelson |
| 6,565,605 | B2 | 5/2003 | Goble et al. |
| 6,572,622 | B1 | 6/2003 | Shäfer et al. |
| 6,579,318 | B2 | 6/2003 | Varga et al. |
| 6,607,487 | B2 | 8/2003 | Chang et al. |
| 6,635,059 | B2 | 10/2003 | Randall et al. |
| 6,641,614 | B1 | 11/2003 | Wagner |
| 6,660,224 | B2 | 12/2003 | Lefebvre et al. |
| 6,663,669 | B1 | 12/2003 | Reiley |
| 6,669,698 | B1 | 12/2003 | Tromanhauser et al. |
| 6,682,563 | B2 | 1/2004 | Scharf |
| 6,682,567 | B1 | 1/2004 | Schroeder |
| 6,716,245 | B2 | 4/2004 | Pasquet et al. |
| 6,723,099 | B1 | 4/2004 | Goshert |
| 6,743,256 | B2 | 6/2004 | Mason |
| 6,746,451 | B2 | 6/2004 | Middleton et al. |
| 6,824,564 | B2 | 11/2004 | Crozet |
| 6,827,670 | B1 | 12/2004 | Stark et al. |
| 6,835,208 | B2 | 12/2004 | Marchosky |
| 6,855,166 | B2 | 2/2005 | Kohrs |
| 6,855,167 | B2 | 2/2005 | Shimp et al. |
| 6,860,902 | B2 | 3/2005 | Reiley |
| 6,872,187 | B1 | 3/2005 | Stark et al. |
| 6,875,236 | B2 | 4/2005 | Reiley |
| 6,902,567 | B2 | 6/2005 | Del Medico |
| 6,908,465 | B2 | 6/2005 | von Hoffmann et al. |
| 6,945,448 | B2 | 9/2005 | Medlin et al. |
| 6,972,019 | B2 | 12/2005 | Michelson |
| 6,974,461 | B1 | 12/2005 | Wolter |
| 7,011,660 | B2 | 3/2006 | Sherman et al. |
| 7,087,056 | B2 | 8/2006 | Vaughan |
| 7,087,058 | B2 | 8/2006 | Cragg |
| 7,108,828 | B2 | 9/2006 | Lefebvre et al. |
| 7,144,399 | B2 | 12/2006 | Hayes et al. |
| 7,163,560 | B2 | 1/2007 | Mason |
| 7,192,447 | B2 | 3/2007 | Rhoda |
| 7,201,775 | B2 | 4/2007 | Gorensek et al. |
| 7,208,222 | B2 | 4/2007 | Rolfe et al. |
| 7,217,291 | B2 | 5/2007 | Zucherman et al. |
| 7,229,448 | B2 | 6/2007 | Goble et al. |
| 7,235,101 | B2 | 6/2007 | Berry et al. |
| 7,235,105 | B2 | 6/2007 | Jackson |
| 7,247,157 | B2 | 7/2007 | Prager et al. |
| 7,255,712 | B1 | 8/2007 | Steinberg |
| 7,303,563 | B2 | 12/2007 | Poyner et al. |
| 7,331,995 | B2 | 2/2008 | Eisermann et al. |
| 7,396,360 | B2 | 7/2008 | Lieberman |
| 7,410,501 | B2 | 8/2008 | Michelson |
| 7,416,537 | B1 | 8/2008 | Stark et al. |

(56) References Cited

U.S. PATENT DOCUMENTS

| | | |
|---|---|---|
| 7,458,991 B2 | 12/2008 | Wang et al. |
| 7,465,317 B2 | 12/2008 | Malberg et al. |
| 7,520,898 B2 | 4/2009 | Re et al. |
| 7,537,616 B1 | 5/2009 | Branch et al. |
| 7,575,600 B2 | 8/2009 | Zucherman et al. |
| 7,621,939 B2 | 11/2009 | Zucherman et al. |
| 7,635,447 B2 | 12/2009 | Hamman et al. |
| 7,637,954 B2 | 12/2009 | Michelson |
| 7,641,697 B2 | 1/2010 | Reiley |
| 7,648,509 B2 | 1/2010 | Stark |
| 7,666,209 B2 | 2/2010 | Zucherman et al. |
| 7,670,383 B1 | 3/2010 | Brown et al. |
| 7,704,279 B2 | 4/2010 | Moskowitz et al. |
| 7,713,290 B2 | 5/2010 | Vaughan |
| 7,740,795 B2 | 6/2010 | Wang et al. |
| 7,771,441 B2 | 8/2010 | Cerundolo |
| 7,789,895 B2 | 9/2010 | Heinz |
| 7,794,465 B2 | 9/2010 | Marik et al. |
| 7,799,081 B2 | 9/2010 | McKinley |
| 7,819,869 B2 | 10/2010 | Godara et al. |
| 7,824,404 B2 | 11/2010 | Godara et al. |
| 7,837,732 B2 | 11/2010 | Zucherman et al. |
| 7,837,734 B2 | 11/2010 | Zucherman et al. |
| 7,846,162 B2 | 12/2010 | Nelson et al. |
| 7,850,690 B2 | 12/2010 | Frigg et al. |
| 7,850,719 B2 | 12/2010 | Gournay et al. |
| 7,850,732 B2 | 12/2010 | Heinz |
| 7,909,871 B2 | 3/2011 | Abdou |
| 7,918,891 B1 | 4/2011 | Curran et al. |
| 7,922,765 B2 | 4/2011 | Reiley |
| 7,935,116 B2 | 5/2011 | Michelson |
| 7,942,903 B2 | 5/2011 | Moskowitz et al. |
| 7,963,970 B2 | 6/2011 | Marino et al. |
| 7,972,363 B2 | 7/2011 | Moskowitz et al. |
| 7,972,382 B2 | 7/2011 | Foley et al. |
| 7,985,255 B2 | 7/2011 | Bray et al. |
| 8,034,114 B2 | 10/2011 | Reiley |
| 8,034,115 B2 | 10/2011 | Reiley |
| 8,048,164 B2 | 11/2011 | Reiley |
| 8,070,782 B2 | 12/2011 | McKay |
| 8,075,561 B2 | 12/2011 | Wolter |
| 8,083,796 B1 | 12/2011 | Raiszadeh et al. |
| 8,088,163 B1 | 1/2012 | Kleiner |
| 8,128,666 B2 | 3/2012 | Falahee |
| 8,162,981 B2 | 4/2012 | Vestgaarden |
| 8,187,332 B2 | 5/2012 | McLuen |
| 8,202,305 B2 | 6/2012 | Reiley |
| 8,221,428 B2 | 7/2012 | Trieu |
| 8,231,661 B2 | 7/2012 | Carls et al. |
| 8,308,779 B2 | 11/2012 | Reiley |
| 8,308,794 B2 | 11/2012 | Martinson et al. |
| 8,317,862 B2 | 11/2012 | Troger et al. |
| 8,343,189 B2 | 1/2013 | Assell et al. |
| 8,343,219 B2 | 1/2013 | Allain et al. |
| 8,348,950 B2 | 1/2013 | Assell et al. |
| 8,388,667 B2 | 3/2013 | Reiley |
| 8,414,648 B2 | 4/2013 | Reiley |
| 8,425,570 B2 | 4/2013 | Reiley |
| 8,425,603 B2 | 4/2013 | Reichen et al. |
| 8,439,925 B2 | 5/2013 | Marino et al. |
| 8,444,693 B2 | 5/2013 | Reiley |
| 8,454,618 B2 | 6/2013 | Stark |
| 8,470,004 B2 | 6/2013 | Reiley |
| 8,470,037 B2 | 6/2013 | Re et al. |
| 8,480,755 B2 | 7/2013 | Reiley |
| 8,491,572 B2 | 7/2013 | Martinson et al. |
| 8,491,653 B2 | 7/2013 | Zucherman et al. |
| 8,496,712 B2 | 7/2013 | Reiley |
| 8,501,690 B2 | 8/2013 | Stark |
| 8,518,120 B2 | 8/2013 | Glerum |
| 8,551,171 B2 | 10/2013 | Johnson et al. |
| 8,562,651 B2 | 10/2013 | Metcalf et al. |
| 8,579,912 B2 | 11/2013 | Isaza et al. |
| 8,585,744 B2 | 11/2013 | Duggal et al. |
| D697,209 S | 1/2014 | Walthall, Jr. et al. |
| 8,623,062 B2 | 1/2014 | Kondrashov |
| 8,740,912 B2 | 6/2014 | Stark |
| 8,778,026 B2 | 7/2014 | Mauldin |
| 8,808,305 B2 | 8/2014 | Kleiner |
| 8,808,336 B2 | 8/2014 | Duggal et al. |
| 8,808,377 B2 | 8/2014 | Donner |
| 8,808,380 B2 | 8/2014 | Fox et al. |
| 8,808,389 B2 | 8/2014 | Reiley |
| 8,821,546 B2 | 9/2014 | Vaughan |
| 8,840,651 B2 | 9/2014 | Reiley |
| 8,882,818 B1 | 11/2014 | Vestgaarden |
| 8,894,708 B2 | 11/2014 | Thalgott et al. |
| 8,945,224 B2 | 2/2015 | Trieu |
| 8,979,928 B2 | 3/2015 | Donner |
| 8,992,579 B1 | 3/2015 | Gustine et al. |
| 9,017,407 B2 | 4/2015 | Donner |
| 9,039,765 B2 | 5/2015 | Trieu |
| 9,039,768 B2 | 5/2015 | Voellmicke |
| 9,044,321 B2 | 6/2015 | Mauldin |
| 9,060,815 B1 | 6/2015 | Gustine et al. |
| 9,119,732 B2 | 9/2015 | Schifano |
| 9,149,286 B1 | 10/2015 | Greenhalgh |
| 9,186,155 B2 | 11/2015 | Katzman et al. |
| 9,254,130 B2 | 2/2016 | Hollis |
| 9,283,084 B1 | 3/2016 | O'Hara |
| 9,333,090 B2 | 5/2016 | Donner et al. |
| 9,381,045 B2 | 7/2016 | Donner et al. |
| 9,421,109 B2 | 8/2016 | Donner et al. |
| 9,452,065 B1 | 9/2016 | Lawson |
| 9,474,538 B2 | 10/2016 | Foley |
| 9,480,511 B2 | 11/2016 | Butters |
| 9,486,264 B2 | 11/2016 | Reiley |
| 9,554,909 B2 | 1/2017 | Donner et al. |
| 9,700,356 B2 | 7/2017 | Donner et al. |
| 9,717,539 B2 | 8/2017 | Donner et al. |
| 9,757,154 B2 | 9/2017 | Donner et al. |
| 9,788,961 B2 | 10/2017 | Donner et al. |
| 9,795,396 B2 | 10/2017 | Donner et al. |
| 9,801,546 B2 | 10/2017 | Donner et al. |
| 9,820,783 B2 | 11/2017 | Donner et al. |
| 9,826,986 B2 | 11/2017 | Donner et al. |
| 9,833,265 B2 | 12/2017 | Donner et al. |
| 9,833,320 B2 | 12/2017 | Donner et al. |
| 9,931,212 B1 | 4/2018 | Donner et al. |
| 9,936,983 B2 | 4/2018 | Mesiwala |
| 9,949,835 B2 | 4/2018 | Donner |
| 9,949,843 B2 | 4/2018 | Reiley |
| 10,034,676 B2 | 7/2018 | Donner |
| 10,058,430 B2 | 8/2018 | Donner et al. |
| 10,064,727 B2 | 9/2018 | Donner et al. |
| 10,064,728 B2 | 9/2018 | Donner et al. |
| 10,130,477 B2 | 11/2018 | Donner et al. |
| 10,136,995 B2 | 11/2018 | Donner et al. |
| 10,159,573 B2 | 12/2018 | Donner |
| 10,179,014 B1 | 1/2019 | Menmuir |
| 10,245,087 B2 | 4/2019 | Donner et al. |
| 10,265,176 B2 | 4/2019 | Donner et al. |
| 10,292,720 B2 | 5/2019 | Donner |
| 10,314,710 B2 | 6/2019 | Donner et al. |
| 10,321,945 B2 | 6/2019 | Schifano |
| 10,335,197 B2 | 7/2019 | Donner et al. |
| 10,383,664 B2 | 8/2019 | Donner et al. |
| 10,433,880 B2 | 10/2019 | Donner et al. |
| 10,441,318 B2 | 10/2019 | Donner et al. |
| 10,492,688 B2 | 12/2019 | Donner et al. |
| 10,492,802 B2 | 12/2019 | Donner et al. |
| 2001/0000532 A1* | 4/2001 | Michelson ........... A61B 17/025 606/80 |
| 2001/0005796 A1 | 6/2001 | Zdeblick et al. |
| 2001/0018616 A1 | 8/2001 | Schwab |
| 2001/0020143 A1 | 9/2001 | Stark et al. |
| 2002/0029784 A1 | 3/2002 | Stark et al. |
| 2002/0032484 A1 | 3/2002 | Hyde, Jr. |
| 2002/0068941 A1 | 6/2002 | Hanson |
| 2002/0068977 A1 | 6/2002 | Jackson |
| 2002/0082701 A1 | 6/2002 | Zdeblick et al. |
| 2002/0087161 A1 | 7/2002 | Randall et al. |
| 2002/0103487 A1 | 8/2002 | Errico |
| 2002/0147461 A1 | 10/2002 | Aldrich et al. |

(56) References Cited

U.S. PATENT DOCUMENTS

| | | |
|---|---|---|
| 2002/0147496 A1 | 10/2002 | Belef et al. |
| 2002/0183846 A1 | 12/2002 | Kuslich et al. |
| 2003/0114931 A1 | 6/2003 | Lee et al. |
| 2003/0124486 A1 | 7/2003 | McDevitt |
| 2003/0181981 A1 | 9/2003 | Lemaire |
| 2003/0208202 A1 | 11/2003 | Falahee |
| 2004/0073216 A1 | 4/2004 | Lieberman |
| 2004/0097932 A1* | 5/2004 | Ray, III ............ A61B 17/1757 606/86 A |
| 2004/0127988 A1 | 7/2004 | Goble et al. |
| 2004/0162558 A1 | 8/2004 | Hegde et al. |
| 2004/0162616 A1 | 8/2004 | Simonton |
| 2004/0186482 A1 | 9/2004 | Kolb et al. |
| 2004/0193271 A1 | 9/2004 | Fraser |
| 2004/0199256 A1 | 10/2004 | Wang |
| 2004/0220668 A1 | 11/2004 | Eisermann et al. |
| 2004/0228901 A1 | 11/2004 | Trieu |
| 2004/0249675 A1 | 12/2004 | Stark et al. |
| 2004/0260286 A1 | 12/2004 | Ferree |
| 2005/0043660 A1 | 2/2005 | Stark et al. |
| 2005/0101887 A1 | 5/2005 | Stark et al. |
| 2005/0113652 A1 | 5/2005 | Stark et al. |
| 2005/0131539 A1 | 6/2005 | Kohrs |
| 2005/0149192 A1 | 7/2005 | Zucherman et al. |
| 2005/0154391 A1 | 7/2005 | Doherty et al. |
| 2005/0203515 A1 | 9/2005 | Doherty et al. |
| 2005/0216088 A1 | 9/2005 | McKinley et al. |
| 2005/0240264 A1 | 10/2005 | Tokish, Jr. et al. |
| 2005/0245925 A1 | 11/2005 | Iki et al. |
| 2005/0261775 A1 | 11/2005 | Baum |
| 2005/0267482 A1 | 12/2005 | Hyde, Jr. |
| 2005/0273099 A1 | 12/2005 | Baccelli et al. |
| 2006/0036251 A1 | 2/2006 | Reiley |
| 2006/0054171 A1 | 3/2006 | Dall |
| 2006/0058876 A1 | 3/2006 | McKinley |
| 2006/0069438 A1 | 3/2006 | Zucherman et al. |
| 2006/0085068 A1 | 4/2006 | Barry |
| 2006/0089716 A1 | 4/2006 | Felix |
| 2006/0095134 A1 | 5/2006 | Trieu et al. |
| 2006/0129244 A1 | 6/2006 | Ensign |
| 2006/0147332 A1 | 7/2006 | Jones et al. |
| 2006/0161154 A1 | 7/2006 | McAfee |
| 2006/0167547 A1 | 7/2006 | Suddaby |
| 2006/0229729 A1 | 10/2006 | Gordon |
| 2007/0027543 A1 | 2/2007 | Gimble et al. |
| 2007/0055374 A1 | 3/2007 | Copf, Jr. et al. |
| 2007/0155588 A1 | 7/2007 | Stark et al. |
| 2007/0156241 A1 | 7/2007 | Reiley et al. |
| 2007/0162134 A1 | 7/2007 | Marnay et al. |
| 2007/0179610 A1 | 8/2007 | Biedermann |
| 2007/0179621 A1 | 8/2007 | McClellan, III et al. |
| 2007/0198093 A1 | 8/2007 | Brodke et al. |
| 2007/0225714 A1 | 9/2007 | Gradl |
| 2007/0239164 A1 | 10/2007 | Prager et al. |
| 2007/0239278 A1 | 10/2007 | Heinz |
| 2007/0265621 A1 | 11/2007 | Matthis et al. |
| 2007/0270879 A1 | 11/2007 | Isaza et al. |
| 2007/0270968 A1 | 11/2007 | Baynham |
| 2007/0276501 A1 | 11/2007 | Betz et al. |
| 2007/0293949 A1 | 12/2007 | Salerni et al. |
| 2007/0299445 A1 | 12/2007 | Shadduck |
| 2007/0299525 A1 | 12/2007 | Binotto |
| 2008/0015704 A1 | 1/2008 | Gradl |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0039843 A1 | 2/2008 | Abdou |
| 2008/0045968 A1 | 2/2008 | Yu et al. |
| 2008/0065215 A1 | 3/2008 | Reiley |
| 2008/0133016 A1 | 6/2008 | Heinz |
| 2008/0140082 A1 | 6/2008 | Erdem et al. |
| 2008/0140207 A1 | 6/2008 | Olmos |
| 2008/0154314 A1 | 6/2008 | McDevitt |
| 2008/0183293 A1 | 7/2008 | Parry et al. |
| 2008/0228276 A1 | 9/2008 | Mathews et al. |
| 2008/0262621 A1 | 10/2008 | Gorek |
| 2008/0281425 A1 | 11/2008 | Thalgott et al. |
| 2008/0288081 A1 | 11/2008 | Scrafton et al. |
| 2008/0300685 A1 | 12/2008 | Carls et al. |
| 2009/0018660 A1 | 1/2009 | Roush |
| 2009/0024174 A1 | 1/2009 | Stark |
| 2009/0024217 A1 | 1/2009 | Levy |
| 2009/0043394 A1 | 2/2009 | Zdeblick et al. |
| 2009/0062914 A1 | 3/2009 | Marino |
| 2009/0076553 A1 | 3/2009 | Wolter |
| 2009/0088849 A1 | 4/2009 | Armstrong et al. |
| 2009/0099659 A1 | 4/2009 | Oh |
| 2009/0105833 A1 | 4/2009 | Hovda et al. |
| 2009/0105834 A1 | 4/2009 | Hovda et al. |
| 2009/0131986 A1 | 5/2009 | Lee et al. |
| 2009/0132035 A1 | 5/2009 | Roth et al. |
| 2009/0149957 A1 | 6/2009 | Burd et al. |
| 2009/0192621 A1 | 7/2009 | Winslow et al. |
| 2009/0204215 A1 | 8/2009 | McClintock |
| 2009/0216276 A1 | 8/2009 | Pasquet |
| 2009/0248163 A1 | 10/2009 | King et al. |
| 2009/0259261 A1 | 10/2009 | Reiley |
| 2009/0259316 A1 | 10/2009 | Ginn et al. |
| 2009/0281579 A1 | 11/2009 | Weaver |
| 2009/0287254 A1 | 11/2009 | Nayet et al. |
| 2009/0306671 A1 | 12/2009 | McCormack et al. |
| 2010/0057204 A1 | 3/2010 | Kadaba |
| 2010/0094290 A1 | 4/2010 | Vaidya |
| 2010/0100135 A1 | 4/2010 | Phan |
| 2010/0106200 A1 | 4/2010 | Stark |
| 2010/0121160 A1 | 5/2010 | Stark et al. |
| 2010/0137910 A1 | 6/2010 | Cawley et al. |
| 2010/0137919 A1 | 6/2010 | Wolter |
| 2010/0145397 A1 | 6/2010 | Overes |
| 2010/0152785 A1 | 6/2010 | Forton et al. |
| 2010/0168798 A1 | 7/2010 | Clineff |
| 2010/0168861 A1 | 7/2010 | Yundt |
| 2010/0179552 A1 | 7/2010 | Wolter |
| 2010/0185292 A1 | 7/2010 | Hochschuler |
| 2010/0191088 A1 | 7/2010 | Anderson |
| 2010/0191100 A1 | 7/2010 | Anderson |
| 2010/0204795 A1 | 8/2010 | Greenhalgh |
| 2010/0204796 A1 | 8/2010 | Bae |
| 2010/0211176 A1 | 8/2010 | Greenhalgh |
| 2010/0217086 A1 | 8/2010 | Deshmukh |
| 2010/0268228 A1 | 10/2010 | Petersen |
| 2010/0286779 A1 | 11/2010 | Thibodeau |
| 2010/0286785 A1 | 11/2010 | Grayson |
| 2010/0292796 A1 | 11/2010 | Greenhalgh |
| 2010/0292800 A1 | 11/2010 | Zubok |
| 2010/0305702 A1 | 12/2010 | Michelson |
| 2010/0305704 A1 | 12/2010 | Messerli |
| 2010/0324607 A1 | 12/2010 | Davis |
| 2010/0331981 A1 | 12/2010 | Mohammed |
| 2011/0034957 A1 | 2/2011 | Biedermann |
| 2011/0046737 A1 | 2/2011 | Teisen |
| 2011/0071568 A1 | 3/2011 | Ginn et al. |
| 2011/0071635 A1 | 3/2011 | Zhang et al. |
| 2011/0087294 A1 | 4/2011 | Reiley |
| 2011/0093074 A1 | 4/2011 | Glerum |
| 2011/0098816 A1 | 4/2011 | Jacob et al. |
| 2011/0098817 A1 | 4/2011 | Eckhardt et al. |
| 2011/0118796 A1 | 5/2011 | Reiley |
| 2011/0160866 A1 | 6/2011 | Laurence |
| 2011/0172774 A1 | 7/2011 | Varela |
| 2011/0184518 A1 | 7/2011 | Trieu |
| 2011/0184519 A1 | 7/2011 | Trieu |
| 2011/0184520 A1 | 7/2011 | Trieu |
| 2011/0185306 A1 | 7/2011 | Aravamudan |
| 2011/0213221 A1 | 9/2011 | Roche |
| 2011/0230968 A1 | 9/2011 | Perisic |
| 2011/0238181 A1 | 9/2011 | Trieu |
| 2011/0264233 A1 | 10/2011 | Song |
| 2011/0295272 A1 | 12/2011 | Assell et al. |
| 2012/0010714 A1 | 1/2012 | Moskowitz et al. |
| 2012/0022535 A1 | 1/2012 | Mayer et al. |
| 2012/0022595 A1 | 1/2012 | Pham et al. |
| 2012/0029641 A1 | 2/2012 | Curran et al. |

(56) References Cited

U.S. PATENT DOCUMENTS

| | | |
|---|---|---|
| 2012/0032808 A1 | 2/2012 | Cherubini |
| 2012/0035729 A1 | 2/2012 | Glerum |
| 2012/0065548 A1 | 3/2012 | Morgan |
| 2012/0083883 A1 | 4/2012 | Ginn |
| 2012/0116454 A1 | 5/2012 | Edidin et al. |
| 2012/0116806 A1 | 5/2012 | Stark et al. |
| 2012/0150300 A1 | 6/2012 | Nihalani |
| 2012/0185049 A1 | 7/2012 | Varela |
| 2012/0209388 A1 | 8/2012 | Curran et al. |
| 2012/0253406 A1 | 10/2012 | Bae |
| 2012/0259370 A1 | 10/2012 | Vaidya |
| 2012/0271200 A1 | 10/2012 | Martinson et al. |
| 2012/0271424 A1 | 10/2012 | Crawford |
| 2012/0316565 A1 | 12/2012 | Stark |
| 2012/0323285 A1 | 12/2012 | Assell et al. |
| 2013/0006361 A1 | 1/2013 | Glerum |
| 2013/0018427 A1 | 1/2013 | Pham et al. |
| 2013/0023994 A1 | 1/2013 | Glerum |
| 2013/0030456 A1 | 1/2013 | Assell et al. |
| 2013/0035724 A1 | 2/2013 | Fitzpatrick |
| 2013/0035727 A1 | 2/2013 | Datta |
| 2013/0053854 A1 | 2/2013 | Schoenefeld et al. |
| 2013/0053902 A1 | 2/2013 | Trudeau |
| 2013/0053964 A1 | 2/2013 | Talwar |
| 2013/0060337 A1 | 3/2013 | Petersheim et al. |
| 2013/0066426 A1 | 3/2013 | Martinson et al. |
| 2013/0085535 A1 | 4/2013 | Greenhalgh et al. |
| 2013/0090735 A1 | 4/2013 | Mermuys et al. |
| 2013/0116790 A1 | 5/2013 | Seifert |
| 2013/0123850 A1 | 5/2013 | Schoenefeld et al. |
| 2013/0123923 A1 | 5/2013 | Pavlov et al. |
| 2013/0144343 A1 | 6/2013 | Arnett et al. |
| 2013/0144393 A1 | 6/2013 | Mutchler |
| 2013/0158669 A1 | 6/2013 | Sungarian |
| 2013/0173004 A1 | 7/2013 | Greenhalgh |
| 2013/0197590 A1 | 8/2013 | Assell et al. |
| 2013/0218215 A1 | 8/2013 | Ginn et al. |
| 2013/0226181 A1 | 8/2013 | Assell et al. |
| 2013/0231746 A1 | 9/2013 | Ginn et al. |
| 2013/0238093 A1 | 9/2013 | Mauldin |
| 2013/0245703 A1 | 9/2013 | Warren et al. |
| 2013/0245763 A1 | 9/2013 | Mauldin |
| 2013/0253650 A1 | 9/2013 | Ashley |
| 2013/0282012 A1 | 10/2013 | Stark |
| 2013/0295202 A1 | 11/2013 | Stark |
| 2013/0296953 A1 | 11/2013 | Mauldin |
| 2013/0297035 A1 | 11/2013 | Reiley |
| 2014/0012330 A1 | 1/2014 | Johnson, II et al. |
| 2014/0012340 A1 | 1/2014 | Beck et al. |
| 2014/0031934 A1 | 1/2014 | Trieu |
| 2014/0039628 A1 | 2/2014 | DeLurio et al. |
| 2014/0046380 A1 | 2/2014 | Asfora |
| 2014/0074175 A1 | 3/2014 | Ehler et al. |
| 2014/0100662 A1 | 4/2014 | Patterson et al. |
| 2014/0114415 A1 | 4/2014 | Tyber |
| 2014/0135850 A1 | 5/2014 | Parent et al. |
| 2014/0135927 A1 | 5/2014 | Pavlov et al. |
| 2014/0156007 A1 | 6/2014 | Pabst et al. |
| 2014/0207240 A1 | 7/2014 | Stoffman |
| 2014/0249581 A1 | 9/2014 | Stachniak |
| 2014/0257294 A1 | 9/2014 | Gedet et al. |
| 2014/0257399 A1 | 9/2014 | Rezach |
| 2014/0257408 A1 | 9/2014 | Trieu et al. |
| 2014/0257411 A1 | 9/2014 | Rezach |
| 2014/0257486 A1 | 9/2014 | Alheidt |
| 2014/0277463 A1 | 9/2014 | Yerby |
| 2014/0277478 A1 | 9/2014 | Moore |
| 2014/0277504 A1 | 9/2014 | Forton et al. |
| 2014/0288601 A1 | 9/2014 | Baynham |
| 2014/0336775 A1 | 11/2014 | Reiley |
| 2014/0343678 A1 | 11/2014 | Suddaby et al. |
| 2015/0080972 A1 | 3/2015 | Chin |
| 2015/0105828 A1 | 4/2015 | Reckling |
| 2015/0112444 A1 | 4/2015 | Aksu |
| 2015/0250612 A1 | 9/2015 | Schifano |
| 2015/0327872 A1 | 11/2015 | Assell |
| 2016/0081809 A1 | 3/2016 | Schneider |
| 2016/0081810 A1 | 3/2016 | Reiley |
| 2016/0120661 A1 | 5/2016 | Schell |
| 2016/0128838 A1 | 5/2016 | Assell |
| 2016/0157897 A1 | 6/2016 | Vaidya |
| 2016/0287171 A1 | 10/2016 | Sand |
| 2016/0310188 A1 | 10/2016 | Marino et al. |
| 2016/0310197 A1 | 10/2016 | Black et al. |
| 2017/0007409 A1 | 1/2017 | Mauldin |
| 2017/0296344 A1 | 10/2017 | Souza |
| 2017/0296346 A1 | 10/2017 | Assell |
| 2017/0325845 A1 | 11/2017 | Donner et al. |
| 2018/0008428 A1 | 1/2018 | Larson |
| 2018/0092669 A1 | 4/2018 | Donner et al. |
| 2018/0104071 A1 | 4/2018 | Reckling |
| 2018/0296347 A1 | 10/2018 | Hamzey |
| 2018/0303520 A1 | 10/2018 | Rajpal |
| 2018/0325675 A1 | 11/2018 | Donner |
| 2018/0325676 A1 | 11/2018 | Donner |
| 2018/0360608 A1 | 12/2018 | Aksu |
| 2019/0209011 A1 | 7/2019 | Donner et al. |
| 2019/0343640 A1 | 11/2019 | Donner et al. |

FOREIGN PATENT DOCUMENTS

| | | |
|---|---|---|
| CN | 201073333 Y | 6/2008 |
| CN | 201139628 | 10/2008 |
| CN | 201275132 | 7/2009 |
| CN | 201275133 | 7/2009 |
| CN | 201275134 | 7/2009 |
| CN | 202235633 U | 5/2012 |
| DE | 102013011322 A1 | 5/2014 |
| EP | 1663037 B1 | 6/2006 |
| JP | 2007-275592 | 10/2007 |
| KR | 10-1037206 | 5/2011 |
| RU | 2364359 C1 | 8/2009 |
| WO | WO 1993/008745 A1 | 5/1993 |
| WO | WO 1995/023559 | 9/1995 |
| WO | WO 1995/031947 | 11/1995 |
| WO | WO 1998/048717 | 11/1998 |
| WO | WO 01/30264 A2 | 5/2001 |
| WO | WO 2001/095823 A1 | 12/2001 |
| WO | WO 2002/067759 A2 | 9/2002 |
| WO | WO 02/085182 A2 | 10/2002 |
| WO | WO 2006/020463 A1 | 2/2006 |
| WO | WO 2006/099270 | 9/2006 |
| WO | WO 2007/022790 A1 | 3/2007 |
| WO | WO 2007/115295 A2 | 10/2007 |
| WO | WO 2008/011410 A2 | 1/2008 |
| WO | WO 2008/088685 A2 | 7/2008 |
| WO | WO 2008/089537 A1 | 7/2008 |
| WO | WO 2009/011774 A2 | 1/2009 |
| WO | WO 2009/029074 A1 | 3/2009 |
| WO | WO 2009/108318 A2 | 9/2009 |
| WO | WO 2010/045749 A1 | 4/2010 |
| WO | WO 2010/065015 A1 | 6/2010 |
| WO | WO 2010/108166 A1 | 9/2010 |
| WO | WO 2011014135 A2 | 2/2011 |
| WO | WO 2011/056690 A2 | 5/2011 |
| WO | WO 2011/066053 A2 | 6/2011 |
| WO | WO 2011/087912 A1 | 7/2011 |
| WO | WO 2011/091349 A2 | 7/2011 |
| WO | WO 2012/015976 A1 | 2/2012 |
| WO | WO 2013/020123 A2 | 2/2013 |
| WO | WO 2013/166496 A1 | 11/2013 |
| WO | WO 2014/055529 A2 | 4/2014 |
| WO | WO 2014/074853 A1 | 5/2014 |

OTHER PUBLICATIONS

Atlihan et al. Anatomy of the Posterior Illiac Crest as a Reference to Sacral Bar Insertion. *Clin Orthop* 2004;418:141-145.

Baria, Dinah, "Sacroiliac Joint Biomechanics and Effects of Fusion" (2010). Open Access Dissertations. Paper 466. http://scholarlyrepository.miami.edu/oa_dissertations, 179 pages.

(56) References Cited

OTHER PUBLICATIONS

Belanger, et al. "Sacroiliac Arthrodesis Using a Posterior Midline Fascial Splitting Approach and Pedicle Screw Instrumentation: A New Technique." Journal of Spinal Disorders, vol. 14 No. 2, pp. 118-124, 2001.
Buchowski, et al. "Functional and Radiographic Outcome of Sacroiliac Arthrodesis for the Disorders of the Sacroiliac Joint." The Spine Journal, 5, 2005, pp. 520-528.
Cecil et al. Projection of the S2 Pedicle Onto the Posterolateral Surface of the Ilium: A Technique for Lag Screw Fixation, Sacral Fractures or Sacroiliac Joint Dislocations. Spine 1996;21(7):875-878.
Chang et al. Low Profile Pelvic Fixation. Spine 2009;34(5):436-440.
Dall et al., Surgery for the Painful, Dysfunctional Sacroiliac Joint, Springer International Publishing, Switzerland, 2015.
Dayer R. et al. Pelvic fixation for neuromuscular scoliosis deformity correction. Curr Rev Musculoskelet Med (2012) 5:91-101.
DePuy Spine. ISOLA® Spinopelvic System, Surgical Technique. c. 2003 DePuy Spine, Inc., 28 pages.
Ebraheim, et al. "A Posterior Approach for Inspection of Reduction of Sacroiliac Joint Disruption." Surg. Radiol. Anat., 1999, 21(5), pp. 305-307.
Ebraheim, et al. "Anatomic considerations for Posterior Approach to the Sacroiliac Joint." Spine, 21(23), Dec. 1, 1996, pp. 2709-2712.
Garrido B.J. et al. Navigated placement of iliac bolts: description of a new technique. The Spine Journal 11 (2011) 331-335.
Giannikas, et al. "Sacroiliac Joint Fusion for Chronic Pain: A Simple Technique Avoiding the Use of Metalwork." Eur. Spine J, 13, 2004, pp. 253-256.
Globus Medical. Revere® Addition® Sacroiliac Components, Surgical Technique. c. 2012 Globus Medical, 64 pages.
Globus Medical. SI-LOK™ Sacroiliac Joint Fixation System, Surgical Technique. c. 2011 Globus Medical, 44 pages.
Globus Medical. Secure-C Cervical Artificial Disc. Copyright 2014.
Guner, et al. "Anterior Sacroiliac Fusion. A New Video-Assisted Endoscopic Technique." Surgical Laparoscopy & Endoscopy. 1998; vol. 8, No. 3, pp. 233-236.
LDR. Avenue® L Lateral Lumbar Cage. Sep. 2011, 3 pages.
LDR. ROI-A™ Anterior Approach Implant. Apr. 2008, 2 pages.
LDR. Surgical Technique ROI-C™ Anterior Cervical Cage. Apr. 2010, 15 pages.
Lee et al. Trajectory of Transsacral Iliac Screw for Lumbopelvic Fixation. J Spinal Disord Tech 2011;24(3):151-156.
Lehman, Jr. et al. Advantage of Pedicle Screw Fixation Directed Into the Apex of the Sacral Promontory Over Bicortical Fixation. Spine 2002;27(8):806-811.
Liebergall, Meir (Iri) M.D., Lumbosacral and Spinopelvic Fixation, Lippincott-Raven, Philadelphia, PA, 1996, Chap. 48, "Sacroiliac Joint Fusion," pp. 611-618.
Luk et al. A Stronger Bicortical Sacral Pedicle Screw Fixation Through the S1 Endplate. Spine 2005;30(5):525-529.
Margulies, J.Y. et al., Movement, Stability & Low Back Pain, The essential role of the pelvis, Churchill Livingstone, London, 1997, Chapters 44-47, "Surgical Fusion of the Spine to the Sacrum, etc.," pp. 555-593.
Marotta N. et al. A novel minimally invasive presacral approach and instrumentation technique for anterior L5-S1 intervretebral disectomy and fusion. Neurosurg Focus, vol. 20, Jan. 2006, 8 pages.
Martin et al. Sacropelvic Fixation: Two Case Reports of a New Percutaneous Technique. Spine 2011;36(9):E618-21.
McLauchlan, et al. "Sacral and Iliac Articular Cartilage Thickness and Cellularity: Relationship to Subchrondral Bone End-Plate Thickness and Cancellous Bone Density." Rheumatology 2002; 41:375-380.
Medtronic Sofamor Danek. Colorado 2™ Sacro-Iliac Fixation, Surgical Technique. © 2003 Medtronic Sofamor Danek USA, Inc.
Medtronic Sofamor Danek. Colorado 2™The New Revolution, Surgical Technique. © 2000 Medtronic Sofamor Danek, Inc.
Mendel et al. The Lateral Sacral Triangle—A Decision Support for Secure Transverse Sacroiliac Screw Insertion. Injury J. Care Injured 2010;42(2011):1164-1170.
Moshirfar et al. Pelvic Fixation in Spine Surgery. The Journal of Bone & Joint Surgery 2005;87-A(2 Suppl):89-106.
O'Brien et al. An Anatomic Study of the S2 Iliac Technique for Lumbopelvic Screw Placement. Spine 2009;34(12):E439-E442.
O'Brien et al. Feasibility of Minimally Invasive Sacropelvic Fixation. Spine 2010;35(4):460-464.
O'Brien et al. Sacropelvic Instrumentation: Anatomic and Biomechanical Zones of Fixation. Seminars in Spine Surgery 2004;16(2):76-90.
Ouellet et al. Surgical Anatomy of the Pelvis, Sacrum, and Lumbar Spine Relevant to Spinal Surgery. Seminars in Spine Surgery 2004 Elsevier Inc.;16:91-100.
Pan W. et al. The invention of an iliosacral screw fixation guide and its preliminary clinical application. Orthopaedic Surgery (2012), vol. 4, No. 1, pp. 55-59.
Puhakka, et al. "MR Imaging of the Normal Sacroiliac Joint with Correlation to Histology." Skeletal Radiol., 33, 2004, pp. 15-28.
SI-BONE iFuse Implant System, Surgical Technique Manual. c. 2011 SI-BONE, Inc., 35 pages.
SI-BONE iFuse Implant System™. SI-BONE, Inc. 2010, 4 pages.
Signus Medizintechnik GmbH. DIANA Operationstechnik. Rev. May 1, 2010, 20 pages.
Sponseller P.D. et al. Low profile pelvic fixation with the sacral alar iliac technique in the pediatric population improves results at two-year minimum follow-up. Spine. 2010; vol. 35, No. 20, pp. 1887-1892.
Stark J. G. et al. The history of sacroiliac joint arthrodesis: a critical review and introduction of a new technique. Current Orthopaedic Practice, vol. 22, No. 6, Nov./Dec. 2011, pp. 545-557.
Stark. "The Diagnosis and Treatment of Sacroiliac Joint Abnormalities." Current Orthopedic Practice, 21(4), Jul./Aug. 2010, pp. 336-347.
Synthes GmbH. Sacral Bars. Fixation of the posterior pelvis in cases of fractures or sacroiliac joint dislocations. © Apr. 2009 Synthes, Inc.
Synthes Spine. ProDisc-C Total Disc Replacement. Product Information. © 2008 Synthes, Inc., 14 pages.
Synthes Spine. SynFix-LR System. Instruments and implants for stand-alone anterior lumbar interbody fusion (ALIF). Technique Guide. © 2008 Synthes, Inc., 45 pages.
Synthes Spine. ProDisc-L Total Disc Replacement. For replacement of a diseased and/or degenerated intervertebral disc of the lumbosacral regions. Technique Guide. Copyright 2006.
Synthes Spine. Universal Spinal System (USS) Polyaxial and Iliosacral Spine Fixation. A versatile system for posterior stabilization of spinal segments. Technique Guide, c. 2009 Synthes, Inc., 61 pages.
Szadek, et al. "Possible Nociceptive Structures in the Sacroiliac Joint Cartilage: An Immunohistochemical Study." Clinical Anatomy, 23, 2010, pp. 192-198.
Tenon Medical, Catamaran SI Joint Implant, http://tctig.com/projects (last visited Nov. 19, 2014).
Tifix® Technology Pressure Plate Technology: Multidirectional Locking Technology Titanium Plate and Screw Systems, General & Specific Instructions. litos/GmbH & Co. KG, Rev: Sep. 9, 2008.
Tobler W.D. et al. The presacral retroperitoneal approach for axial lumbar interbody fusion. J Bone Joint Surg [Br], vol. 93-B, No. 7, Jul. 2011, pp. 955-960.
Ugur, et al. "New Needle Holder Facilitates Percutaneous Fluoroscopy-Guided Sacroiliac Puncture." Acta Radiologica, 2006, 47(5), pp. 481-483.
Vanelderen, et al. "Evidence-Based Medicine. Evidence-Based Interventional Pain Medicine According to Clinical Diagnoses. 13. Sacroiliac Joint Pain." Pain Practice, 10(5), 2010, pp. 470-478.
Waisbrod, et al. "Sacroiliac Joint Arthrodesis for Chronic Lower Back Pain." Arch. Orthop. Trauma Surg., 106, 1987, pp. 238-240.
Wise, et al. "Minimally Invasive Sacroiliac Arthrodesis. Outcomes of a New Technique." Spinal Disord. Tech., 21(8), Dec. 2008, pp. 579-584.
Yin, et al. "Sensory Stimulation-Guided Sacroiliac Joint Radiofrequency Neurotomy: Technique Based on Neuroanatomy of the Dorsal Sacral Plexus." Spine 2003; vol. 28, No. 20, pp. 2419-2425.

(56) References Cited

OTHER PUBLICATIONS

Zyga Technology, Inc. SImmetry Sacroiliac Joint Fusion System, Surgeon Didactic, c. 2012 Zyga Technology, Inc., 45 pages.
Zyga Technology, Inc. SImmetry Sacroiliac Joint Fusion System, Technique Guide, known at least as early as Mar. 1, 2013, 20 pages.

* cited by examiner

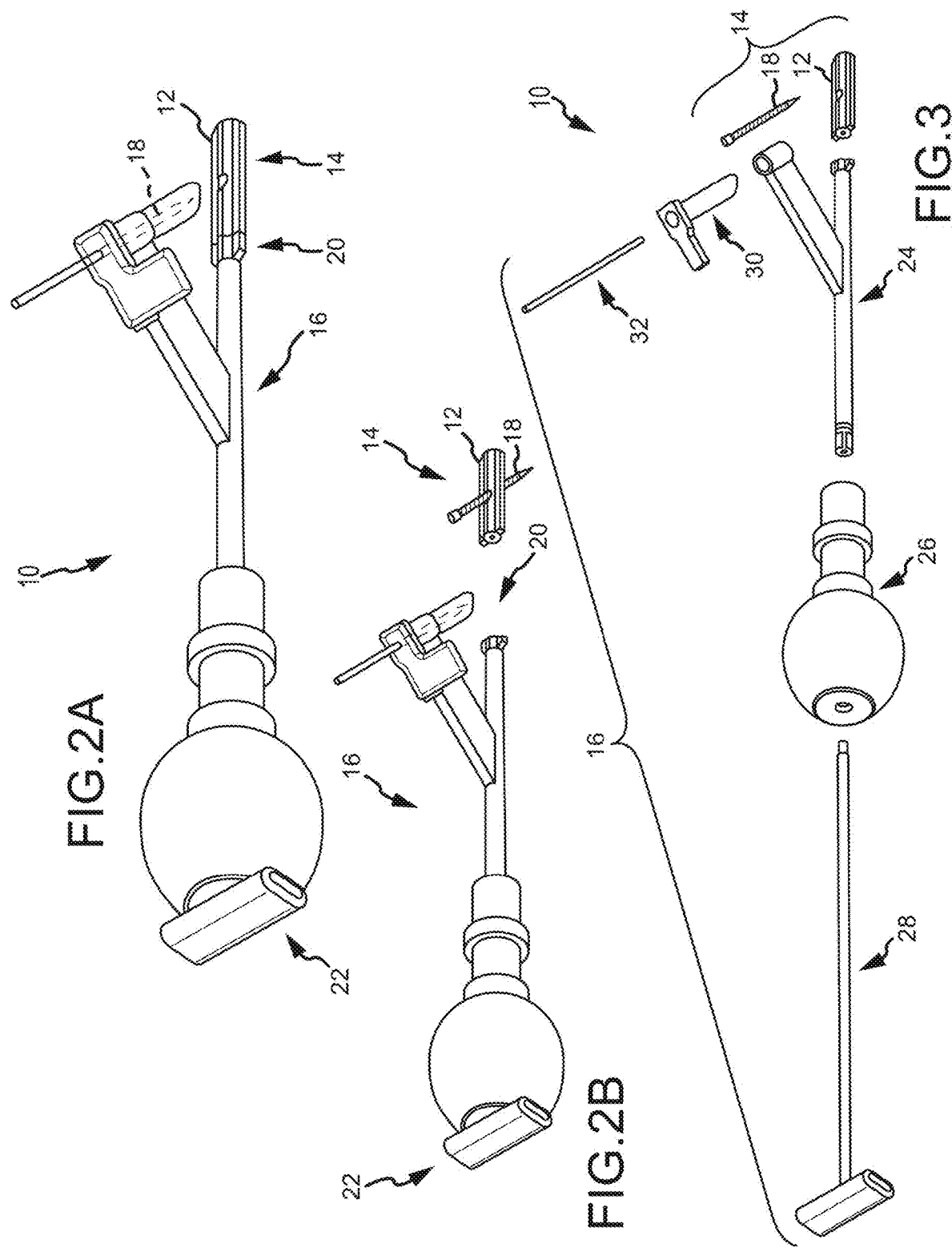

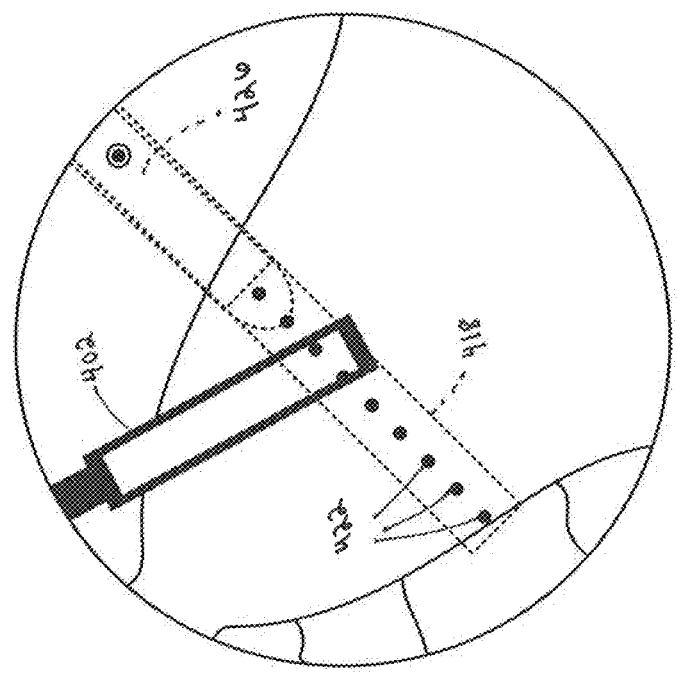
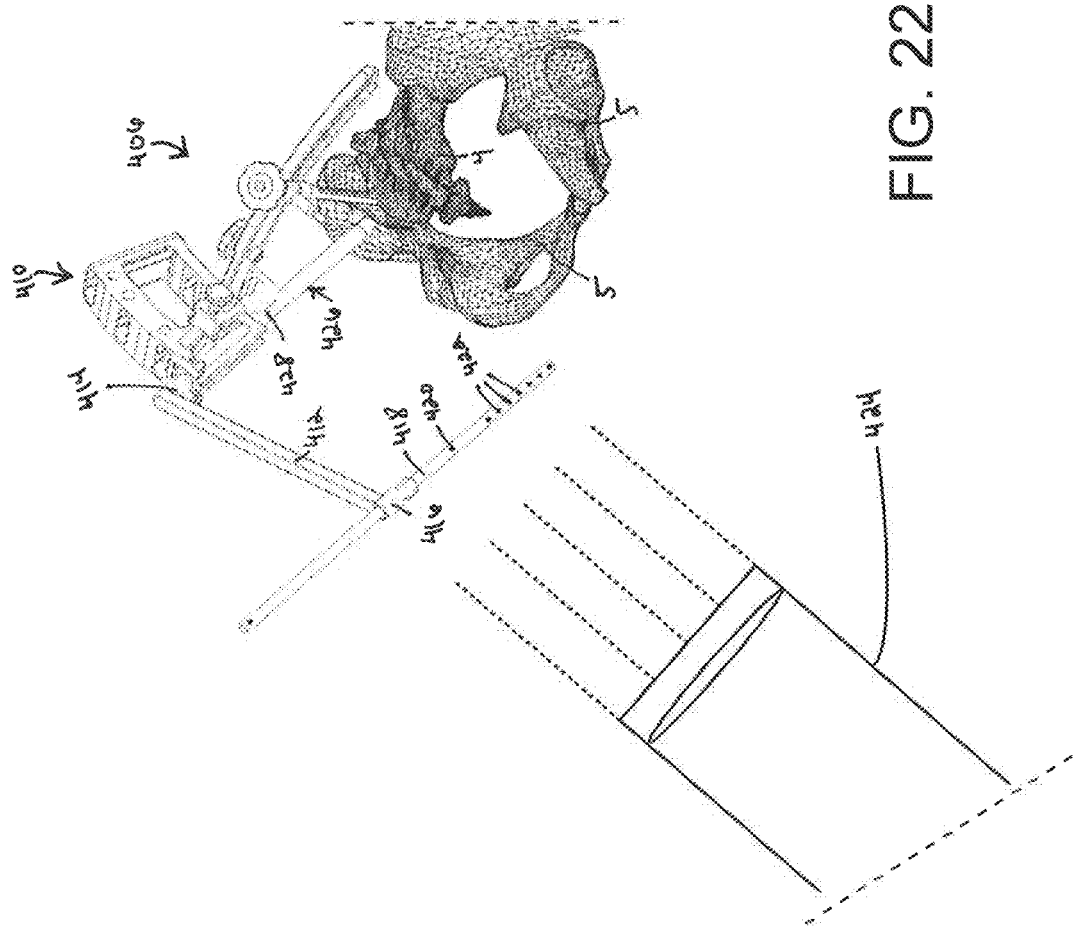
FIG. 22

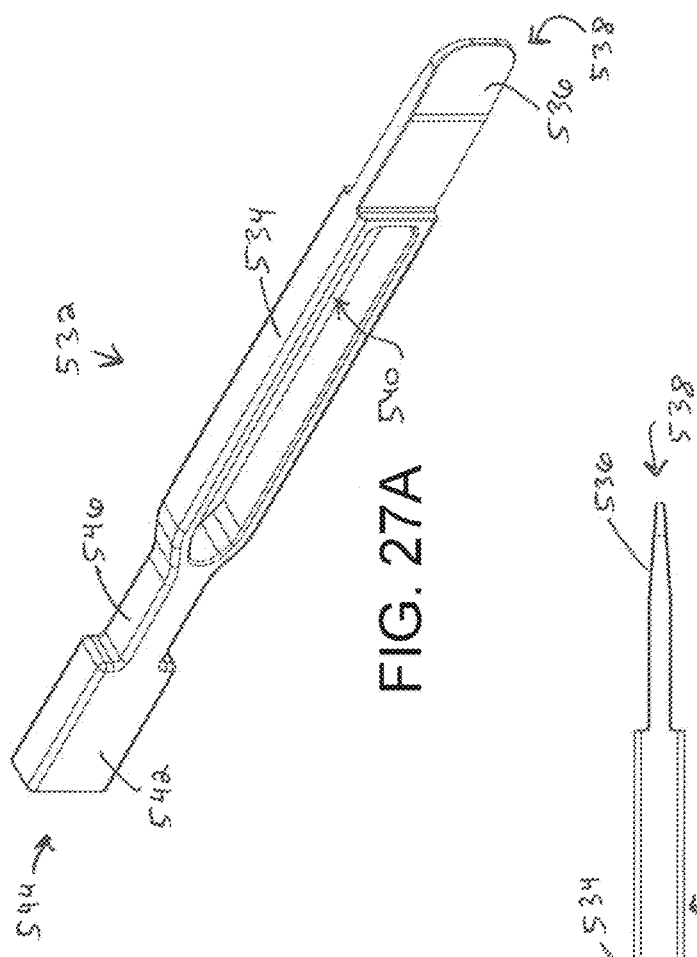
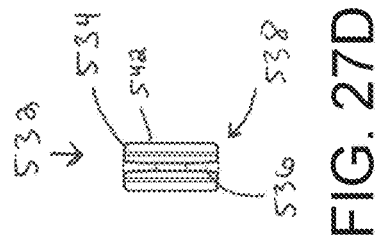
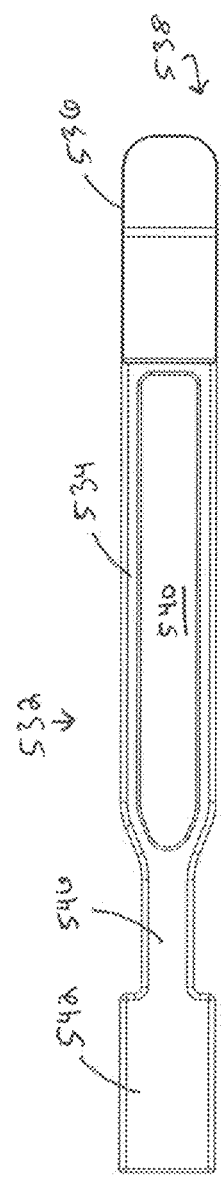
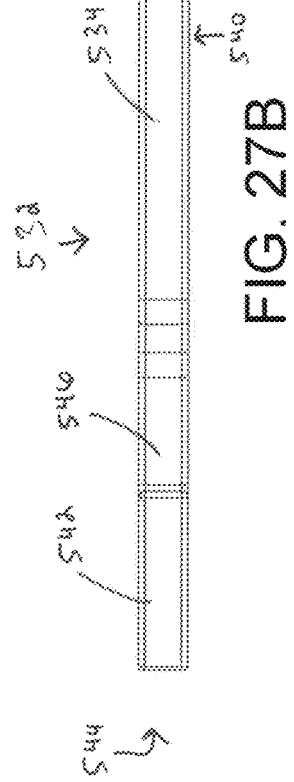
FIG. 27A
FIG. 27B
FIG. 27C
FIG. 27D

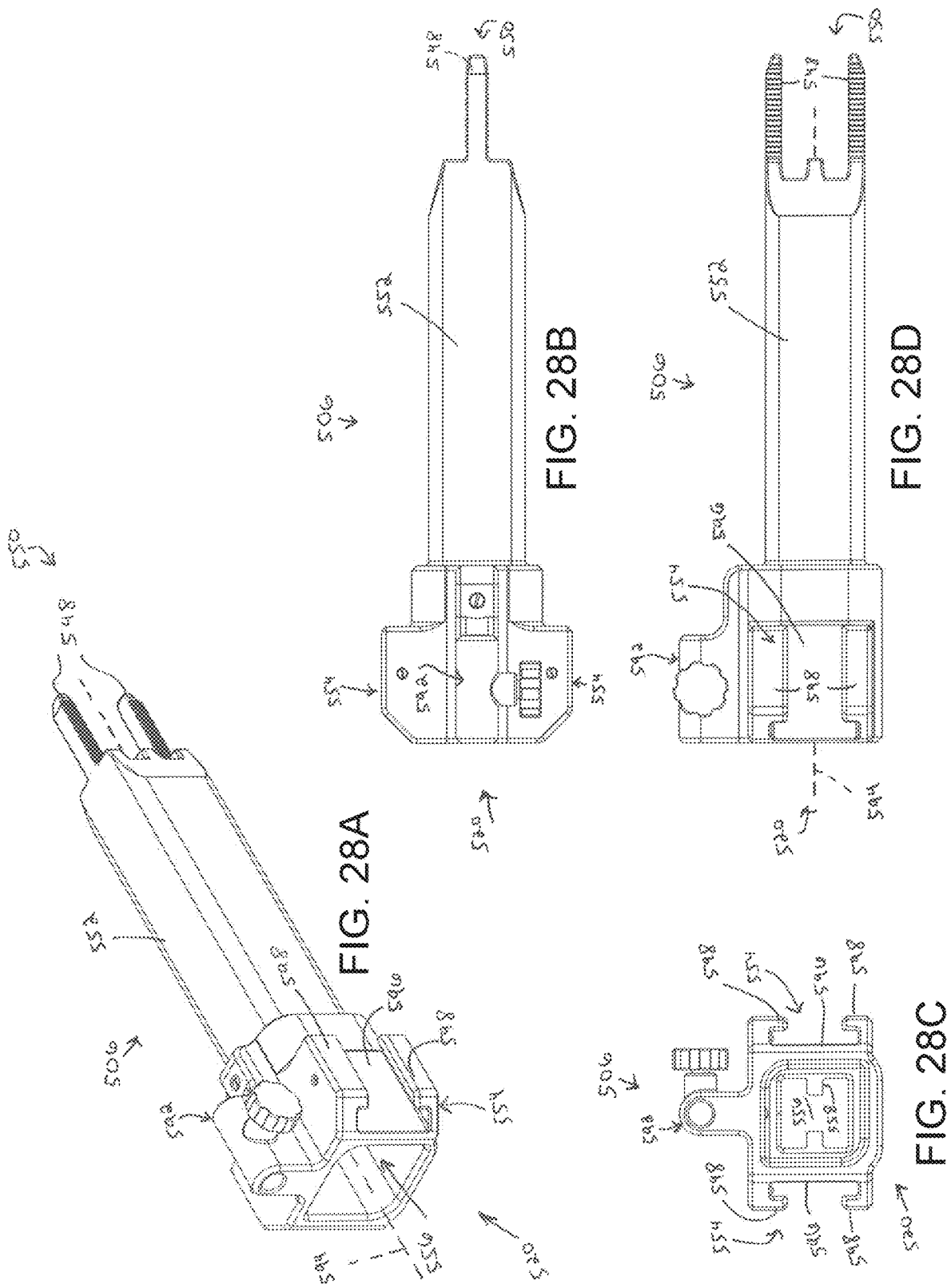

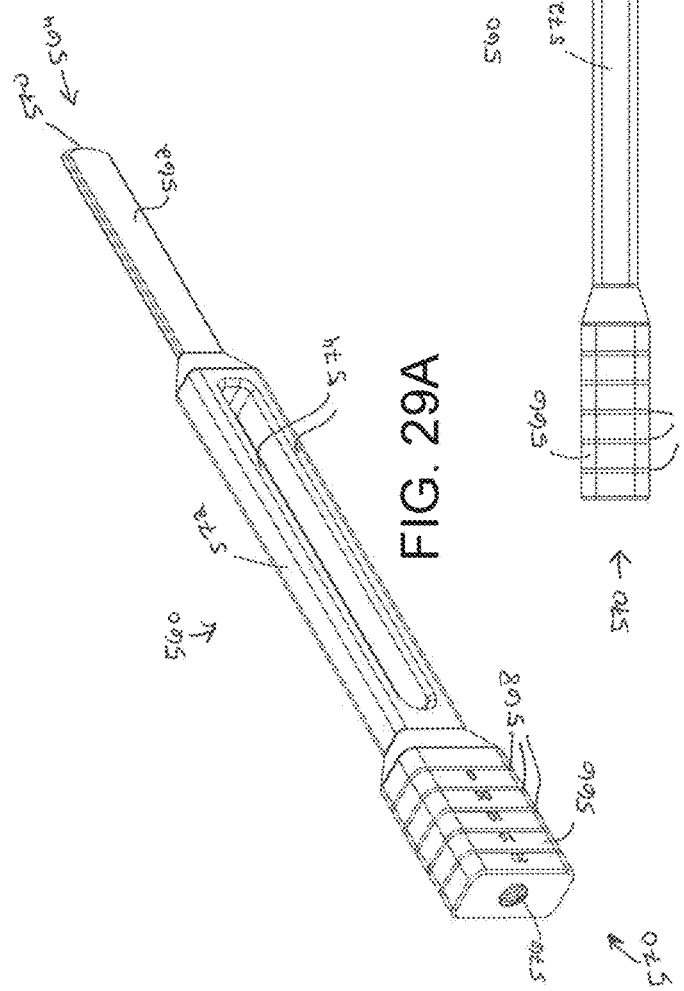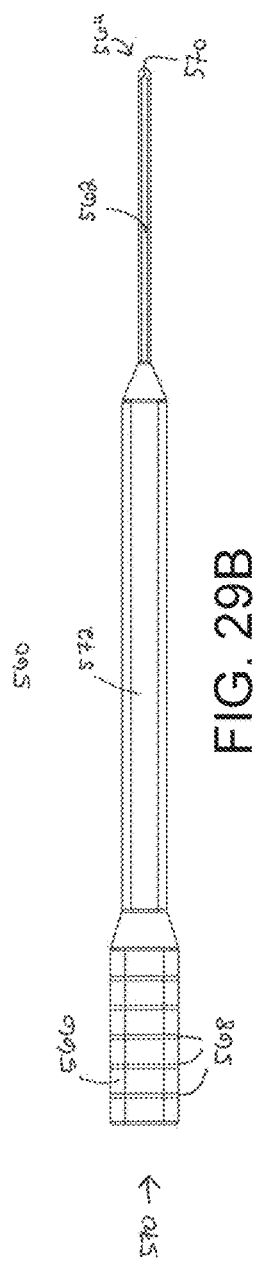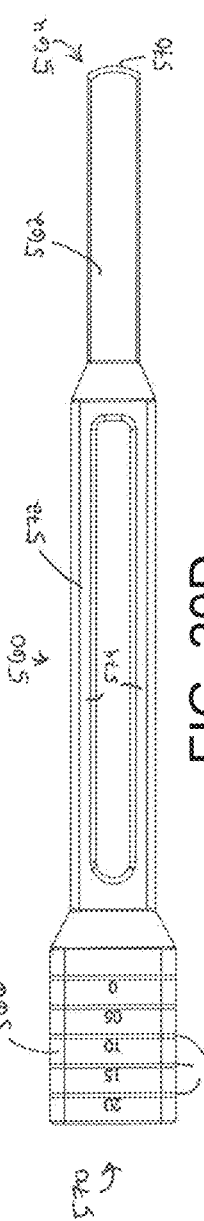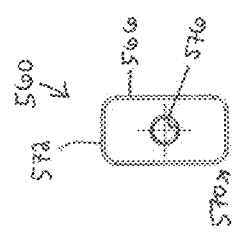

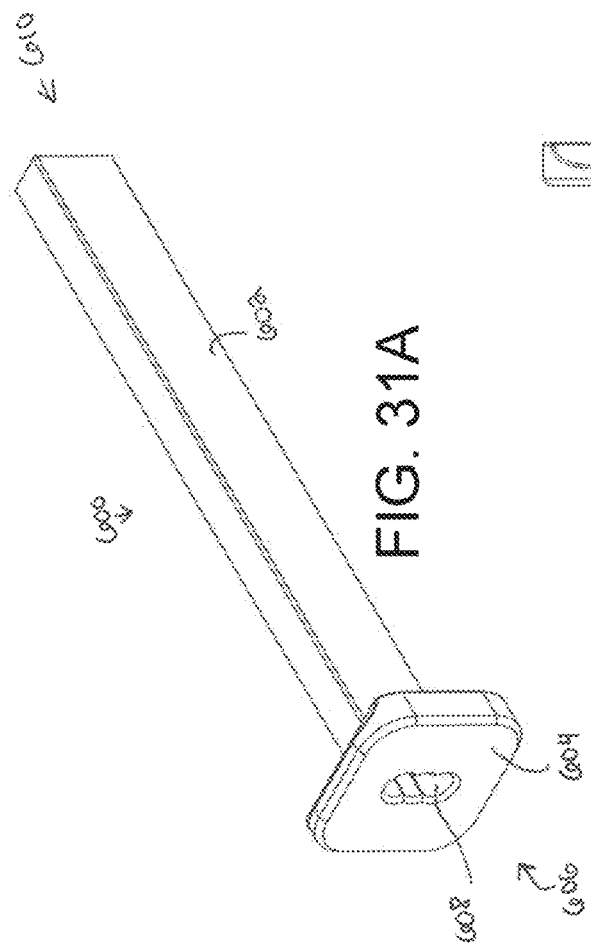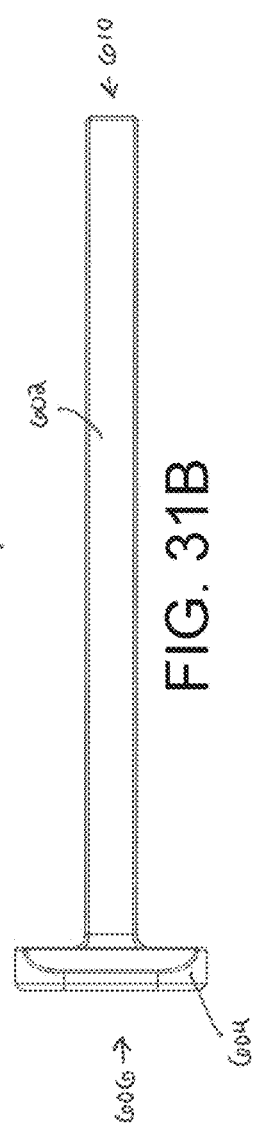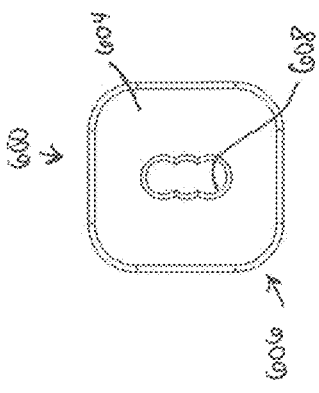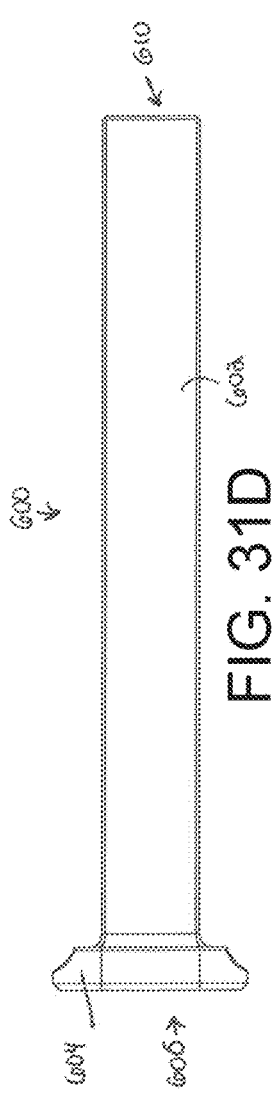

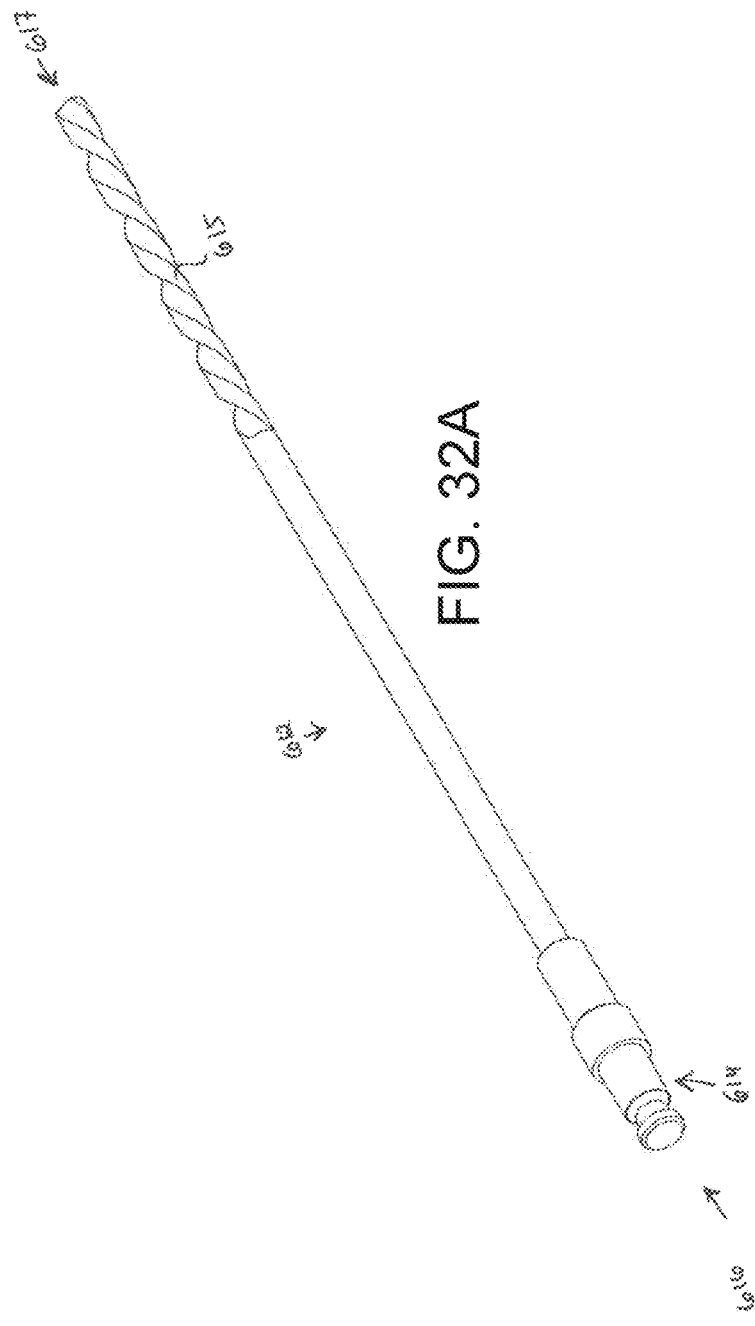
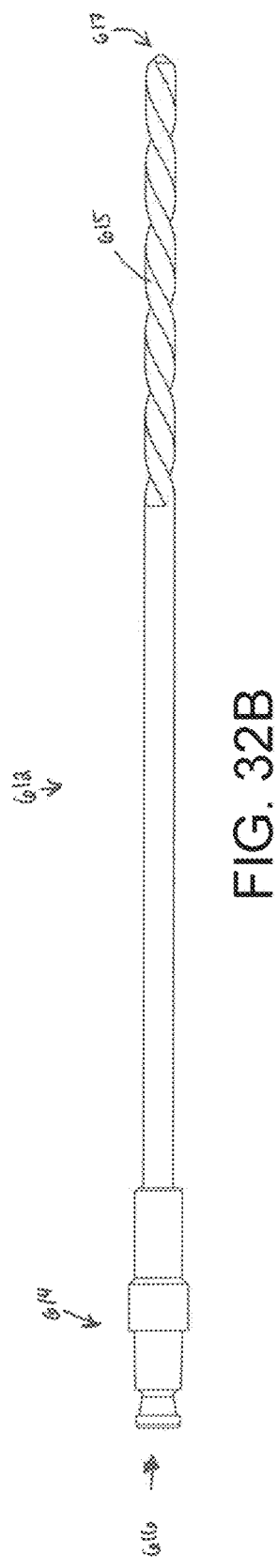
FIG. 32A
FIG. 32B

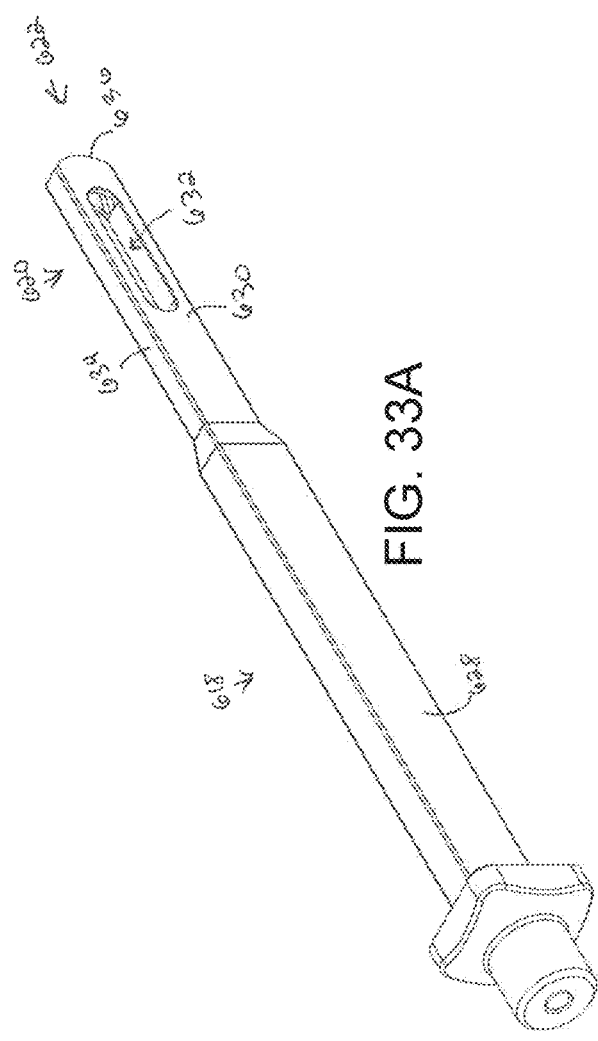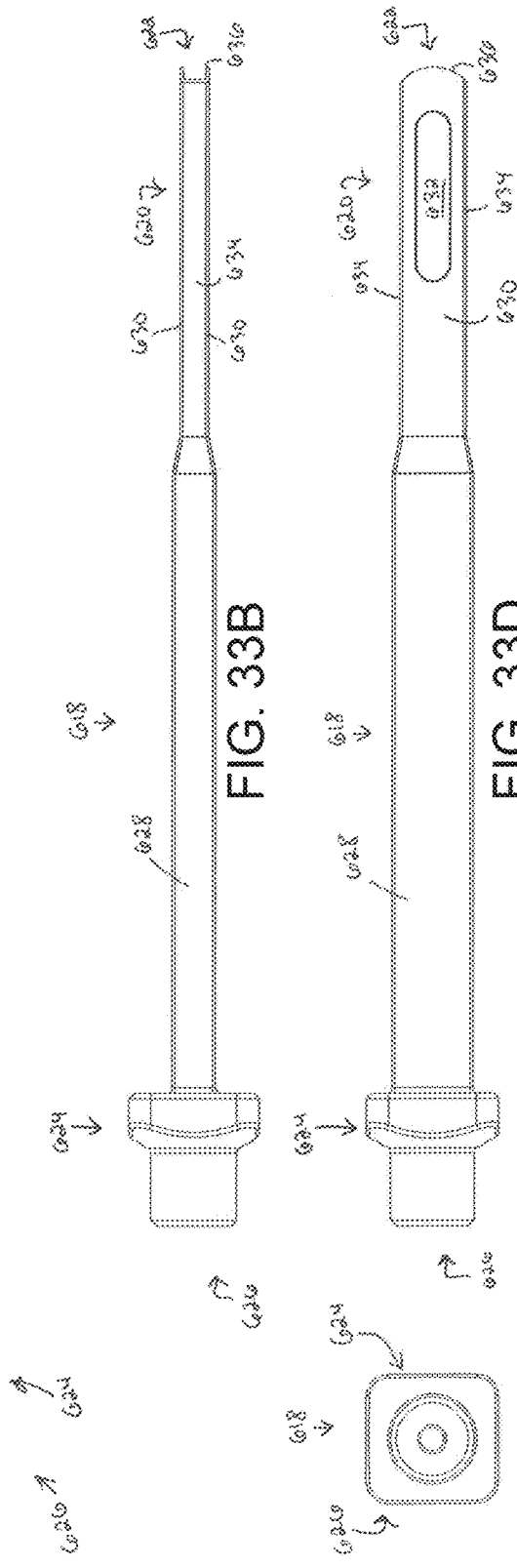

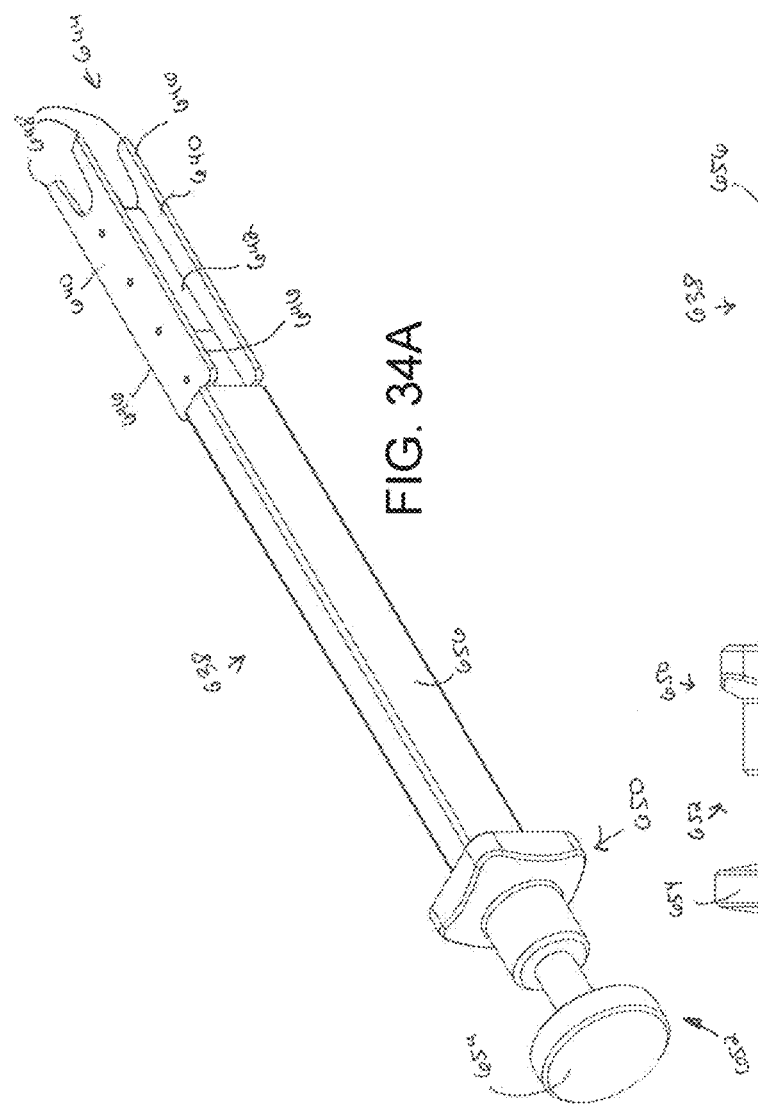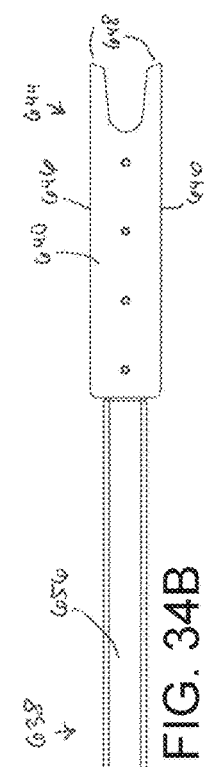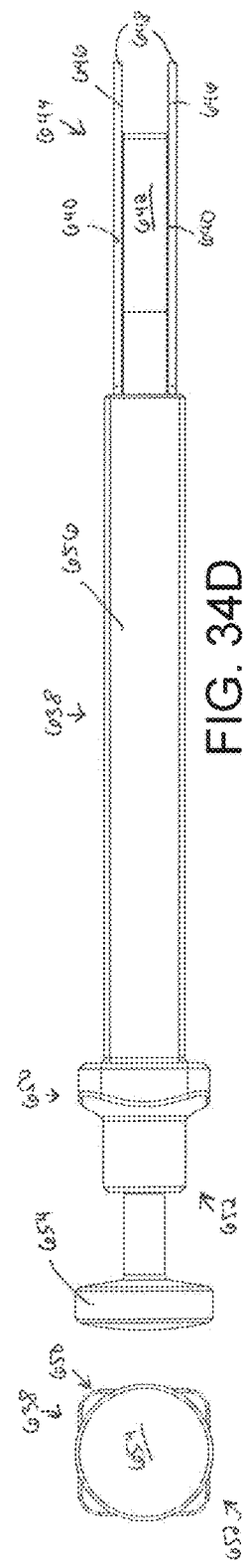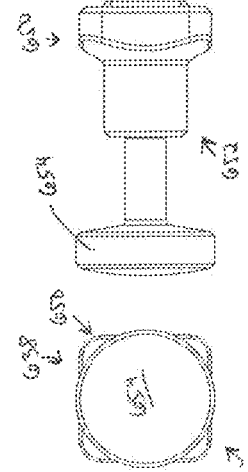

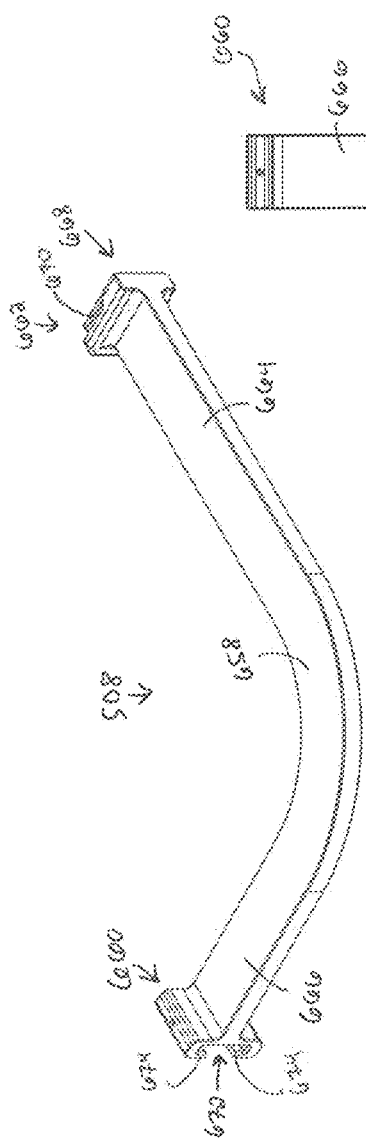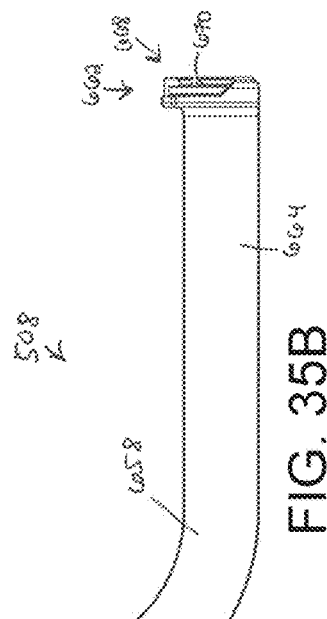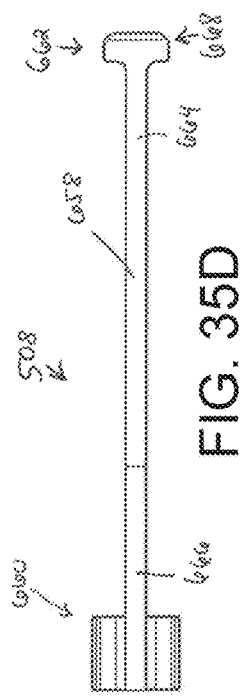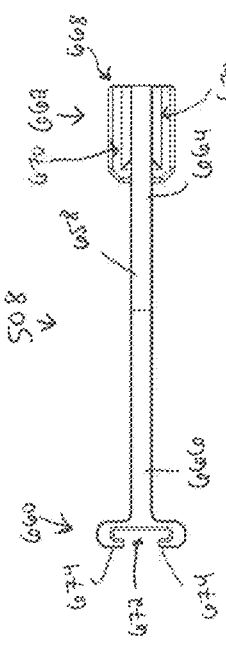

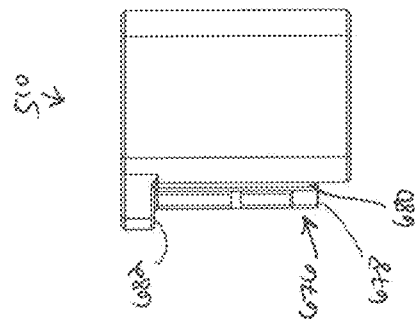
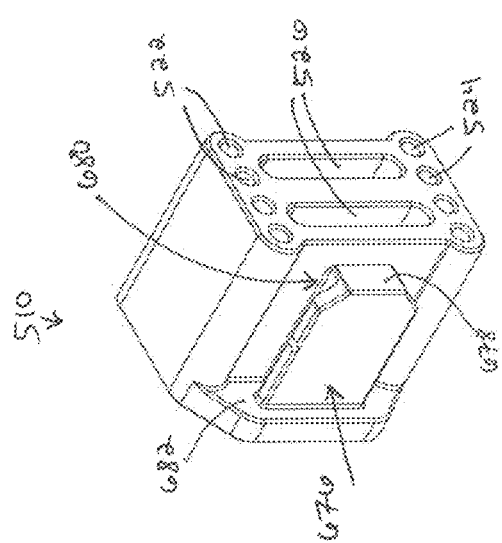
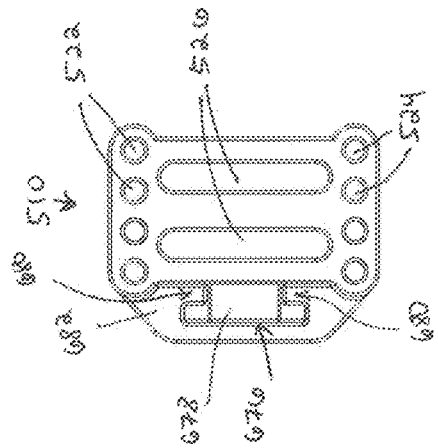
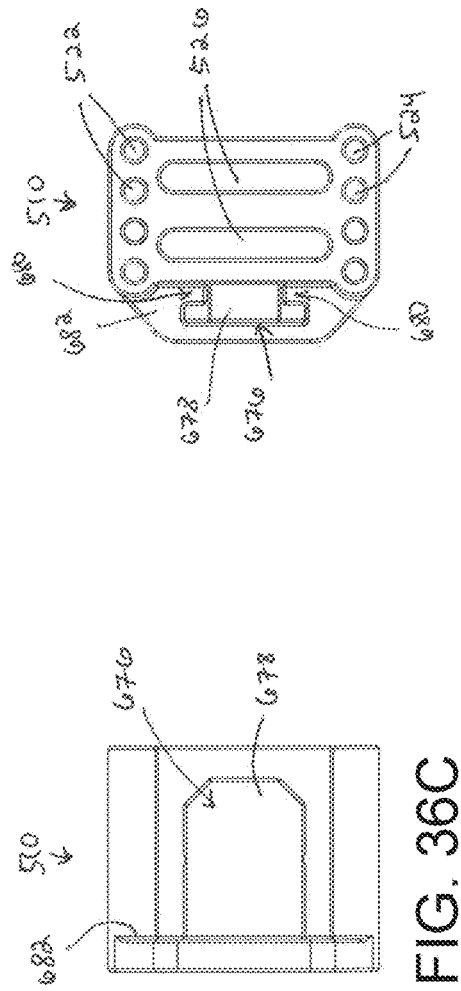

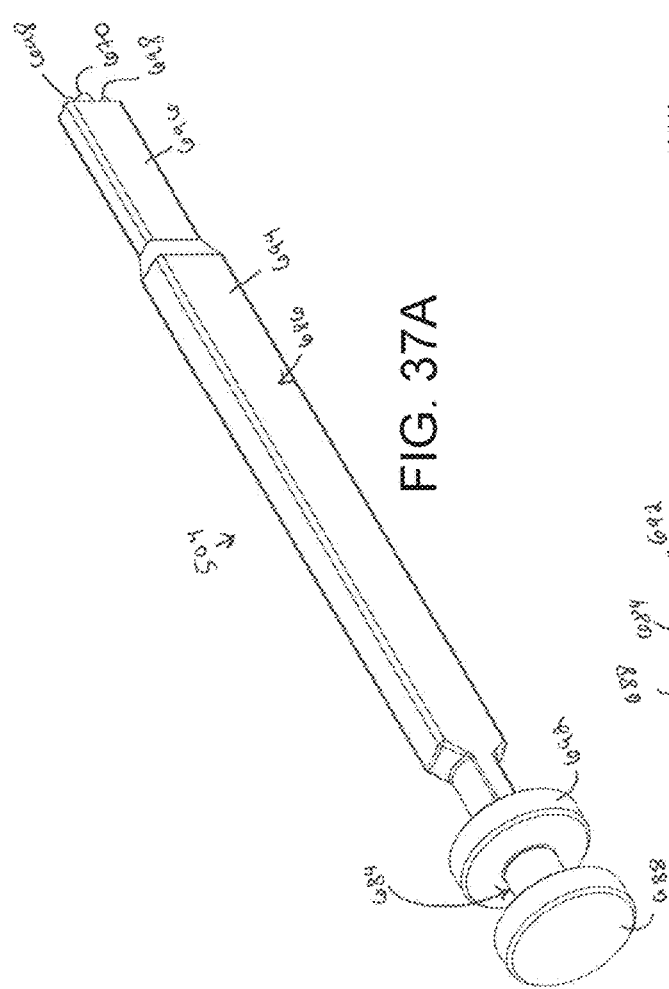
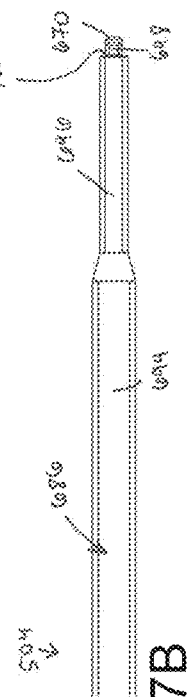
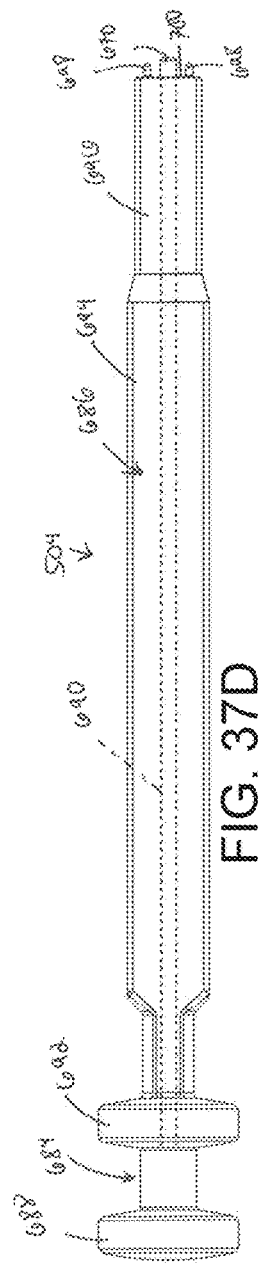
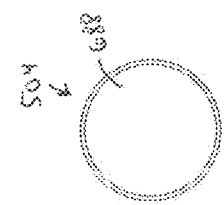
FIG. 37A
FIG. 37B
FIG. 37C
FIG. 37D

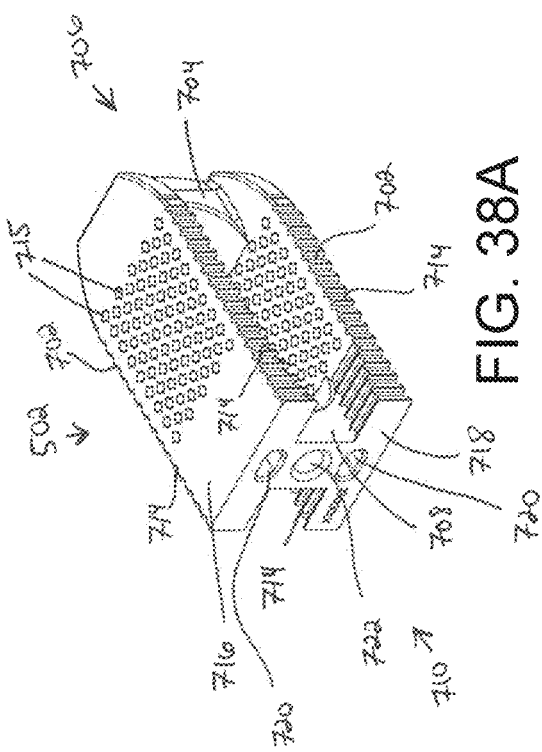
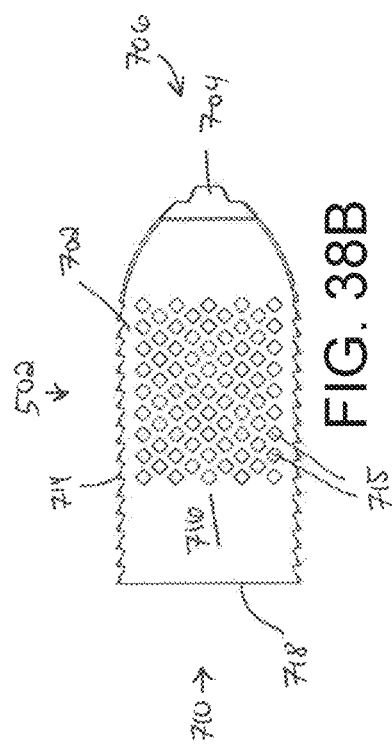
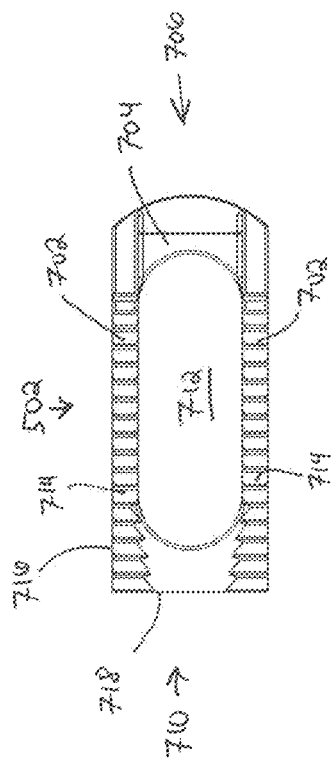
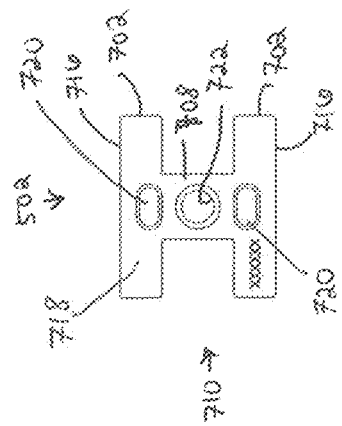
FIG. 38A
FIG. 38B
FIG. 38C
FIG. 38D

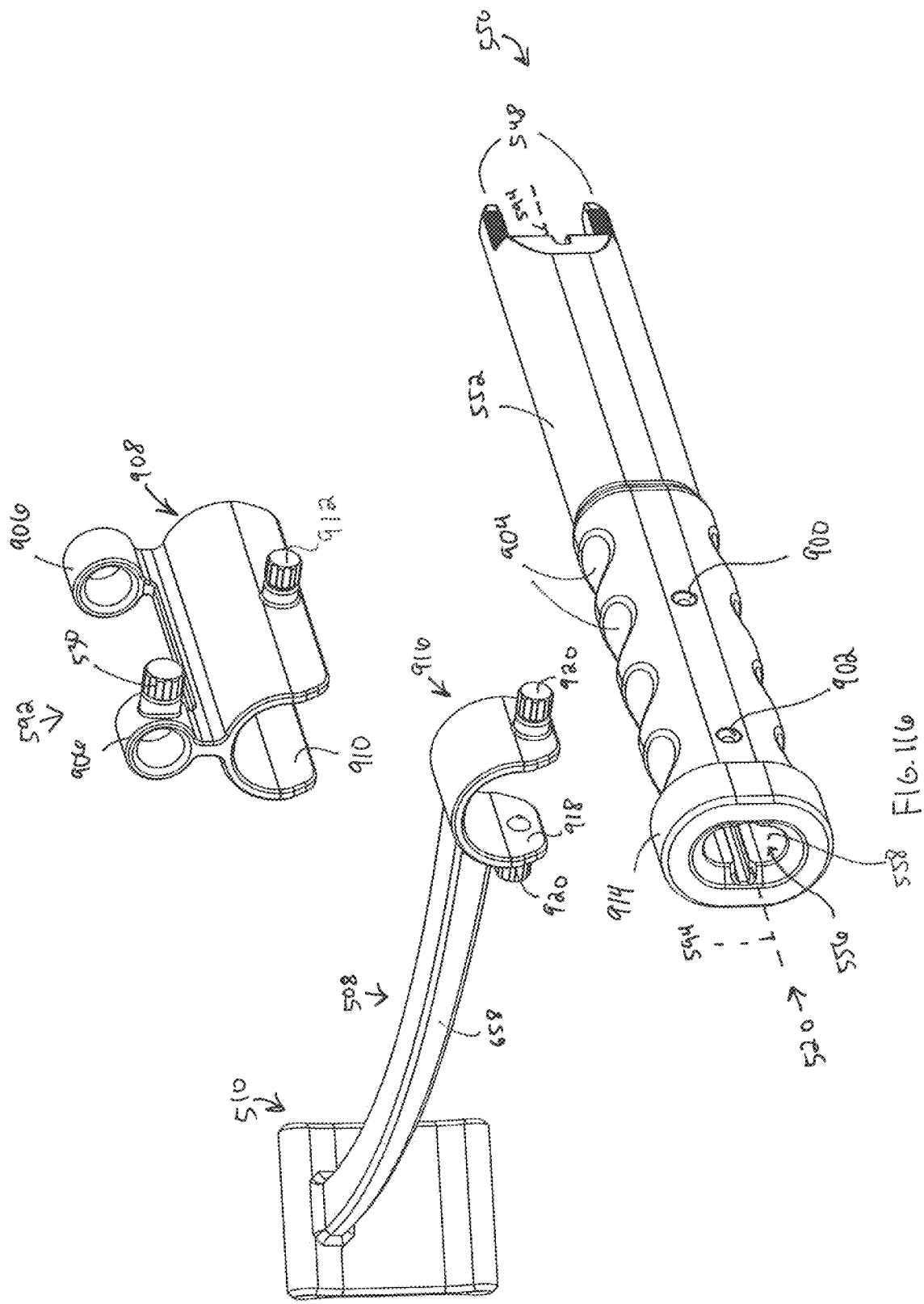

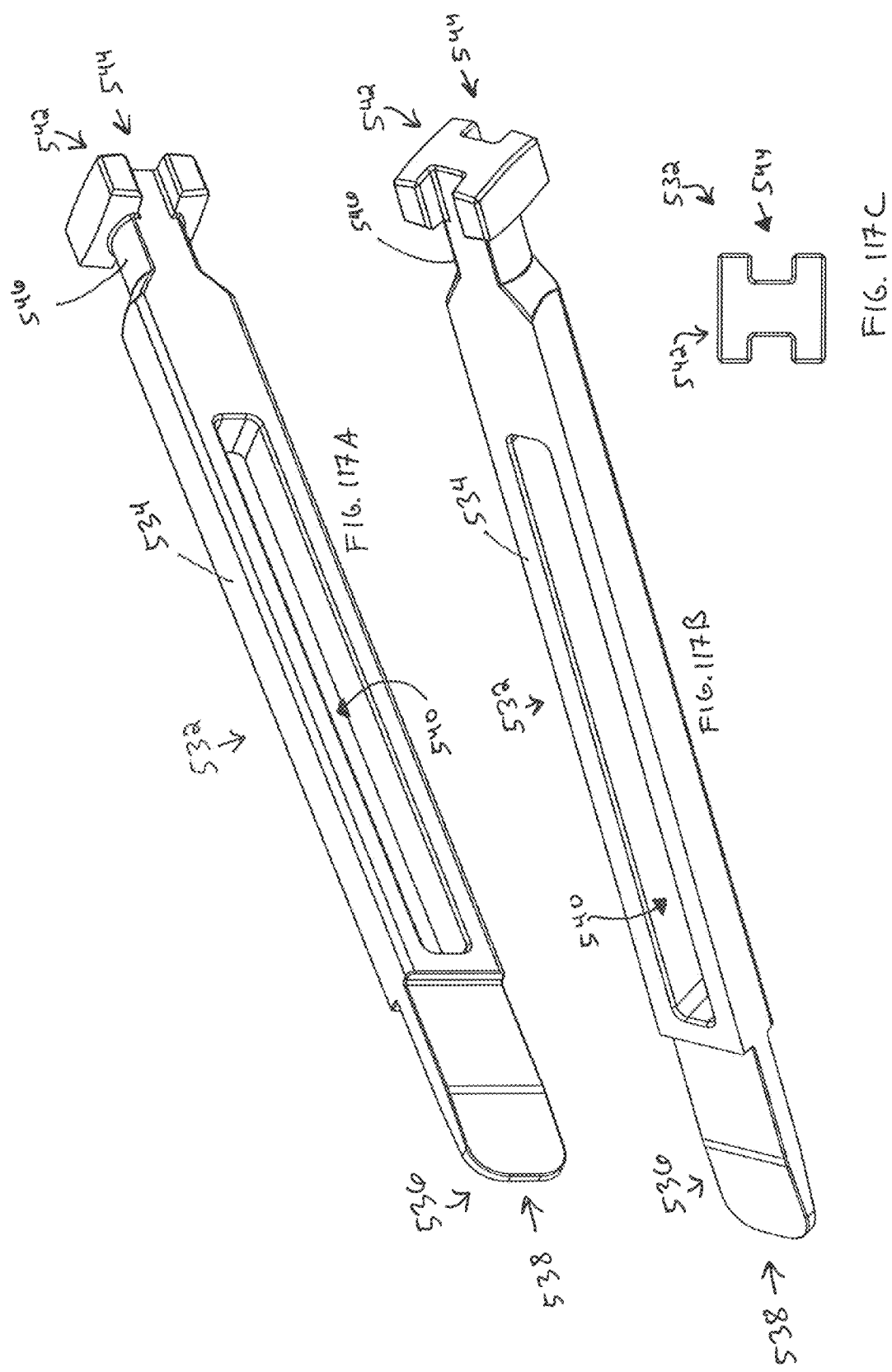

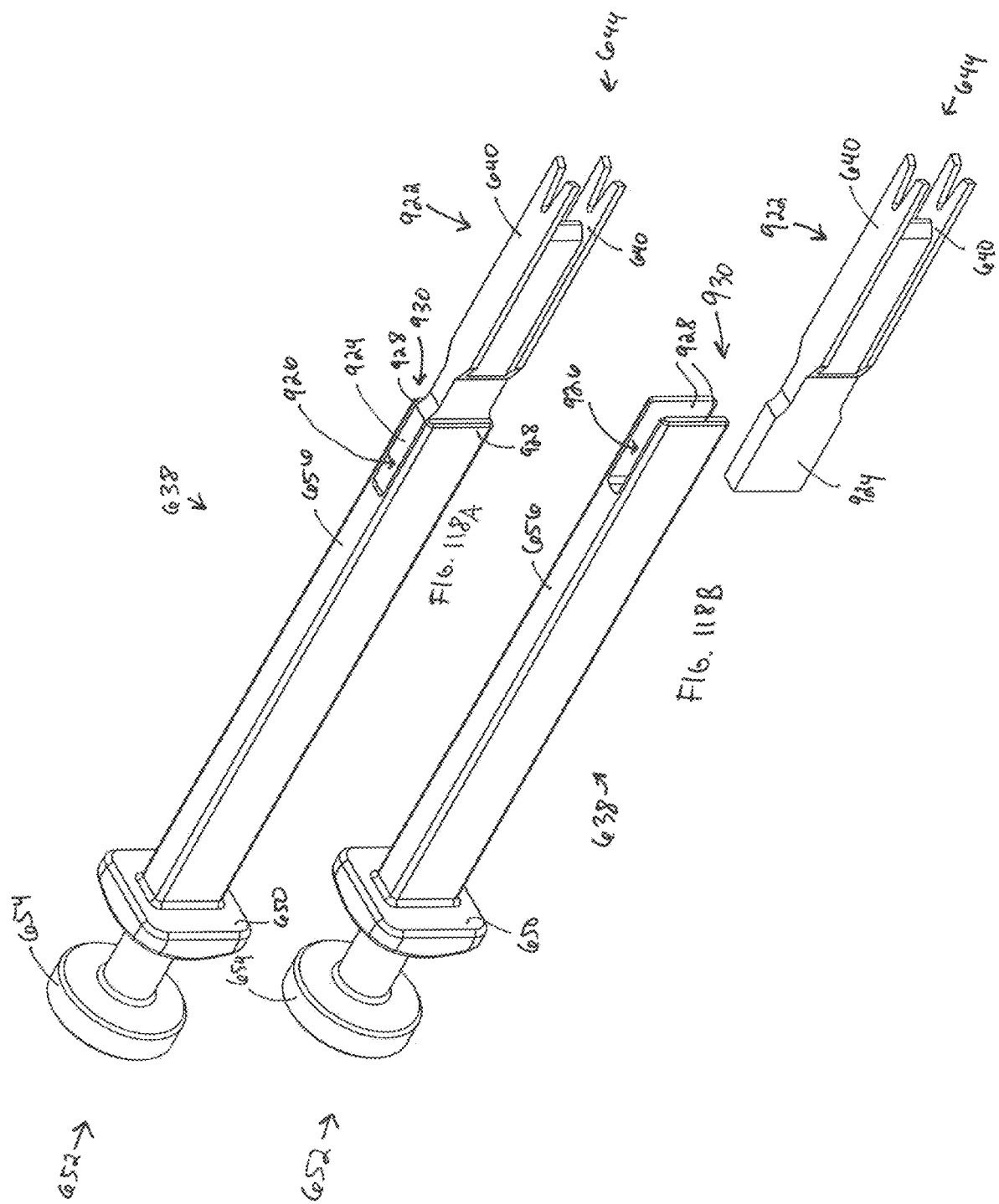

SYSTEMS FOR AND METHODS OF PREPARING AND FUSING A SACROILIAC JOINT

CROSS-REFERENCE TO RELATED APPLICATIONS

The present application claims priority under 35 U.S.C. § 119 to U.S. Provisional Patent Application Numbers: 62/559,386 filed Sep. 15, 2017; 62/608,476 filed Dec. 20, 2017; 62/609,095 filed Dec. 21, 2017; 62/632,635 filed Feb. 20, 2018; and 62/640,026 filed Mar. 8, 2018. All of the aforementioned U.S. Provisional Patent Applications are hereby incorporated by reference in their entireties into the present application.

TECHNICAL FIELD

Aspects of the present disclosure relate to medical apparatus and methods. More specifically, the present disclosure relates to devices and methods for preparing and fusing a sacroiliac joint for fusion.

BACKGROUND

The sacroiliac joint is the joint between the sacrum and the ilium of the pelvis, which are joined by ligaments. In humans, the sacrum supports the spine and is supported in turn by an ilium on each side. The sacroiliac joint is a synovial joint with articular cartilage and irregular elevations and depressions that produce interlocking of the two bones.

Pain associated with the sacroiliac joint can be caused by traumatic fracture dislocation of the pelvis, degenerative arthritis, sacroiliitis an inflammation or degenerative condition of the sacroiliac joint, osteitis condensans ilii, or other degenerative conditions of the sacroiliac joint. Currently, sacroiliac joint fusion is most commonly advocated as a surgical treatment for these conditions. Fusion of the sacroiliac joint can be accomplished by several different conventional methods. However, while each of these methods has been utilized for fixation and fusion of the sacroiliac joint over the past several decades, substantial problems with respect to the fixation and fusion of the sacroiliac joint remain unresolved.

A significant problem with certain conventional methods for fixation and fusion of the sacroiliac joint may be that the surgeon has to make a substantial incision in the skin and tissues for direct access to the sacroiliac joint involved. These invasive approaches allow the sacroiliac joint to be seen and touched directly by the surgeon. Often referred to as an "open surgery", these procedures have the attendant disadvantages of requiring general anesthesia and can involve increased operative time, hospitalization, pain, and recovery time due to the extensive soft tissue damage resulting from the open surgery.

A danger to open surgery using an anterior approach can be damage to the L5 nerve root, which lies approximately two centimeters medial to the sacroiliac joint or damage to the major blood vessels. Additionally and as seen in FIG. 1, which depicts a conventional fusion procedure (immobilization of the articular surfaces of the sacroiliac joint in relation to one another) on a sacroiliac joint 1, one or more screws or implants 2 are implanted transversely across the articular surfaces 3 and through the sacrum 4 and the ilium bones 5. That is, the joint 1 is immobilized by placement of a fusion device 2 transverse to or across a plane defined by articular surfaces 3 of the sacroiliac joint space.

Use of trans-sacroiliac and S1 pedicle-iliac bone implants can also involve the risk of damage to the lumbosacral neurovascular elements. Damage to the lumbosacral neurovascular elements as well as delayed union or non-union of the sacroiliac joint by use of these procedures may require revision surgery to remove all or a portion of the implants or repeat surgery as to these complications.

Another significant problem with conventional procedures utilizing minimally invasive small opening procedures can be that the procedures are technically difficult, requiring biplanar fluoroscopy of the articular surfaces of the sacroiliac joint and extensive surgical training and experience. Despite the level of surgical training and experience, there is a substantial incidence of damage to the lumbosacral neurovascular elements. Additionally, sacral anomalies can further lead to mal-placement of implants leading to damage of surrounding structures. Additionally, these procedures are often performed without fusion of the sacroiliac joint, which does not remove the degenerative joint surface and thereby does not address the degenerative condition of the sacroiliac joint, which may lead to continued or recurrent sacroiliac joint pain.

Another significant problem with conventional procedures can be the utilization of multiple trans-sacroiliac elongate implants, which do not include a threaded surface. This approach requires the creation of trans-sacroiliac bores in the pelvis and nearby sacral foramen, which can be of relatively large dimension and which are subsequently broached with instruments, which can result in bone being impacted into the pelvis and neuroforamen.

The creation of the trans-sacroiliac bores and subsequent broaching of the bores requires a guide pin, which may be inadvertently advanced into the pelvis or sacral foramen, resulting in damage to other structures. Additionally, producing the trans-sacroiliac bores, broaching, or placement of the elongate implants may result in damage to the lumbosacral neurovascular elements, as above discussed. Additionally, there may be no actual fusion of the articular portion of the sacroiliac joint, which may result in continued or recurrent pain requiring additional surgery.

Another substantial problem with conventional procedures can be that placement of posterior extra-articular distracting fusion implants and bone grafts may be inadequate with respect to removal of the articular surface or preparation of cortical bone, the implant structure and fixation of the sacroiliac joint. The conventional procedures may not remove sufficient amounts of the articular surfaces or cortical surfaces of the sacroiliac joint to relieve pain in the sacroiliac joint. The conventional implant structures may have insufficient or avoid engagement with the articular surfaces or cortical bone of the sacroiliac joint for adequate fixation or fusion. The failure to sufficiently stabilize and fuse the sacroiliac joint with the conventional implant structures and methods may result in a failure to relieve the condition of sacroiliac joint being treated. Additionally, conventional methods of driving apart a sacrum and ilium may lead to mal-alignment of the sacroiliac joint and increased pain.

Improvements to sacroiliac joint fusion involve systems and methods for non-transverse delivery of an implant into the sacroiliac joint are described in U.S. Patent Applications: Ser. No. 12/998,712, filed May 23, 2011 entitled SACROILIAC JOINT FIXATION FUSION SYSTEM; Ser. No. 13/236,411, filed Sep. 19, 2011 entitled SYSTEMS FOR AND METHODS OF FUSING A SACROILIAC JOINT;

and Ser. No. 13/475,695, filed May 18, 2012, entitled SYSTEMS FOR AND METHODS OF FUSING A SACROILIAC JOINT; and Ser. No. 13/945,053, filed Jul. 18, 2013, entitled SYSTEMS FOR AND METHODS OF FUSING A SACROILIAC JOINT; and Ser. No. 13/946,790, filed Jul. 19, 2013, entitled SYSTEMS FOR AND METHODS OF FUSING A SACROILIAC JOINT; and Ser. No. 14/216,975, filed Mar. 17, 2014, entitled SYSTEMS AND METHODS FOR FUSING A SACROILIAC JOINT AND ANCHORING AN ORTHOPEDIC APPLIANCE; and Ser. No. 14/447,612, filed Jul. 31, 2014, entitled SYSTEMS FOR AND METHODS OF FUSING A SACROILIAC JOINT. All of application Ser. Nos. 12/998,712, 13/236,411, 13/475,695, 13/945,053, 13/946,790, 14/216,975, and 14/447,612 are herein incorporated by reference in their entirety. In certain instances, it may be desirable to prepare the surfaces of the sacroiliac joint prior to implantation of the fusion device, e.g., the intra-articular or extra-articular surfaces. While surgical preparation tools may exist for procedures in other areas of the body, tools for preparing the sacroiliac joint for fusion are lacking. Thus, the systems and methods discussed herein address the challenges in preparing the sacroiliac joint for fixation and fusion.

SUMMARY

One implementation of the present disclosure may take the form of a surgical preparation tool for preparing a sacroiliac joint having a sacrum and an ilium for a surgical procedure.

Aspects of the present disclosure may include a system for performing a fusion procedure on a sacroiliac joint defined between a sacrum and an ilium. In certain instances, the system may include a working cannula that may include a proximal end, a distal end, a tubular body extending between the proximal and distal ends, a cannula passageway defined within the tubular body and having a cannula axis extending there through, a pair of prongs coupled to the tubular body and extending distally there from, an anchor arm engagement structure coupled to the tubular body, and a pin guide coupled to the tubular body and defining a pin passageway having a guidance axis there through that may be generally parallel with the cannula axis.

In certain instances, the pair of prongs may lie in a plane that intersects the cannula axis.

In certain instances, the pair of prongs may lie in a plane that intersects the guidance axis.

In certain instances, the pair of prongs may lie in a plane that intersects the cannula axis and the guidance axis.

In certain instances, the tubular body may include an inner surface that defines the cannula passageway, the inner surface including a pair of protrusions extending inward from opposite sides of the inner surface.

In certain instances, the system further may include an anchor arm including a cannula engagement structure configured to couple to the anchor arm engagement structure of the working cannula, the anchor arm further may include an anchor block engagement structure, and an elongate member coupled to the anchor block engagement structure and the cannula engagement structure.

In certain instances, the system further may include an anchor block including an anchor arm engagement structure configured to couple to the anchor block engagement structure of the anchor arm, the anchor block may include a plurality of guide holes extending through the anchor block and configured to guide a pin along a trajectory.

In certain instances, the anchor block further may include at least one guide slot having an elongated opening extending there through, the at least one guide slot configured to guide a tool along a plurality of trajectories that are limited to those generally within a plane defined by the elongated opening.

In certain instances, the tool may include a pin.

In certain instances, the system further may include a standoff may include a tubular body configured to be positioned within the passageway of the working cannula at the proximal end.

In certain instances, the standoff further may include an inner surface including a pair of protrusions extending inward from opposite sides of the inner surface, wherein, when the standoff may be positioned within the passageway of the working cannula the pair of protrusions of the standoff and working cannula, respectively, are collinear with each other.

In certain instances, the system further may include an implant arm may include an implant retainer and an arm member, the implant retainer may include a shaft having a threaded end configured to couple to a joint implant, the arm member may include a passageway for receiving the shaft of the implant retainer therein.

In certain instances, the system further may include the joint implant.

In certain instances, the joint implant may include an implant body including at least one planar member extending a length between a proximal end and a distal end, and an opening extending through the implant body.

In certain instances, the implant body defines X-shaped cross-section.

In certain instances, the joint implant further may include a flange coupled to the implant body, the flange being generally perpendicular to the implant body, the at least one planar member may include a first planar member, the opening extending through the first member.

In certain instances, the inner surface of the tubular body of the working cannula may be keyed to a cross-sectional shape of a joint implant to permit passage of the joint implant there through.

In certain instances, the system further may include the joint implant.

In certain instances, the tubular body may include an inner surface that defines the cannula passageway, the inner surface defining a non-circular perimeter.

In certain instances, the system further may include an anchor arm including a cannula engagement structure configured to couple to the anchor arm engagement structure of the working cannula, the anchor arm further may include an anchor block engagement structure, and an elongate member coupled to the anchor block engagement structure and the cannula engagement structure.

In certain instances, the system further may include an anchor block including an anchor arm engagement structure configured to couple to the anchor block engagement structure of the anchor arm, the anchor block may include a plurality of guide holes extending through the anchor block and configured to guide a pin along a trajectory.

In certain instances, the system further may include an implant arm that may include an implant retainer and an arm member, the implant retainer may include a shaft having a threaded end configured to couple to a joint implant, the arm member may include a passageway for receiving the shaft of the implant retainer therein, wherein, movement of the implant arm and the joint implant may be independent of movement of the working cannula, the anchor arm, and the anchor block.

Aspects of the present disclosure may include a method of performing a fusion procedure on a sacroiliac joint defined between a sacrum and an ilium, where the sacroiliac joint may include an articular region, and the ilium may include a posterior superior iliac spine (PSIS) and a posterior inferior iliac spine (PIIS). In certain instances, the method may include: inserting a distal tip of a working cannula between the sacrum and the ilium via a posterior access. The distal tip may include a pair of prongs separated from each other by a distance. The working cannula may include a tubular body, a cannula passageway extending through the tubular body, a pin guide coupled to the tubular body and defining a pin passageway having a guidance axis there through that may be generally parallel with the cannula axis, and an anchor arm engagement structure. The method may further include inserting a guide pin into the ilium, securing the guide pin to the pin guide, inserting a joint implant through the cannula passageway and at least partially into the articular region of the sacroiliac joint, coupling a cannula engagement structure of an anchor arm to the anchor arm engagement structure of the working cannula, coupling an anchor block to the anchor arm, the anchor block may include a plurality of guide holes extending there through, inserting a pin through one of the plurality of guide holes and into the ilium along a trajectory defined by the one of the plurality of guide holes, and guiding a bone anchor into the ilium via guidance by the pin.

In certain instances, the method further may include inserting a distal portion of a cutting tool through the cannula passageway and into the sacroiliac joint so as to prepare the sacrum and the ilium for insertion of the joint implant.

In certain instances, the cutting tool may include at least one tool from a group may include a rasp, a drill bit, a saw blade, and a box osteotome.

In certain instances, securing the guide pin to the pin guide may be via a screw lock of the pin guide.

In certain instances, the tubular body may include an inner surface that defines the cannula passageway, the inner surface including a pair of protrusions extending inward from opposite sides of the inner surface.

In certain instances, the method further may include decoupling the anchor block from the anchor arm prior to guiding the bone anchor into the ilium by the pin.

In certain instances, the method further may include decoupling the cannula engagement structure of the anchor arm and the anchor arm engagement structure of the working cannula prior to guiding the bone anchor into the ilium by the pin.

In certain instances, the guide pin may be inserted into the PSIS of the ilium.

In certain instances, the method further may include removing bone material from the PSIS in preparation for inserting the guide pin therein.

In certain instances, the method further may include implanting the bone material into at least one or both of the joint implant and the sacroiliac joint.

In certain instances, the joint implant may be inserted at least partially into the articular region of the sacroiliac joint via a posterior access region defined between the PSIS and the PIIS.

Aspects of the present disclosure may include a system for preparing a sacroiliac joint having a sacrum and an ilium for a surgical procedure. The system may include: a plurality of pins; a tissue protector or working cannula; a depth gauge; a guide block standoff; a drill guide block; a tool guide block; a plurality of keel drill blocks; a joint implant; and a delivery tool.

In certain instances, the plurality of pins may be configured to be inserted along a plane of the sacroiliac joint in generally a parallel fashion between a PSIS and a PIIS.

In certain instances, the tissue protector may include a generally block shaped body having four inner walls defining a generally square throughway, an open distal end, an open proximal end, a first pin hole passageway for receiving a first of the plurality of pins there through, a second pin hole passageway for receiving a second of the plurality of pins there through, and a transverse attachment point for a handle or other structure, the first and second pin hole passages being on opposite sides of the body and not obscuring the square throughway, the tissue protector configured to be delivered up to a posterior boundary of the sacroiliac joint via the first and second pins being received in the first and second pin hole passages, respectively.

According to particular embodiments, the tissue protector may have an inner wall configuration which provides an singular fixturing arrangement or an indexable fixturing arrangement relative to the various inserts, jigs, guide blocks or tools which engage the inner walls in order to provide a precise singular orientation or set of orientations, respectively, of the inserts, jigs, guide blocks or tools. The inner walls may comprise at least one of curved surfaces or planar surfaces. For example, a singular orientation of a drill guide block having multiple drill guide bores may align the multiple drill guide bores to all be generally coplanar with the plane of the sacroiliac joint while preventing a second orientation, for example, where the multiple drill guide bores are all aligned generally perpendicular with the plane of the sacroiliac joint. For example, a set of orientations may include providing an arrangement such that the drill guide block and the tool guide block may be oriented within the tissue protector in only two orientations, a first orientation being a mirror of a second orientation such that the guide blocks are able to be placed in the tissue protector in a zero degree orientation or a 180 degree orientation while, for example, preventing a 90 degree orientation or 270 degree orientation thereby improving precision between steps of the procedure by design in order to avoid unintentional misorientation of any of the cutting or implantation steps.

According to particular embodiments, the tissue protector may have a transverse attachment point for a handle or other structure (e.g. to allow attachment to a surgical table either directly or via an (e.g., FISSO brand) articulating arm surgical tool holder).

In certain instances, the depth gauge guide block may be configured to fit longitudinally within or nest within the four inner walls of the tissue protector via insertion through the open proximal end of the tissue protector, the depth gauge guide block may include a generally block like structure with a plurality of longitudinal through-bores extending there through, the plurality of longitudinal through-bores configured to receive depth pins there through to gauge, e.g.: at least one of i) a depth of the sacroiliac joint at different points along an anterior border of the joint, ii) the distance up to an entry point of the articular portion of the SI joint adjacent the distal end of the tissue protector, or iii) the distance up to the cortical surface of the ilium or sacrum adjacent the distal end of the tissue protector.

In certain instances, the guide block standoff may be configured to couple to the depth gauge guide block or other components of the system so as to limit a depth of insertion to a desired amount. The system may comprise multiple sizes of guide block standoffs which are configured to limit a depth of insertion to preselected desired amounts which may be selected based on information obtained from measurements while using either the depth gauge guide block or a separate depth gauge without the use of a depth gauge guide block.

In certain instances, the drill guide block may be configured to fit longitudinally within or nest within the four inner walls of the tissue protector via insertion through the open proximal end of the tissue protector, the drill guide block may include a generally block like structure with a drill guide bore extending longitudinally there through, when the drill guide block is nested within the tissue protector, the bore is oriented to guide a drill along a predetermined path relative to the tissue protector and first and second pins.

According to particular embodiments, the drill guide block may comprise at least one of a single drill guide bore, two or more spaced apart drill guide bores, two or more overlapping drill guide bores, a slot drill guide bore or a curved slot drill guide bore.

In certain instances, the tool guide block configured to fit longitudinally within or nest within the four inner walls of the tissue protector via insertion through the open proximal end of the tissue protector, the tool guide block may include a generally block like structure with a particularly shaped longitudinal passageway having a cross-sectional shape that generally matches a cross-sectional shape of an implant to be delivered or that permits passage of the implant and a plurality of tools there through, the plurality of tools may include: an osteotome having a pair of oppositely oriented longitudinal projections projecting from an outer surface of the osteotome, the projections configured to fit within the longitudinal passageway; a rasp having a pair of oppositely oriented longitudinal projections projecting from an outer surface of the rasp; a broach guide having a pair of oppositely oriented longitudinal projections projecting from an outer surface of the broach guide; and a broach having multiple cutting edges and configured to cut the sacrum and ilium with a stroke from the broach (or a series of progressively larger broaches; or a chisel or series of progressively larger chisels).

In certain instances, the plurality of keel drill blocks, each configured to fit longitudinally within or nest within the four inner walls of the tissue protector via insertion through the open proximal end of the tissue protector, each of the plurality of keel drill blocks may include a longitudinal through bores defining a pattern and spaced a certain distance apart, the through bores configured to guide a drill in forming a portion of an implant receiving space in the sacrum or the ilium, the plurality of keel drill blocks being arranged in progressively larger or more spaced apart through bores. For example, the pattern of a first keel drill block may have the bores located furthest away from a longitudinal axis of the first keel drill block such that when employed the drill holes are located in the sacrum and ilium at the terminal edges of the keel portion of the implant receiving space; and, for example, the pattern of a second keel drill block may have the bores located closer to a midline of the keel drill block such that when employed the drill holes are located in the sacrum and ilium adjacent the holes at the terminal edges of the keel portion of the implant receiving space and closer to the plane of the sacroiliac joint such that after using one or more keel drill blocks a drilled out implant receiving space approximates at least a portion of a net shape of the implant.

In certain instances, the joint implant may be configured to couple to an implant arm and be delivered through the longitudinal passageway of the tool guide block, the joint implant may include a planar top member, a planar bottom member, a distal member connecting a distal portion of the top and bottom member, and a proximal member connecting a proximal portion of the top and bottom member, the joint implant defining a transverse passageway between the distal and proximal members for receiving an anchor or biocompatible material therein.

In certain instances, the delivery tool may include the implant arm, an anchor arm, and an adjustment arm coupling the implant arm and anchor arm, the anchor arm may include a through bore configured to guide the placement of an anchor to a predetermined position and orientation relative to the joint implant; the adjustment arm configured to arcuately extend and retract so as to change an angle of delivery of the anchor relative to the joint implant, the through bore of the anchor arm configured to guide preparation tools including an awl, a center drill, a drill bit, a spatulate tipped tool, a ball-end tool (for providing tactile feedback of whether the bore formed in the bones terminates in soft tissue or within the bones), depth gauge, tap for a screw implant (or broach for a non-threaded implant), and screw driver (or other implantation tool) for progressively preparing the bones of the sacrum or the ilium for delivery of the anchor.

In certain instances, the delivery tool further may include a guide block insertion tool configured to couple to the adjustment arm, the guide block insertion tool may include a plurality of through holes of differing orientation for inserting the anchor arm there through, the differing orientation configured to orient the anchor arm in different trajectories relative to the joint implant.

In certain instances, the guide block insertion tool may be custom manufactured for a particular patient based off of pre-operative imaging studies in order to provide custom configurations, orientations and trajectories of the through holes such that various tools and implants may be delivered via the custom through holes to arrive at preselected locations within the patient.

In certain instances, the drill guide block further may include another drill guide bore positioned inferior, and in-line with the drill guide bore.

In certain instances, the cross-sectional shape of the longitudinal passageway may include an I-beam shape with an additional midline cross through the I-beam shape.

In certain instances, the cross-sectional shape of the longitudinal passageway may include an X shape.

In certain instances, the cross-sectional shape of the longitudinal passageway may include a + shape.

In certain instances, the adjustment arm may include a closed tubular structure, e.g., having a circular, oval, polygonal, rectangular, square, half round, half oval, or other hybrid partially planar/partially arcuate or curved cross section shape.

In certain instances, the adjustment arm may include non-tubular structural beam shape structures to resist torsional and bending forces, e.g., a I-beam, Tee bar or channel "[" cross section shape.

In certain instances, the system may further may include a trial implant configured to couple to the implant arm and to be delivered through the longitudinal passageway of the tool guide block into the implant receiving space prior to cutting the sacrum and ilium using the broach. For example, the trial implant may have a net shape which approximates the shape of the implant or only partial approximates the shape of the implant, e.g., only the intraarticular portion of the implant without the "keels" or other members extending beyond the implant receiving space within the joint plane.

In certain instances, the trial implant may include a radiolucent body within which one or more radiopaque markers are disposed.

In certain instances, the system may further may include a radiographic guidance system adapted to be received by the delivery tool, the radiographic guidance system may include a plurality of adjustable members and a plurality of radiopaque markers, the adjustable members movable to align the radiopaque markers with a radiographic system and a point of interest related to implantation of the anchor.

In certain instances, the point of interest is a structural feature of the trial implant.

In certain instances, the point of interest is an anatomical feature of one of the sacrum and the ilium.

In certain instances, the plurality of adjustable members may include: a plunger adapted to be rotationally coupled to the delivery tool; a depth gauge; and a guide arm coupled to each of the plunger and the depth gauge, the depth gauge being translatable relative to the guide arm.

In certain instances, the depth gauge may include one or more first radiopaque markers of the plurality of radiopaque markers.

In certain instances, the first radiopaque markers are distributed along a distal portion of the depth gauge in a predetermined pattern such that the first radiopaque markers may be used to measure a distance relative to the point of interest in a radiographic image when the first radiopaque markers are aligned with a radiographic system and the point of interest.

In certain instances, when the plunger is disposed within one of the through bore of the anchor arm or a through hole of the guide bloc insertion tool, a distal end of the plunger extends to an anchor implantation location.

In certain instances, the depth gauges may include one or more first radiopaque markers of the plurality of radiopaque markers, the plunger may include one or more second radiopaque markers of the plurality of radiopaque markers, and aligning the radiopaque markers with the radiographic system and the point of interest further includes aligning the one or more first radiopaque markers with the one or more second radiopaque markers.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 2A is an isometric view of a first embodiment of a system for fusing a sacroiliac joint.

FIG. 2B is the same view as FIG. 2A, except the delivery tool and implant assembly are decoupled from each other.

FIG. 3 is the same view as FIG. 2A, except the system is exploded to better illustrate its components.

FIG. 8 is a medial view of a sacrum and ilium with a nearest ilium removed so as to clearly view a parallel pin guide and three pins extending there through.

FIG. 22 is an isometric view of a radiographic system in use with the implant trial, the elongate plunger, and a close-up view of a radiographic image.

FIGS. 27A-27D are respectively isometric, top, side, and front views of a joint finder.

FIGS. 28A-28D are respectively isometric, top, back, and side views of a working cannula or tissue protector.

FIGS. 29A-29D are respectively isometric, top, back, and side views of a depth gauge.

FIGS. 31A-31D are respectively isometric, top, back, and side views of a drill guide insert.

FIGS. 32A-32B are respectively isometric and side views of a drill bit.

FIGS. 33A-33D are respectively isometric, top, back, and side views of a box osteotome.

FIGS. 34A-34D are respectively isometric, top, back, and side views of a dual chisel blade (or broach, saw blade or other cutting profile) broach.

FIGS. 35A-35D are respectively isometric, top, back, and side views of an anchor arm.

FIGS. 36A-36D are respectively isometric, top, side, and front views of an anchor block.

FIGS. 37A-37D are respectively isometric, top, back, and side views of an implant arm.

FIGS. 38A-38D are respectively isometric, top, back, and side views of a joint implant.

FIG. 116 is proximal isometric view of the exemplary working cannula, the anchor arm, and pin guide uncoupled from each other.

FIGS. 117A-117C are, respectively, a pair of isometric side views and a back view of a joint finder.

FIGS. 118A and 118B are, respectively, side isometric and side isometric exploded views of a broach.

DETAILED DESCRIPTION

Figure 1:
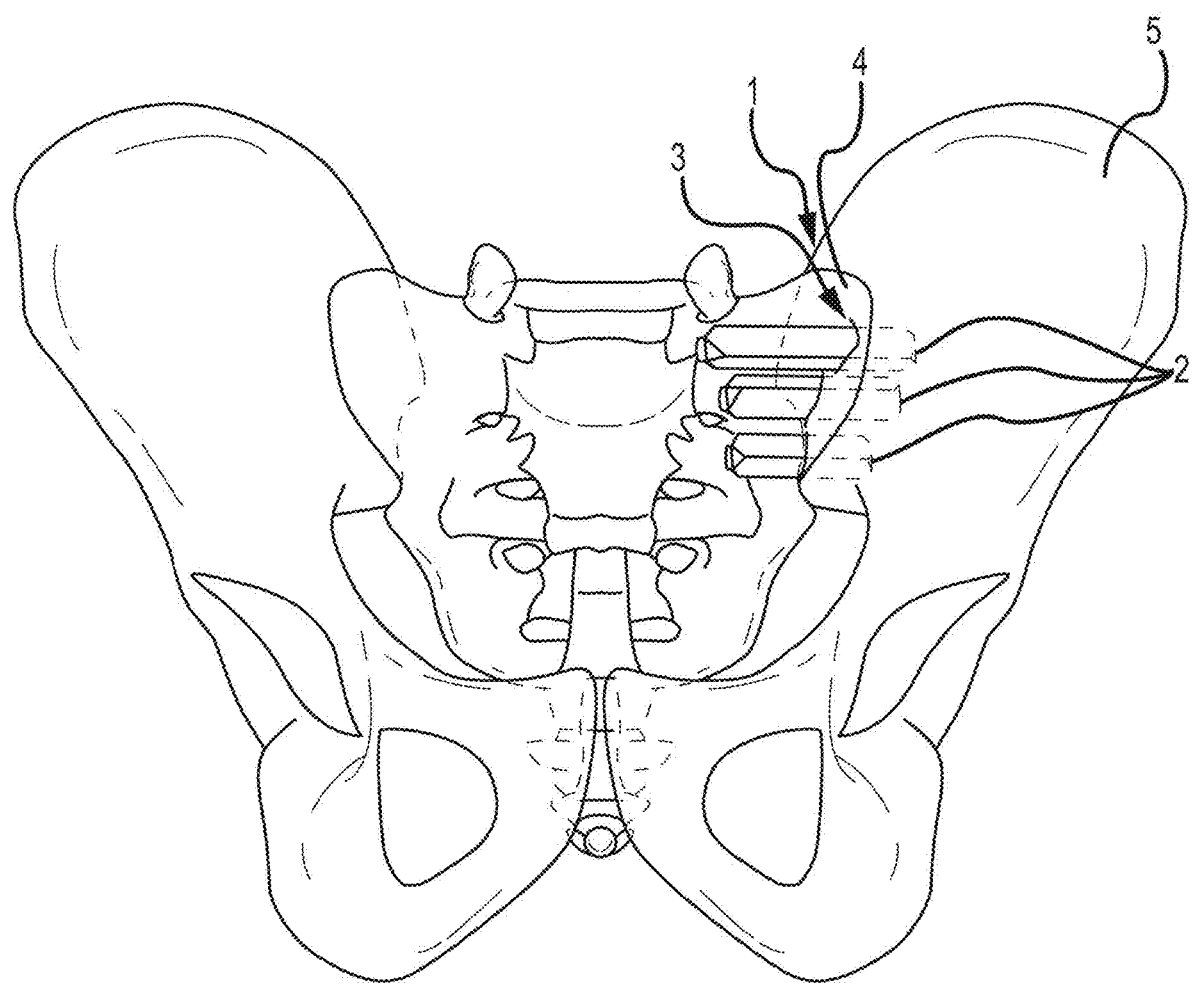
FIG. 1 is an anterior view of the pelvic region and a conventional method and device for stabilizing the sacroiliac joint.

The present application incorporates by reference the following patent applications in their entireties: Ser. No.

12/998,712 filed on May 23, 2011; Ser. No. 13/135,381 filed on Jul. 1, 2011; Ser. No. 14/127,119 filed on Dec. 17, 2013; Ser. No. 13/236,411 filed on Sep. 19, 2011; Ser. No. 13/475,695 filed on May 18, 2012; Ser. No. 13/945,053 filed on Jul. 18, 2013; Ser. No. 13/946,790 filed on Jul. 19, 2013; Ser. No. 14/344,876 filed on Mar. 13, 2014; Ser. No. 14/216,975 filed on Mar. 17, 2014; Ser. No. 14/681,882 filed on Apr. 8, 2015; Ser. No. 15/061,524 filed on Mar. 4, 2016; Ser. No. 15/178,244 filed on Jun. 9, 2016; Ser. No. 15/178,291 filed on Jun. 9, 2016; Ser. No. 15/216,472 filed on Jul. 21, 2016; Ser. No. 15/664,608 filed on Jul. 31, 2017; Ser. No. 15/664,862 filed on Jul. 31, 2017; Ser. No. 14/514,221 filed on Oct. 14, 2014, now U.S. Pat. No. 9,826,986; Ser. No. 14/723,384 filed on May 27, 2015; Ser. No. 14/567,956 filed on Dec. 14, 2014; Ser. No. 14/447,612 filed Jul. 31, 2014; Ser. No. 14/413,318 filed Jan. 7, 2015; Ser. No. 15/418,633 filed on Jan. 27, 2017; 62/608,476 filed Dec. 20, 2017; 62/609,095 filed Dec. 21, 2017; 62/632,635 filed Feb. 20, 2018; and 62/640,026 filed Mar. 8, 2018.

Implementations of the present disclosure involve a system for preparing a sacroiliac joint for fusion. In particular, the system may include a preparation tool for removing articular cartilage from the sacroiliac joint space, abrading of the articular surfaces to enhance bony fusion, and removal of portions of the cortical, subchondral or cancellous bone for implantation of a fusion device. The preparation tool may include an anchoring arm that is configured to direct an anchoring element for transverse delivery through the sacroiliac joint space. The anchor may be delivered into the joint space before, during, or after the joint space is prepared for implant delivery. Alternatively, an implant may not be delivered into the joint and instead, e.g., bone paste or slurry may be introduced into the prepared sacroiliac joint before or after anchor placement. And, the anchor may be delivered cranial, caudal, in front of, behind, above, below, next to, up to, near, adjacent, away from, through, or in-line with the eventual placement of the implant. The preparation tool is configured to quickly, accurately and reliably prepare the joint space for insertion of an implant.

Implementations of the present disclosure may further include radiographic tools adapted to confirm placement of the joint implant and anchors prior to their implantation. According to particular embodiments, a radiographic tool may include a radiographic implant template (not shown) positioned near, up to or within the patient's body in order to approximate the orientation, location, size, configuration and implantation trajectory of the implant and employed either: i) prior to the incision of the patient's skin, ii) prior to the preparation of the sacroiliac joint, iii) prior to the creation of the central portion of the implant receiving space, iv) prior to the creation of substantially the entire implant receiving space, v) after placement of a pin or other guidance instrument (e.g., joint finder) into the sacroiliac joint, vi) after the preparation of the sacroiliac joint, vii) after the creation of the central portion of the implant receiving space, viii) after the creation of substantially the entire implant receiving space; for example, the implant template may include a shape comprising a cross section of the implant and may further comprise an overlapping pattern of implant sizes or configurations in order to determine, e.g., desired implant size or configuration in relation to the sacroiliac joint an surrounding anatomy. As an example, such tools may be used after removing articular cartilage but prior to abrading or otherwise removing the cortical, subchondral or cancellous bone of the joint. The tools may be used before making cuts for keels or other members extending beyond the portion of the implant at the plane of the joint and after preparing the plane of the sacroiliac joint in order to create at least a portion of the implant receiving space, which, e.g., may approximate the shape and size of the portion of the implant to be situated therein and, e.g., may be configured to accommodate a cylindrical body, a rectangular body. In other aspects the implant receiving space may be fully prepared before employing the radiographic tools. The radiographic tools generally include radiopaque markers or structures that are viewable using a radiography system, such as a fluoroscope or X-ray. By aligning the radiopaque markers/structures with anatomical features of the patient or other radiopaque elements of the tools, parameters for implanting the anchors (such as anchor configuration and size, location, orientation, and depth) may be determined and confirmed prior to the substantial tissue removal required for implanting the joint implant and/or the anchor.

I. System for Fusion of the Sacroiliac Joint

To begin a detailed discussion of an exemplary system 10 for delivering an implant 12 into the sacroiliac joint, reference is made to FIGS. 2A-3. FIG. 2A is an isometric view of the system 10. FIG. 2B is the same view as FIG. 2A, except an implant assembly 14 of the system 10 is separated from a delivery tool 16 of the system 10. FIG. 3 is the same view as FIG. 2A, except the system 10 is shown exploded to better illustrate the components of the system 10.

As can be understood from FIGS. 2A and 2B, the system 10 includes a delivery tool 16 and an implant assembly 14 for implanting at the sacroiliac joint via the delivery tool 16, the implant assembly 14 being for fusing the sacroiliac joint. As indicated in FIG. 3, the implant assembly 14 includes an implant 12 and an anchor element 18 (e.g., a bone screw or other elongated body). As discussed below in greater detail, during the implantation of the implant assembly 14 at the sacroiliac joint, the implant 12 and anchor element 18 are supported by a distal end 20 of the delivery tool 16, as illustrated in FIG. 2A. The delivery tool 16 is used to deliver the implant 12 into the sacroiliac joint space. The delivery tool 16 is then used to cause the anchor element 18 to extend through the ilium, sacrum and implant 12 generally transverse to the sacroiliac joint and implant 12. The delivery tool 16 is then decoupled from the implanted implant assembly 14, as can be understood from FIG. 2B. As illustrated in FIG. 3, the delivery tool 16 further includes a proximal end 22 opposite the distal end 20, an arm assembly 24, a handle 26, an implant retainer 28, a sleeve 30 and a trocar or guidewire 32. While in the embodiment of FIGS. 2A-3, the delivery tool 16 is fixed and non-adjustable and configured to deliver the anchoring element 18 in a single orientation relative to the implant 12, the delivery tool 16 may be adjustable and configured to deliver the anchoring element 18 within a range of orientations relative to the implant 12 that will orient the anchoring element 18 either within a bore of the implant 12, or adjacent implant 12, e.g., as described in U.S. patent application Ser. No. 14/447,612, filed Jul. 31, 2014, entitled SYSTEMS FOR AND METHODS OF FUSING A SACROILIAC JOINT, which is hereby incorporated by reference in its entirety or as described by an of the other applications reference in this application.

Figure 6:
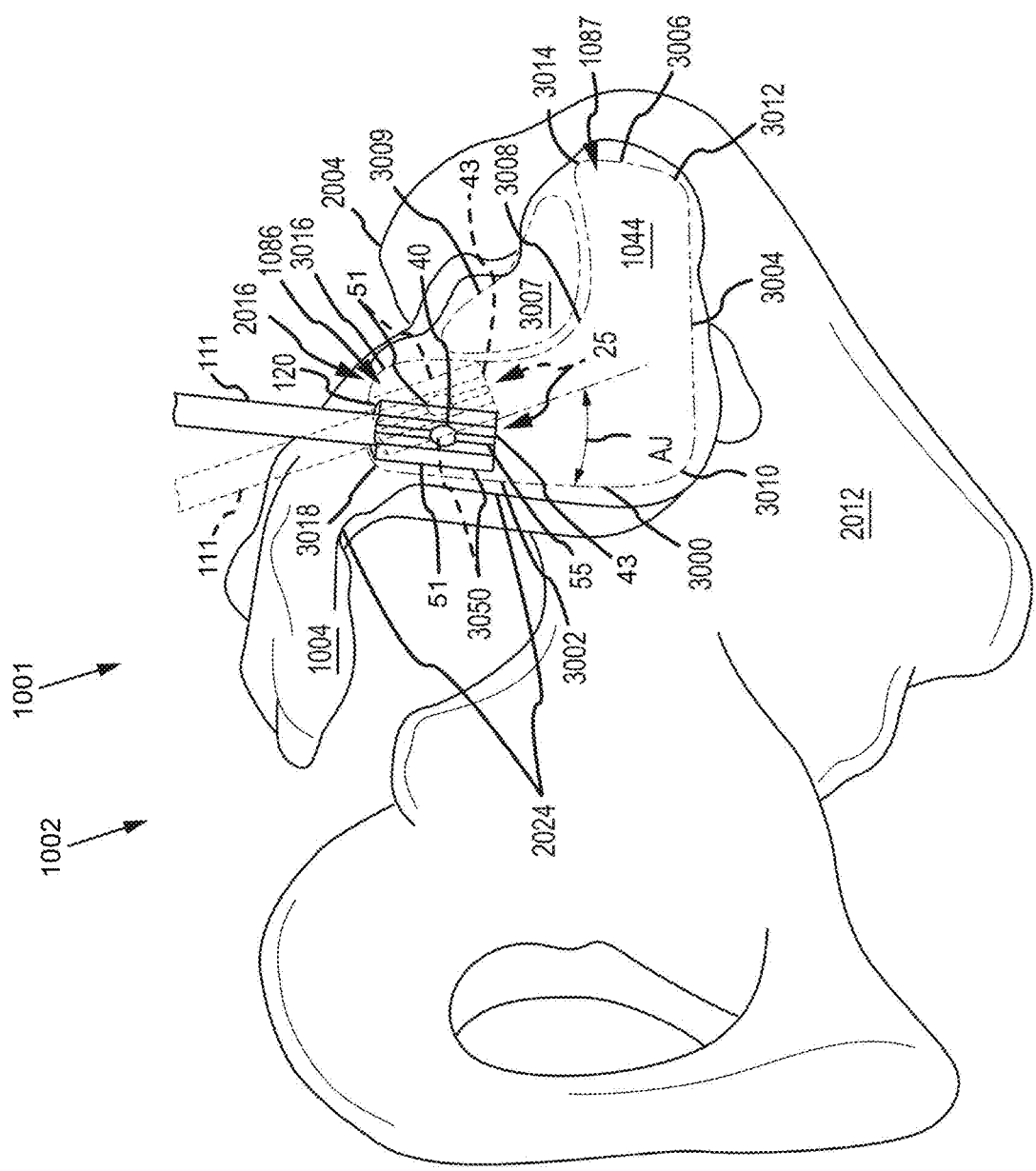
FIG. 6 is an enlarged view of the hip region where the nearest ilium is removed to show the sacroiliac joint space boundary defined along the sacrum and an implant positioned for implantation within the joint space.

In particular embodiments, and with reference to FIG. 6, first and second articular faces of the implant 25 may be selected to match the contour of the joint space of the sacroiliac joint within which the implant 12/25 is to be inserted. For example, the sacral, medial or first articular face of the implant 25 may be configured to be generally convex to match the contour of a sacral auricular boney surface or to match the contour of an extra-articular region of a sacrum (e.g., a sacral fossa). In one aspect and referring to portions of the anatomy shown FIG. 6, the sacral, medial or first articular face of the implant may be generally a surface negative of the articular surfaces 1016 of the extra-articular region 3007 and/or articular region 1044 of the sacrum 1004. As another example, the lateral, iliac or second articular face of the implant 12 may be configured to be generally concave to match the contour of an iliac auricular boney surface or to match the contour of an extra-articular region of an ilium (e.g., an iliac tuberosity). In one aspect, the lateral, iliac or second articular face of the implant 12/25 may be generally a surface negative of the articular surfaces 1016 of the extra-articular region 3007 and/or articular region 1044 of the ilium 1005.

To begin a discussion of implant delivery into the sacroiliac joint articular region 1044, reference is made to FIG. 6, which is a close-up lateral side view of the pelvis or hip region 1002 of a patient 1001 with a nearest ilium 1005 removed in order to show the sacroiliac joint boundary 3000 defined along the sacrum 1004 and outlining the sacroiliac joint articular region 1044, and an implant 25 positioned for implantation within the sacroiliac joint articular region 1044. The opposite ilium 1005 is visible, including the landmarks of the posterior superior iliac spine 2004 and the tubercle of the iliac crest 2012, among other landmarks.

As seen in FIG. 6, boundaries along the sacroiliac joint articular region 1044 include an inferior boundary segment 3002, an anterior boundary segment 3004, a superior boundary segment 3006, and a posterior boundary segment 3008. The inferior boundary segment 3002 is immediately adjacent, and extends along, the sciatic notch 2024.

The inferior boundary segment 3002 and anterior boundary segment 3004 intersect to form an anterior-inferior corner 3010. The anterior boundary segment 3004 and superior boundary segment 3006 intersect to form an anterior-superior corner 3012. The superior boundary segment 3006 and posterior boundary segment 3008 intersect to form a superior-posterior corner 3014. The posterior boundary segment 3008 and posterior inferior access region 2016 intersect to form a superior-posterior corner 3016 of the posterior inferior access region 2016. The inferior boundary segment 3002 and posterior inferior access region 2016 intersect to form an inferior-posterior corner 3018 of the posterior inferior access region 2016.

The inferior boundary segment 3002 extends between corners 3010 and 3018. The anterior boundary segment 3004 extends between corners 3010 and 3012. The superior boundary segment 3006 extends between corners 3012 and 3014 and provides an access into the cranial portion 1087 of the sacroiliac joint. The posterior boundary segment 3008 extends between corners 3014 and 3016. The posterior inferior access region 2016 extends between corners 3016 and 3018 and provides an access into the caudal region 1086 of the sacroiliac joint. The posterior boundary segment 3008 separates articular region 1044 and extra-articular region 3007, which includes the sacral fossa on the sacrum 1004 and the corresponding iliac tuberosity on the ilium 1005 and defined by the extra-articular region boundary 3009.

In one aspect and as seen in FIG. 6, the implant 25 may be coupled to a distal end 120 of an implant arm 111 of a delivery tool and delivered via the implant arm 111 into the caudal region 1086 of the sacroiliac joint articular region 1044. As shown via the implant 25 and implant arm 110 shown in solid lines, in one embodiment, the implant 25 enters the posterior inferior access region 2016, and is further advanced into the caudal region 1086 of the sacroiliac joint articular region 1044, in an orientation such that the implant arm 110 and wide planar members 51 are in the joint plane and the longitudinally extending edge 3050 of the wide planar member 51 next to the inferior boundary segment 3002 is generally parallel to, and immediately adjacent to, the inferior boundary segment 3002. Thus, the distal end 43 of the implant is heading generally perpendicular to, and towards, the anterior boundary segment 3004. A bore 40 of the implant 25 is oriented transversely to the longitudinally extending edge 3050 of the planar member 51, and extends transversely to the joint plane when implanted. As seen in FIG. 6, the bore 40 may extend through the planar member 55, which is oriented generally transverse to the wide planar member 51.

As shown in FIG. 6 via the implant 25 and implant arm 110 shown in dashed lines, in one embodiment, the implant 25 enters the posterior inferior access region 2016, and is further advanced into the caudal region 1086 of the sacroiliac joint articular region 1044, in an orientation such that the implant arm 111 and wide planar members 51 are in the joint plane and the longitudinally extending edge 3050 of the wide planar member 51 next to the inferior boundary segment 3002 is somewhere between being generally parallel to the inferior boundary segment 3002 (as illustrated by the solid-lined implant 25 in FIG. 6) or forming an angle AJ with the inferior boundary segment 3002 of up to approximately 50 degrees. Thus, the distal end 43 of the implant shown in dashed lines can be said to head anywhere from generally perpendicular to, and towards, the anterior boundary segment 3004 to heading generally towards the superior-anterior corner 3012, or points in between.

In one embodiment, the implant 25 may be first directed into the joint space as illustrated by the solid-lined implant 25 in FIG. 6 after which the implant 25 is rotated within the joint space to be positioned somewhere between, and including, angled position depicted by the dashed-lined implant 25. In other embodiments, the implant 25 may be first directed into the joint space as illustrated by the dashed-lined implant 25 in FIG. 6 after which the implant 25 is rotated within the joint space to be positioned somewhere between, and including, the parallel position depicted by the solid-lined implant 25. Thus, an implant 25 may be delivered non-transversely (i.e., within the joint and not across the joint) into the caudal region 1086, the cranial portion 1087, or partially within each of the caudal and cranial regions 1086, 1087 of the sacroiliac joint articular region 1044. Further details of the implant delivery can be found in related applications, mentioned previously, such as for example U.S. patent application Ser. No. 12/998,712, which is incorporated by reference herein in its entirety.

Figure 4:
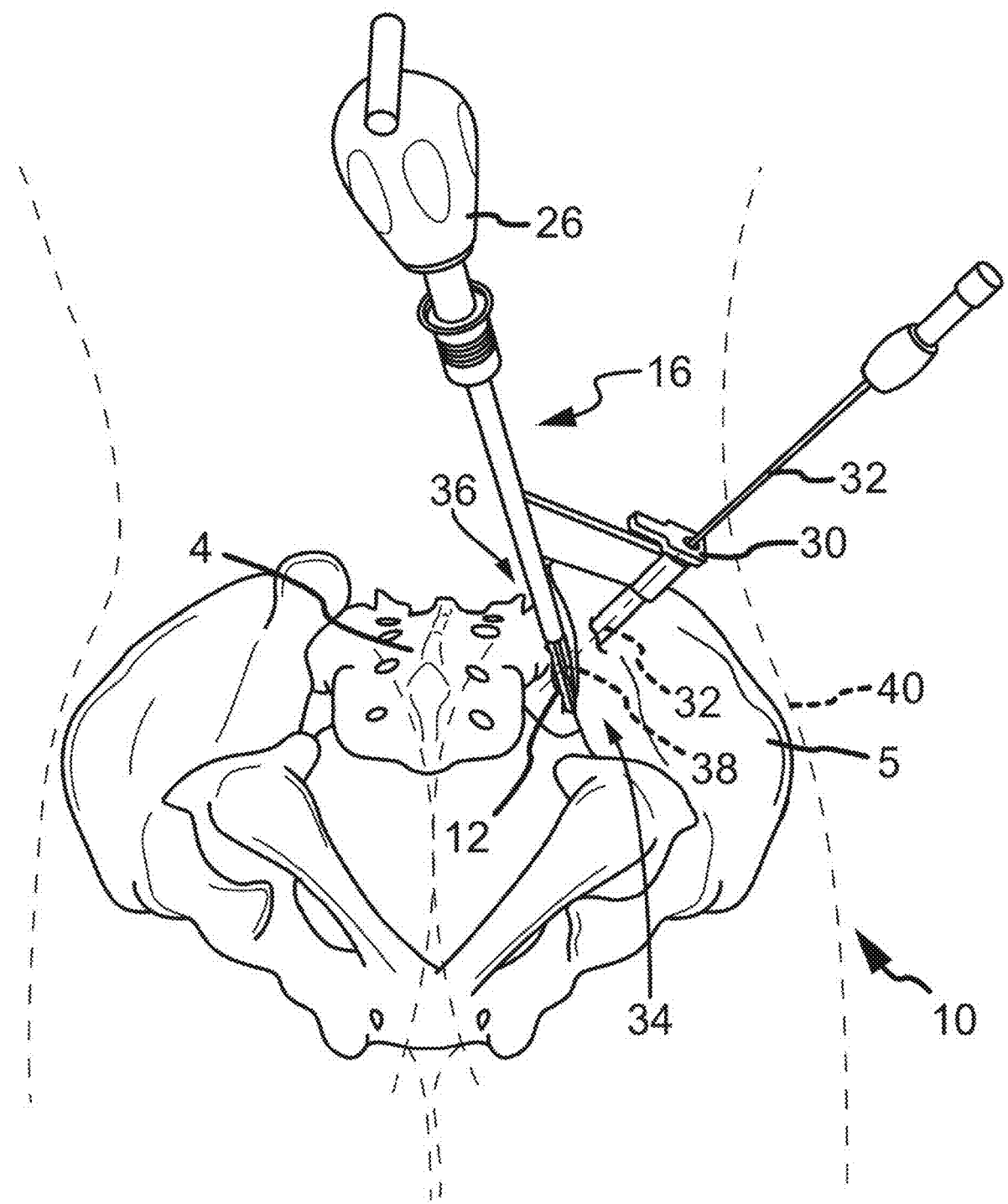
FIG. 4 is a posterior-inferior view of a sacroiliac joint with a patient body shown in broken line.
Figure 5:
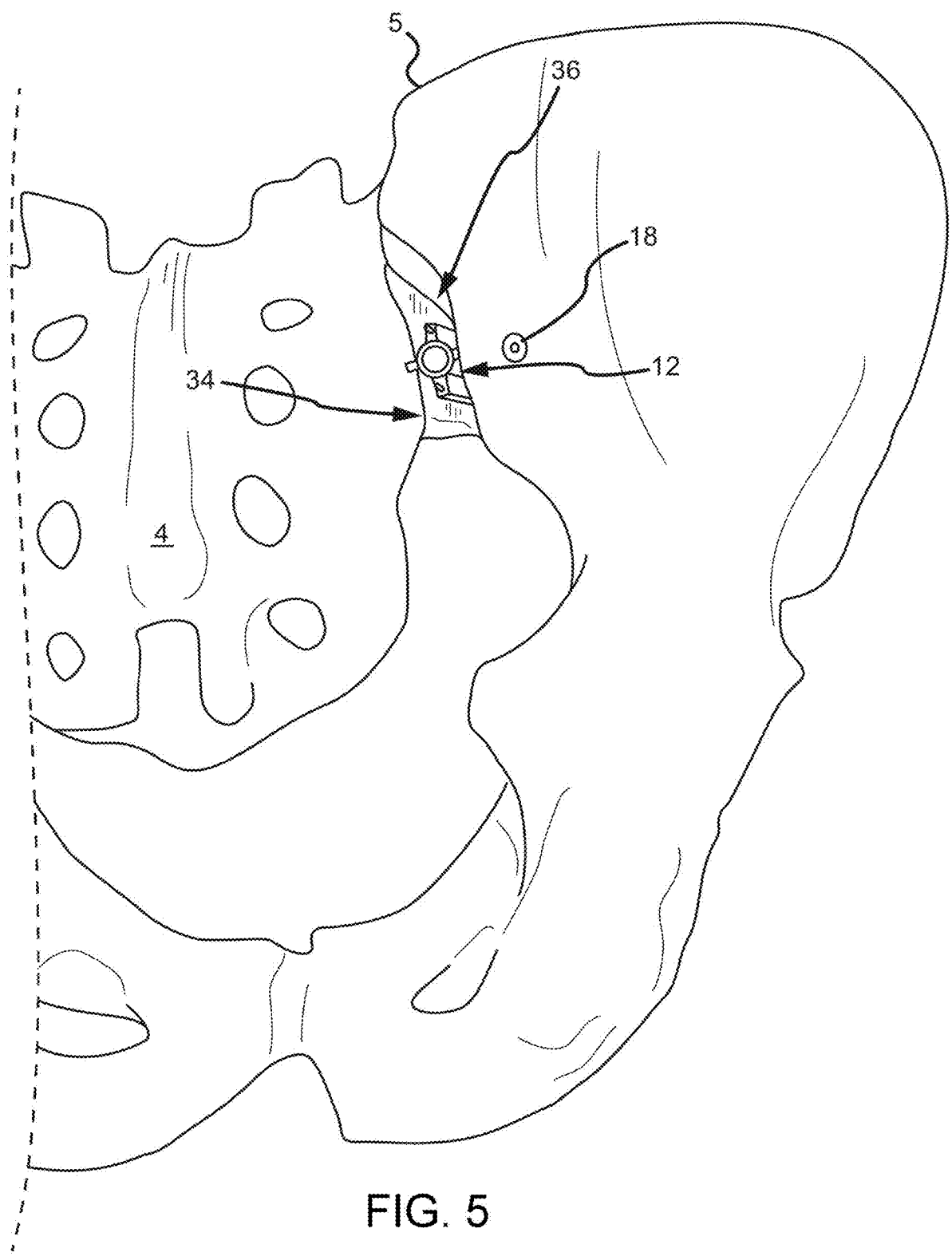
FIG. 5 is a close-up view of the implant and anchor element in the sacroiliac joint.

A system as described in FIGS. 2A-3 may be used in a surgical procedure via a posterior approach, as seen in FIGS. 4-6. As can be understood from FIG. 4, which is a posterior-inferior view of a sacroiliac joint 36 with a patient 40 shown in broken line, the delivery tool 16 is positioned to deliver the implant 12 into a caudal region 34 of the sacroiliac joint 36 and the anchoring element 18 through the ilium 5 and into the bore 38 of the implant 12. Referring to FIG. 5, the implant 12 and anchoring element 18 have been inserted into the caudal region 34 of the sacroiliac joint 36 and the delivery tool 16 has been removed.

With further reference to the bony anatomy shown in FIG. 6, a system as described herein may be used in a surgical procedure via an anterior approach (e.g., such that the surgical pathway includes traversing an anterior boundary segment 3004 and/or traversing an anterior-inferior corner 3010) and may further include positioning an implant into a sacroiliac joint such that: 1) the implant longitudinal axis a) is generally parallel to a sacroiliac joint inferior boundary segment 3002, or b) points towards a posterior superior iliac spine, or c) point towards a posterior inferior iliac spine, or d) points toward a sacroiliac extra-articular region; or, 2) the distal end of the implant generally lies within a) a caudal region of the sacroiliac joint articular region, or b) an extra-articular portion of the sacroiliac joint, or c) a cranial portion or cephlad region of the sacroiliac joint articular region.

Additionally, a system as described herein may be used in a surgical procedure via an approach which includes a surgical pathway which transverses a sacroiliac joint inferior boundary segment 3002, e.g., as described in U.S. patent application Ser. No. 13/945,053, filed Jul. 18, 2013, entitled SYSTEMS AND METHODS OF FUSING A SACROILIAC JOINT, which is hereby incorporated by reference in its entirety. A surgical procedure via this pathway may further include positioning an implant into a sacroiliac joint such that: 1) the implant longitudinal axis a) is transverse to a sacroiliac joint inferior boundary segment 3002, or b) points towards a posterior superior iliac spine, or c) point towards a posterior inferior iliac spine, or d) points toward a sacroiliac extra-articular region, or e) points towards a sacroiliac joint anterior boundary segment 3004, or f) points towards either superior boundary segment corner 3014 or 3012 or somewhere in-between; or, 2) the distal end of the implant generally lies within a) a caudal region of the sacroiliac joint articular region, or b) an extra-articular portion of the sacroiliac joint, or c) a cranial portion or cephlad region of the sacroiliac joint articular region.

Furthermore, in an aspect, an implant 12 may be inserted along a generally arcuate path. Accordingly, a surgical preparation technique and tools may be utilized while operating in an arcuate path. The implant arcuate path may follow and generally match the surgical preparation arcuate path and the path arc may include a radius of between approximately 3 cm to 6 cm. The portion of the path having an arcuate path including a radius of between approximately 3 cm to 6 cm may reside substantially in the plane of the sacroiliac joint or in a plane in close proximity and generally parallel thereto. Furthermore, the arcuate path may generally or substantially reside in sacroiliac joint articular region 1044. Additionally, an implant may be selected for use during the procedure which substantially matches the radius or curvature of the arcuate or curved insertion path or surgical preparation path.

According to a particular aspect, after drilling or otherwise producing an opening through an ilium (or sacrum) leading toward or into a sacroiliac joint, a sleeve may guide (alone or along with another cannulated tool, e.g., a needle) a bone paste, bone marrow aspirate, stem cells, allograft or any biocompatible material or substance into the sacroiliac joint space via a path with a trajectory which may be generally transverse to the plane of the sacroiliac joint. The sleeve may be caused to form a seal with a bone defining the sacroiliac joint, e.g. the ilium. The seal may be created by impacting a proximal end of sleeve which may, for example, cause the sleeve to slightly penetrate the cortex of the outer table of the ilium. Alternatively, a cannulated tool such as a large gauge needle or tube may either be interference fit within a hole in the ilium or the needle or tube may have a threaded distal end which may be threaded into the bore formed in the ilium. A plunger or bone tamp may be forced through a sleeve to advance the bone paste or other material into the sacroiliac joint space, adjacent/around the implant and/or into the bone graft window of the implant.

Subsequently, an anchor such as a bone screw may be advanced via the sleeve into engagement with an opening formed in the ilium and driven across the sacroiliac joint and further into the sacrum. Alternatively, a bone plug may be positioned into the opening formed in the ilium in order to occlude the passageway between the outer cortex of the ilium and the implanted bone paste or other material positioned which had be positioned generally in the plane of the joint.

As such, the systems and methods described herein are directed to preparing the sacroiliac joint for surgical fusion procedures of this type and others.

II. System for Preparing the Sacroiliac Joint for Fusion

A. First Embodiment of Surgical Access Devices, Surgical Preparation Tools, Implant Delivery Tool and Implant.

Reference is now made to FIGS. 7-12 in the present application. Additional figures and description for the tools and methods of use can be found in Provisional Patent Application Nos. 62/559,386 filed Sep. 15, 2017, 62/609,095 filed Dec. 21, 2017, 62/632,635 filed Feb. 20, 2018, and 62/640,026 filed Mar. 8, 2018. Each of the aforementioned provisional patent applications are hereby incorporated by reference in their entireties.

Various surgical access devices, surgical preparation tools and assemblies, delivery instrumentation and implants will be discussed herein. These tools and assemblies may be used by themselves or in combination with each other. Additionally, features of a particular embodiment are non-limiting and may be incorporated into any or all other embodiments without departing from the teachings in this disclosure.

Figure 7:
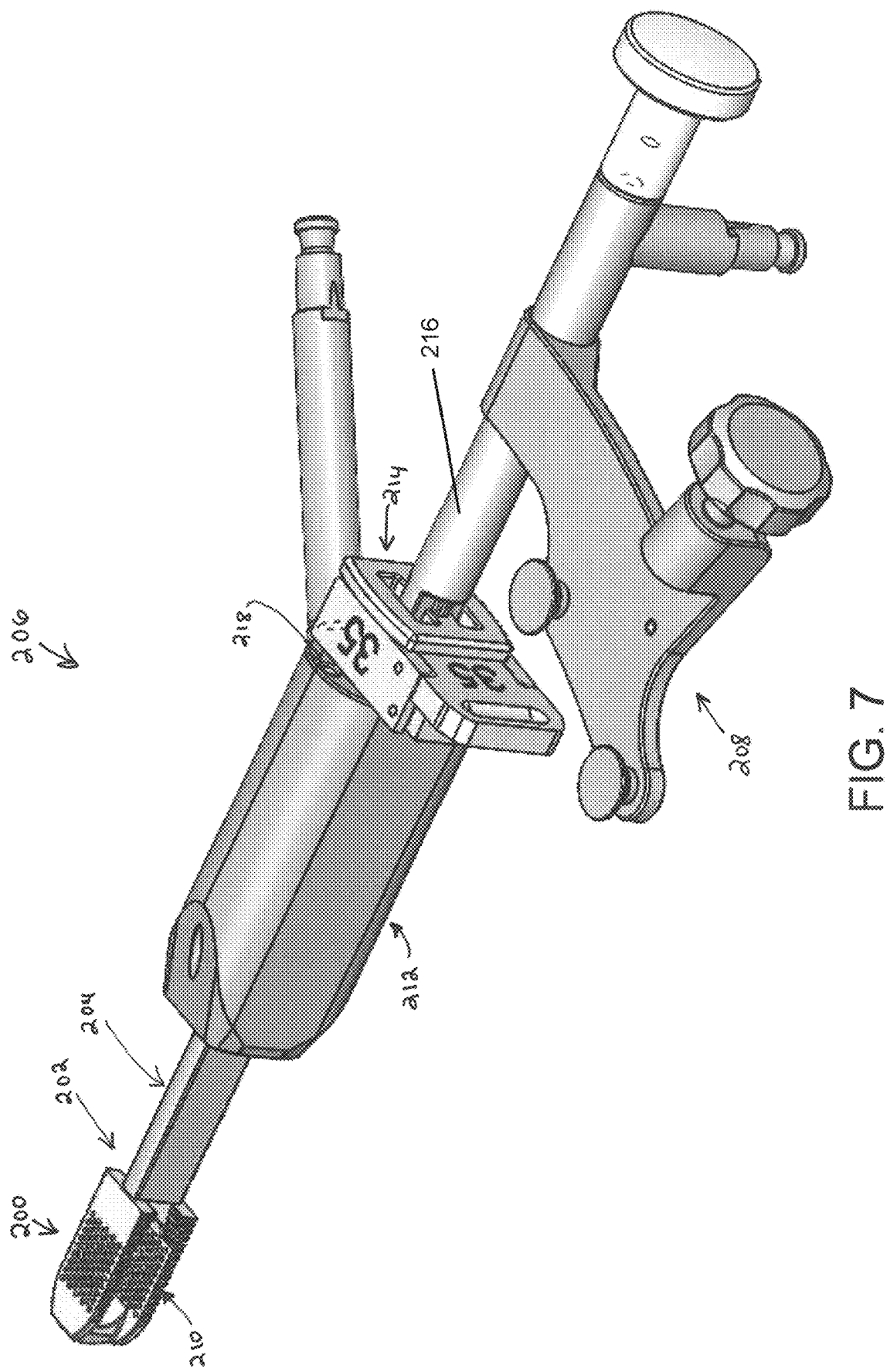
FIG. 7 is an isometric view of a delivery tool with an implant arm coupled to an implant, where the implant arm extends through a working cannula.
Figure 9:
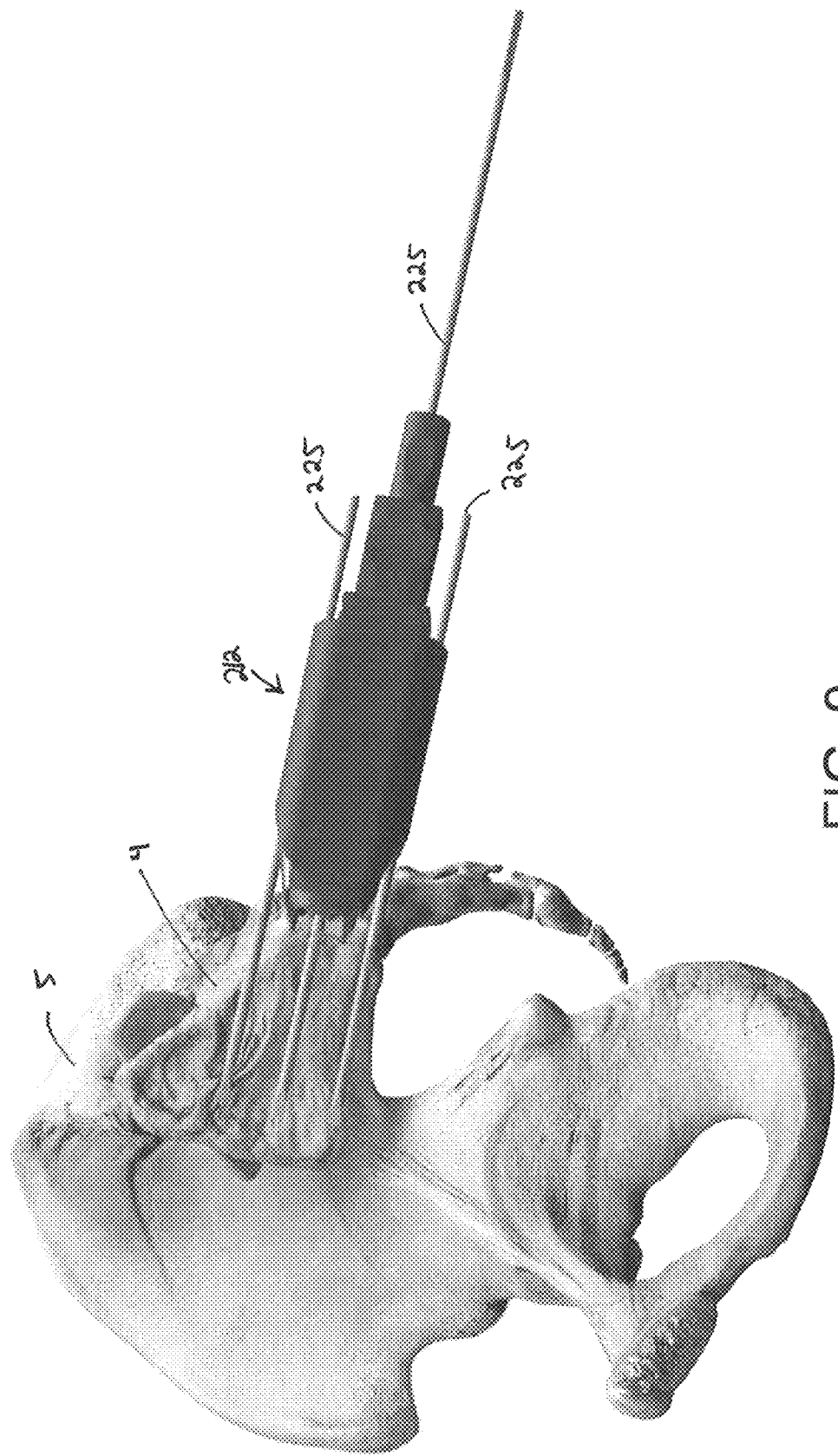
FIG. 9 is the medial view of the sacrum and ilium of FIG. 8, but with a working cannula in position via guidance by the three pins.
Figure 10:
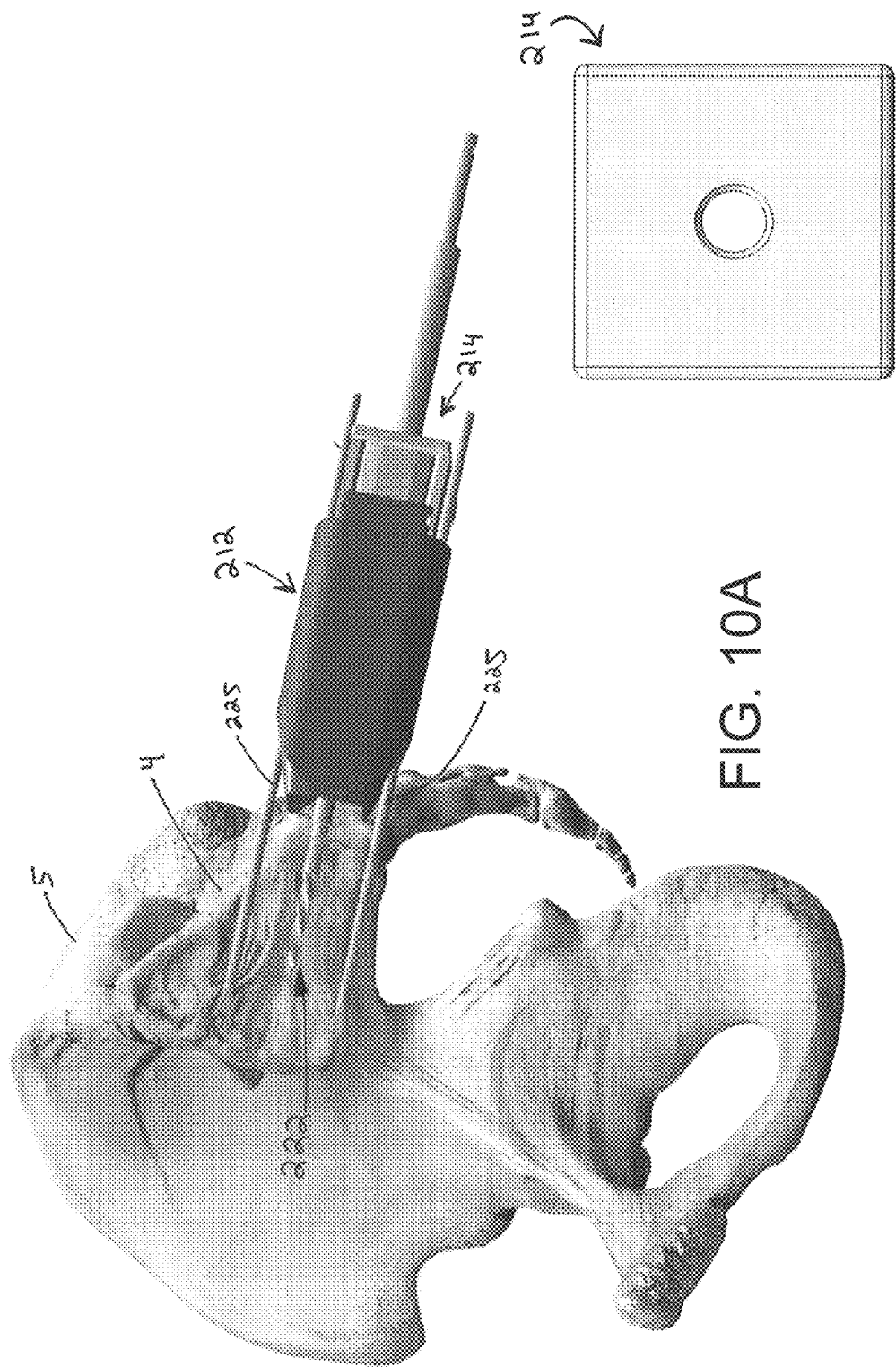
FIG. 10A is the medial view of the sacrum and ilium of FIG. 8, and with a drill guide block positioned within the working cannula, and a drill being guided by the drill guide block with depth being limited by a standoff.
FIG. 10B is a rear view of the drill guide block.
Figure 11:
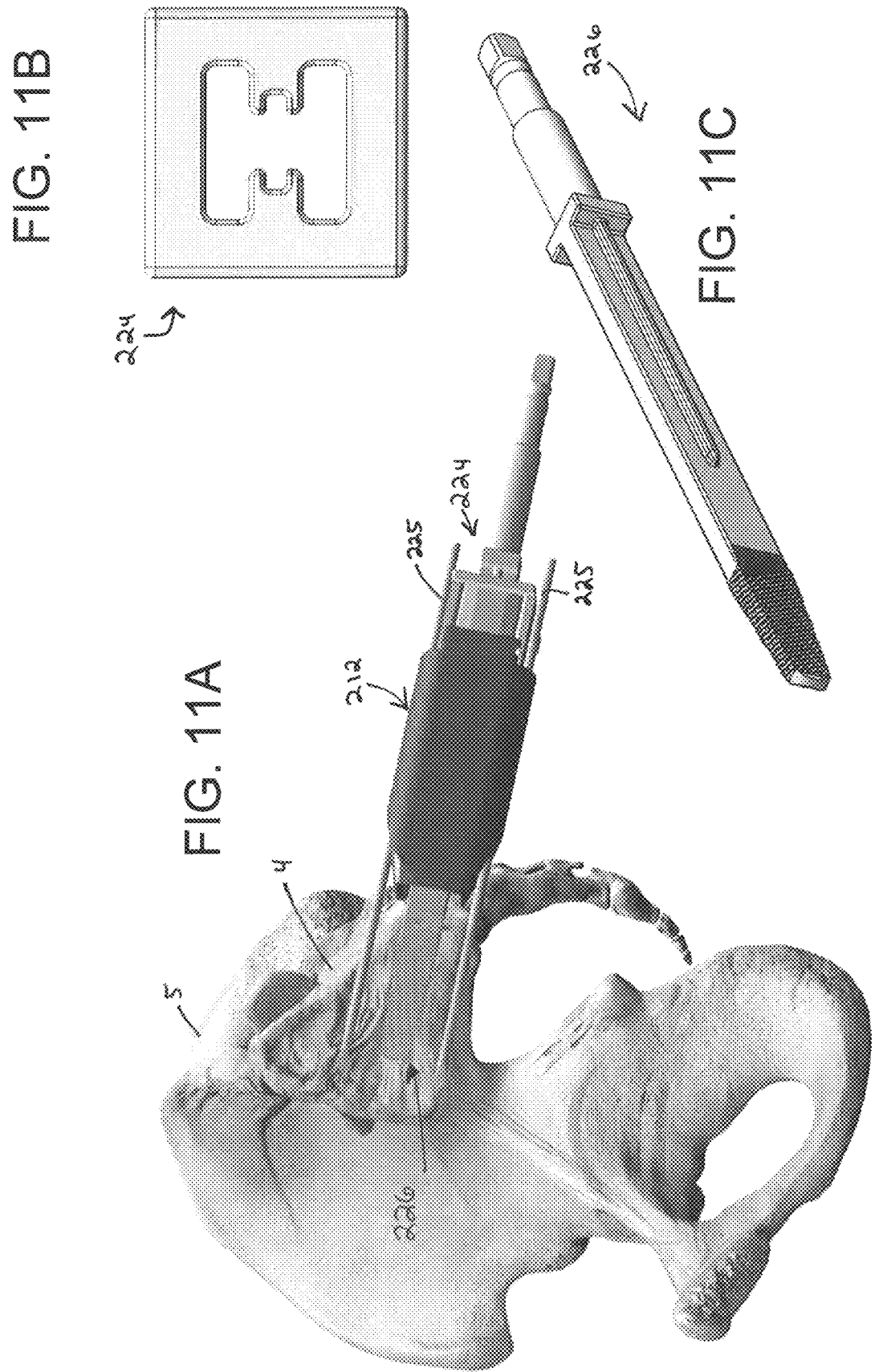
FIG. 11A is the medial view of the sacrum and ilium of FIG. 8, and with a rasp positioned within the working cannula with depth being limited by a standoff.
FIG. 11B is a rear view of a tool guide block for fitting within the working cannula and guiding various tools.
FIG. 11C is an isometric view of a rasp.
Figure 12:
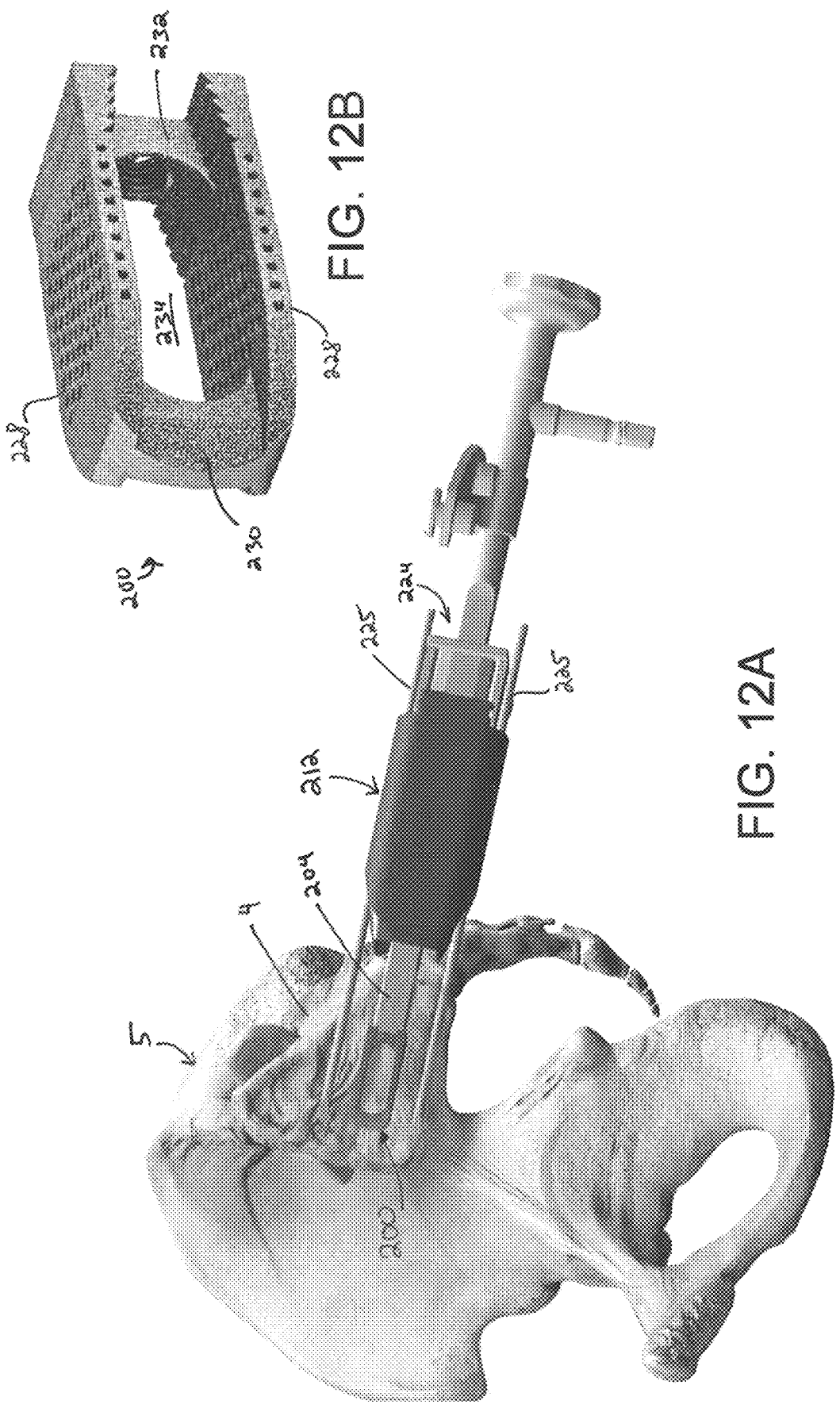
FIG. 12A is the medial view of the sacrum and ilium of FIG. 8, and with the implant coupled to the implant arm of the delivery tool, where the implant arm is positioned within the tool guide block and the working cannula with depth being limited by a standoff.
FIG. 12B is an isometric view of an exemplary joint implant.
Figure 13:
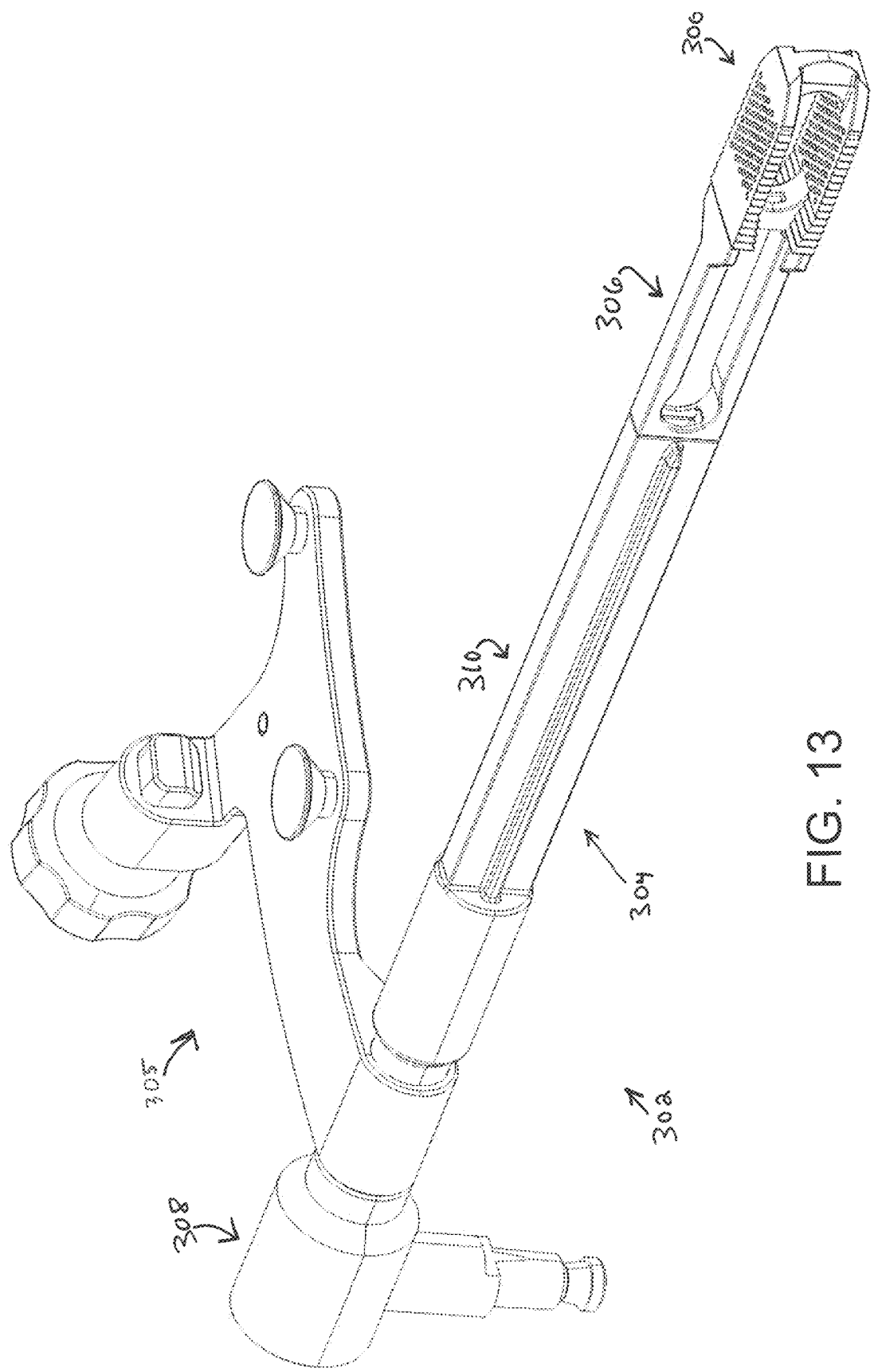
FIG. 13 is an isometric view of a delivery tool and an implant.

Exemplary embodiments of a system for sacroiliac joint fusion may be seen in FIG. 7. In the figure, a joint implant 200 is coupled to a distal end 202 of an implant arm 204 of a delivery tool 206. The implant arm 204 may extend from the joint implant 200 and an anchor arm 208 coupled to the implant arm 204. The anchor arm 208 may deliver an anchor (not shown) in a predetermined position relative to the joint implant 200. In certain instances, the anchor (not shown) may be delivered through a transverse opening or window 210 in the joint implant 200. As seen in FIG. 7, the implant arm 204, as well as various other joint preparation tools, may extend through a working cannula 212 (otherwise known as a tissue protector). The working cannula 212 protects the patient's surrounding tissue and provides a passageway to the joint for the insertion of various tools and the implant 200. The working cannula 212 may include a longitudinal passageway, a superior lumen 218 extending longitudinally, an inferior lumen (not shown in FIG. 7) extending longitudinally on an opposite side of the passageway and an attachment shaft extending off the exterior of the working cannula, either permanently fixed thereto or removably coupled thereto and configured to couple with a handle or with a fixture configured to also couple with the operating table or a surgical robot and in some instances may extend transverse to the length of the working cannula and may include an angle of about 90 degrees or about 45 degrees as shown in FIG. 7 and/or may have a bayonet or dog legged configuration. According to particular embodiments, the attachment shaft may be positioned medially over the sacrum and given the orientation of the plane of the sacroiliac joint and the presence of the patient's tissue, the 45 degree angle of the attachment shaft as shown in FIG. 7 permits sufficient clearance from the skin for a handle to extend therefrom or for a coupling mechanism to attach thereto. The superior and inferior lumens 218 may accept joint pins inserted into the joint, as seen in FIG. 9. Alternatively, the working cannula may be configured similar to the tissue protector of the systems shown is FIGS. 23, 28 and 39, e.g., the working cannula may include a pair of prongs, spikes, or projections at a distal end thereof instead of having superior and inferior lumens for accepting joint pins described above, or wherein the working cannula includes a lateral side having an angled opening that extends into the passageway.

Various inserts 214 may be positioned within the working cannula 212 to guide the delivery of various instruments, respectively. For example, as seen in FIG. 7, the shaft 216 of the implant arm 204 may be keyed to a corresponding shape of the insert 214 such that the implant arm 204 is prevented from rotating relative to the insert 214. This ensures the correct rotational alignment of the implant 200 upon delivery into the joint. It is noted, the working cannula 212 may be secured to the operating room table during the surgical procedure to ensure it is in a fixed position as described above.

Figure 68:
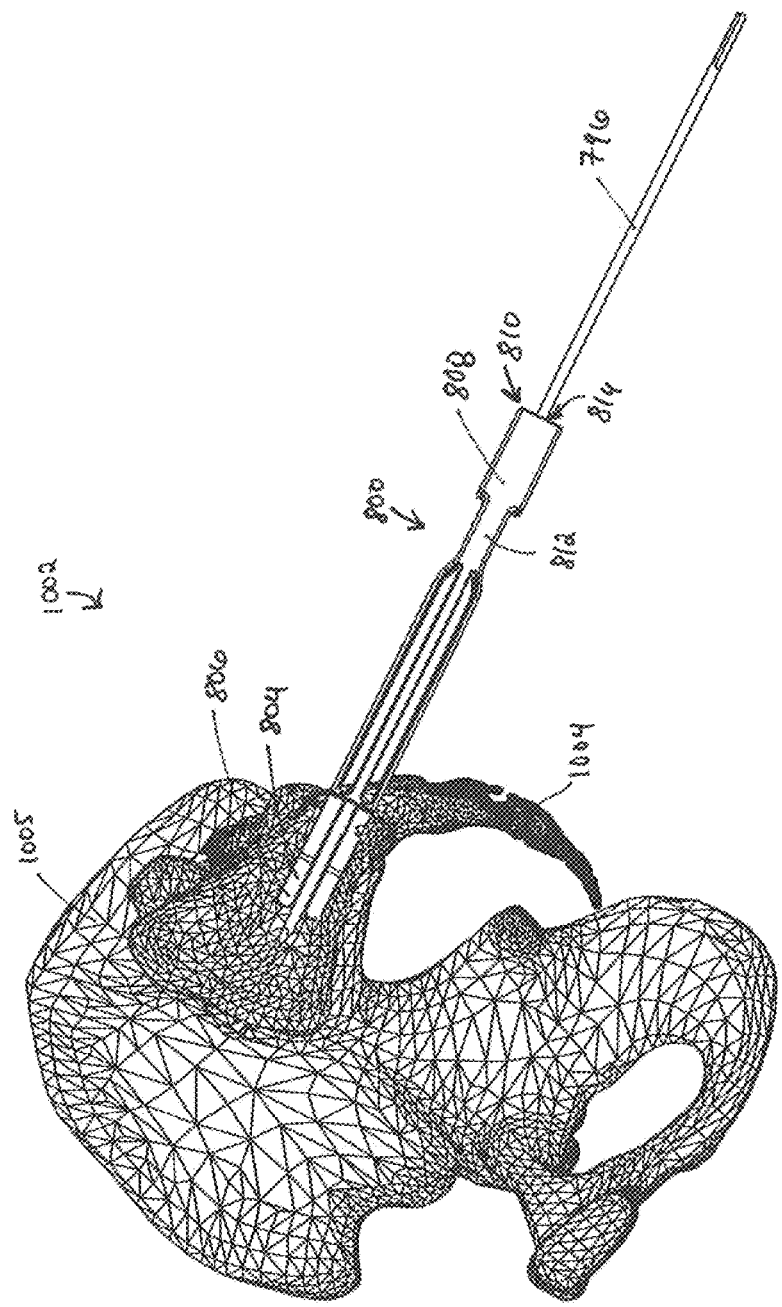
FIG. 68 is a side view of a pelvis with the nearest ilium removed, and a cannulated joint finder positioned over the pin and in the sacroiliac joint.
Figure 75:
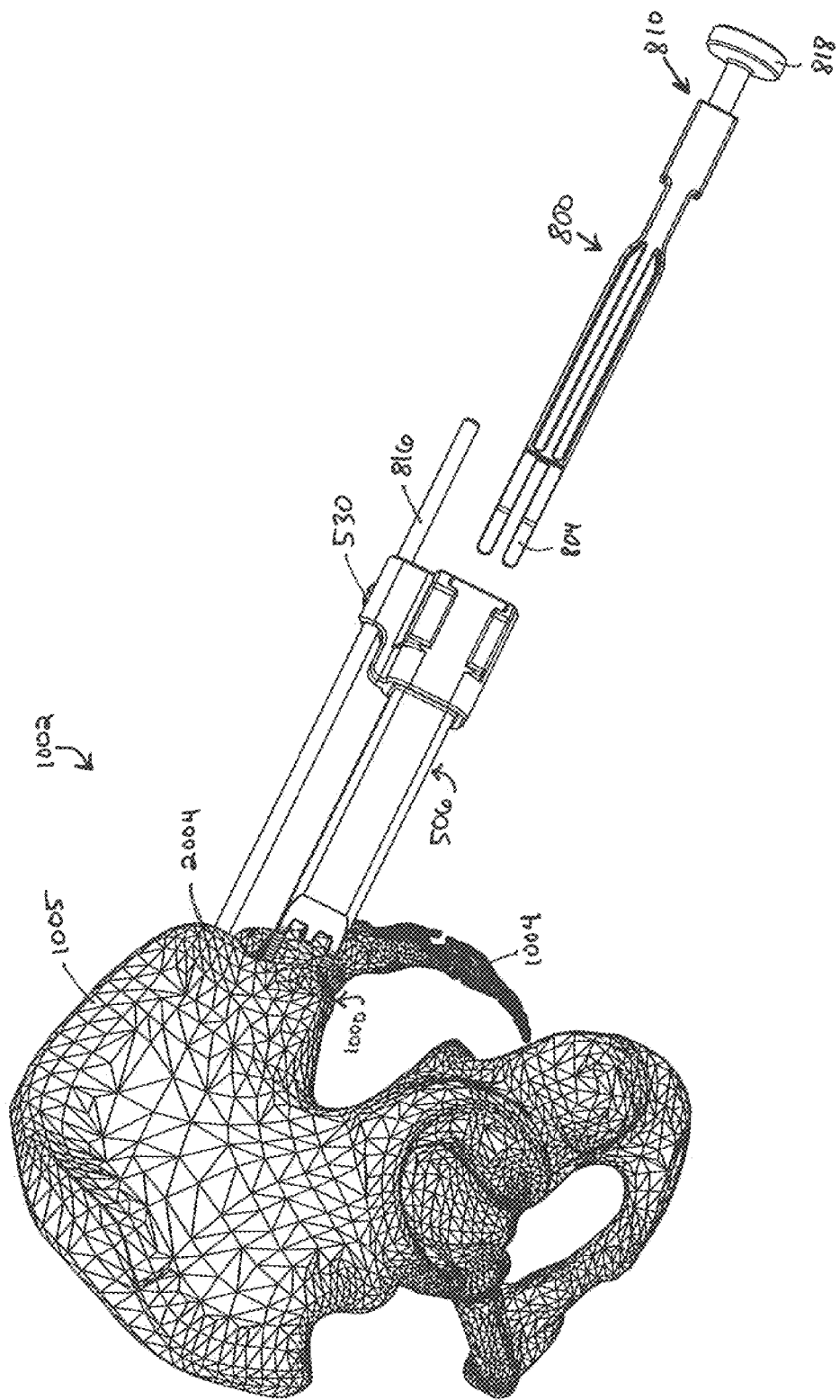
FIG. 75 is a side view of the pelvis with the cannulated joint finder removed via the slide hammer from within the working cannula, which is still in the joint.

FIGS. 8-9, 10A, 11A, and 12A illustrate an exemplary method of preparing a joint, and delivering an implant into a joint. To begin a surgical procedure on the SI joint, the PSIS and PIIS landmarks may be identified. The plane of the articular portion may be identified with a first pin or probe. Additionally or alternatively, a spatula probe (e.g., the joint finder as shown in FIGS. 27A-27D or as shown in FIGS. 68 and 75) may be advanced into the SI joint while orienting the flat distal tip parallel to the plane of the articular portion. In some embodiments the shaft extending proximally from the flat distal tip may be cylindrical, while in other embodiments the shaft may be non-circular in cross section or the shaft or the proximal end may have a clocked or indexed configuration such that further tools may be coupled with or otherwise engaged with the non-circular or clocked or indexed portion such that they act as an orientation reference providing discrete positions or orientation of the further tools relative to the flat distal tip and therefor the plane of the articular portion of the joint.

Figure 8:
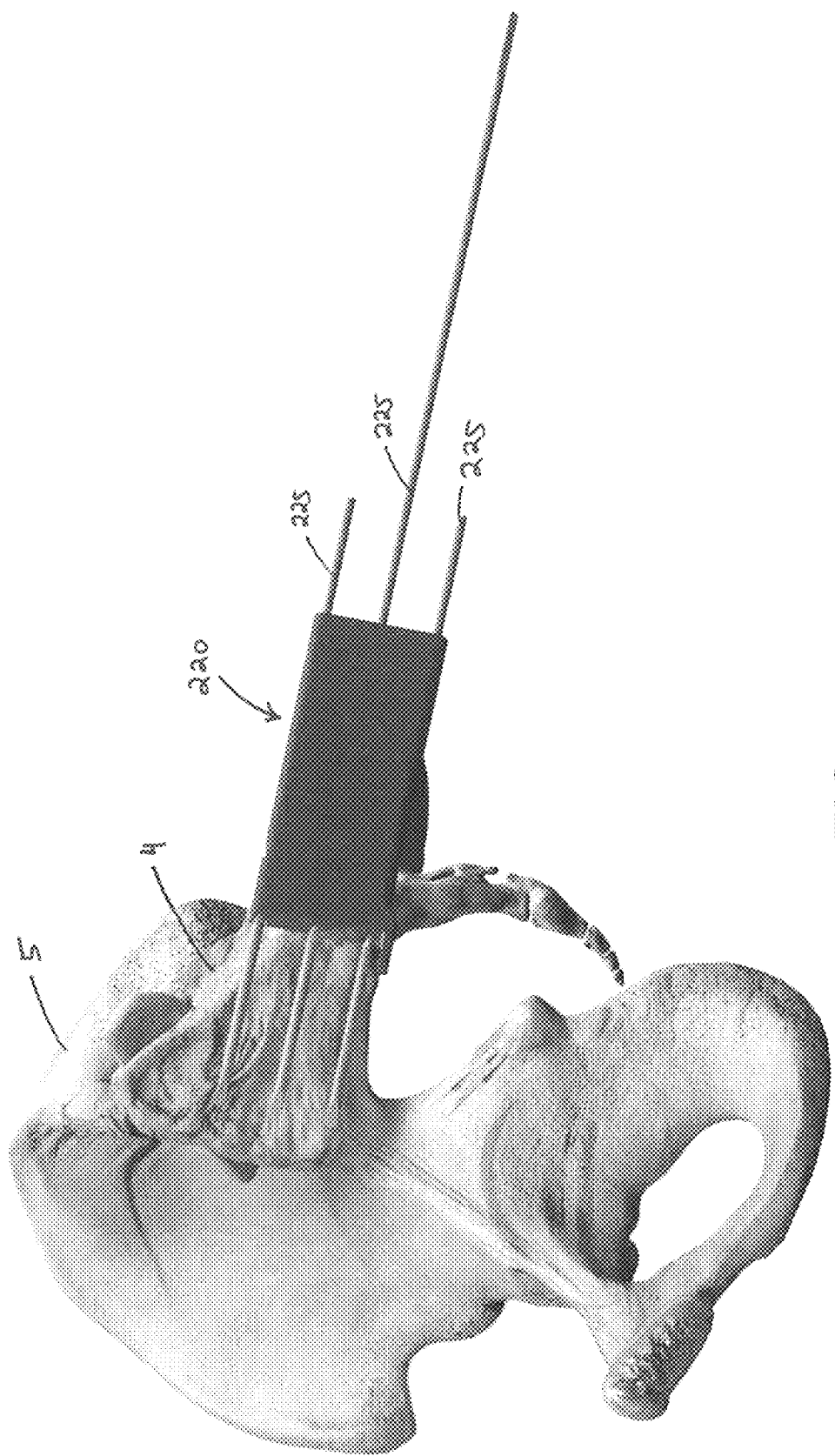

A parallel pin guide 220 may be advanced over the pin 225 at FIG. 8 (or the spatula probe). The pin guide 220 may be a thin rectangular block with multiple through-holes (either circular or non-circular in cross-section) extending longitudinally there through as seen in FIG. 8 to accommodate multiple pins. Once the parallel pin guide is positioned over the first pin 225, the two remaining guides are configured to align a superior and an inferior pin 225, 225 into the joint in a predetermined relation to the first pin 225. As illustrated in FIG. 8, the second pin/probe 225 and the third pin/probe 225 may be located superior and inferior of the first pin 225 and may generally correspond to the PSIS and the PIIS, respectively. Following placement of the pins, the pin guide may be removed.

After removal of the pin guide 220, the pins 225 may be used to guide various tools for dilating soft tissue adjacent the sacroiliac joint and for introducing the working cannula 212, as shown in FIG. 9. In certain applications, the first pin 225 is removed after introduction of the working cannula 212 and the working cannula may be subsequently fixed to an operating table or other fixture in the vicinity of the patient or held using a handle extending from the working cannula. FIG. 10A, for example, illustrates a working cannula 212 in place with the first pin 225 removed. A drill guide insert or block 214 that may be used to guide drill bits, or pins, among other tools, may be inserted into the working cannula 212. The drill guide insert 214 may guide a drill bit along predetermined paths in order to remove tissue from the articular portion of the sacroiliac joint. FIG. 10B illustrates a first drill guide block 214 with a single through-bore. Once inserted into the working cannula 212, a drill bit 222 of a drill assembly, may be inserted through the drill guide block to remove tissue from within the articular portion of the joint. Guide block standoffs may be used as part of the system described herein to control the depth to which tools are inserted into a patient. Such standoffs may be used, for example, in conjunction with the drill guide blocks to control the insertion depth of the drill assembly.

In certain implementations, multiple drill guide blocks may be used to guide the drill bit of the drill assembly to various locations to remove additional tissue. Following removal of tissue from the articular portion of the sacroiliac joint, the exposed bone may subsequently be prepared for implantation of a joint implant. In certain implementations, such a process generally includes cutting away or otherwise removing cortical bone and filing the exposed bone to bleeding bone in order to promote healing and bone growth over the joint implant. To facilitate such procedures, the system disclosed herein may also include a tool guide block shaped to fit within the tissue protector when inserted through the open proximal end of the tissue protector.

As illustrated in FIGS. 11A-11C, the tool guide block 224 in FIG. 11B generally includes a block-like structure defining a longitudinal passageway through which tools may be inserted. Such tools may include, without limitation, osteotomes, rasps 226 (as seen in FIG. 11C) or similar tools to further prepare the joint for fusion or delivery tools for delivering the joint implant to the implantation location. The longitudinal passageway may be shaped to allow only substantially longitudinal movement of corresponding tools shaped to be inserted into the longitudinal passageway. For example, in the illustrated implementation, the longitudinal passageway of the tool guide block has a cross-sectional shape defining a passageway that is substantially "I"-shaped but with an additional midline cross-bore through the "I" shape. This cross-sectional shape substantially matches that of various tools so as to prevent the tools from rotating within the tool guide block and within the joint.

With respect to further preparation of the sacroiliac joint, such tools may include an osteotome, a starting rasp, and a finishing rasp. Each of the osteotome, the starting rasp, and the finishing rasp may have longitudinal bodies having projections such that the cross-section of the longitudinal bodies substantially matches the passageway of the tool guide block.

Following preparation of the articular surfaces, a broach may be used to cut slots into the surfaces for receiving keels or other features of the joint implant. To do so, a broaching assembly may be used in conjunction with the tool guide block to cut the keel slots.

After formation of the keel slots, an additional procedure may be undertaken to remove tissue by additional drilling. Accordingly, the system may further include each of a keel drill assembly and one or more keel guide blocks corresponding to locations in which additional tissue or bone is to be removed. The keel guide blocks may include longitudinal bores distributed in a predetermined pattern and at predetermined distances relative to each other in order to guide the keel drill assembly to the necessary locations within the implant receiving space. In certain implementations, the system may include a range of keel guide blocks, each of which having progressively larger or more spaced apart longitudinal through-bores.

FIGS. 12A and 12B depict the joint implant 200 coupled to the implant arm 204, and delivered into the sacroiliac joint. As seen in FIG. 12A, the implant arm 204 extends through the working cannula 212, which is supported in place by the pins 225 generally extending into the joint at the PSIS and PIIS, respectively.

Further details of an example joint implant 200 are illustrated in FIG. 12B. The example joint implant 200 includes each of a planar top member 228 and a planar bottom member (also referred to herein as keels) 228, a distal member 230 connecting a distal portion of the top and bottom members 228, and a proximal member 232 connecting a proximal portion of the top and bottom members 228. The joint implant 200 further defines a transverse passageway 234 between the distal and proximal members 230, 232 for receiving an anchor or biocompatible material.

In certain implementations, biocompatible material may be disposed within the joint implant 200 using a bone injection block and associated tools for packing the transverse passageway 234.

Following placement of the joint implant within the implant receiving space, an anchor may be delivered transversely to or across the joint to additionally stabilize the joint.

B. Second Embodiment of a Delivery Tool, Insertion Tools, and a Joint Implant

Reference is made to FIGS. 13-17 in the present application. An exemplary embodiment of a joint implant 300 may be seen in FIG. 13. As seen in the figure, the joint implant 300 includes a pair of keels or planar members coupled together at a distal end by a distal intra-articular or connecting member, and coupled together at a proximal end by a proximal intra-articular or connecting member. In certain embodiments the planar members are only coupled together at the distal end either by a proximal intra-articular member or at a proximal end without any intra-articular member such that the implant resembles a staple having wide planar legs. Each of the pair of keels may be a mirror image of each other. The pair of keels may include inner surfaces or faces that face each other, and outer surfaces or faces that are opposite each other. The inner and outer faces of the pair of keels may be bounded by a tapered distal edge, lateral side edges that may be jagged, serrated, or saw-like, and a linear proximal edge. The pair of keels may include a plurality of passageways that extend from the outer surfaces to the inner surfaces. The inner surfaces of the keels may taper towards each other at the proximal end and may include a series of ridges or serrations that inhibit migration of the implant once it is implanted in the sacroiliac joint. The distal intra-articular member may be tapered at the distal tip so as to ease insertion into the sacroiliac joint.

Figure 93:
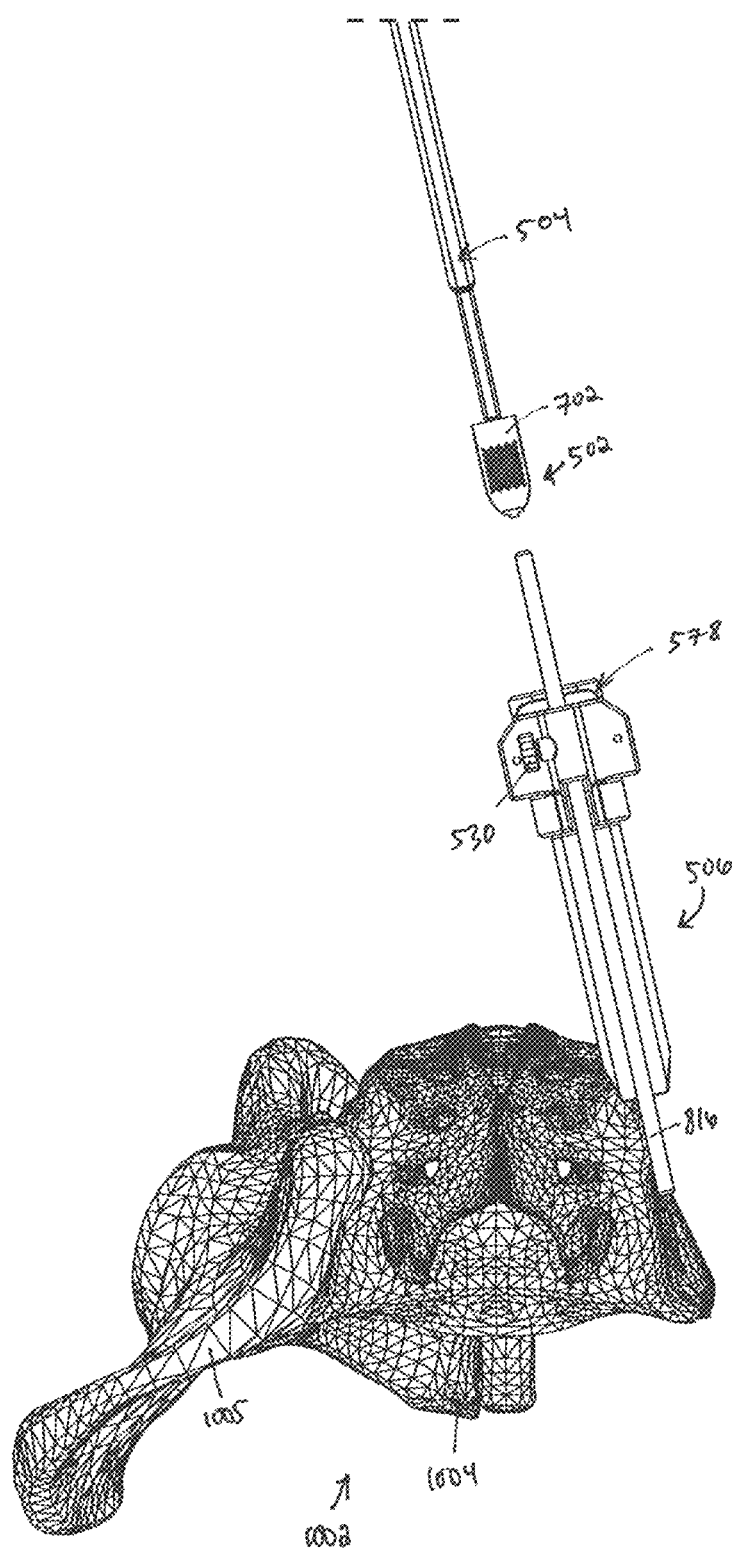
FIG. 93 is a superior view of the joint implant coupled with an implant arm positioned proximate of the working cannula.

The proximal end of the joint implant includes a tool interface that includes an elongated slot defined in a proximal side of the proximal intra-articular member. The tool interface may be used in conjunction with a distal end of an implant arm of a delivery tool to couple the joint implant and the implant arm together. As seen in FIG. 93 of U.S. 62/609,095 filed Dec. 21, 2017 and hereby incorporated by reference in its entirety, the tool interface defines a rectangular perimeter on the proximal end of the joint implant. The top and bottom portions of the rectangular perimeter define lipped edges for supporting a portion of an implant arm, which will be subsequently described in more detail.

Figure 14:
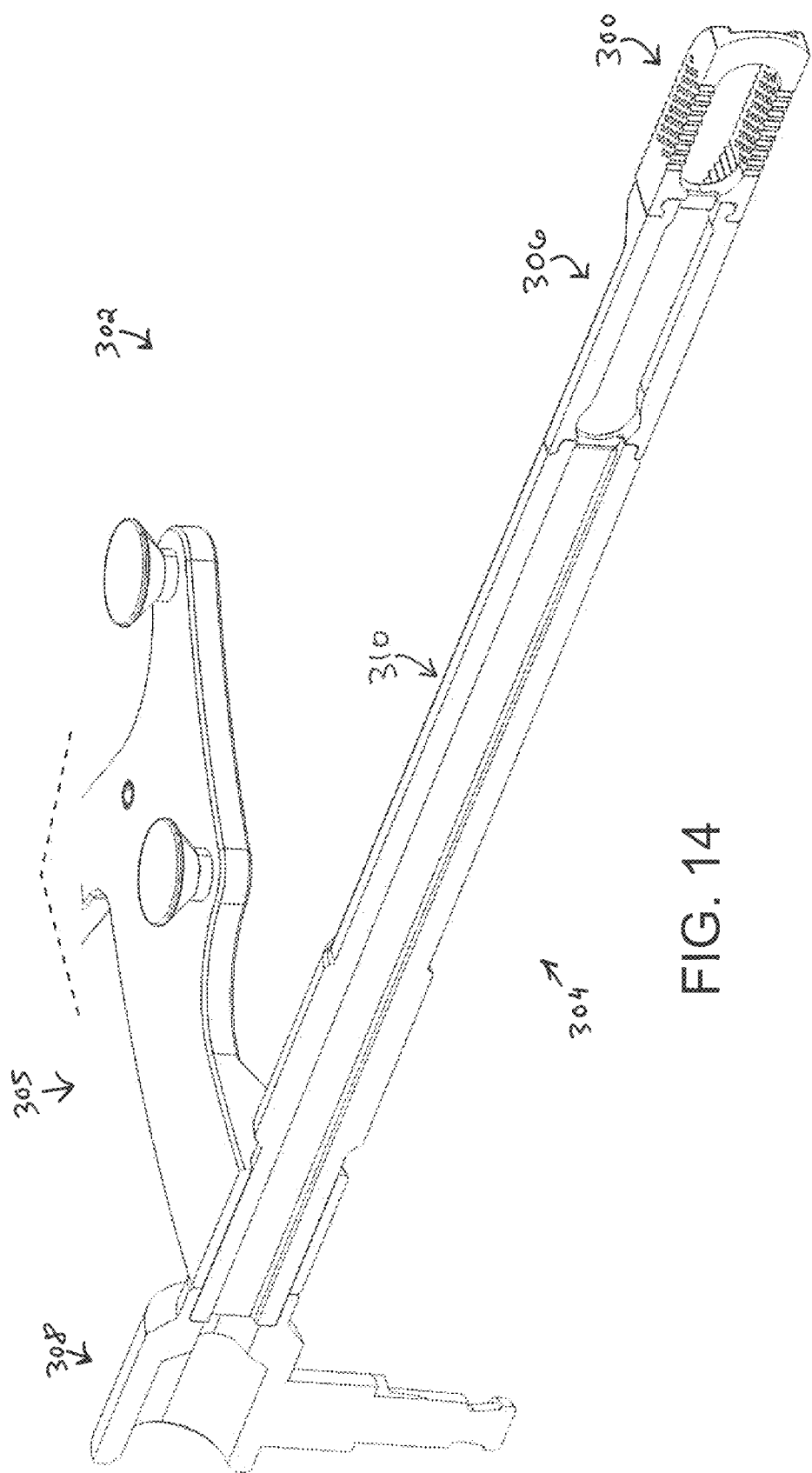
FIG. 14 is a cross-sectional isometric view of the delivery tool and implant.

As seen in the longitudinal cross-sectional view of FIG. 14, and moving distally from a proximal most boundary, the lipped edges of the tool interface includes a proximal facing ramped portion that ramps inwardly to a planar longitudinal portion. The planar longitudinal portion transitions to a distal facing ramped portion. The distal faced ramped portion transitions to another planar longitudinal portion, which then transitions to a proximal facing planar portion. The proximal facing planar portion is perpendicular to the planar longitudinal portion. Central within the proximal facing planar portion is a rectangular opening and a passageway that extends into a window or opening defined between the inner ends of the proximal intra-articular member and the distal intra-articular member. As seen in the cross-sectional view of FIG. 14, the window is pill shaped with arcuate ends defined by the ends of the proximal intra-articular member and the distal intra-articular member, and planar, parallel sides defined by the inner sides of the pair of planar members.

In certain instances, the joint implant may be implanted, inserted, or delivered into the sacroiliac joint such that the intra-articular members are positioned generally within the plane of the sacroiliac joint, and the planar members extend across the joint and into the sacrum and the ilium.

Figure 15:
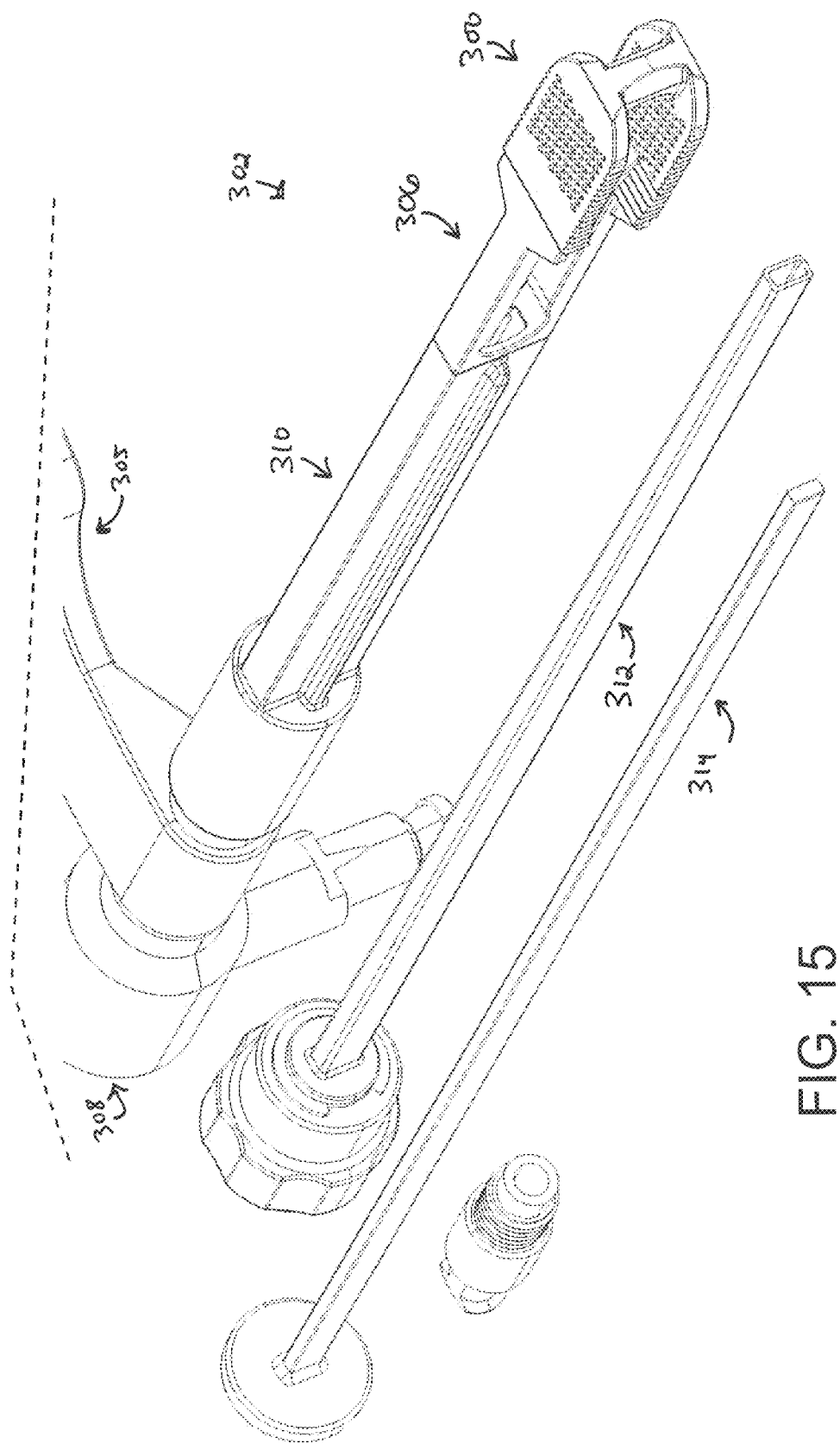
FIG. 15 is an isometric view of the implant arm, the implant, a cannula insertion tool, a tamp insertion tool, and a luer lock adapter.

The delivery tool 302 may include an implant arm 304 (alternatively called an insertion arm) and an anchor arm 305 extending off of the implant arm 304. As seen in FIG. 15, the implant arm 304 may include a distal member 306, a proximal member 308, and an intermediate member 310. A cylindrical proximal end of the intermediate member may be fitted through a tubular portion of the anchor arm, and the proximal member may couple to the cylindrical proximal end of the intermediate member to couple the implant arm to the anchor arm.

The proximal member 308 includes a distal opening for receiving the proximal cylindrical end of the intermediate member 310. The distal opening is defined in a cylindrical body. And coupled to the cylindrical body is an attachment rod terminating in a large Hudson connection configured to attach to a handle extending away from a cylindrical sidewall of the cylindrical body. A lumen extends through the cylindrical body, and is coaxial with the distal opening.

The intermediate member 310 can be seen in FIG. 15, and it includes the cylindrical proximal end, and a rectangular tube that extends distally from the cylindrical proximal end. A pair of fins extend outward from the long sides of the rectangular tube, and also extend a length of the rectangular tube. A lumen extends through the intermediate member from the cylindrical proximal end to the distal end of the rectangular tube. The lumen of the intermediate member 310 is coaxial with the lumen of the proximal member 308 such that tools and material (e.g., biocompatible material) may be passed through the pair of lumens.

A pair of prongs extends distally out of the distal opening of the rectangular tube. The pair of prongs are positioned at opposite ends of the distal opening (i.e., the short ends of the rectangular tube). The pair of prongs is configured to couple the intermediate member 310 to the distal member 306.

The distal member 306 includes a pair of distally extending prongs that are coupled at a proximal end to a plate. At a distal end of each of the prongs are laterally extending wings. The wings are positioned such that they generally lie in the same plane as the pair of planar members of the joint implant when the distal member is coupled to the joint implant. The wings may be dimensioned such that the height is less than the height of the planar members of the implant such that when the distal member disengages the implant and are deflected towards one another they will still fit within the track cut into the bone the implant followed.

The pair of prongs are spaced-apart from each other and are open at the distal end. At a proximal end of the distal member, the distal member forms a semi-cylindrical outline on a distal side of the plate and in between the prongs. This shape may permit the prongs to flex inward and extend outward away from each other so as to couple and uncouple with the joint implant. The plate includes a lumen extending longitudinal there through that is coaxial with the lumens of the intermediate member and the proximal member. In this way, tools can be inserted through the respective lumens of the proximal member, intermediate member, and distal member, and also inserted into the window of the joint implant via the passageway within the tool interface. Such insertion of the tool can be accomplished while the implant arm is coupled to the joint implant because the lumens are centrally positioned, and the coupling of the joint implant and the distal member avoids obstructing the lumens.

Each of the prongs includes a tab that extends distally off of its respective prong. The tabs are configured to selectively engage and release the tool interface of the proximal end of the joint implant 300.

In certain instances, a neutral condition (i.e., unstressed state, unflexed) of the distal member 306 may be when the prongs are parallel with each other. In the neutral position, the prongs may be flexed inward towards each other, via an applied force, in order to permit the tabs to fit within the tool interface opening. Once the tabs are within the tool interface opening, the prongs may rebound or expand back to the neutral position. Once coupled with the joint implant 300, the distal member 306 may be configured such that it exerts opposing forces on the joint implant so as to ensure a secure connection between the joint implant and the distal member.

In certain instances, a neutral condition (i.e., unstressed state, unflexed) of the distal member 306 may be when the prongs are non-parallel with each other. In an example, the neutral condition may be when the prongs converge towards each other. As will be discussed subsequently, a tool (e.g., engagement tool) may be used to forcibly move the prongs to a parallel condition so as to secure the connection between the joint implant and the distal member. The tool may then be removed, after implantation of the joint implant, in order to decouple the joint implant and the distal member. In another example, the neutral condition may be when the prongs diverge away from each other each other in a non-parallel condition. A tool (e.g., engagement tool) may be used to flex the prongs to a less than parallel condition so as to permit coupling of the joint implant and the distal member. Once coupled, prongs of the joint implant may exert a force on the joint implant by attempting to expand back to its neutral state. After implantation of the joint implant, the tool may be used again to decouple the joint implant and the distal member.

Figure 16:
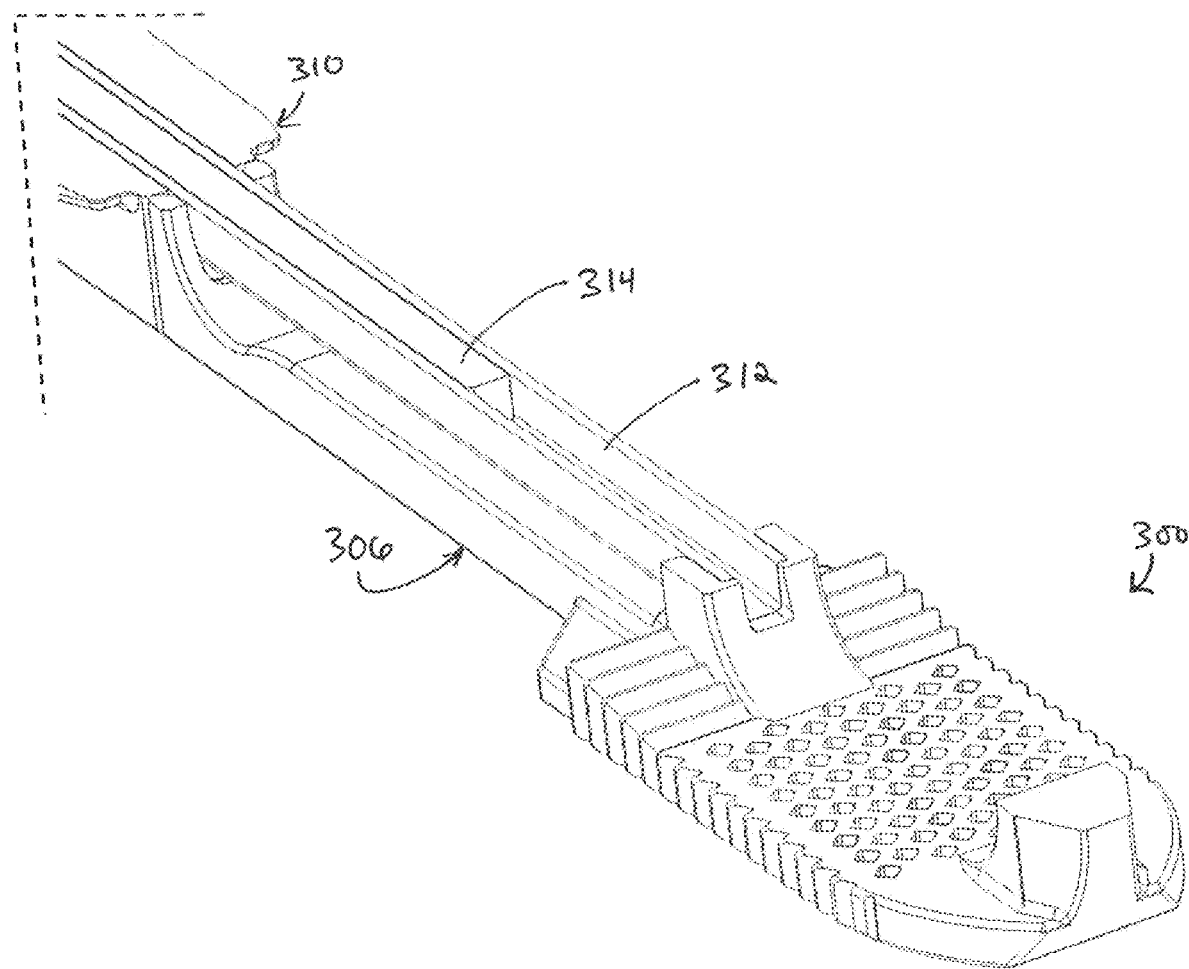
FIG. 16 is a close-up, cross-sectional, isometric view of the implant and the distal member of the implant arm with the cannula insertion tool (fully inserted) and tamp insertion tool (partially inserted) nested therein.

FIGS. 15-16 show various types of insertion tools that may be used in conjunction with the implant arm 304. To begin, a solid or non-cannulated engagement tool (not shown) for inserting through the implant arm 304 is shown in FIG. 15. The engagement tool includes a cylindrical section at a proximal end (optional male threads not shown), and an elongate member with a rectangular cross-section extending distally from the cylindrical section. The cylindrical section may include a sealing flange at a proximal most point. There is no lumen extending through the non-cannulated engagement tool. The engagement tool may be advanced through a lumen of the arm knob such that the sealing flange is received within and seals relative to the lumen of the arm knob. A ring clip may be used to secure an arm knob onto the cylindrical section positioned adjacent and distal to the sealing flange thereby fixing the location of the arm knob on the engagement tool while allowing the arm knob to rotate freely around the cylindrical section. In particular, the clip may snap into a cylindrical groove near the distal end of the cylindrical section thereby allowing the threading of the arm knob into the recess of the body proximal part of the insertion tool (optional female threads not shown) via rotational forces while allowing the rectangular volume of the engagement arm to not rotate yet still translate along the length of the insertion tool.

The length of the elongate member of the engagement tool is such that it may be received up to the distal end, and in between, the prongs of the distal member 306 so as to restrict the prongs from flexing inward towards each other. Thus, the engagement tool may ensure a secure connection between the joint implant and the distal member of the implant arm, for example, during delivery of the joint implant into the sacroiliac joint. Upon delivery, the engagement tool may be retracted from the implant arm to permit decoupling of the joint implant form the implant arm.

Moving on to another insertion tool, a cannula insertion tool 312 for inserting through the implant arm is shown in FIGS. 15-16. The cannula insertion tool 312 includes a cylindrical section at a proximal end (optional male threads not shown), and a tubular member with a rectangular cross-section extending distally from the cylindrical section. The cylindrical section may include a sealing flange at a proximal most point. The cylindrical section may include a proximal opening at the proximal end that is larger than the lumen of the tubular member, which extends from within the cylindrical section to a distal opening at the distal end of the tubular member. The proximal opening at the proximal end opens up to a female threaded bore within the cylindrical section configured to receive the luer lock adapter described below. The cannula insertion tool 312 may be advanced through a lumen of the arm knob such that the sealing flange is received within and seals relative to the lumen of the arm knob. A ring clip may be used to secure an arm knob onto the cylindrical section. In particular, the clip may snap into the cylindrical groove near the distal end of the cylindrical section. Generally, the arrangement between the cylindrical section and the arm knob are the same as described above for the engagement tool. The coupled arm knob and cannula may then be inserted through the lumens of the implant arm's proximal member, intermediate member, and distal member. When received therein, the arm knob may be engaged with the proximal end of the cylindrical body of the proximal member.

A luer lock adapter may be inserted, external threads first, into the female threaded bore of the cylindrical section, and a syringe may be engaged with the opposite end of the luer lock adapter. Thus, the luer lock adapter provides a fluid connection to the implant through the tubular member of the cannula insertion tool for the dispensing of biological material therein. Alternatively, a funnel may be engaged with proximal opening of the cannula insertion tool for the dispensing of biological material therein. The funnel may have a male threaded defined on the exterior tip of the nozzle of the funnel configured to thread into the female threaded bore of the cylindrical section. Another insertion tool that may be used in conjunction with the cannula insertion tool 312 is a tamp insertion tool 314, which is shown in FIGS. 15 and 16. The tamp insertion tool 314 may include a cylindrical body at a proximal end and a thin elongate member with a rectangular cross-section extending from the cylindrical body. The elongate member may be configured to be inserted within the tubular member of the cannulated insertion tool 312 via the proximal opening at the proximal end of the cylindrical section (after the luer lock has been removed) so as to advance material (e.g., biological material such as bone paste, bone graft, etc.) through the tubular member of the cannula insertion tool 312, and deposit the material through the lumen within the tool interface of the joint implant 300 and into the window of the joint implant 300. As such, the size of the elongate member may be sized to fit just within the passage of the tubular member so as to act like a plunger within a syringe in moving the material through the cannula insertion tool to the joint implant.

Figure 17:
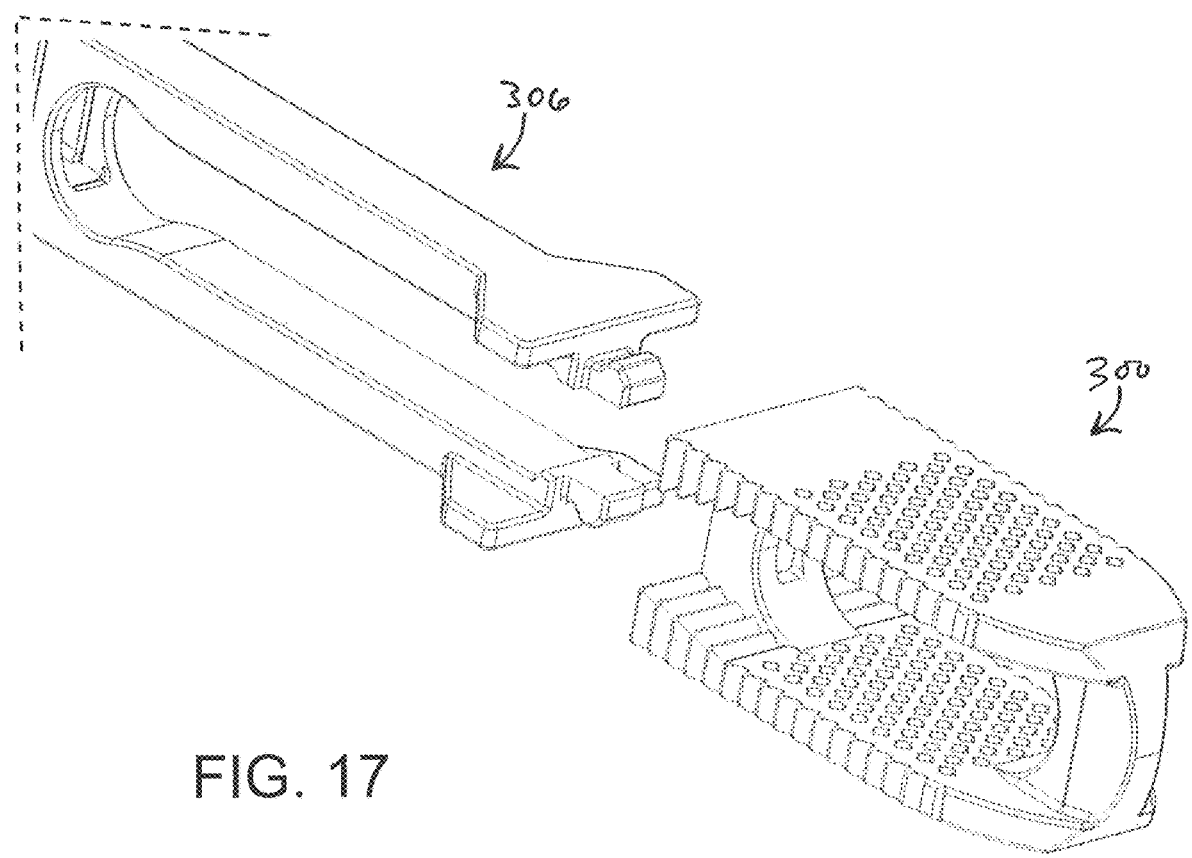
FIG. 17 is a close-up isometric view of the implant uncoupled from the distal member of the implant arm.

FIG. 17 shows an isometric view of the distal member and the joint implant uncoupled from each other. As seen in FIG. 17, the distal member is aligned with the joint implant in a way that the tabs at the distal end of the prongs will be received within the tool interface of the joint implant when the distal member and the joint implant converge. In this particular orientation, the distal member is in a neutral condition where the prongs are generally parallel to each other. The distal member may be distally advanced relative to the joint implant and the tabs may engage and be secured to the tool interface portion of the joint implant because of the complimentary geometry of the tabs and the tool interface.

As seen in FIG. 16, which is a longitudinal cross-sectional views along a plane that is parallel to a plane of the planar members of the joint implant, the distal end of the tubular member of the cannula insertion tool 312 abuts against the proximal facing planar portion of the tool interface. In this fully distal position, the geometry on the inside of the tubular member matches the geometry of the passageway through the tool interface and into the window of the joint implant 300.

FIG. 16 also depicts the tamp insertion tool 314 being inserted within the cannula insertion tool 312 so as to distally advance the biological material within the tubular member and into the window of the joint implant 300. As seen in FIG. 16, the tamp insertion tool is partially advanced so as to be about halfway along a length of the distal member. Note the biological material is not shown in FIG. 16.

FIG. 17 depicts the uncoupling of the joint implant 300 from the distal member 306 following insertion of the biological material into the window of the joint implant 300. To accomplish the uncoupling, the tamp insertion tool 314 and the cannula insertion tool 312 may be retracted; then, the implant arm 304 may be proximally pulled relative to the joint implant 300, which is securely implanted within the joint. The complementary geometry of the tabs of the distal member and the lipped edges of the tool interface may permit such decoupling merely by providing an opposing force between the distal member and the joint implant. And without the tubular member of the cannula insertion tool positioned within the distal member 306, the prongs may be permitted to flex inward to permit the uncoupling.

A kit comprising the aforementioned tools or implant may further include a particular volume of biological material which approximately corresponds to the volume of the bone graft window of the implant. Optionally, the particular volume may significantly exceed the volume of the bone graft window such that the bone graft window of the implant may be filled and then flow out into the joint space adjacent the implant via openings in the planar members.

III. Radiographic Tools for Use During Preparation for Fusion of the Sacroiliac Joint As described in previous sections, implantation of a joint implant for fusion of the sacroiliac joint includes preparation of a joint receiving space. Such preparation includes removing articular cartilage; removing cortical, subchondral or cancellous bone of the joint (such as by cutting or abrading the joint surfaces); and then cutting slots, drilling holes, or similar features into the exposed boney tissue to receive keels or other structural elements of the joint implant. Once prepared, the joint implant is delivered into the prepared joint space and one or more anchors are delivered across the joint and into the ilium and sacrum. Additional anchors may also be implanted to provide additional stability of the treated joint. Implantation of the anchors may also include preparation of the corresponding screw holes such as by drilling pilot holes or removing additional tissue within or surrounding the anchor implantation locations. Notably, many of the procedures for preparing the implant receiving space materially affect the sacrum and/or ilium such that misplacement of the anchors may not be readily correctable. In light of the foregoing, systems in accordance with this disclosure may include a radiographic guidance system 400 configured to allow a surgeon to evaluate and confirm implant trajectories, implant configurations, implant sizes, screw (or other anchor) trajectories and screw lengths prior to preparing the screw holes.

The radiographic guidance system 400 includes a trial implant 402 that is coupled to the distal end of an implant arm of a delivery tool. The trial implant 402 may be disposed within the implant receiving space of the joint prior to fully preparing the articular surfaces of the sacrum and ilium. By doing so, the trial implant 402 may be used to assess and verify the placement of the final joint implant prior to substantial alteration of the articular surfaces.

Figure 18:
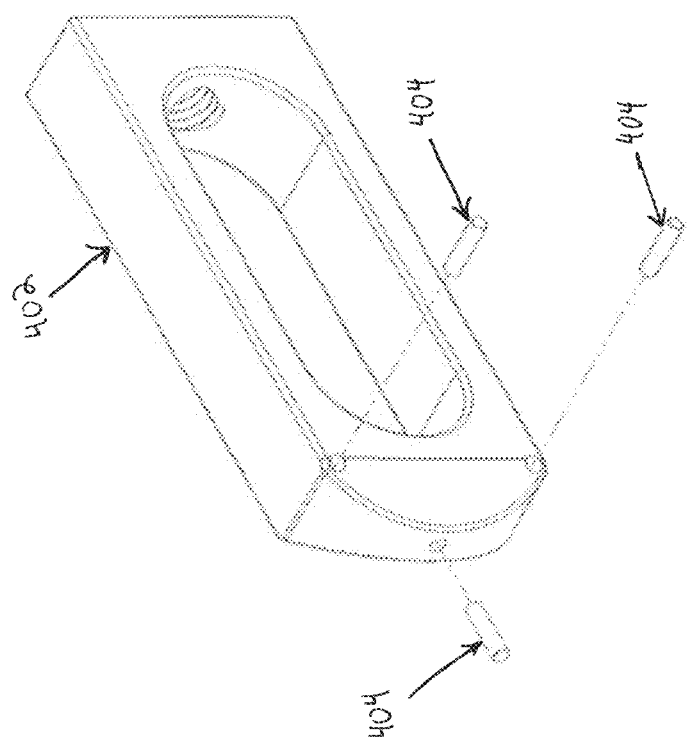
FIG. 18 is an isometric view of an implant trial with radiographic markers.

An example of a trial implant 402 is shown in FIG. 18. As shown, the trial implant 402 generally conforms to the size and shape of the joint implant 300, of FIGS. 13-17, among others, used to actually fuse the sacrum and ilium but lacks the keels of the joint implant 300. Accordingly, the trial implant 402 can be disposed within the joint space prior to forming the slots or grooves of the implant receiving space required to receive the keels of the joint implant 300.

The trial implant 402 may include a body formed from a radiolucent material (such as PEEK or Radel) with radiopaque markers 404 coupled to or disposed within the body. For example, the trial implant 402 in FIG. 18 includes pins 404 formed of a radiopaque material (such as tantalum or titanium) and that are inserted into the radiolucent body at the distal tip, and upper and lower distal corners. In other implementations, the radiopaque markers 404 may instead be in the form of, among other things, beads, bands, rings, or strips disposed within or coupled to the body of the trial implant 402. The radiopaque markers 404 may be disposed at various locations of the trial insert including, without limitation, at corners of the trial implant 402, along the outer perimeter of the trial implant 402, along a bone graft window perimeter of the trial implant 402, at a centroid of the trial implant 402, or at or along any other feature of the trial implant 402.

Figure 19:
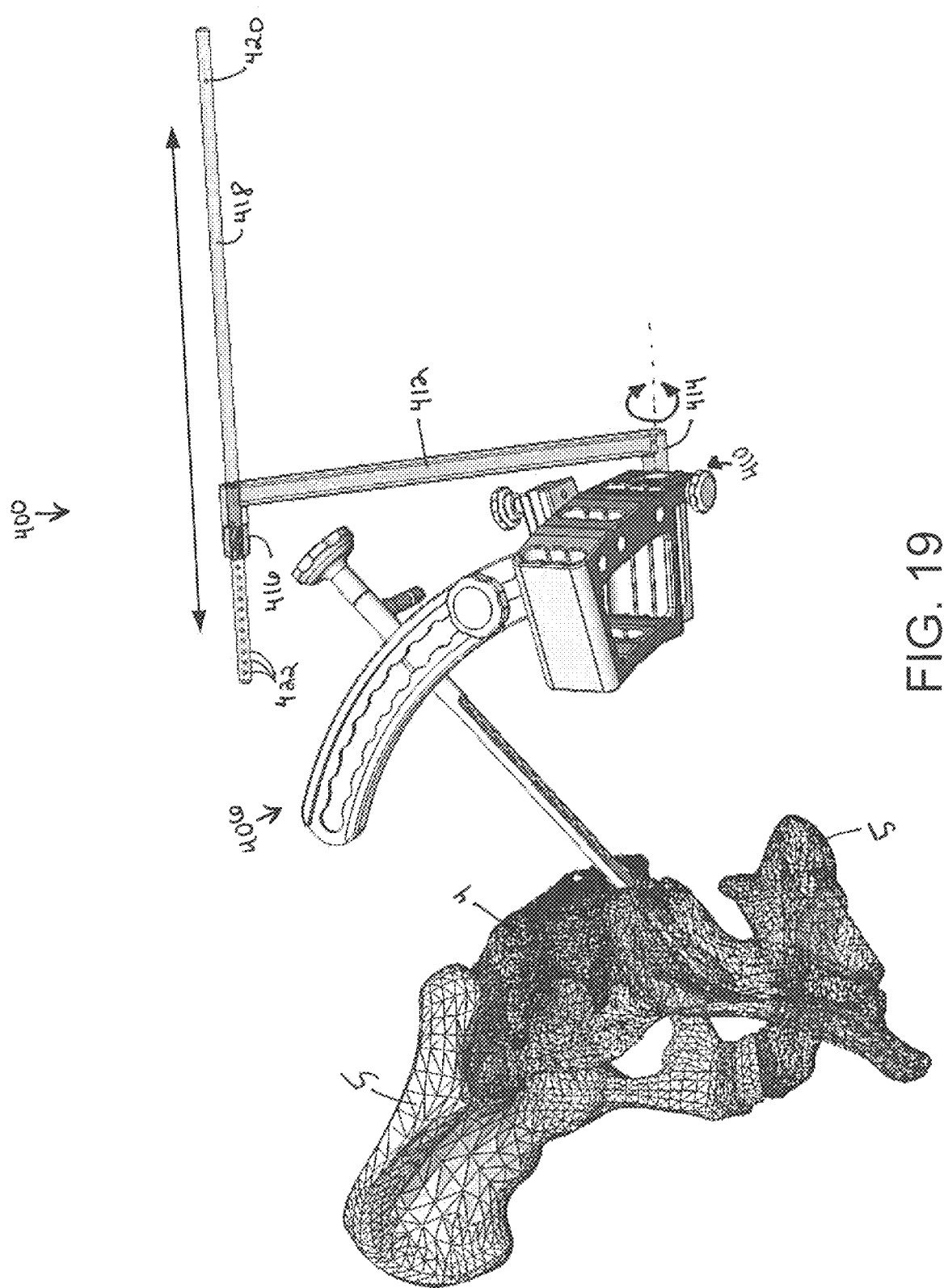
FIG. 19 is an isometric view of a radiographic system in use with the implant trial.
Figure 20:
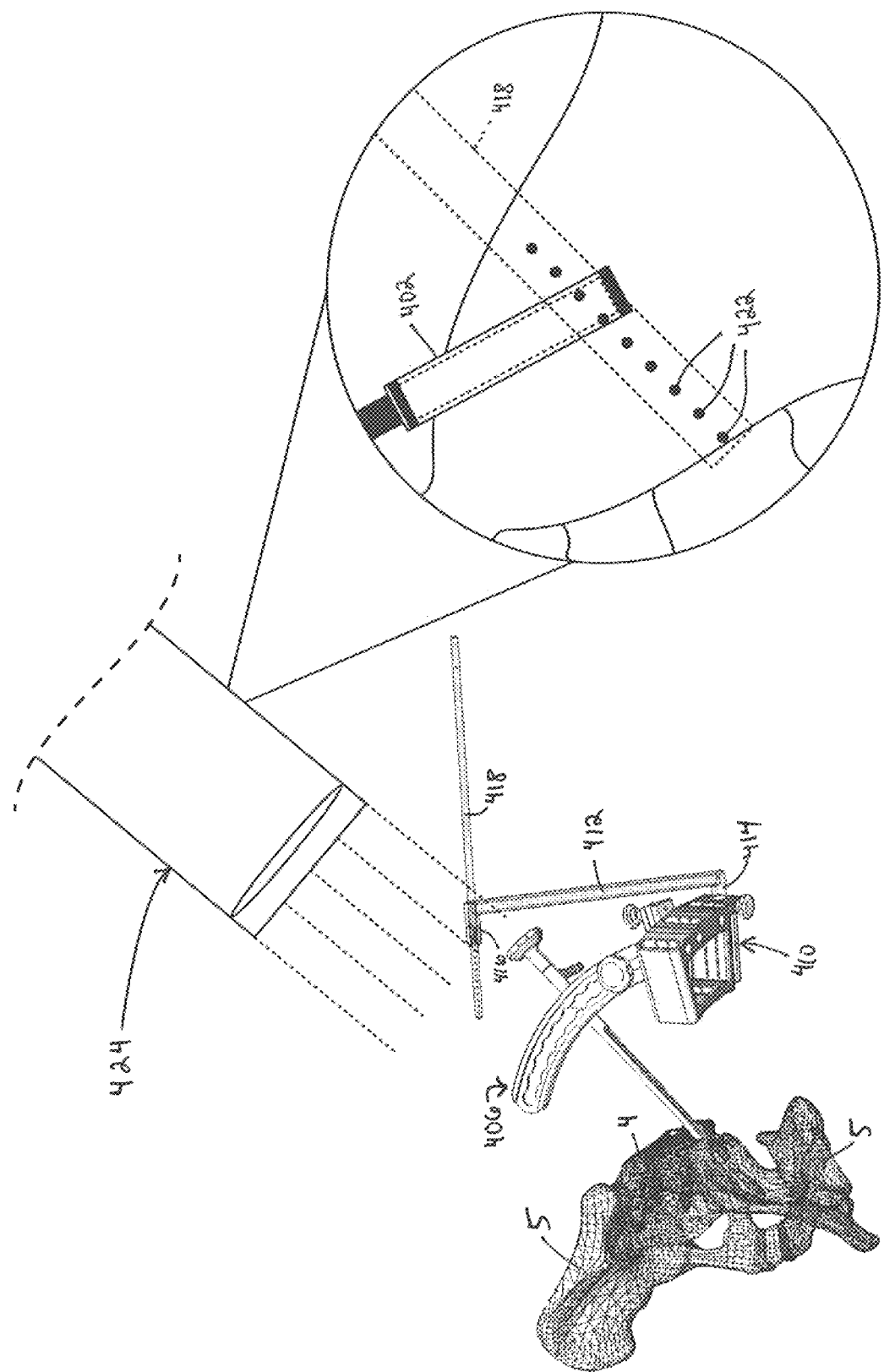
FIG. 20 is an isometric view of a radiographic system in use with the implant trial, and a close-up view of a radiographic image.

The trial implant 402 may be delivered into the sacroiliac joint using the same delivery tool for delivering the joint implant as previously described, as described below regarding any implant coupling instrument or a dedicated (e.g., radiolucent Radel) shaft may be removably or permanently coupled (either multi-piece construction or constructed from a single piece of material) with the trial implant. As illustrated in FIGS. 19-20, the delivery tool 406 may include an implant arm 408 having a distal end to which the trial implant 402 is coupled and inserted into the sacroiliac joint. Guide pins, tissue protectors, and other components that may be used in conjunction with the delivery tool are omitted from FIGS. 19-20 for clarity. During placement of the trial implant 402, multiple x-rays or similar images may be taken to determine the location and orientation of the trial 402 and other components of the radiographic guidance system. Such images may include, without limitation, one or more views including, an anteroposterior view, a lateral view, an inlet view, an outlet-oblique view, Judet views of the pelvis, an internal (obturator) oblique view, a Ferguson view, an external (iliac) oblique view, or other relevant views.

The features used to align or otherwise position the radiopaque markers of the guidance system may include, without limitation, structural elements of the trial implant (such as a centroid of the trial implant, or a radiopaque marker of the trial implant) or anatomical features of the patient. An anatomical feature may, for example, be a portion of the outer cortex of the ilium corresponding to the location of the anchor head once implanted. Other anatomical features of the ilium or sacrum or radiographic boney landmarks that may be used as references for aligning the radiopaque markers of the guidance system include, without limitation, the superimposed greater sciatic notches, the superimposed iliac cortical densities or alar slope, the sacral promontory, the first sacral endplate, the sacral foramina, the arcuate sacral lines, the iliopectineal line, the ilioishial line, the acetabular teardrop lines boney corridors of S1 or S2, the superimposed acetabula, and the ventral and dorsal surfaces of the sacrum. Anatomical features may also include vascular structures, which may be identified using an angiogram or similar imaging system. Examples of such vascular structures include, without limitation, the superior gluteal artery, the internal iliac artery and vein, and the iliolumbar vein.

Placement of the trial insert 402 may be facilitated and/or verified using a radiographic guidance system 400 inserted into or otherwise coupled to the delivery tool 406. In certain aspects, the radiographic guidance system 400 may be inserted into or otherwise coupled to the working cannula 506 (also referred to as a tissue protector), the implant arm 504, the anchor arm 508 (also referred to as an angle arm) or the anchor block 510 of the embodiment shown in FIGS. 23-26 and described below or the similar systems described and shown throughout the rest of the present application or any of the referenced applications. In FIGS. 19-20, for example, the radiographic guidance system 400 is disposed within an anchor arm guide 410 of the delivery tool 406. The radiographic guidance system 400 includes various members that are substantially composed of radiolucent materials. Similar to the trial insert 402, the members of the guidance tool may also include radiopaque markers, such as beads, at predetermined locations that may be used to verify placement of the trial insert.

With reference to FIGS. 19-20, the guidance system 400 includes a guide arm 412 adapted to receive each of a plunger 414 and a collet 416. The collet 416 is adapted in turn to receive a cylindrical depth gauge 418 that may be translated within the collet 416.

The depth gauge 418 includes an elongate body within which radiopaque markers are disposed. For example, the depth gauge 418 may include at least one proximal marker 420 used to facilitate alignment of the depth gauge with radiopaque features of other components of the guidance system or anatomical features. A distal end of the depth gauge may include multiple radiopaque markers 422 disposed at predetermined intervals or otherwise disposed in a predetermined graduated pattern to facilitate taking measurements or evaluating distances using the depth gauge. According to particular alternative embodiments, depth gauge 418 and/or elongated plunger 426 may be constructed entirely or largely from radiopaque materials, e.g., stainless steel and may simply be a Steinmann pin or K-wire.

Referring to FIGS. 19-20, the guidance system 400 is coupled to the delivery system 406 by inserting the plunger 414 into an anchor arm guide 410 of the delivery system 406. Once inserted into the delivery system 406, the guidance tool may be adjusted by rotating the guide arm 412 of the guidance system within the anchor arm guide 410 and/or translating the depth gauge 418 within the collet 416.

A surgeon may align each of a radiographic system (e.g., fluoroscopy machine and the x-ray beam) 424, radiopaque markers 404 of the guidance system 400, and a feature of the trial implant 402 or anatomical feature. Such alignment is generally achieved by manipulation of the guidance system 400 (such as by rotation within the anchor arm guide or translation of the depth gauge) and/or repositioning of the radiographic system 424. When such alignment occurs, the radiopaque markers 420, 422 of the depth gauge 418 may be used to verify placement and orientation of the trial implant 402 and to measure distances between the trial implant 402 and anatomical features, among other things.

Figure 21:
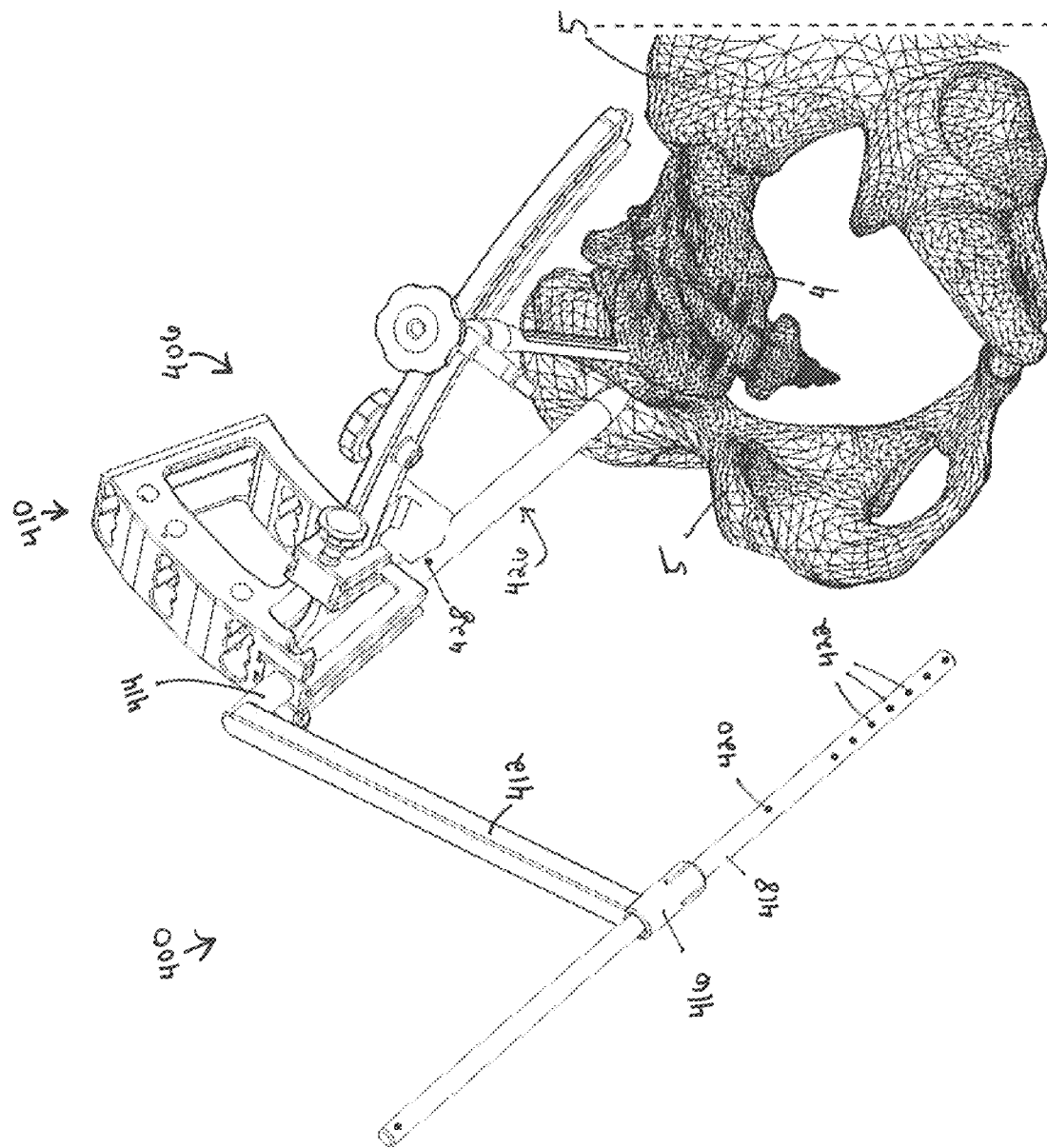
FIG. 21 is an isometric view of a radiographic system in use with the implant trial and an elongate plunger having a radiographic marker.

Once the trial implant is satisfactorily placed, an alternative radiographic guidance system may be used to verify or determine anchor placement, as illustrated in FIGS. 21-22. As illustrated, the guidance system 400 includes an elongated plunger 426, adapted to be inserted through the anchor arm guides 410 of the delivery tool 406 such that a distal end of the elongated plunger 426 reaches the corresponding anchor implantation location associated with the guide hole within which it is inserted. The guidance system 400 further includes a guide arm 412 and a depth gauge 418, where the guide arm 412 is coupled between the depth gauge 418 and the elongated plunger 426.

As illustrated in FIG. 20, the surgeon may align the depth gauge 418 of the guidance system 400 with each of a radiographic system 424 (e.g., emitter and detector of a fluoroscopy machine) and the elongated plunger 426 such that each are generally aligned in the same plane. By doing so, the radiopaque markers of the depth gauge 418 extend along an anchor trajectory that is visible in the corresponding radiographic image. In addition to indicating the trajectory of the anchor, the radiopaque markers of the depth gauge 418 may be used to determine the depth to which an anchor may be delivered, the distance between the anchor and any surrounding anatomical features, and other dimensions relevant to placement of the anchor.

In one example implementation, alignment may be achieved by aligning in the radiographic image a proximal most radiopaque marker 420 of the depth gauge 418 such that it overlays a proximal radiographic marker 428 of the elongated plunger 426 either by rotating and/or translating certain parts guidance system or by adjusting the location and orientation of the beam of the radiographic system 400.

IV. Additional System for Preparing the Sacroiliac Joint for Fusion

Figure 23:
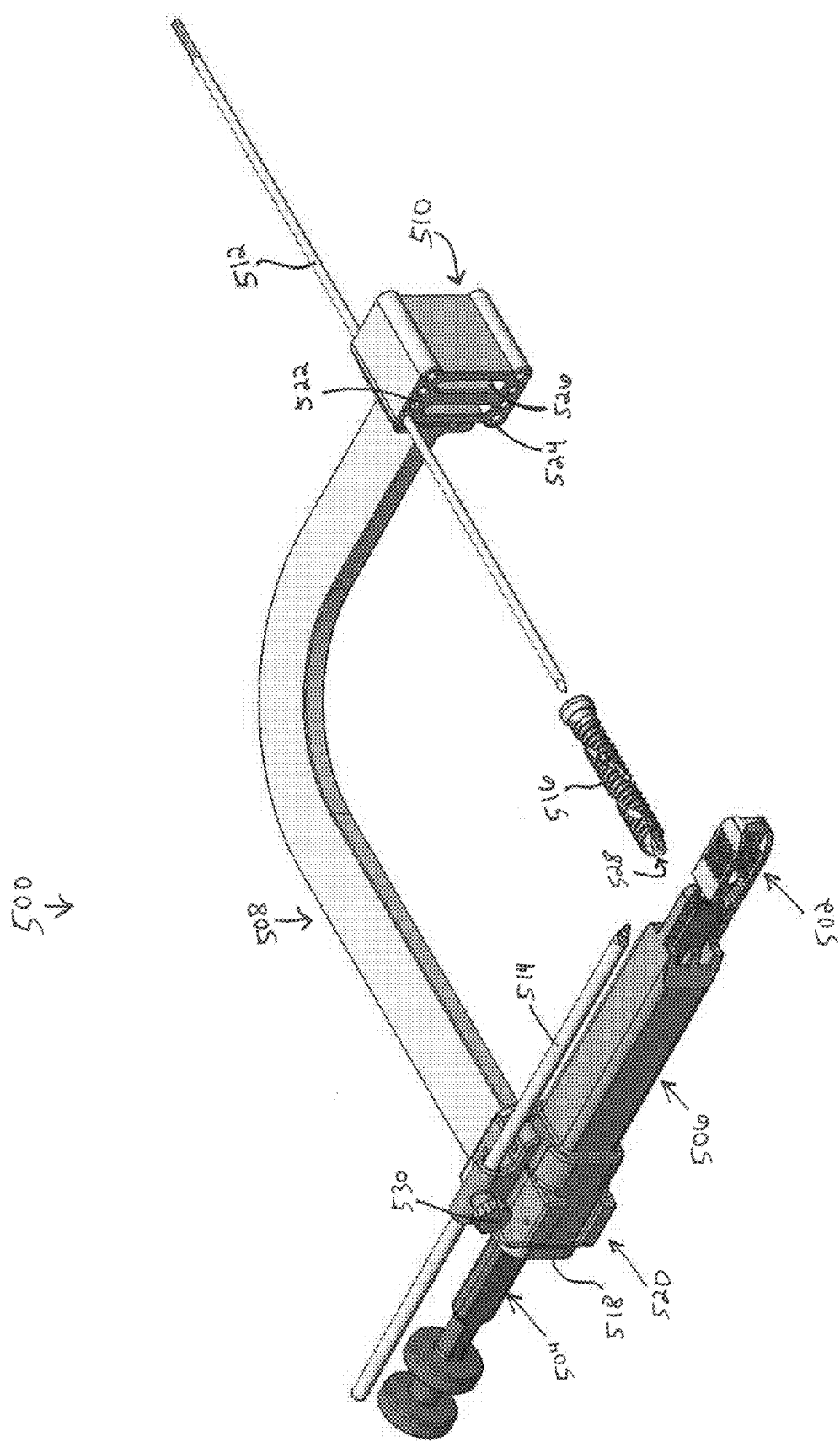
FIG. 23 is a distal isometric view of a sacroiliac joint delivery system.
Figure 24:
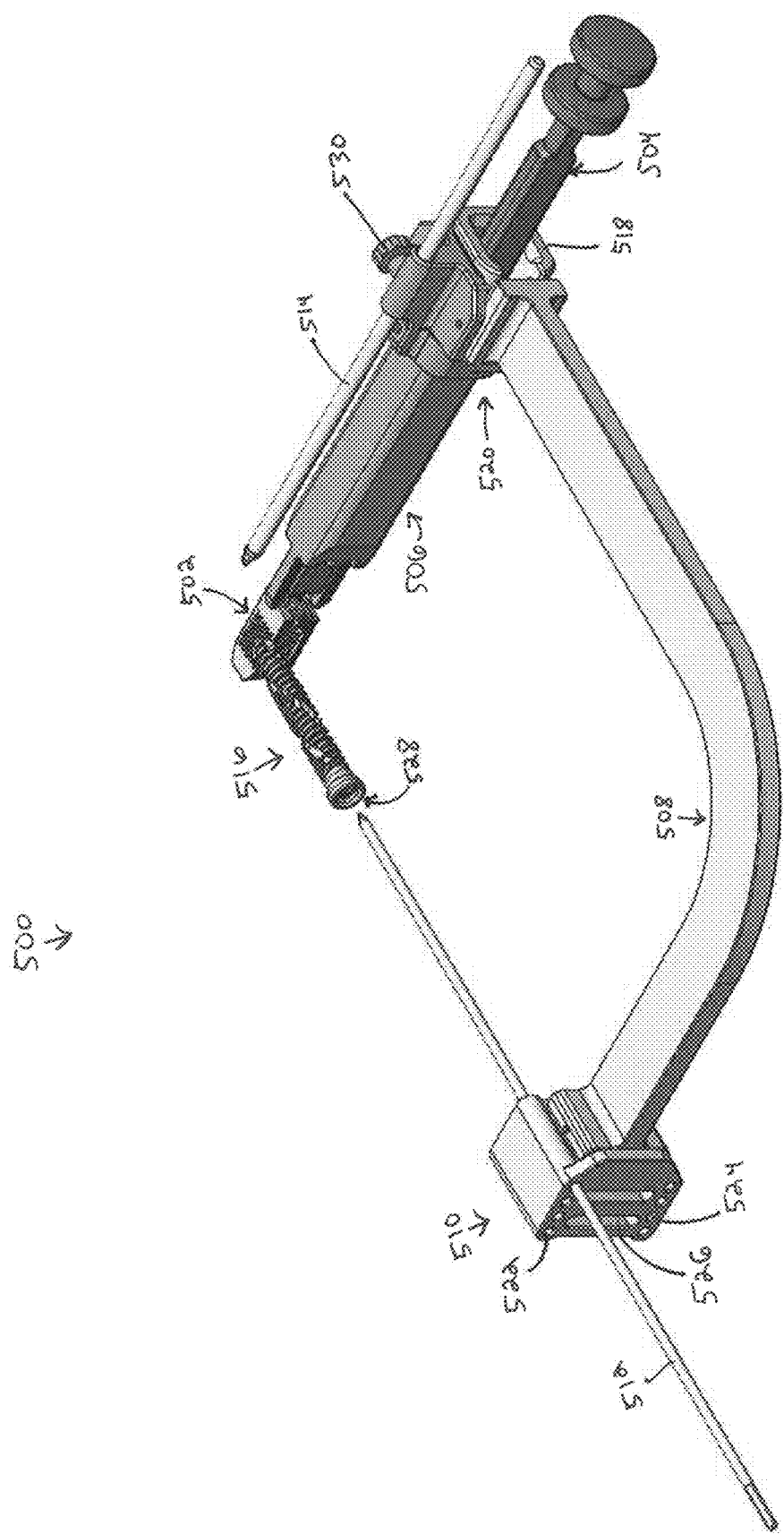
FIG. 24 is a proximal isometric view of the sacroiliac joint delivery system of FIG. 23.
Figure 25:
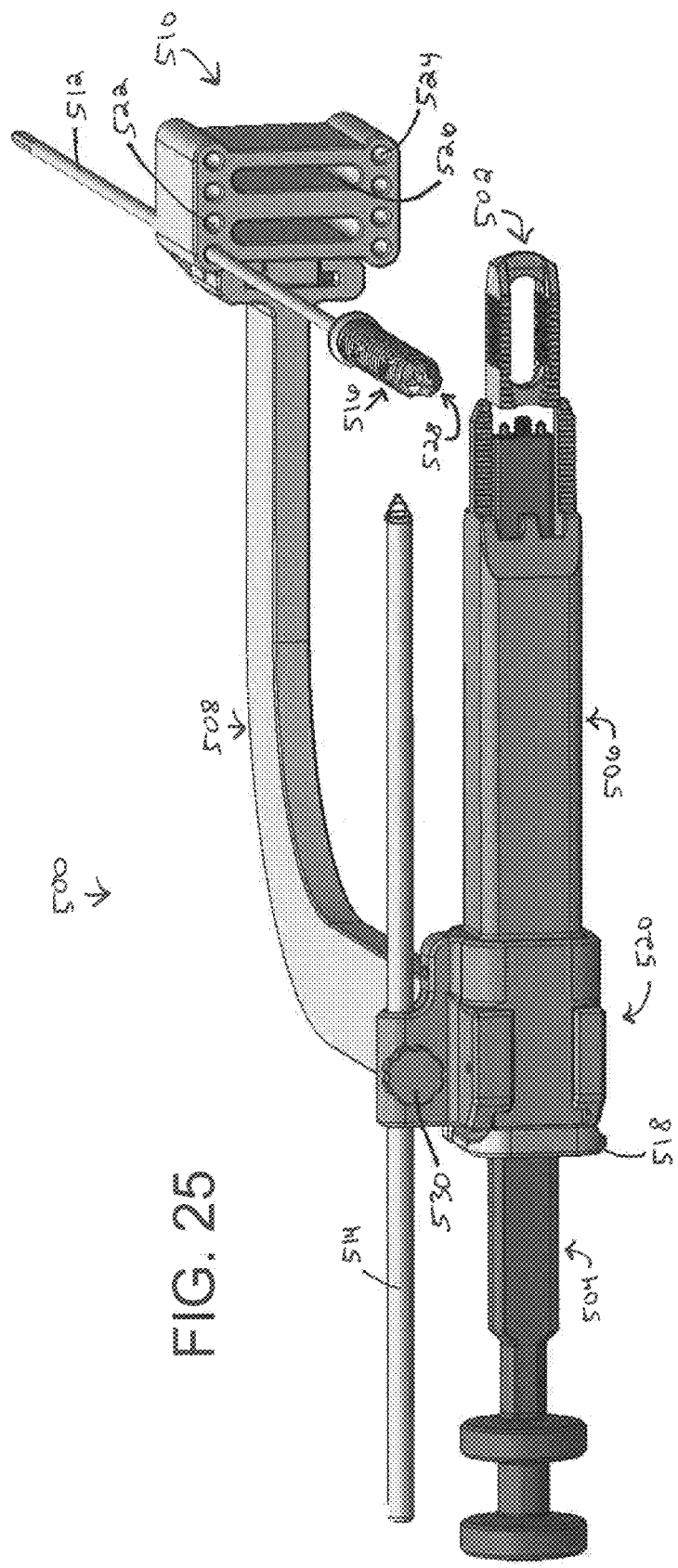
FIG. 25 is a side isometric view of the sacroiliac joint delivery system of FIG. 23.
Figure 26:
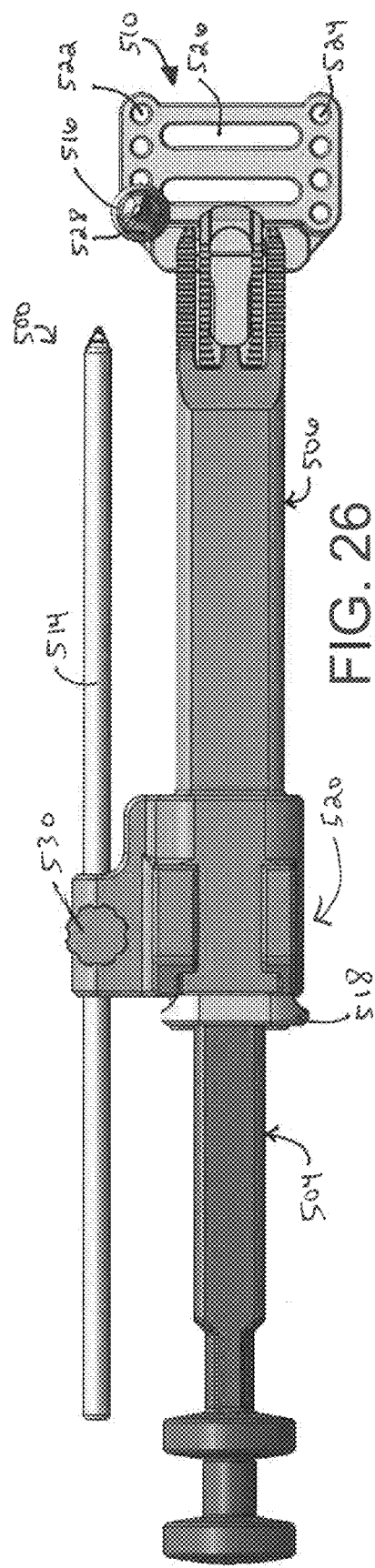
FIG. 26 is a side view of the sacroiliac joint delivery system of FIG. 23, except the joint implant is coupled to the implant arm of the system.

Reference is made to FIGS. 23-26 for a discussion of a sacroiliac joint access, preparation and delivery system 500. FIG. 23 is a distal isometric view of a portion of the components of the system 500. FIG. 24 is a proximal isometric view of the components of the system 500 of FIG. 23. FIG. 25 is an isometric side view of the components of the system 500 of FIG. 23. And FIG. 26 is a side view of the components of the system 500 of FIG. 23, with a joint implant 502 coupled to an implant arm 504 of the system 500.

The preparation and delivery system 500 may include a working cannula 506 (also referred to as a tissue protector), the implant arm 504, the implant 502, an anchor arm 508 (also referred to as an angle arm), an anchor block 510, a pin 512 (also referred to, or may be configured, as a Schanz screw, Steinmann pin, Kirschner wire or K-wire), a guidance pin 514 (also referred to, or may be configured, as a Schanz screw, Steinmann pin, Kirschner wire or K-wire), an anchor 516, and a standoff 518 (also referred to as an insert), among other components not shown in FIGS. 23-26, but shown in subsequent figures.

As seen in FIGS. 23-26, the working cannula 506 connects to the anchor arm 508 at a proximal end 520 thereof. The anchor arm 508 is cantilevered off of the working cannula 506, and is generally angled about at a ninety degree bend. The anchor arm may have numerous different configurations similar to those shown and described in the referenced patent applications or as otherwise described throughout the present application (e.g., having an arcuate bend, various shapes and angles, tubular, telescoping, fixed, adjustable, pivotable, slidable, translatable, rotatable, bendable, indexable, multisegmented, customizable etc.) modified to couple with the working cannula versus the implant arm. The anchor block 510 may be removably coupled to the free end of the anchor arm 508, and may include superior guide holes 522, inferior guide holes 524, and superior-inferior slots 526 extending through the anchor block 510. The superior guide holes 522 may guide a pin 512 in a predefined trajectory relative to the joint implant 502 that is superior to the joint implant 502. The inferior guide holes 524 may guide a pin 512 in a predefined trajectory relative to the joint implant 502 that is inferior to the joint implant 502; or alternatively, when the working cannula and other instruments are flipped approximately 180 degrees to align with the contralateral sacroiliac joint, inferior guide holes 524 may guide a pin 512 in a predefined trajectory relative to the joint implant 502 that is superior to the joint implant 502. The superior-inferior slots 526 may orient a cutting tool or other tool in-line with or adjacent the joint implant 502 while allowing a limited range of trajectories. The anchor block 510 in FIGS. 23-26 generally orient pins and tools perpendicular to the longitudinal axis of the joint implant 502; however, the system 500 may include additional or alternative anchor blocks 510 with guide holes and slots that orient the pins 512 and anchors 516 at different trajectories relative to the joint implant 502.

The pins 512 may guide the delivery of the anchor 516 into the bones of the sacrum, the ilium, and the sacroiliac joint in a transverse orientation relative to the joint implant 502. As seen in the figures, the anchor 516 may include a longitudinal lumen 528 for the pin 512 to extend there through. In this way, the pin 512 may provide an initial path to the bone, and the anchor 516 may be delivered along the trajectory of the pin 512. Upon delivery of the anchor 516 into the bone, the pin 512 may be withdrawn.

The guidance pin 514, e.g., a Schanz screw, may be anchored to the patient's bone, and the pin 514 may be secured in position relative to the working cannula via a screw lock 530. As an example, the guidance pin 514 may be anchored to the portion of the patient's posterior superior iliac spine that extends medially over the posterior access region of the sacroiliac joint. In this way, the working cannula 506 is oriented to guide tools and implants into the articular region of the sacroiliac joint, which is inferior to the portion of the posterior superior iliac spine to which the pin 514 is anchored.

The following discussion is with reference to FIGS. 27-38, which depict various views of the components of the preparation and delivery system 500. To begin, FIGS. 27A-27D are respectively isometric, top, side, and front views of a joint finder 532. As seen in the figures, the joint finder 532 may include an elongate body 534 with spatulate tip 536 at a distal end 538 thereof, a transverse opening 540 extending between sides of the body 534, a rectangular block-like handle 542 at a proximal end 544, and a recessed gripping portion 546 just distal of the block-like handle 542. The spatulate tip 536 may be used to identify the opening or gap between the sacrum and the ilium. Upon identifying the opening or gap between the sacrum and ilium, the spatulate tip 536 may be advanced into the sacroiliac joint.

FIGS. 28A-28D are respectively isometric, top, back, and side views of a working cannula or tissue protector 506. The working cannula 506 may include a pair of prongs, spikes, or projections 548 at a distal end 550 thereof, a tubular body 552 extending proximally from the pair of prongs 548, and a pair of anchor arm engagement structures 554 at the proximal end 520. Within the working cannula 506 is a passageway 556 that extends from the proximal to distal ends 520, 550. An inner surface 558 of the passageway 556 is keyed in the shape of an I-beam or H-beam.

As particularly seen in FIG. 28A, a portion of the inner surface 588 of the passageway 556 at the proximal end 520 is keyed so as to accept a standoff and has a keyed configuration which is different from the keyed passageway discussed above, in particular the proximal end is keyed with a generally square shape with two opposing corners having a substantial radius compared with the other two corners having a comparably small radius, and the tubular body 580 of the standoff has a cross section along a portion of the length of the standoff which matches the shape of the proximal end 520 where the cross section of the tubular body includes a generally square shape with two opposing corners having a substantial radius compared with the other two corners having a comparably small radius, in order to properly align the keyed inner surface 590 of the standoff 578 with the keyed inner surface 588 of the passageway 556, the standoff will be discussed in further detail below in reference to FIGS. 30A-30D. That is, the inner surface 558 of the passageway 556 comprises two differently configured keyed portions which ultimately result in a continuous keyed passageway once the standoff is in position within the proximal end of the working cannula.

The working cannula 506 may additionally include a pin guide 592 and a screw lock 530 at the proximal end 520. The pin guide 592 may be a cylindrical passageway that aligns an axis of a guide pin positioned therein (shown in FIG. 23, for example) in parallel alignment with a longitudinal axis 594 of passageway 556 of the working cannula 506. The guide pin may be secured in position relative to the working cannula 506 by tightening a screw lock 530. As seen in FIGS. 28A-28D, the pin guide 592 is positioned on a superior side of the working cannula 506 so as to guide a guide pin into a portion of the ilium (e.g., posterior superior iliac spine) while aligning the longitudinal axis 594 of the passageway 556 of the working cannula 506 with the articular region of the sacroiliac joint. The pin guide 592 is positioned between the anchor arm engagement structures 554, which are on opposite sides of the working cannula 506.

According to particular embodiments, the pin guide may have a fixed configuration such that the trajectory of the guide pin positioned therethrough is not adjustable or the pin guide may have an adjustable configuration such that the trajectory of the guide pin positioned therethrough is adjustable in at least one plane in order to align the guide pin with the desired boney anatomy without necessitating the reorientation or position of the working cannula longitudinal axis. For example, the pin guide may swivel (reversibly lockable) relative to the rest of the working cannula in order to allow the guide pin to be angled either lateral or medial to the longitudinal axis of the working cannula or even closer to or further away from (e.g., cranial or superior to) the exterior of the working cannula. As another example, the pin guide may translate (e.g., along a track and reversibly lockable) relative to the rest of the working cannula in order to allow the guide pin to be positioned either lateral or medial to the longitudinal axis of the working cannula or even closer to or further away from (e.g., cranial or superior to) the exterior of the working cannula. According to yet further embodiments, the pin guide may be couple to the working cannula with various mechanisms and arrangements that provide various desirable degrees of freedom.

The anchor arm engagement structures 554 may include a T-slot 596 formed by a pair of longitudinally extending tabs 598. The T-slot 596 may receive a corresponding structure of the anchor arm 508 having a T-shaped end portion.

According to certain aspects, the anchor arm engagement structures 554 may include a dovetail slot 596 formed by a pair of longitudinally extending tabs 598. The dovetail slot 596 may receive a corresponding structure of the anchor arm 508 having a dovetail shaped end portion. Whether the anchor arm engagement structures 554 and corresponding structure of the anchor arm 508 have a T-shaped, dovetail shape or an other similar arrangement the female portion may be defined on the working cannula (as shown) or alternatively the male portion may be defined on the working cannula and the female portion on the anchor arm.

Figure 77:
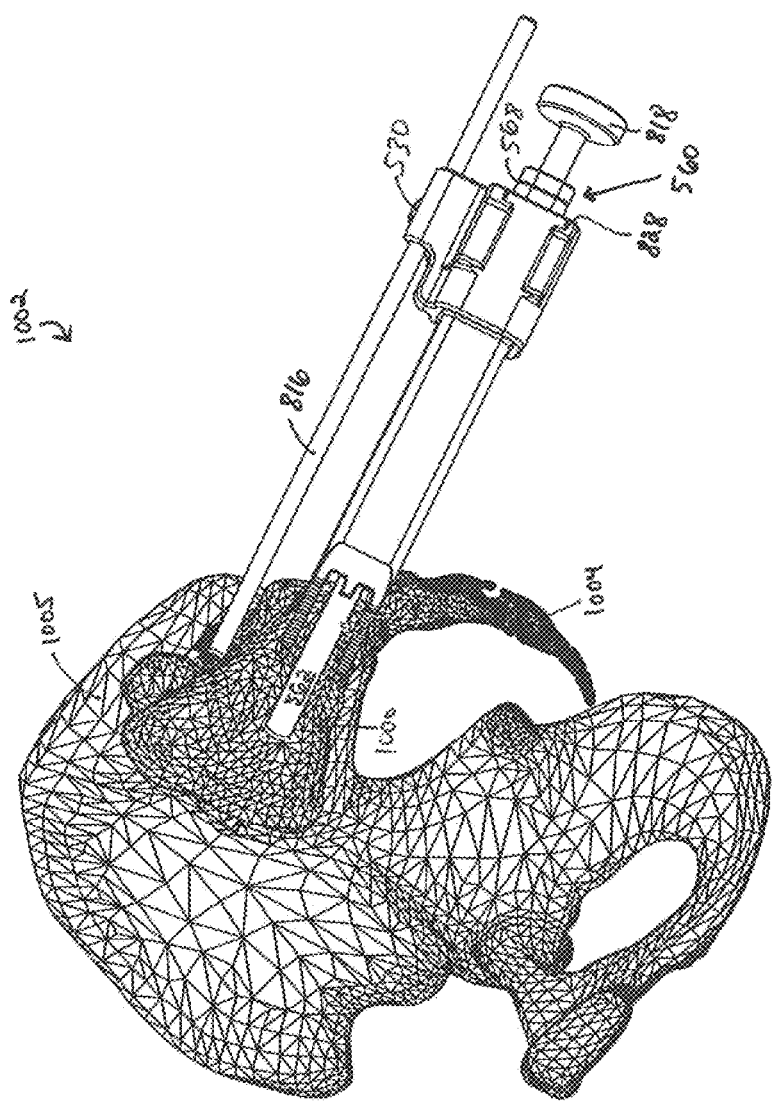
FIG. 77 is a side view of the pelvis with the nearest ilium removed, and the depth gauge positioned through the working cannula and in the joint in order to allow a medical person to evaluate with intra-operative imaging (e.g., with a lateral view) a desired depth of joint preparation and/or desired depth of implant placement (e.g., the joint may be prepared further distally than the desired implant depth in order to prepare more of the joint for fusion and may include packing/tamping bone graft or other biocompatible material distal to the final location of the implant).

FIGS. 29A-29D are respectively isometric, top, back, and side views of a depth gauge 560. As seen in the figures, the depth gauge 560 may include an elongate body 572 with a thin elongate tongue 562 at a distal end 564 thereof. The depth gauge 560 may include a rectangular block-like structure 566 at a proximal end 570 thereof. The structure 566 may include a series of markers 568 indicating a depth or distance away from the distal tip 570 of the tongue 562 or from a different component of the preparation and delivery system 500. The markers 568 may include numerical markers (indicating, for example, millimeters or centimeters, among other units of measurement) and/or physical markers (e.g., indentations in the block-like structure 566) to indicate a depth or distance. For example, the desired depth of implant receiving space preparation or other joint preparation, or implantation depth may be determined by reading the laser marking on the depth gauge from the proximal most surface of the working cannula once the thin elongate tongue is positioned in the sacroiliac joint at a desired location and orientation (e.g., as shown in FIG. 77) in order to select the appropriate corresponding standoff size.

The elongate body 572 may further include an intermediate section including a pair of members 574 interconnected between the block-like structure 566 and the tongue 562. The structure 566 may include a threaded bore 576 at the proximal end 570 for threadably coupling to a button knob having a male end thread.

Figure 30A:
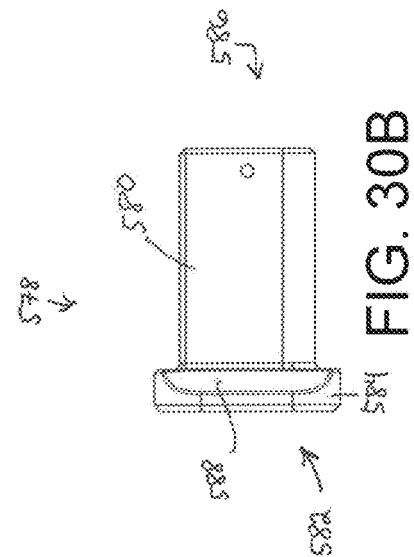
FIGS. 30A-30D are respectively isometric, top, back, and side views of a standoff.
Figure 30B:
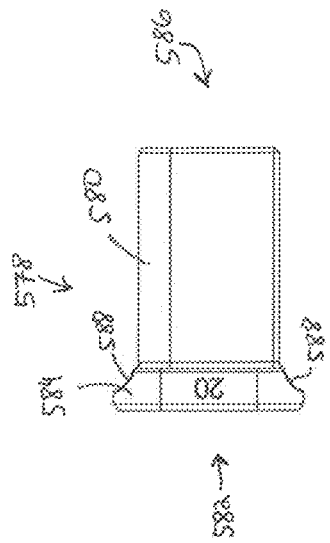
Figure 30C:
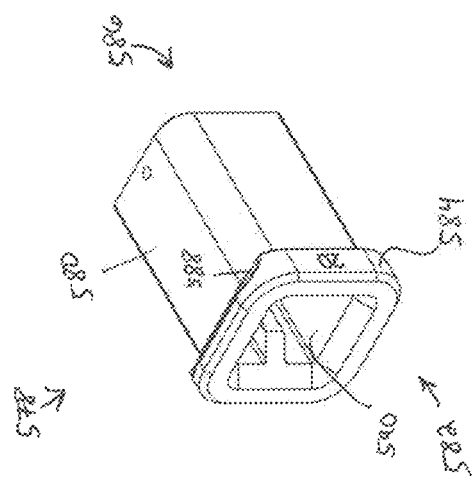
Figure 30D:
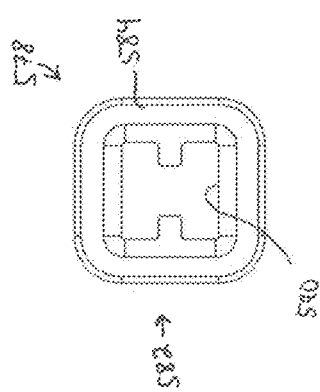

FIGS. 30A-30D are respectively isometric, top, back, and side views of a standoff or insert 578. The standoff 578 may include a tubular body 580 and a flanged base 584 extending outward from the tubular body 580 at a proximal end 582 of the standoff 578. The tubular body 580 extends to a distal end 586 of the standoff 578. As seen in FIGS. 30A-30B, and 30D, the flanged base 584 may include beveled edges 588 along two edges thereof. As seen in FIG. 30C, an inner surface 590 of the standoff 578 is keyed in the shape of an I-beam or H-beam so as to match the inner surface 558 of the passageway 556 of the working cannula 506 when the standoff 578 is positioned within the proximal end 520 of the passageway 556 of the working cannula 506. Once positioned in the working cannula 506, the keyed inner surfaces 590 of the standoff 578 and the inner surface 558 of the working cannula 506 are flush, collinear, or planar with each other.

While the inner surface 590 of the standoff 578 and the inner surface 558 of the passageway 556 of the working cannula 506 may be keyed in a corresponding shape of the joint implant of an I-beam or H-beam, the inner surfaces 590, 558 may be modified to fit a particular shape a joint implant 502 to be implanted. For example, the inner surfaces 590, 558 of the standoff 578 and working cannula 506 may be keyed to an X-shaped cross-section (among other shapes) to permit the joint implant 502 and associated tooling to extend there through. Additionally, other tools described herein may similarly be modified to permit passage through inner surfaces that are keyed to an X-shaped cross-section. For instance, joint preparation tools may similarly be modified to prepare the joint space for the implantation of an implant of a particular shape. In the instance of an X-shaped implant 502, a broach may similarly include a cutting surface shape that matches the X-cross-sectional shape of the joint implant 502.

The depth gauge 560, for example, may be used in conjunction with the working cannula 506. The depth gauge 560 may be inserted in the working cannula 506 such that the tongue 562 is oriented vertically. In this orientation, the width of the depth gauge 560 is slightly smaller than a distance between the inner protrusions of the inner surfaces 558 of working cannula 506.

FIGS. 31A-31D are respectively isometric, top, back, and side views of a drill guide insert 600. As seen in the figures, the drill guide insert 600 may include a tubular body 602 having a rectangular cross-section transverse to its length, a flanged base 604 extending outward from the tubular body 602 at a proximal end 606 thereof, and a series of cylindrical guide holes 608 extending longitudinally through the insert 600 from the proximal end 606 to a distal end 610 thereof. As seen in FIGS. 31A and 31C, the drill guide insert 600 includes three guide holes: a superior guide hole; a central guide hole; and an inferior guide hole. In certain instances, the drill guide insert 600 may include a different number and arrangement of guide holes. The drill guide insert 600 as shown herein is designed to align a drill bit along a plane of the sacroiliac joint. When the drill guide insert 600 is positioned within the standoff 578 and the working cannula 506, the series of guide holes 608 are aligned in a plane with the pair of prongs 548 of the working cannula 506.

FIGS. 32A-32B are respectively isometric and side views of a drill bit 612. The drill bit 612 may be sized to fit within the cylindrical guide holes 608 of the drill guide insert 600, and sized to drill out a portion of the articular surfaces of the sacrum and ilium in preparing the sacroiliac joint for a fusion procedure. The drill bit 612 may include a drill engagement structure 614 at a proximal end 616 thereof for coupling to a surgical drill (not shown) or quick connect handle. Additionally, the drill bit 612 may include cutting surface (e.g., flutes) 615 at a distal end 617 thereof. As an example, the drill diameter of the fluted portion may be equal to or less than the diameter to the shank diameter proximal to the fluted portion, and either an adjustable or non-adjustable and fixed (as shown in FIGS. 32A-32B as an increase in diameter of the shank/shaft of the drill bit) drill stop is located between the proximal end 616 and distal end 617 configured and calibrated (and positioned a similar distance with the stops, flanged bases 624/650, of the other tools relative to their distal cutting ends) in order to abut the proximal surface of the standoffs to limit the depth of cutting.

FIGS. 33A-33D are respectively isometric, top, back, and side views of a box osteotome 618. As seen in the figures, the box osteotome 618 may include a four-sided tubular cutting structure 620 at a distal end 622 of the box osteotome 618. A flanged base 624 is at a proximal end 626 of the box osteotome 618, and an elongate intermediate section 628 interconnects the flanged base 624 and the tubular cutting structure 620 at the distal end 622. The flanged base 624 extends outward from the intermediate section 628 so as to prevent the box osteotome 618 from extending beyond a certain position when inserted into the standoff 578 and working cannula 506.

The tubular cutting structure 620 may include a rectangular cross-section transverse to a length, and may include pair of wide surfaces 630 having transverse openings 632 therein, and a pair of narrow surfaces 634 extending between the wide surfaces 630. A distal tip 636 of the tubular cutting structure 620 may include rounded cutting surfaces defined on the wide surfaces 630 and linear cutting surfaces on the narrow surfaces 634.

The box osteotome 618 may be oriented in the working cannula 506 such that the wide surfaces 630 of the tubular cutting structure 620 are vertically aligned. In this way, the wide surfaces 630 are generally parallel with the joint plane of the sacroiliac joint, and the narrow surfaces 634 extend across the sacroiliac joint. The tubular cutting structure 620 may be hollow such that bone material may extend into an inner cavity of the cutting structure 620 as the box osteotome 618 is distally advanced within the joint. The distal advancement may cut the surfaces of the sacrum and ilium and cause a portion of the surfaces to extend into the box osteotome 618.

FIGS. 34A-34D are respectively isometric, top, back, and side views of a dual saw blade broach 638. As seen in the figures, the dual saw blade broach 638 may include, at a distal end 644 thereof, a pair of saw blades 640 opposite each other and coupled together via an intra-articular member 642. The saw blades 640 may be serrated along the long edges 646, and each saw blade 640 may include a pair of distal tips 648 opposite each other. Opposite the saw blades 640, the dual saw blade broach 638 may include a flanged base 650 at a proximal end 652 thereof. A button knob 654 may be coupled to the flanged base 650. An intermediate section 656 including a rectangular member may interconnect the flanged base 650 and the saw blades 640 and intra-articular member 642.

The flanged base 650 is sized and shaped to be prevented from extending beyond the standoff 578 when distally advanced relative to the standoff 578 and working cannula 506. The pair of saw blades 640 are oriented, sized and shaped to fit within the passage defined by the keyed inner surfaces 590, 558 of the standoff 578 and working cannula 506 when the saw blades 640 are oriented horizontally. That is, the intra-articular member 642 may extend vertically between the inner protrusions of the inner surfaces 590, 558 of the standoff 578 and working cannula 506.

The saw blades 640 may match a size and shape of features of a joint implant to be subsequently implanted into the joint. For example, a distance between the pair of saw blades 640 may be the same as a distance between the keels of a joint implant, such as the joint implant shown in FIGS. 23-26. The saw blades 640 may cut a pair of channels into the bones of the sacrum and ilium so as to provide an entry path into the joint for the subsequent delivery of the joint implant. While the dual saw blade broach 638 includes a pair of saw blades 640, the saw blade broach 638 may include a different number and configuration of saw blades 640 to match a particular joint implant.

According to particular embodiments, a final broach may be employed similar in configuration and construction as shown in FIG. 34 yet having saw blades 640 which are thicker and more closely match the thickness of the proximal most portion of the implant keels, which are thicker than the rest of the keels extending the length of the joint implant. The final broach may provide a passageway through the bones defining the sacroiliac joint up to the implant receiving space, the passageway having a set of keel tracks which allow the tapered thicker parts of the keels to pass relatively freely up until or near the proximal end of the implant receiving space. The distance between the distal tips 648 and the flanged base 650 of the final broach is less than the distance between the distal tips 648 and the flanged base 650 of any preceding broach, the distance difference being approximately the length of the implant.

As previously described, the broach 638 may be modified based on the shape of a joint implant 502 to be implanted. For instance, a broach 638 having an X-shaped blade arrangement 640 may be employed to prepare a joint space for the implantation of a joint implant 502 having an X-shaped cross-section. Other cross-sectional shapes of the broach 638 (among other tools) are contemplated herein to match the cross-sectional shape of joint implants 502 to be implanted without limitation.

FIGS. 35A-35D are respectively isometric, top, back, and side views of an anchor arm 508. As seen in the figures, the anchor arm 508 may include a curvate member 658 extending between an anchor block engagement structure 660, and a cannula engagement structure 662. The curvate member 658 may include a proximal section 664 and a distal section 666 that are oriented generally perpendicular to each other. The cannula engagement structure 662 may couple to the anchor arm engagement structure 554 of the working cannula 506, and the anchor block engagement structure 660 may couple to a corresponding structure of the anchor block 510.

The cannula engagement structure 662 of the anchor arm 508 may include a T-shaped end structure 668 extending generally perpendicular to the curvate member 658. The T-shaped end structure 668 may include slots 670 on the top and bottom surfaces thereof that are configured to receive the pair of longitudinally extending tabs 598 of the T-slot 596 of the anchor arm engagement structure 554 of the working cannula 506 so as to couple the anchor arm 508 and the working cannula 506 together.

Opposite the cannula engagement structure 662 is the anchor block engagement structure 660, which may include a T-slot 672 formed by a pair of longitudinally extending tabs 674.

FIGS. 36A-36D are respectively isometric, top, side, and front views of an anchor block 510. The anchor block 510 may be removably coupled to the anchor block engagement structure 660 of the anchor arm 508, and may include superior guide holes 522, inferior guide holes 524, and superior-inferior slots 526 extending through the anchor block 510. The superior guide holes 522 may guide a pin 512 in a predefined trajectory relative to the joint implant 502 that is superior to the joint implant 502. The inferior guide holes 524 may guide a pin 512 in a predefined trajectory relative to the joint implant 502 that is inferior to the joint implant 502.

The anchor block 510 may also include an anchor arm engagement structure 676 including a T-shaped end structure 678 having slots 680 on tops and bottoms thereof for receiving the longitudinally extending tabs 674 of the T-slot 672 of the anchor block engagement structure 660 of the anchor arm 508. The anchor arm engagement structure 676 may also include a proximal stop 682 so as to prevent the T-slot 672 from disengaging by moving proximally beyond the proximal stop 682. While the anchor block 510 depicts a series of four superior guide holes 522, and a series of four inferior guide holes 524, the anchor block 510 may include a different number and orientation of guide holes. For instance, there may be guide holes positioned along the superior-inferior direction between the superior and inferior guide holes 522, 524. And the guide holes may include various trajectories that orient the K-wire in various trajectories relative to the joint implant.

In certain instances, the superior and inferior guide holes 522, 524 may be spaced apart from each other a distance of about 34 mm. And the adjacent guide holes of the superior guide holes 522 and the inferior guide holes 524 may be spaced apart from each other about 6.25 mm.

The superior-inferior slots 526 may be used to guide the K-wire or pin in a variety of trajectories in a superior-inferior direction while restricting the K-wire or pin from moving laterally. In this way, a K-wire or pin may be angled superior, inferior, or in-line (within the transverse opening) with a joint implant 502 coupled to the implant arm 504.

FIGS. 37A-37D are respectively isometric, top, back, and side views of an implant arm 504. As seen in the figures, the implant arm 504 may include an implant retainer 684 and an arm member 686. The implant retainer 684 may include a proximal handle 688, an elongate cylindrical body 690 extending distally from the proximal handle 688, and a threaded distal end 670. The implant retainer 684 may be positioned within and through a cylindrical passageway extending longitudinally through the arm member 686. The arm member 686 may include a proximal handle 692, a central body 694, and a distal body 696. A pair of protrusions 698 extend distally from a distal face 700 of the distal body 696, and may fit within corresponding recesses in a proximal face of the joint implant 502 so as to prevent rotation of the joint implant 502 relative to the arm member 686. The threaded distal end 670 of the implant retainer 684 may extend distally out of the passageway of the arm member 686 and be positioned between the pair of protrusions 698. In this way, the threaded distal end 670 may threadably engage a threaded proximal opening of the joint implant 50 so as to retain the implant 502 against the arm member 686 during delivery of the joint implant into the joint. Accordingly, the implant retainer 684 may rotate within the passageway of the arm member 686 so as to cause the joint implant 502 and the threaded distal end 670 to converge, which causes the joint implant 502 to tighten against the distal face 700 of the distal body 696. Opposite rotation of the implant retainer 684 may cause decoupling of the joint implant 502 and the implant retainer 684.

The implant retainer 684 proximal handle 688 and arm member 686 proximal handle 692 both provide a coupling interface with the slide (or slap) hammer assembly (e.g., see FIG. 74) in order to allow removing the implant from within the sacroiliac joint while still coupled with the implant retainer via a removing force on the proximal handle 688 or in order to assist in the removal of the arm member 686 if it is seized up within the working cannula after the implant retainer has been decoupled from the implant (which will remain within the sacroiliac joint) and removed from within the cylindrical passageway extending longitudinally through the arm member 686.

FIGS. 38A-38D are respectively isometric, top, back, and side views of a joint implant 502. As seen in the figures, the joint implant 502 may include a pair of planar keels or members 702 spaced apart from each other and coupled together via a distal member 704 at a distal end 706, and a proximal member 708 at a proximal end 710. A transverse opening or passageway 712 is defined between the planar members 702, and the distal and proximal members 704, 708.

The planar members 702 may include ridges 714 along its edges, and openings 715 extending through the faces 716 of the members 702. Near the proximal end 710, the planar members may taper inward, and the ridges 714 along the edges may extend onto the inward faces of the planar members 702 at the tapered portion. A proximal face 718 of the joint implant 502 may include a pair of recesses 720 for receiving the protrusions 698 of the arm member 686 of the implant arm 504. The proximal face 718 may also include a central threaded opening 722 for receiving the threaded distal end 670 of the implant retainer 684 of the implant arm 504.

As seen in FIG. 38C, the joint implant 502 defines a generally I-beam or H-beam shape that fits through the keyed inner surfaces 590 of the standoff 578 and the inner surface 558 of the working cannula 506.

Figure 39:
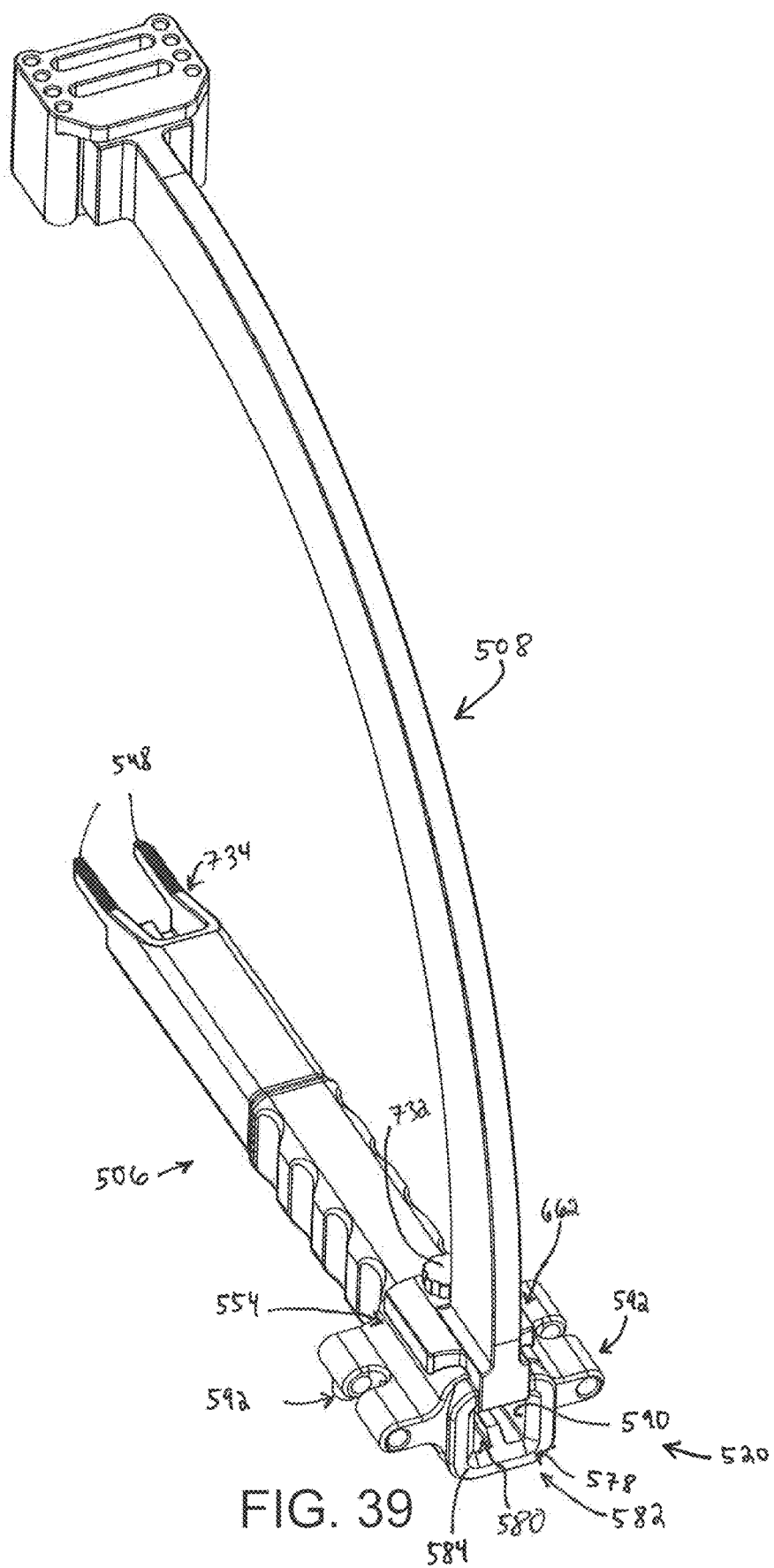
FIG. 39 is an isometric view of an exemplary working cannula and anchor arm removably coupled thereto.
Figure 40:
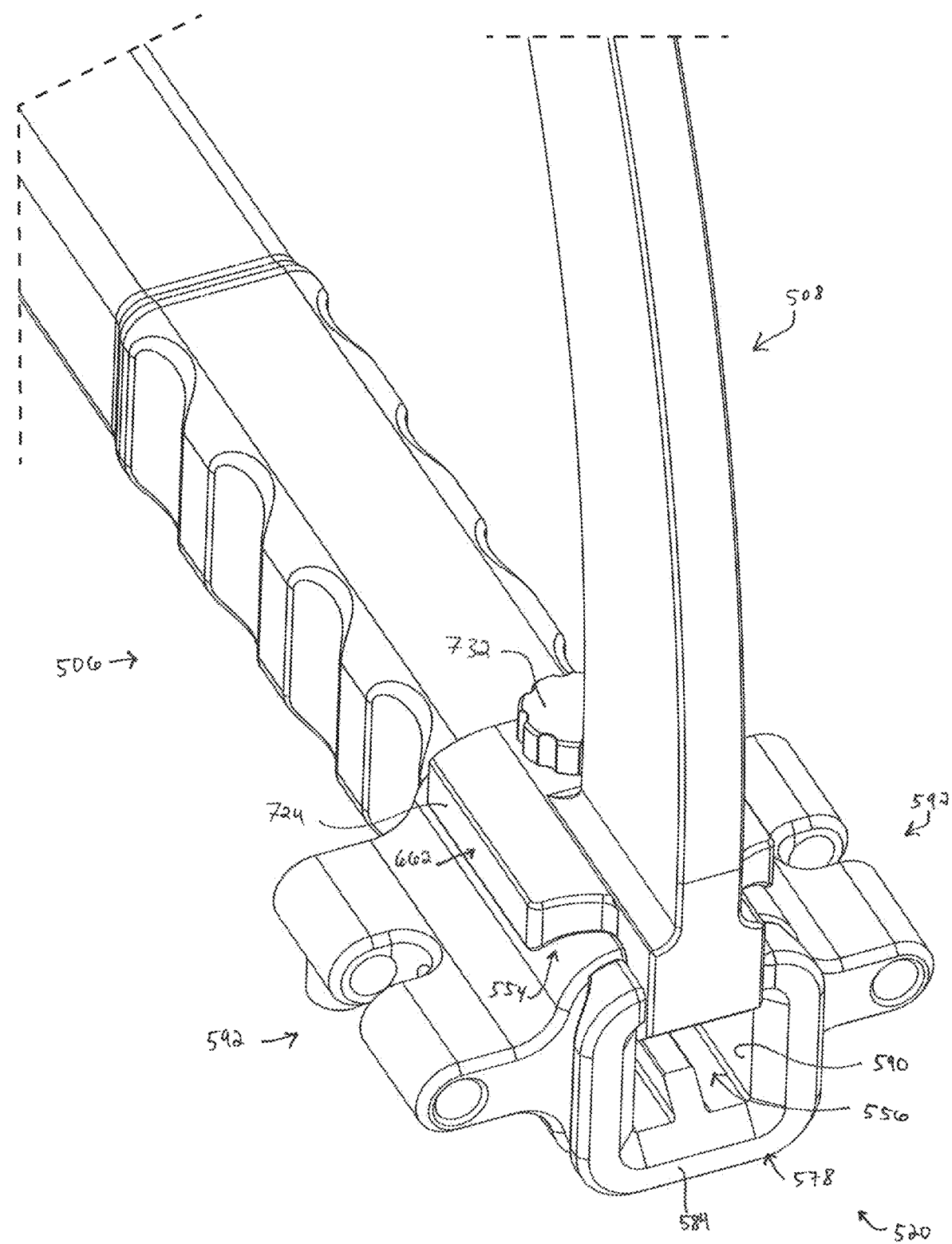
FIG. 40 is a close up, rear isometric view of the connection between the working cannula and the anchor arm.
Figure 41:
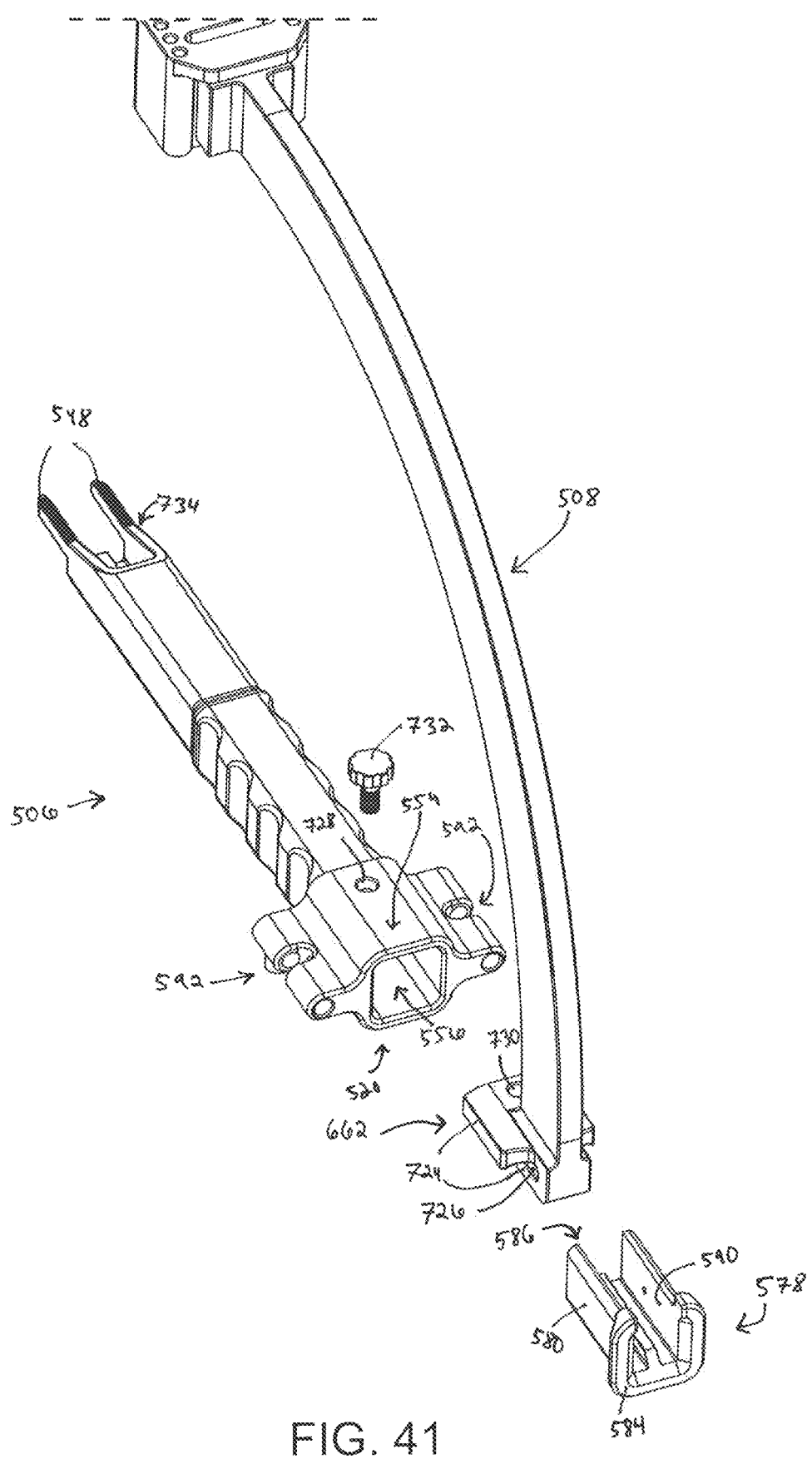
FIG. 41 is an exploded, rear isometric view of the working cannula, anchor arm, and a standoff.
Figure 42:
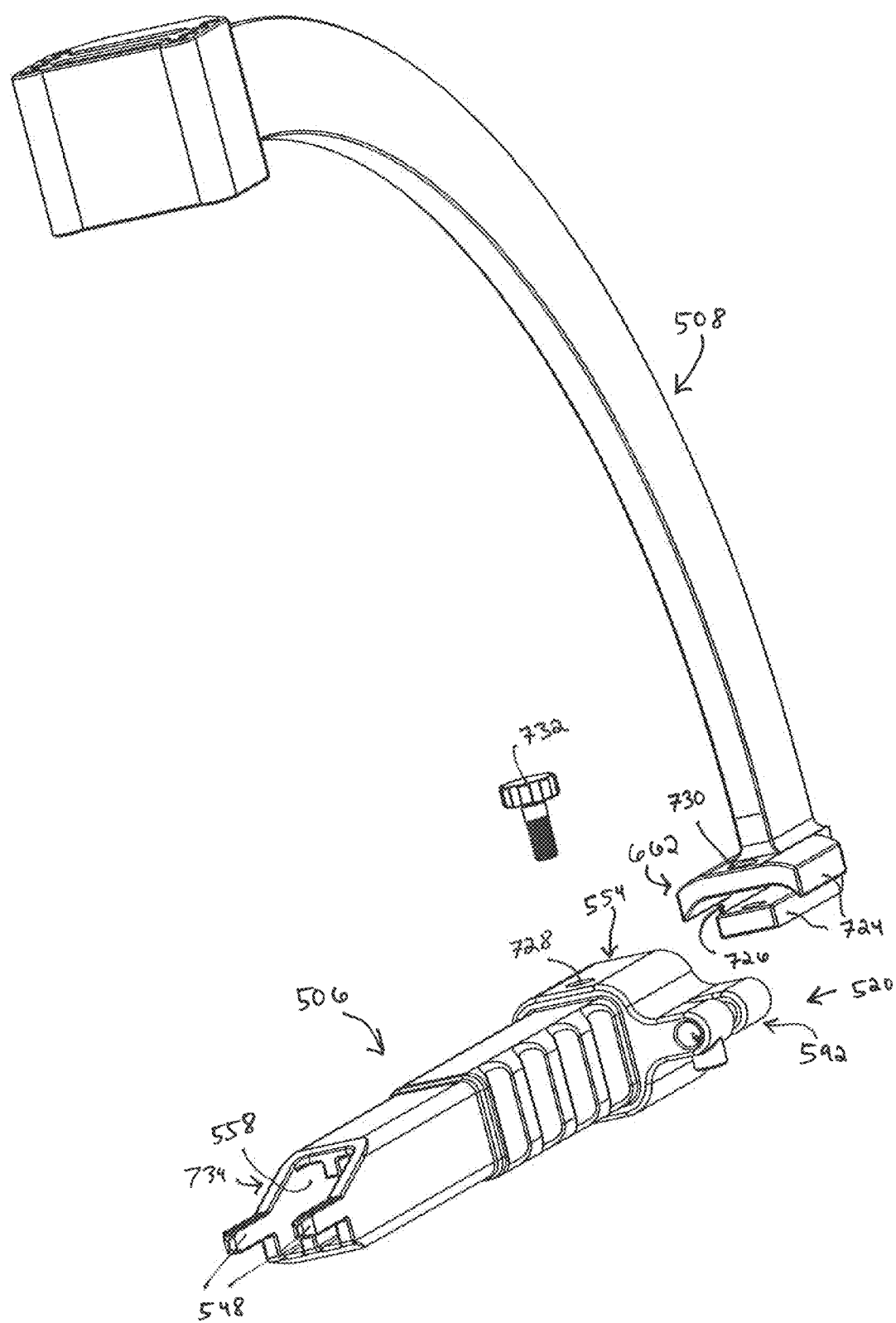
FIG. 42 is an exploded, front isometric view of the working cannula, and anchor arm.
Figure 43:
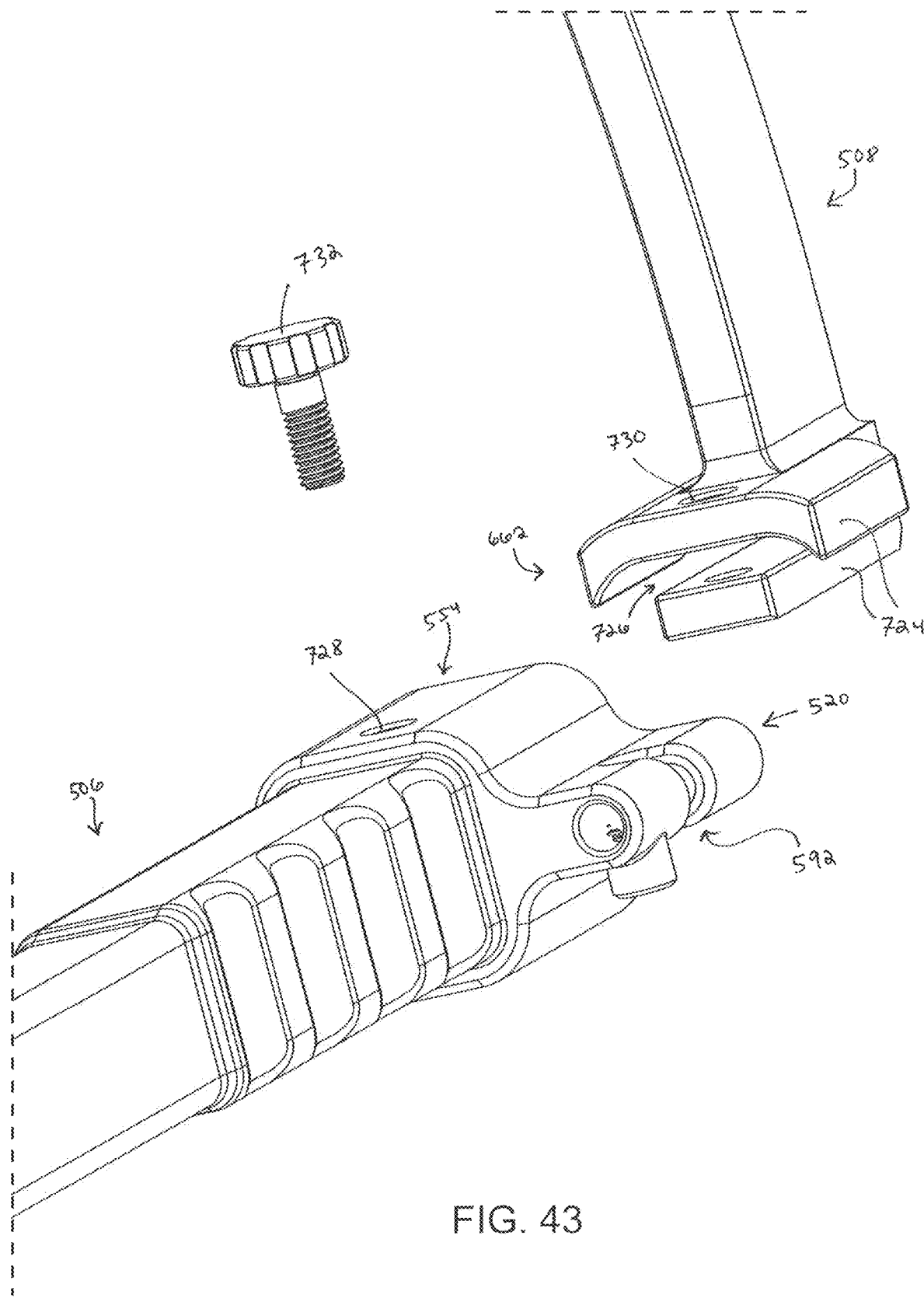
FIG. 43 is a close up view of the working cannula and anchor arm of FIG. 42.
Figure 44:
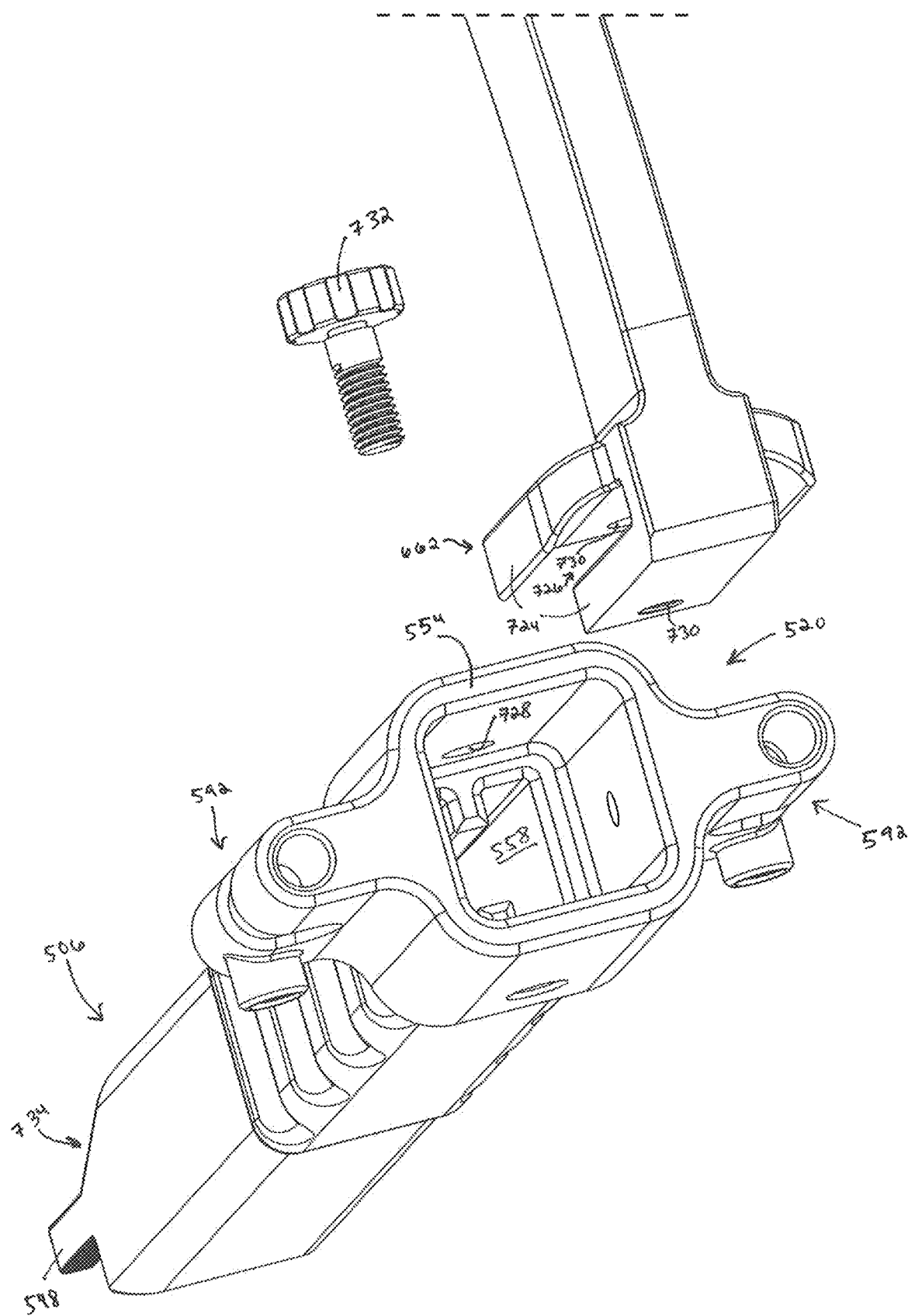
FIG. 44 is a close up, rear isometric view of the working cannula, and anchor arm.

FIGS. 39-46 depict various views of a coupling arrangement between a working cannula 506 and an anchor arm 508. FIG. 39 is an isometric view of an exemplary working cannula 506 and anchor arm 508 coupled thereto. And FIG. 40 is a close up, rear isometric view of the connection between the working cannula 506 and the anchor arm 506. The working cannula 506 may include many of the features as previously shown in FIGS. 28A-28D. As seen in FIGS. 39-41, among others, the working cannula 506 in this instance includes two pin guides 592 positioned between an anchor arm engagement structures 554 which allow the working cannula to be rotated 180 degrees along its axis to treat a contralateral sacroiliac joint while still allowing a guidance pin to be positioned in a PSIS above the treatment site and for the angled opening 734 to be aligned with the sacrum on each joint.

FIG. 41 is an exploded, rear isometric view of the working cannula 506, anchor arm 508, and a standoff 578. As seen in this figure and in FIG. 40, the standoff 578 may include a three sided tubular body 580 and a three sided flanged base 584 extending outward from the tubular body 580 at a proximal end 582 of the standoff 578. The tubular body 580 extends to a distal end 586 of the standoff 578. An inner surface 590 of the standoff 578 is keyed in the shape of an I-beam or H-beam so as to match the inner surface 558 of the passageway 556 of the working cannula 506 when the standoff 578 is positioned within the proximal end 520 of the passageway 556 of the working cannula 506. Once positioned in the working cannula 506, the keyed inner surfaces 590 of the standoff 578 and the inner surface 558 of the working cannula 506 are flush or planar with each other.

Figure 45:
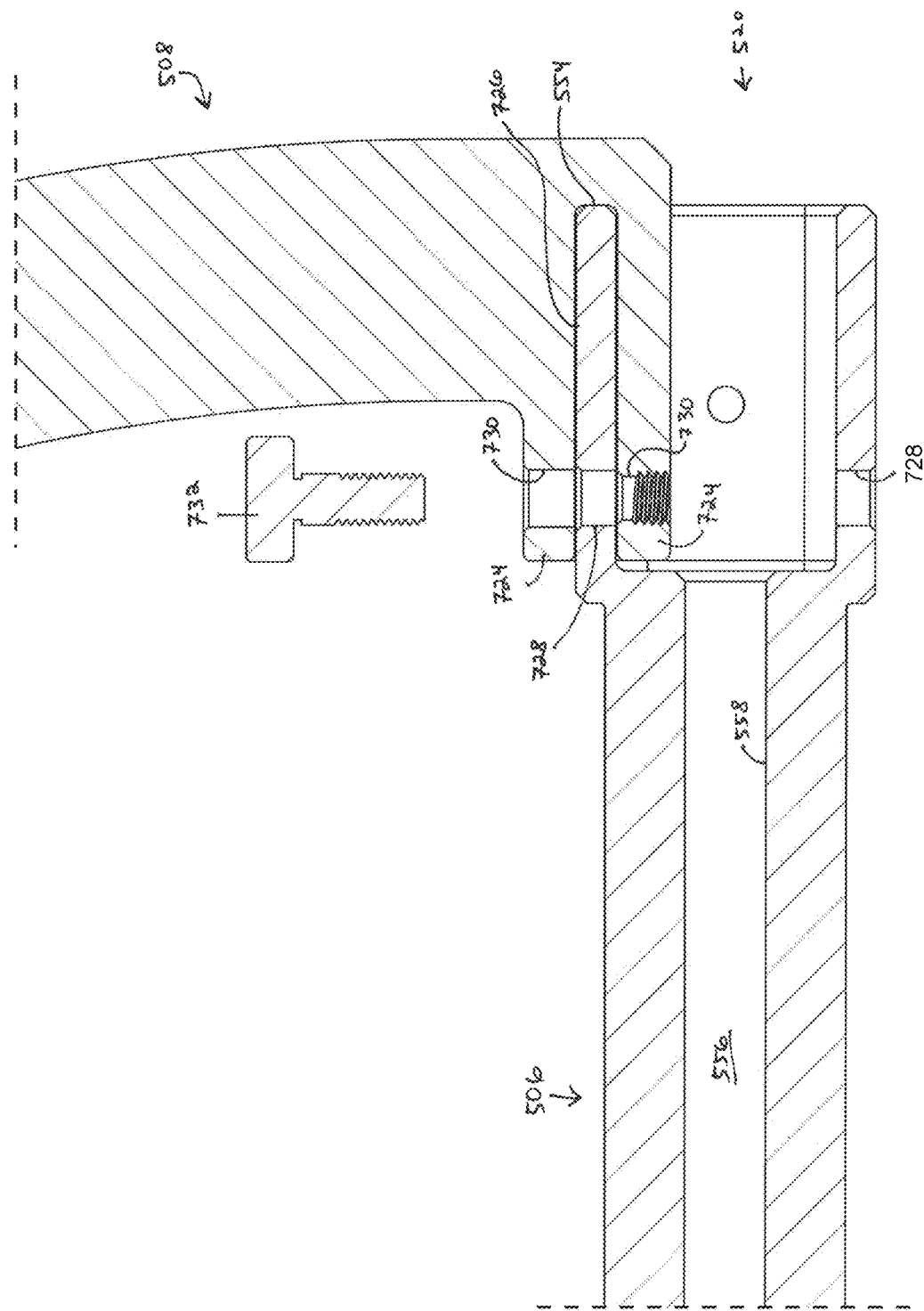
FIG. 45 is a side cross-sectional view of the working cannula and the anchor arm coupled together.

As particularly seen in FIG. 40, the cannula engagement structure 662 of the anchor arm 508 fits within the gap within the three sided standoff 578 when the standoff 578 is positioned within the working cannula 506. More particularly, the cannula engagement structure 662 of the anchor arm 508 may include a pair of generally parallel extension members 724 spaced apart from each other a distance about equal to a thickness of the wall thickness of the working cannula 506 at the proximal end 520. The parallel extension members 724 define a slot 726 there between, and the proximal edge of the working cannula 506 may be fitted within the slot 726. The working cannula 506 may include an opening 728 extending through a thickness thereof at the proximal end 520, and the pair of extension members 724 may also include a pair of openings 730 that coaxially align with the opening 728 in the working cannula 506 when the edge of the working cannula 506 extends within the slot 726 of the cannula engagement structure 662. As seen in FIG. 45, which is a side cross-sectional view of the working cannula 506 and the anchor arm 508 coupled together, the lower opening 730 in the pair of openings 730 on the pair of extension members 724 may be threaded to receive a screw 732 to secure the working cannula 506 and the anchor arm 508 together. There may be two openings 728, for example, as shown in FIG. 45 such that the anchor arm may couple to either side of the working cannula.

Figure 46:
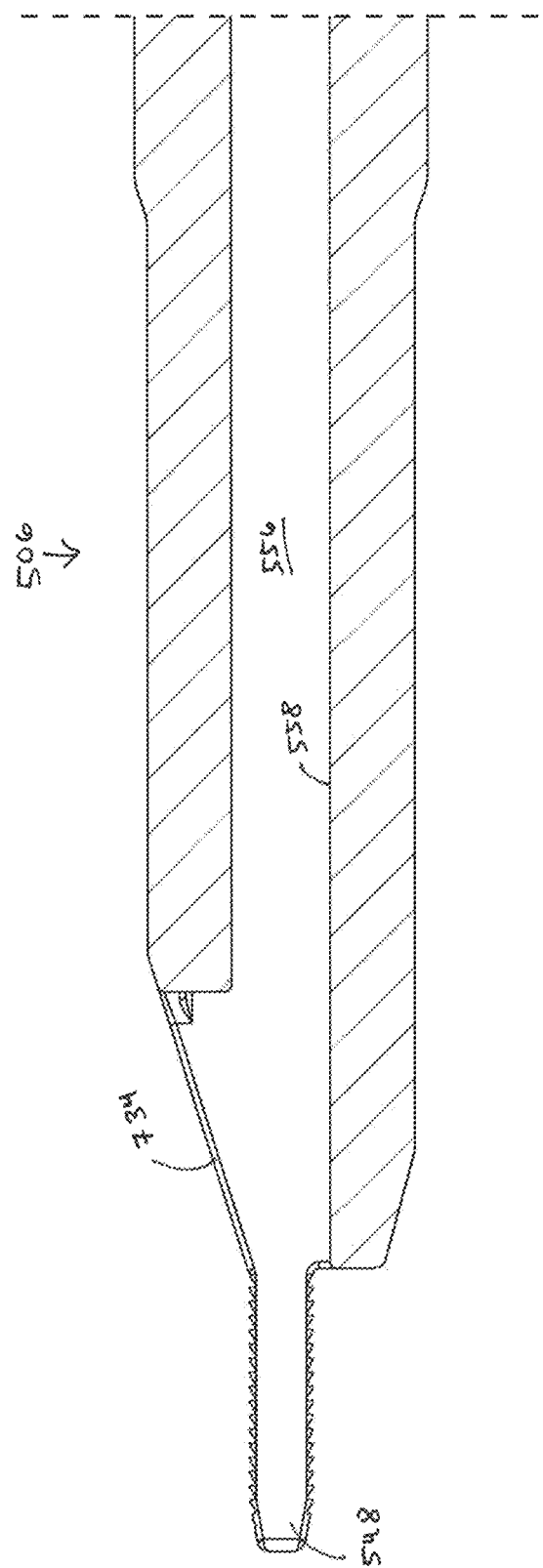
FIG. 46 is a side cross-sectional view of the distal end of the working cannula.

FIG. 46 is a side cross-sectional view of the distal end of the working cannula 506. As seen in the figure, the prong 548 of the working cannula 506 is centrally positioned along the passageway. One lateral side includes an angled opening 734 that extends into the passageway.

Figure 47:
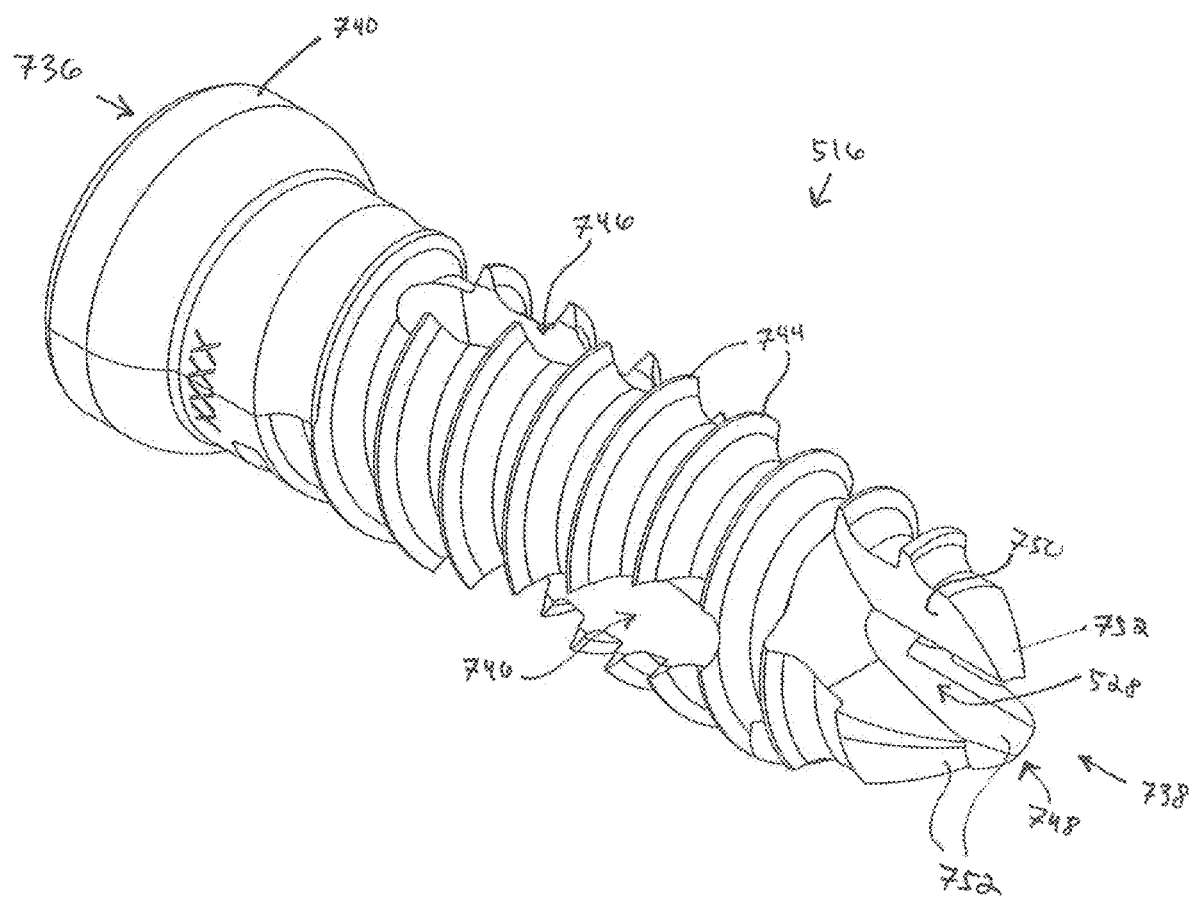
FIG. 47 is an isometric view of a bone anchor.
Figure 48A:
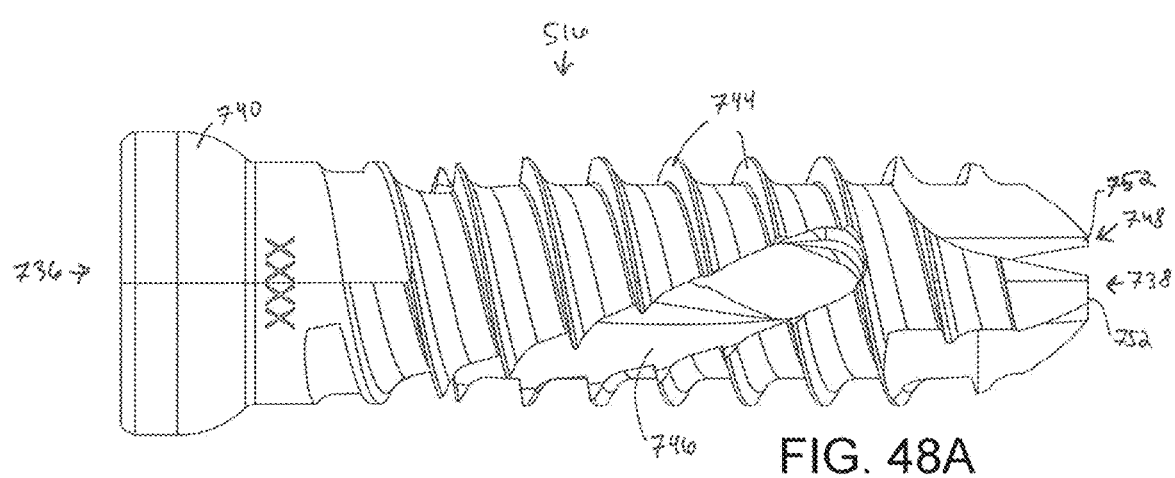
FIGS. 48A-48B are respectively top and side views of the bone anchor of FIG. 47.
Figure 48B:
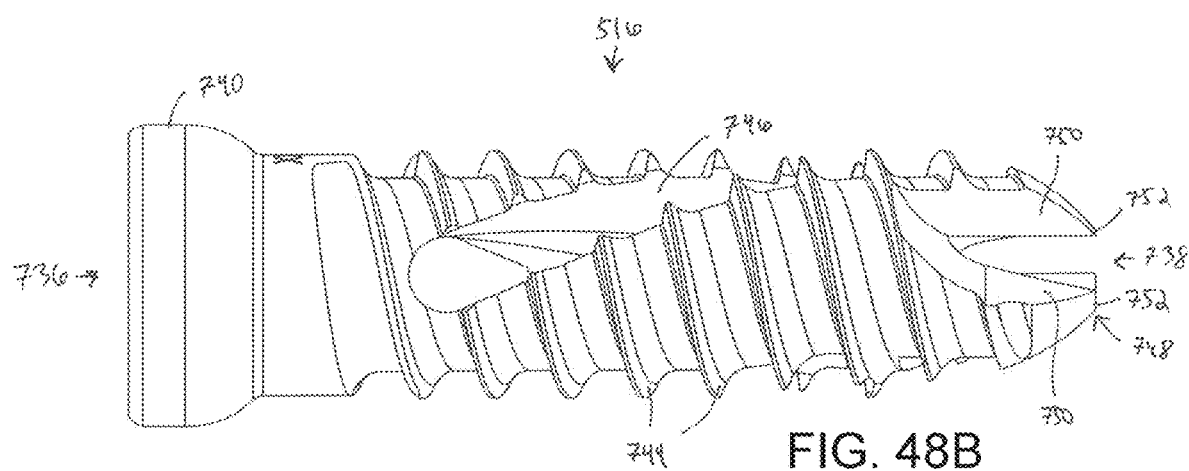
Figure 49A:
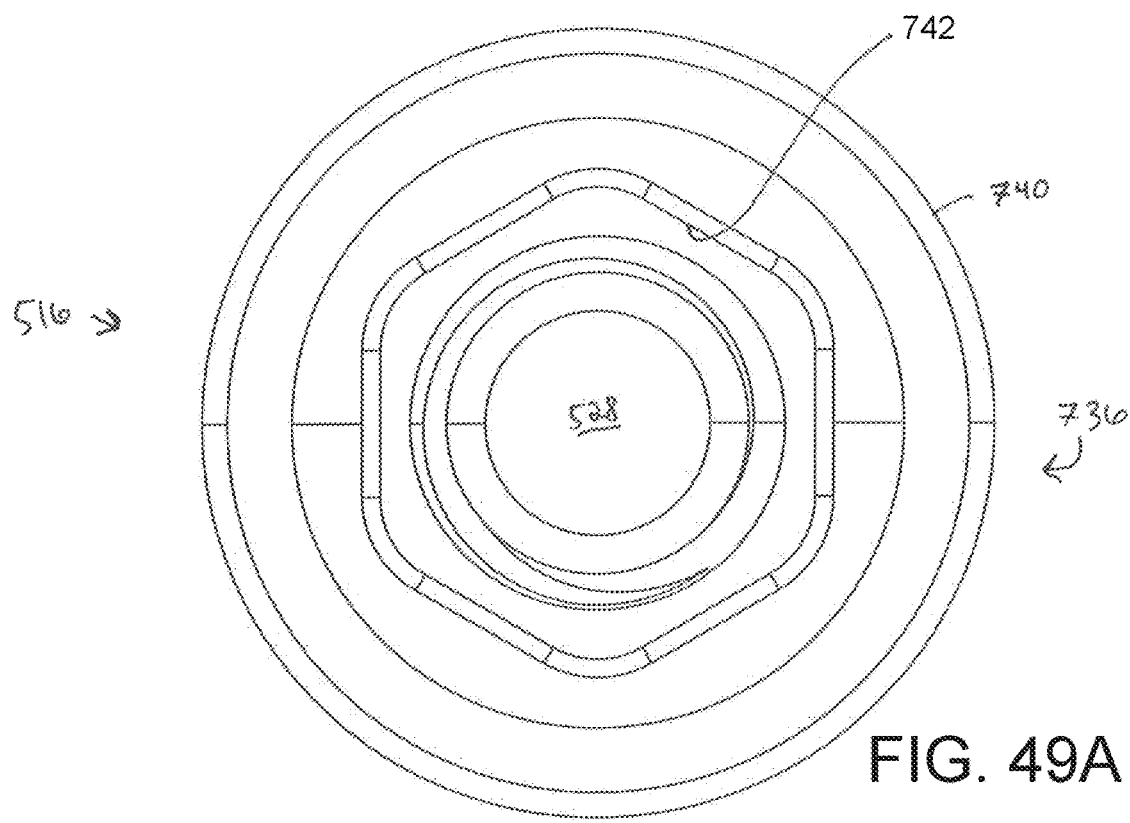
FIGS. 49A-49B are respectively back and front views of the bone anchor of FIG. 47.
Figure 49B:
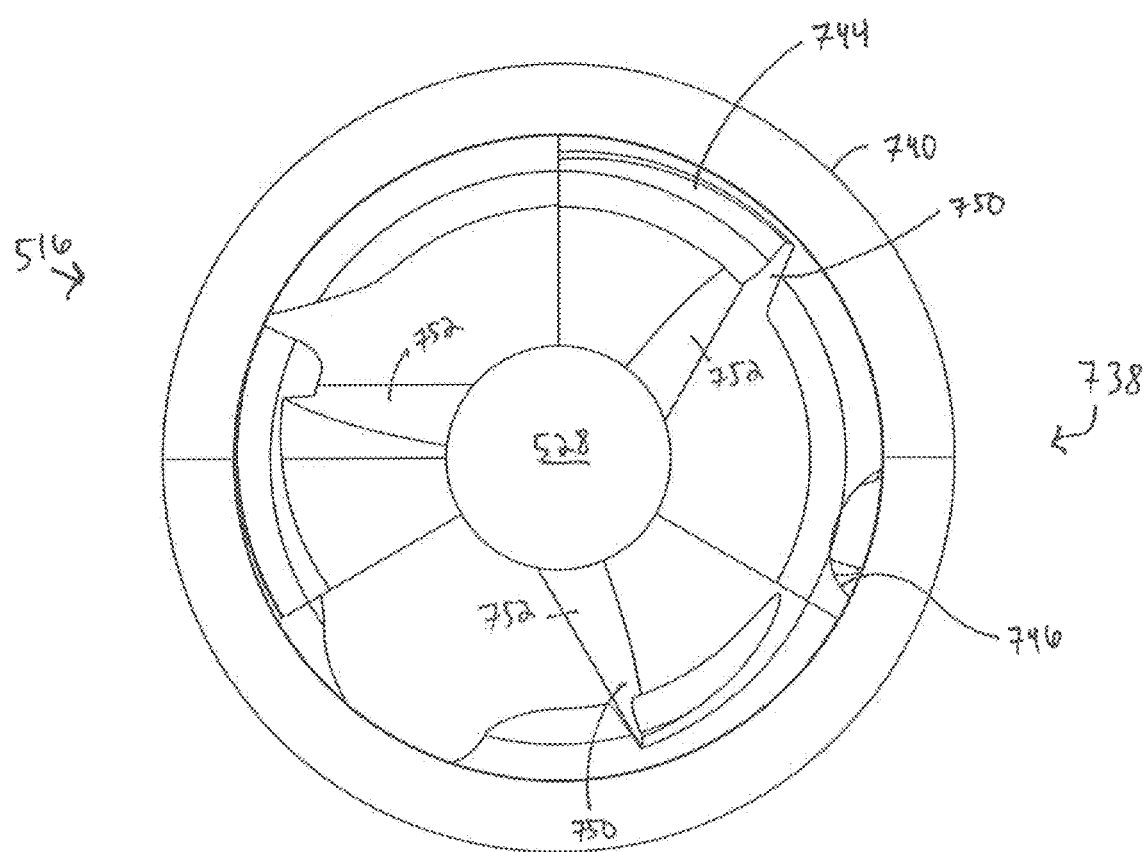

FIG. 47 is an isometric view of a bone anchor 516. FIGS. 48A-48B are respectively top and side views of the bone anchor 516 of FIG. 47. And FIGS. 49A-49B are respectively back and front views of the bone anchor of FIG. 47. The anchor 516 may include a longitudinal lumen 528 extending from a proximal end 736 to a distal end 738. The lumen 528 may receive the pin or K-wire 512 therein so as to guide the anchor 516 in its delivery to the surgical site. The bone anchor 516 may include a body having a bulbous proximal structure 740 including a tool engaging structure 742 such as a hex-key structure and threaded bore formed therein. Extending distally from the bulbous proximal structure 740 is a thread form (e.g., helical) 744 that extends to the distal end 738. The body includes two flutes 746 extending through the thread form 744 into the lumen 528. The flutes 746 extend longitudinally along the body, and spiral around the body as they extend in a distal-proximal direction.

At the distal end 738 of the bone anchor 516 may have a self-tapping, self-drilling tip 748 including partial flutes 750 that define individual screw tips 752. In this way, as the bone anchor 516 is advanced into bone material, the self-drilling tip 748 forms a bore in the bone and forces bone material into the lumen 528 as the anchor is distally advanced.

Figure 50:
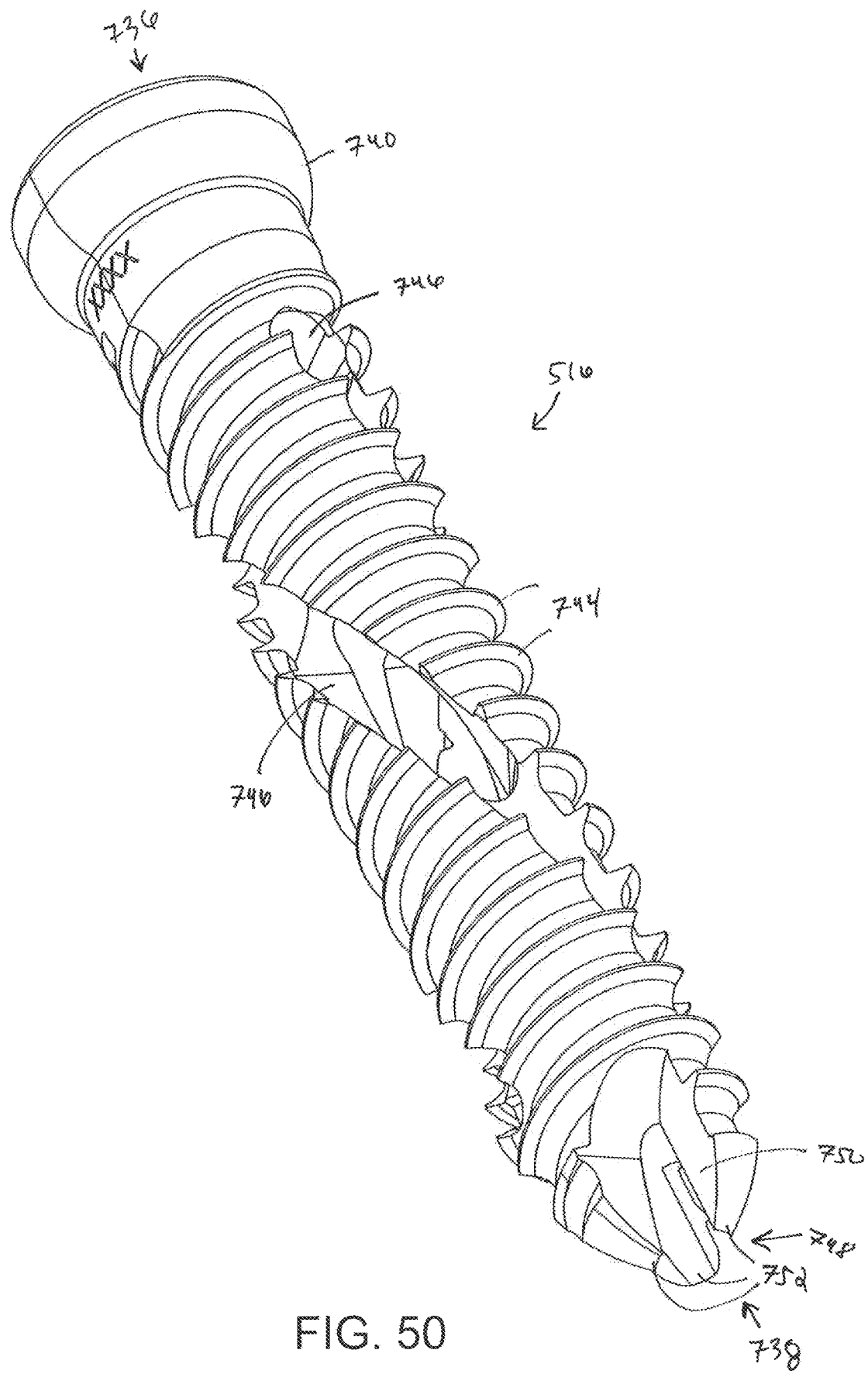
FIG. 50 is an isometric view of a bone anchor.
Figure 51A:
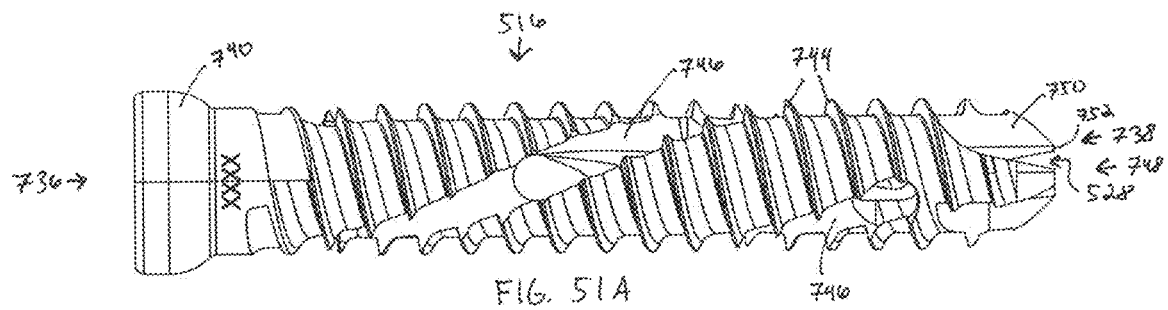
FIGS. 51A-51F are respectively top, first side, second side, third side, back, and front views of the bone anchor of FIG. 50.
Figure 51B:
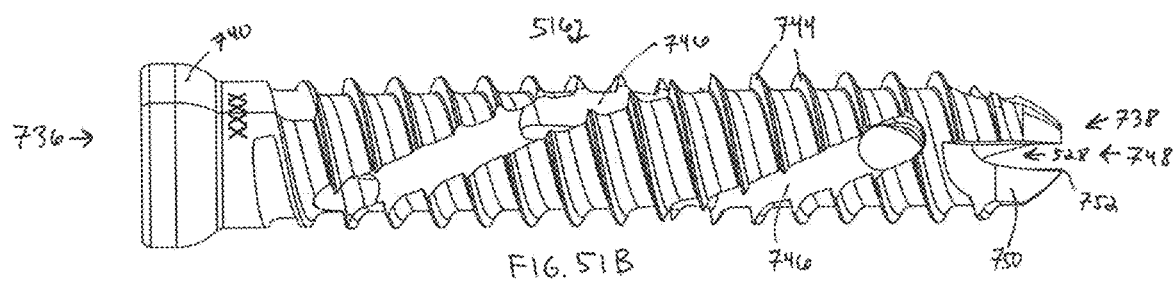
Figure 51C:
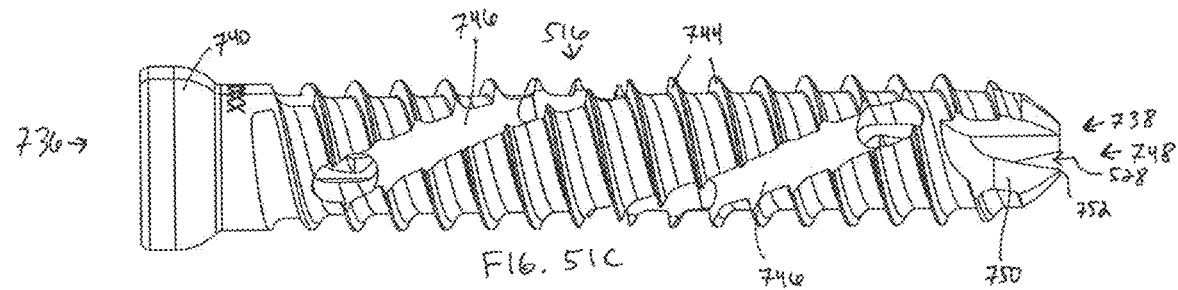
Figure 51D:
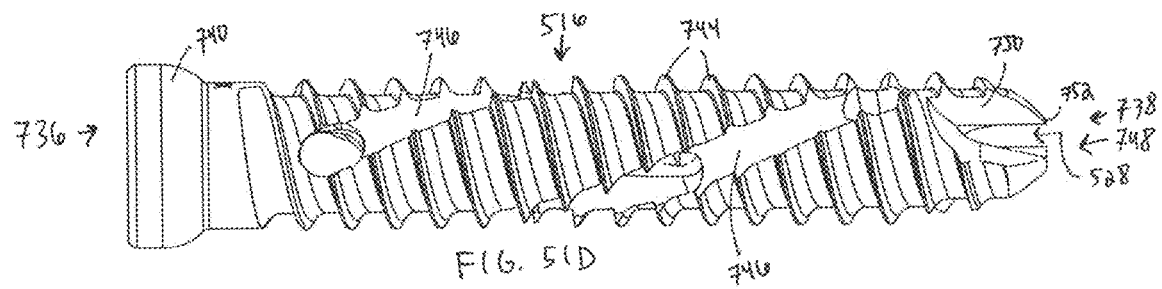
Figure 51E:
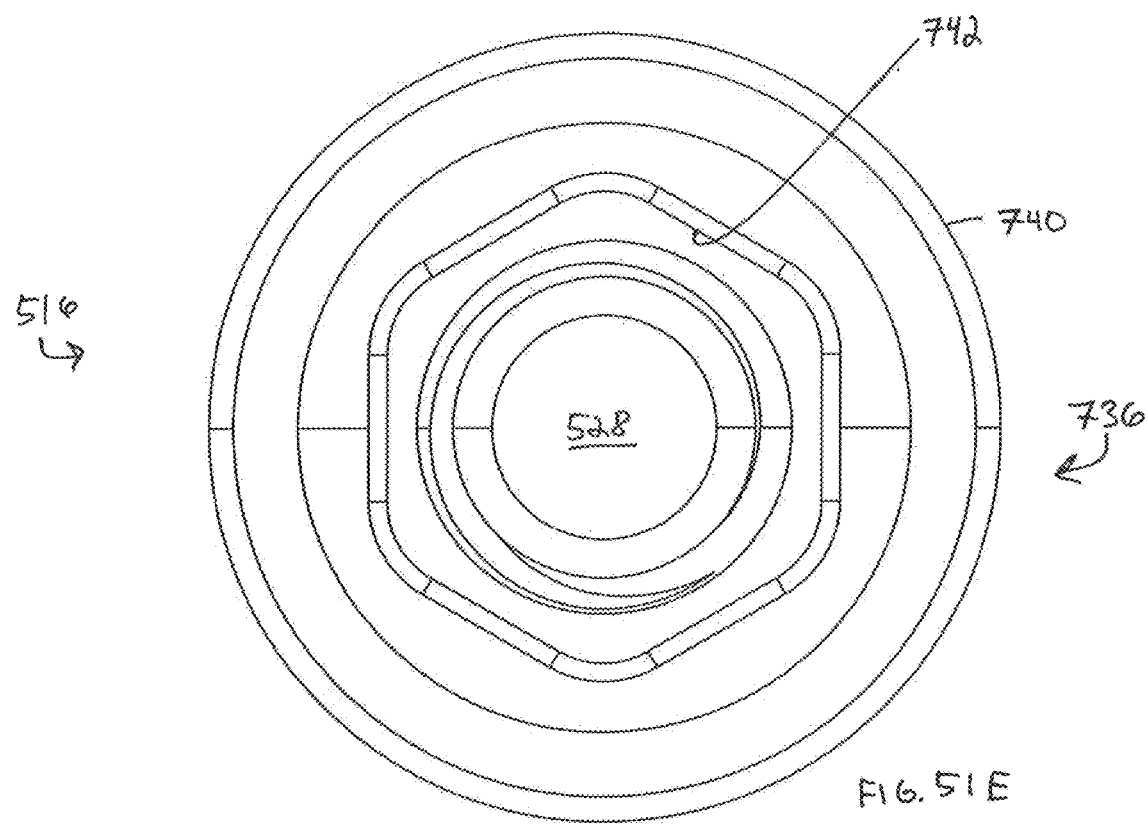
Figure 51F:
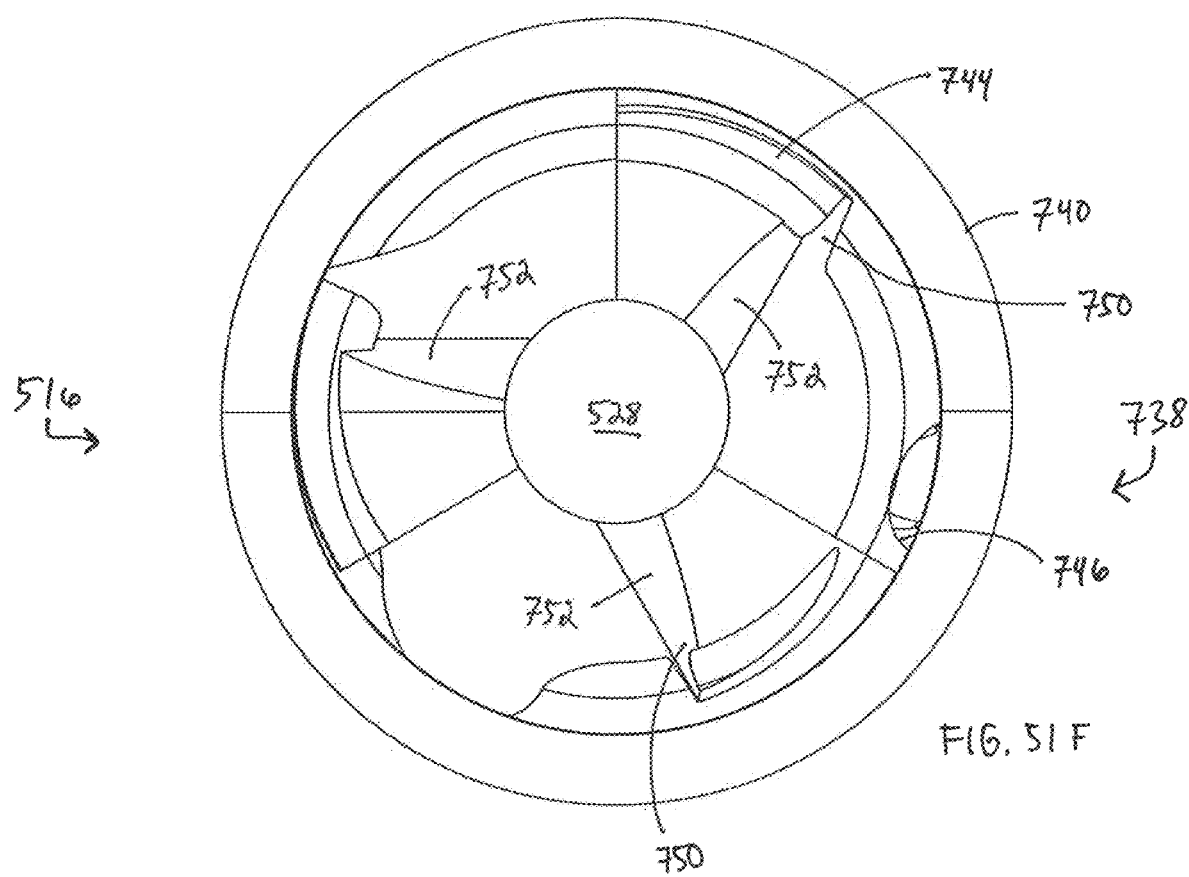
Figure 52:
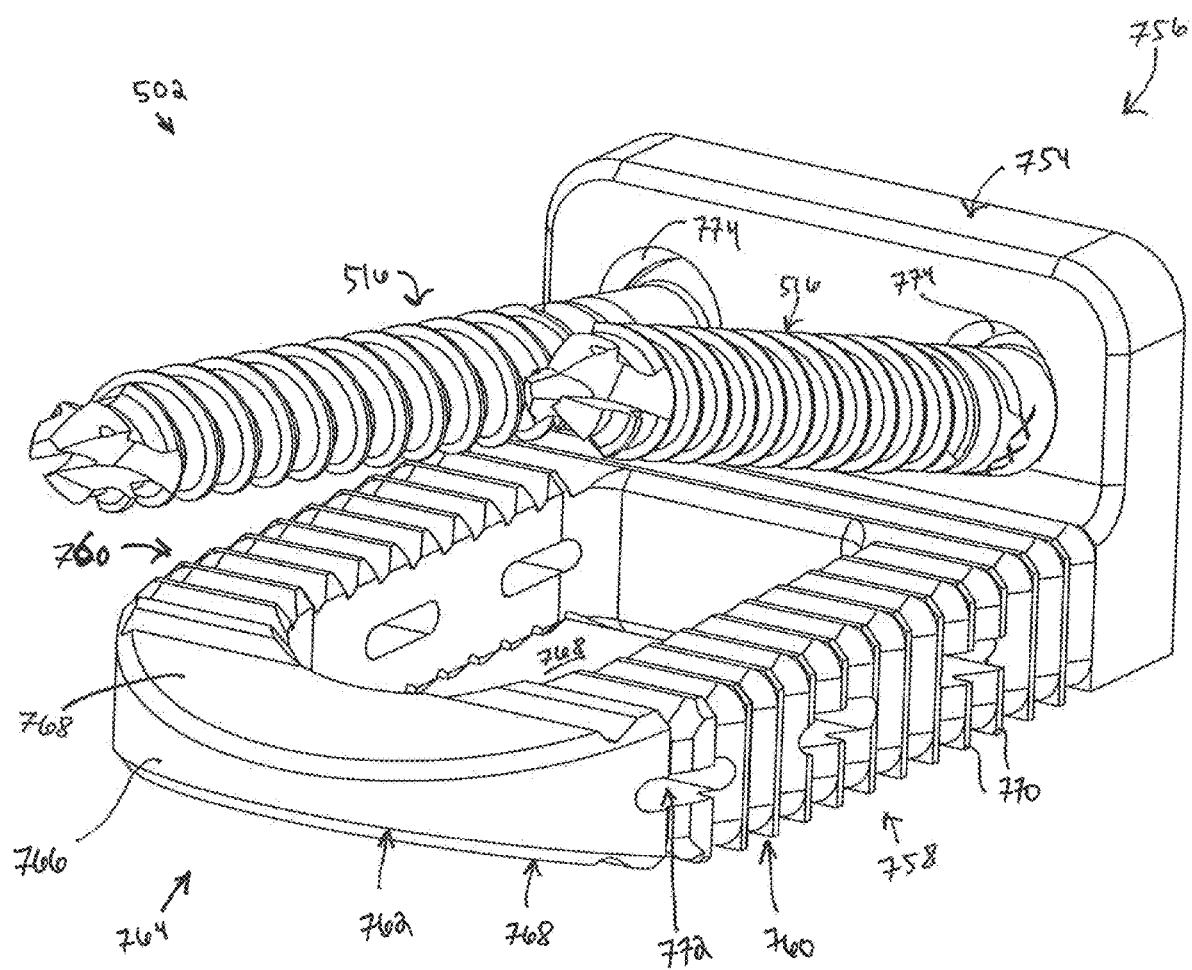
FIGS. 52-56 are respectively front isometric, rear isometric, front, side and top views of a flanged implant.
Figure 53:
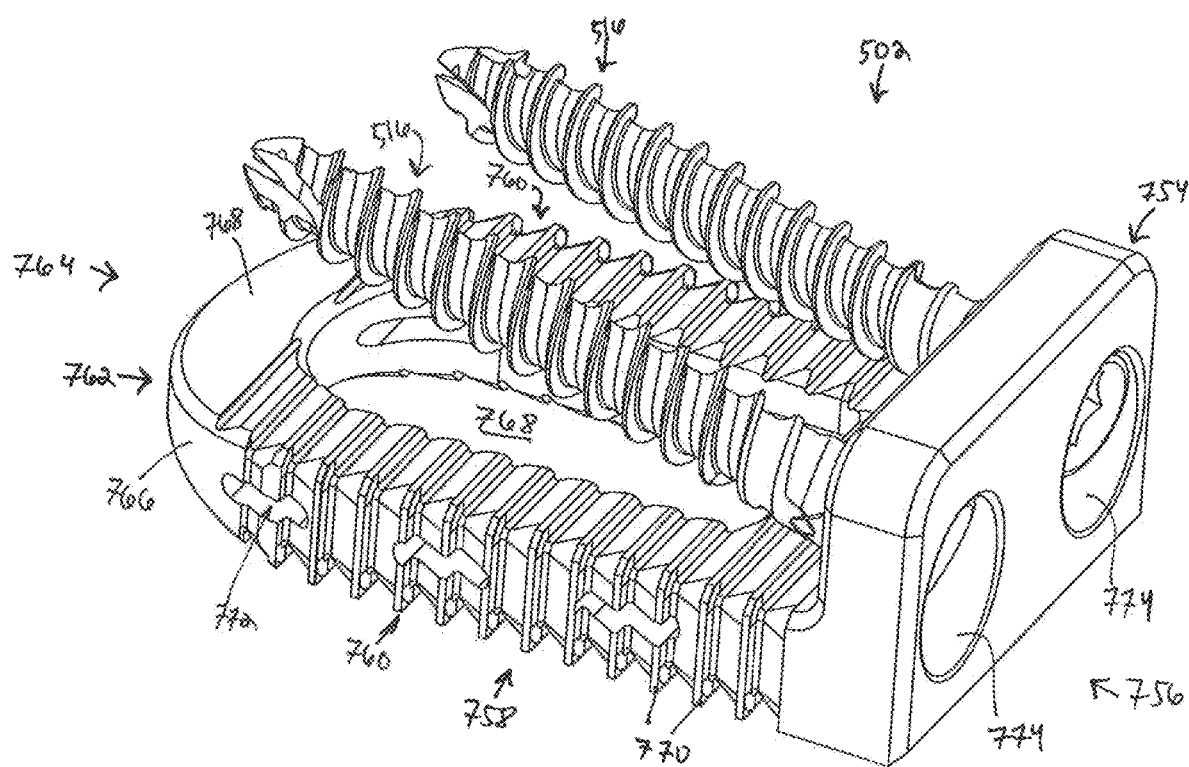

FIG. 50 is an isometric view of a bone anchor 516 in another instance. FIGS. 51A-51F are respectively top, first side, second side, third side, back, and front views of the bone anchor 516 of FIG. 50. As seen in the figures, the bone anchor 516 may include features from the bone anchor 516 in FIGS. 47-49. The bone anchor 516 of FIGS. 50-51C includes a longer body (and thread form 744), a distal slot shaped opening in line with and following the twist of the flutes, a proximal slot shaped opening in line with and following the twist of the flutes, flutes 746 positioned in between the distal and proximal slot shaped openings and a flute portion defining a channel (e.g., having a half circle cross section) extending between both the distal slot shaped opening and flute 746 and the flute and the proximal slot shaped opening which cuts into the screw body through the threads but does not extend into the lumen 528.

Figure 54:
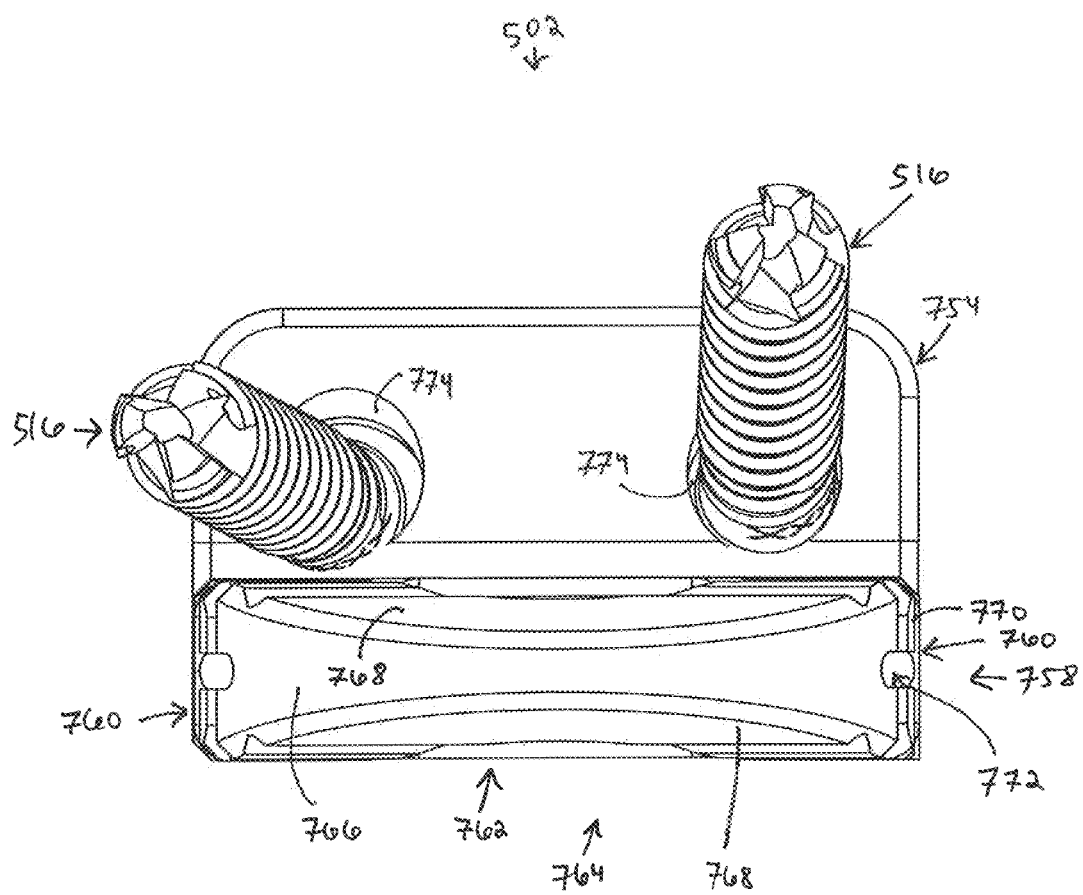
Figure 55:
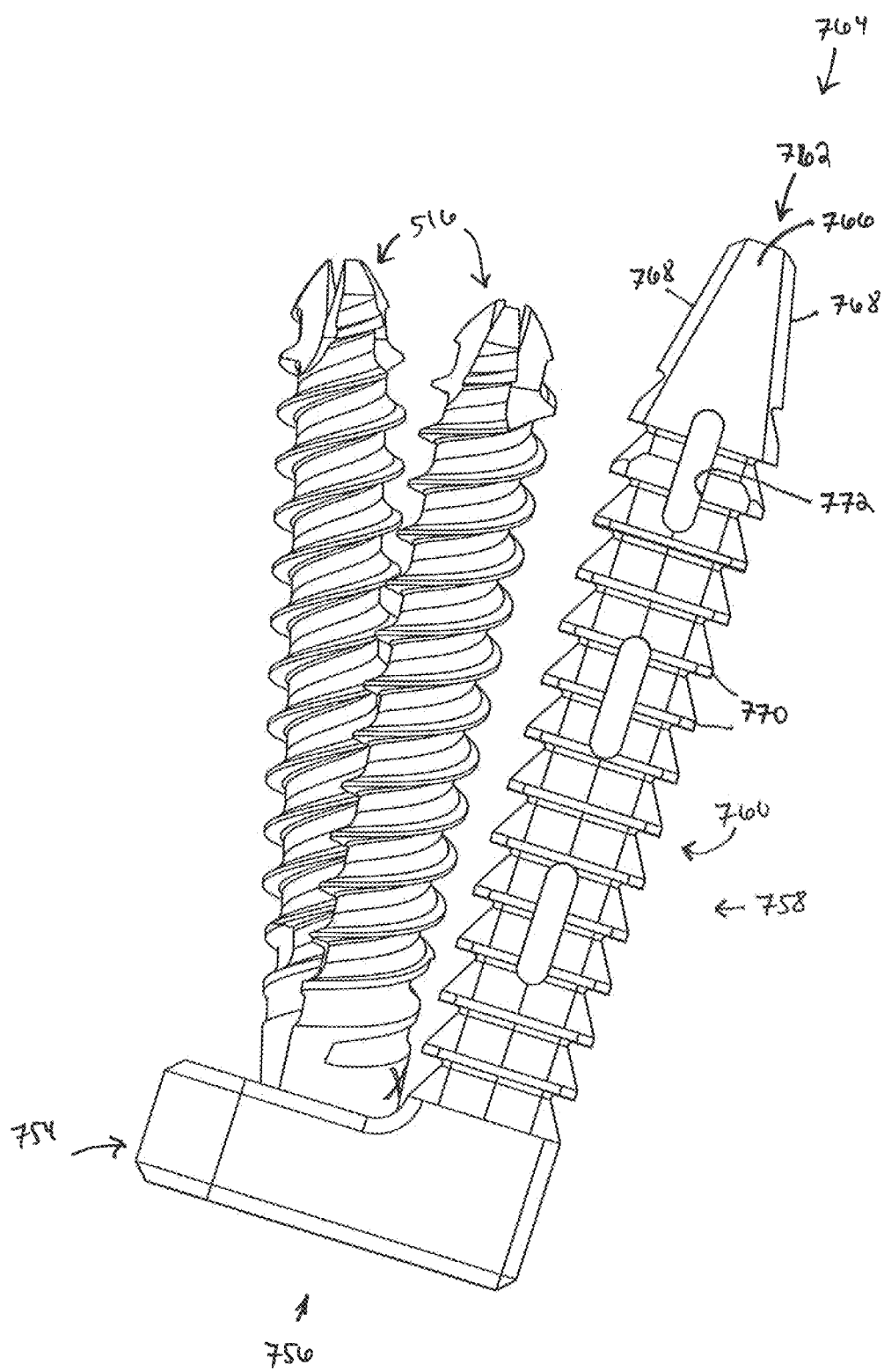
Figure 56:
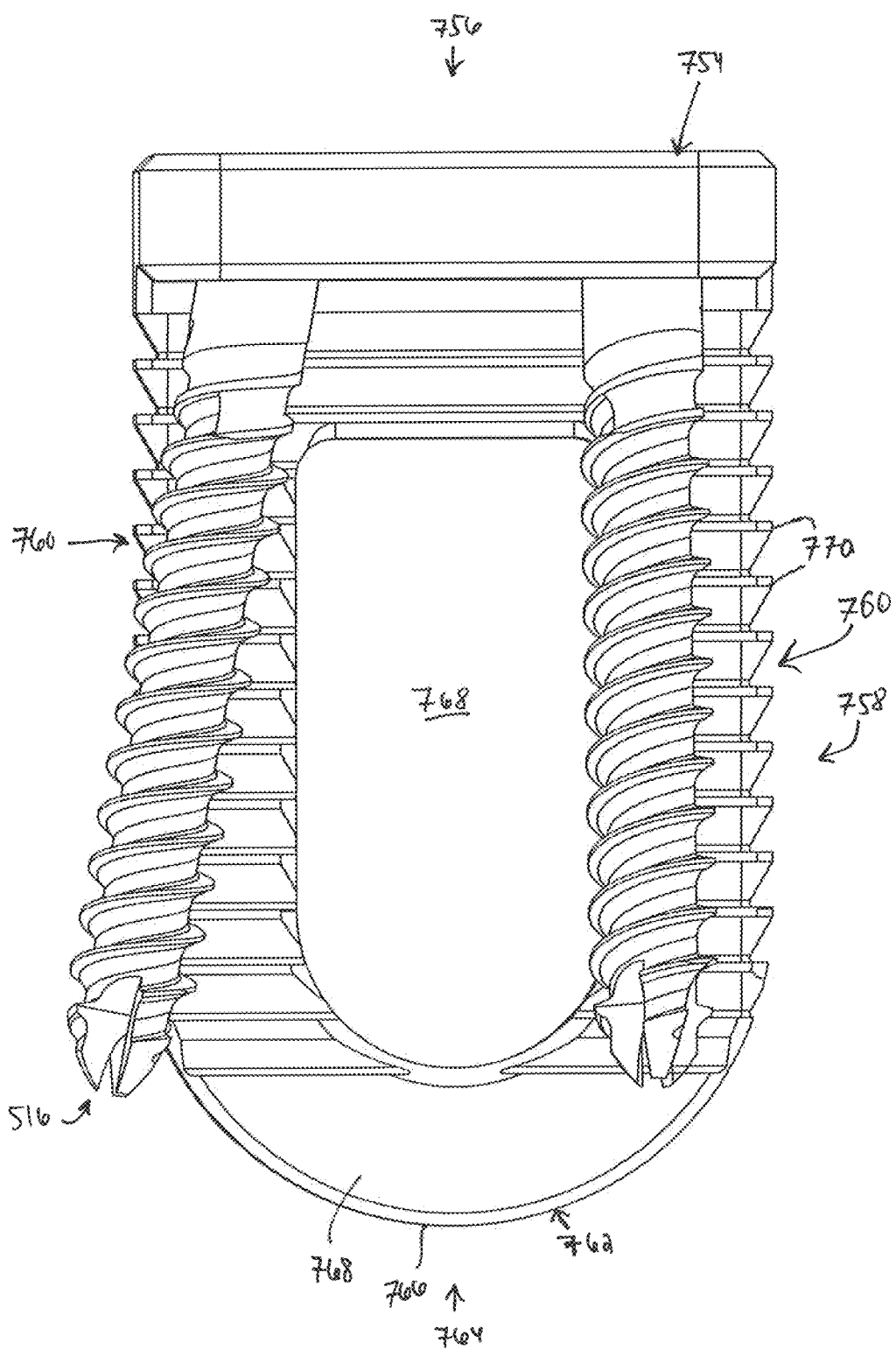

FIGS. 52-56 are respectively front isometric, rear isometric, front, side and top views of a flanged implant 502. As seen in the figures, the flanged implant 502 may include a flange 754 at a proximal end 756, and an implant body 758 extending generally perpendicular relative to the flange 754. The implant body 758 may include a pair of members 760 extending generally perpendicular to the flange 754, and a distal member 762 coupling the pair of members 760 at a distal end 764 thereof. The distal member 762 may include a rounded distal edge 766, as seen in FIG. 56, and a pair of non-parallel or angled surfaces 768, as seen in FIGS. 54-55, that extend distally from the pair of members 760 to the distal edge 766.

The pair of members 760, the distal member 762 and the flange 754 define a superior-inferior opening 768 extending through the implant body 758. As seen in FIG. 56, the superior-inferior opening 768 is rectangular in shape with a rounded distal portion.

The implant body 758 may include ridges 770 extending across the body 758 and in particular across the pair of members 760. The ridges 770 may act as anti-migration elements that prevent the implant body 758 from proximally displacing from its implanted position in the sacroiliac joint. While the figures depict ridges 770 as the anti-migration elements, other surface features may be included on the implant body 758 without departing from the scope of the present disclosure. For example, indentations, serrations, protrusions, surface irregularities, chevron patters, and openings, among others, may be included on the implant body 758 additionally or alternatively to the ridges 770.

As seen in FIGS. 52-55, the pair of members 760 extending between the flange 754 and the distal member 762 includes transverse openings 772 extending there through. In certain instances, there may be three transverse openings 772 spaced apart from each other and extending from an outer surface of the members 760 to an inner surface.

The flange 754 at a proximal end 756 may include a pair of anchor holes 774 extending there through. The anchor holes 774 may be spaced apart from each other, and may be generally positioned superior to the pair of members 760. The anchor holes 774 may include a distal opening that is smaller in diameter to a proximal opening so as to prevent the bulbous proximal end of the anchor 516 from extending through the flange 754. As best seen in FIGS. 52 and 54-56 the anchors 516 may be positioned in a variety of trajectories relative to each other.

Figure 57:
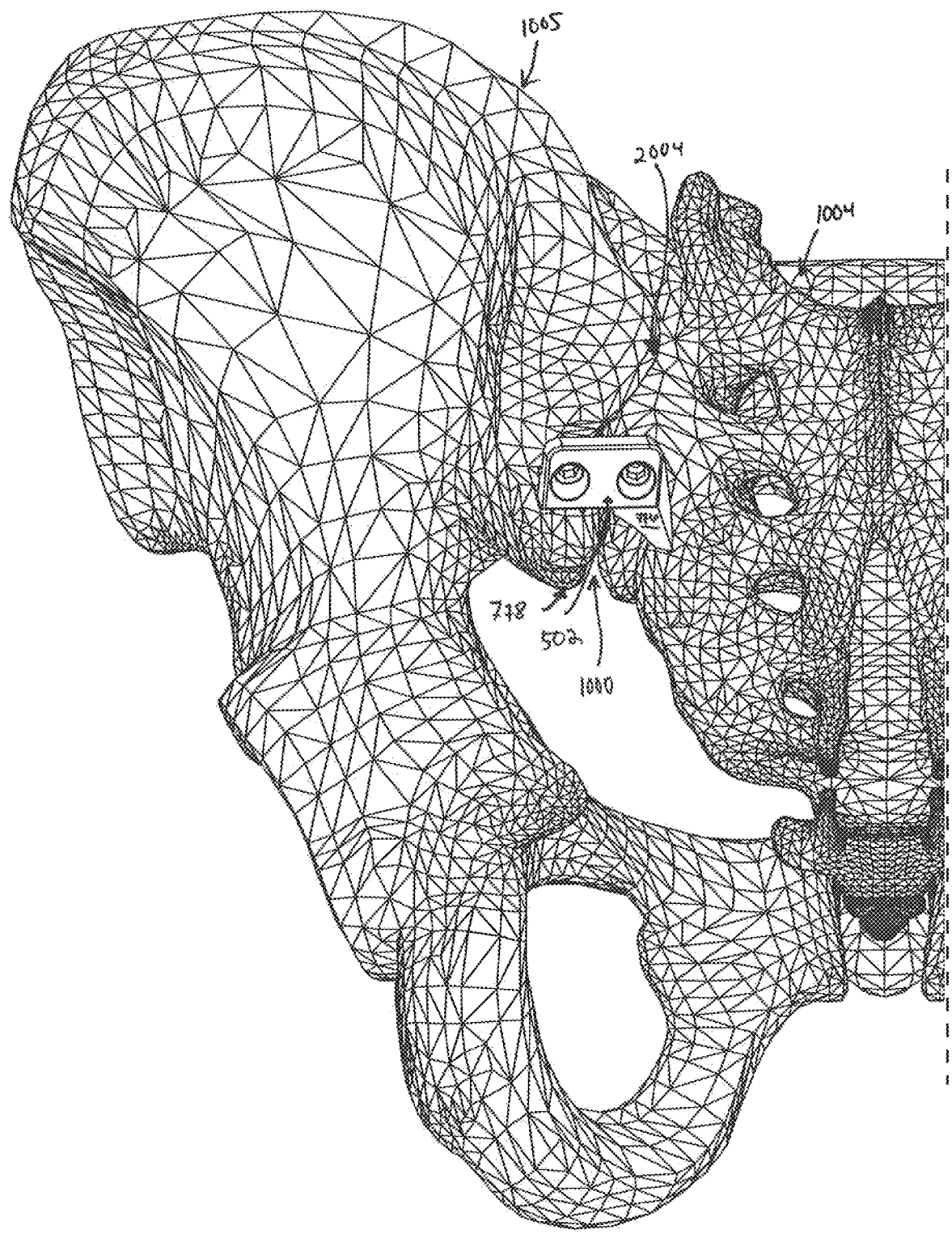
FIG. 57 is a posterior view of the flanged implant bridging across the sacroiliac joint.
Figure 58:
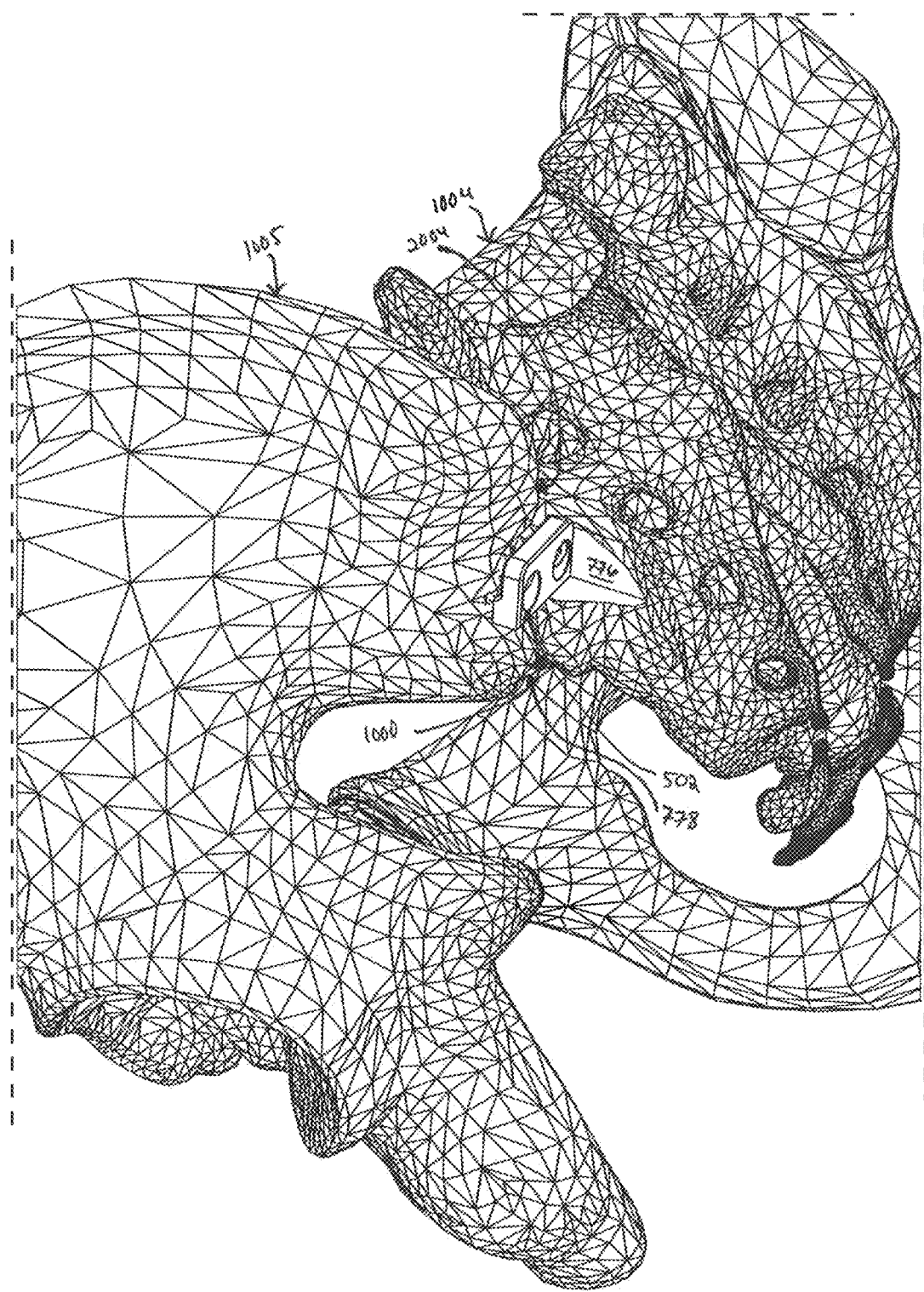
FIG. 58 is a posterior-lateral view of the flanged implant bridging across the sacroiliac joint.

FIGS. 57 and 58 depict the implant 502 of FIGS. 52-56 implanted in a sacroiliac joint 1000 defined between a sacrum 1004 and an ilium 1005. FIG. 57 is a posterior view of the flanged implant 502 bridging across the sacroiliac joint 1000. FIG. 58 is a posterior-lateral view of the flanged implant 502 bridging across the sacroiliac joint 1000. As seen in the figures, the flanged implant 502 is implanted into the sacroiliac joint 1000 via posterior delivery such that a plane defining the implant body 758 is transverse to a joint plane defined by the sacroiliac joint 1000. That is, generally, one of the pair of members 760 is positioned in the ilium 1005 and the other of the pair of members 760 is positioned in the sacrum 1004, whereas the distal member 762 extends across the sacroiliac joint 1000 and into each of the sacrum 1004 and the ilium 1005. And, when the implant body 758 is implanted such that the implant bridges across the joint 1000, one of the anchor holes is positioned over the sacrum 1004, and the other one of the anchor holes is positioned over the ilium 1005. Thus, anchors 516 may be delivered into the sacrum 1004 and the ilium 1005 after the implant is delivered into the joint 1000 to secure the implant 502 in position relative to the bones of the joint 1000.

As seen in FIGS. 57-58, an angled portion 776 of the sacrum 1004 may be removed to make way for the delivery of the implant 502. And as seen in the figures, the implant 502 is generally positioned in between the posterior superior iliac spine 2004 and the posterior inferior iliac spine 778. That is, the implant body 758 may bridge across the articular region 1044 (not shown in FIGS. 57-58) of the joint 1000. And while FIGS. 57-58 depict the implant body 758 positioned in the articular region of the joint, the implant body 758 may alternatively be positioned in the extra-articular region 3007, among other areas of the joint 1000 for implantation.

The joint implant 502 as seen in FIGS. 52-58 may be used with the working cannula 506 and standoff 578 (among other tools such as the anchor arm 508 and implant arm 504, as well as others) as previously described. In such an instance, the inner surface 590 of the standoff 578 and the inner surface 558 of the passageway 556 of the working cannula 506 may be keyed in a corresponding shape of the joint implant 502 in FIGS. 52-58. For example, the inner surfaces 590, 558 of the standoff 578 and working cannula 506 may be keyed to a flanged implant shape to permit the joint implant 502 and associated tooling to extend there through. Additionally, other tools described herein may similarly be modified to permit passage through inner surfaces that are keyed to the flanged implant shaped cross-section.

Figure 59A:
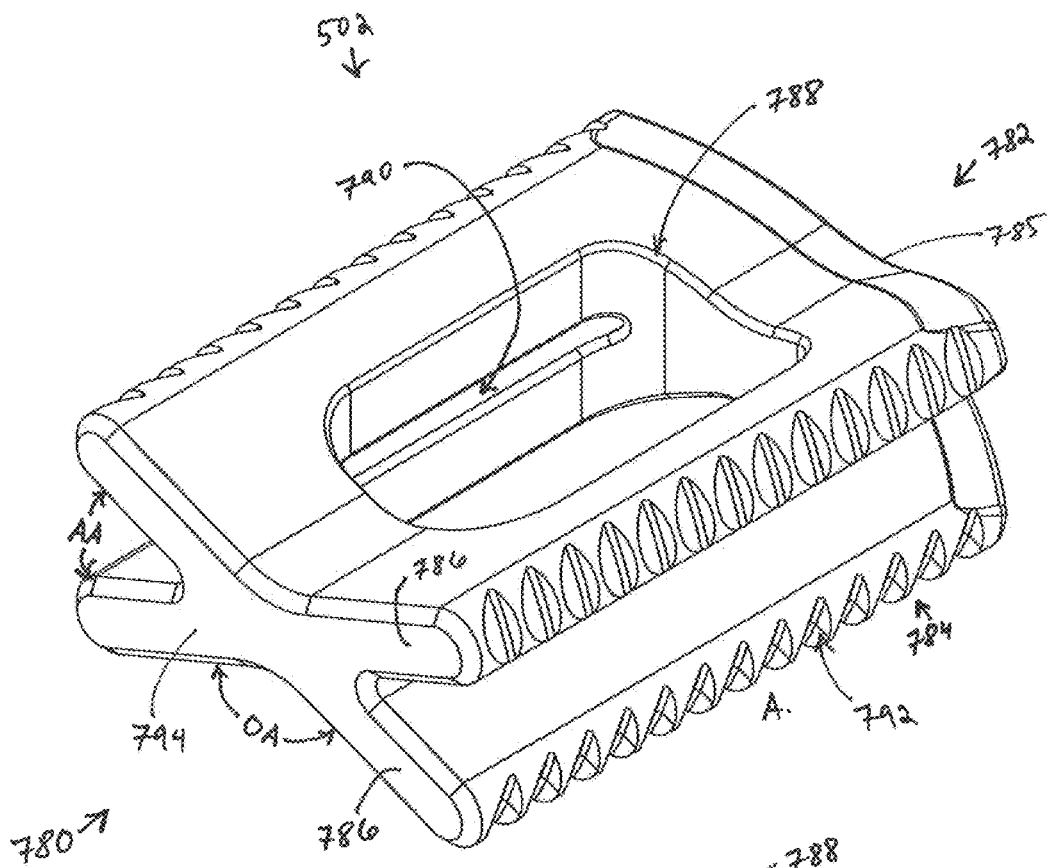
FIGS. 59A-59B are respectively rear isometric, and side isometric views of a joint implant.
Figure 59B:
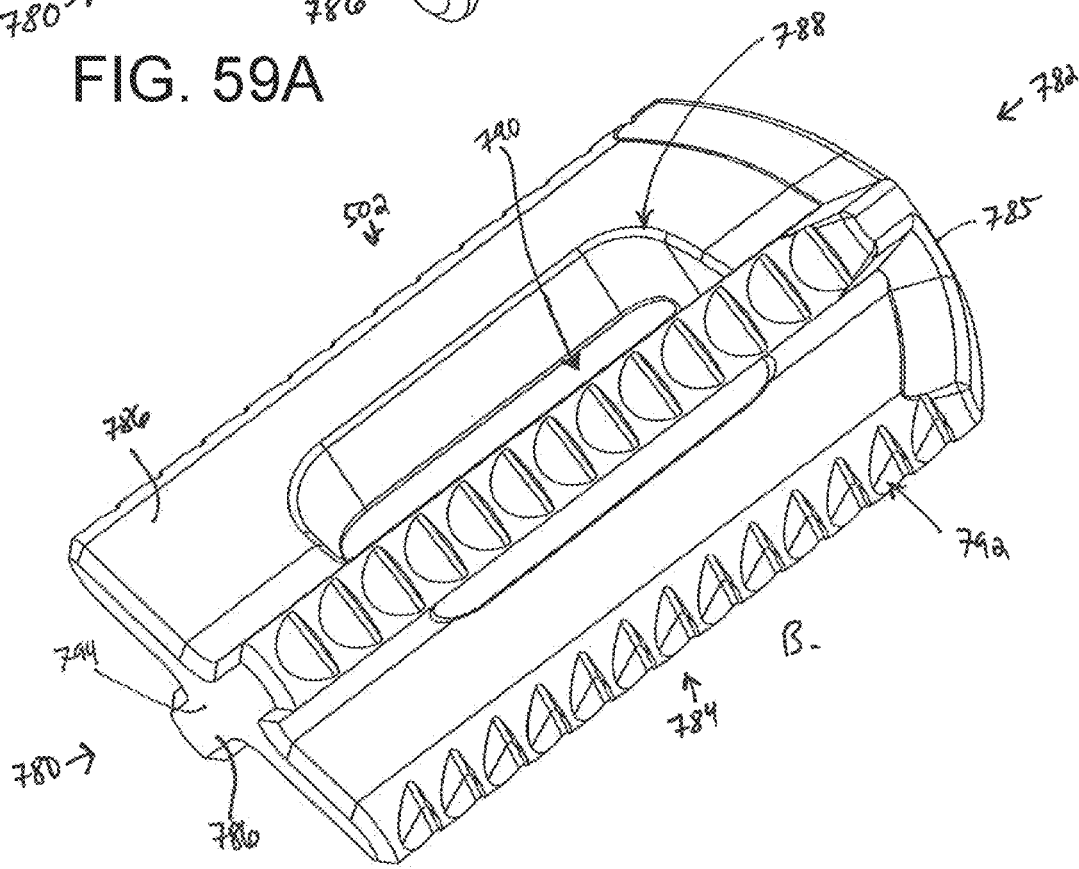
Figure 60A:
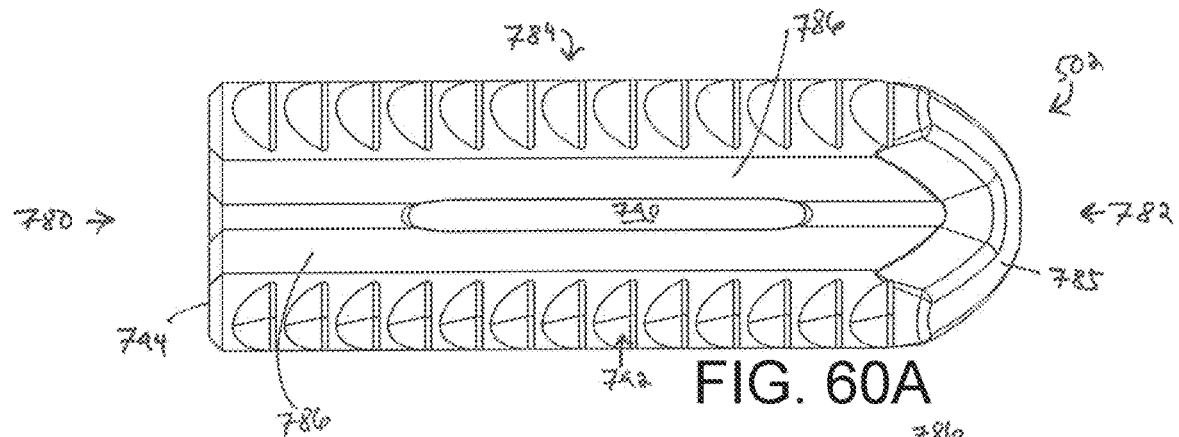
FIGS. 60A-60D are respectively first side, second side, back, and front views of the joint implant of FIGS. 59A-59B.
Figure 60B:
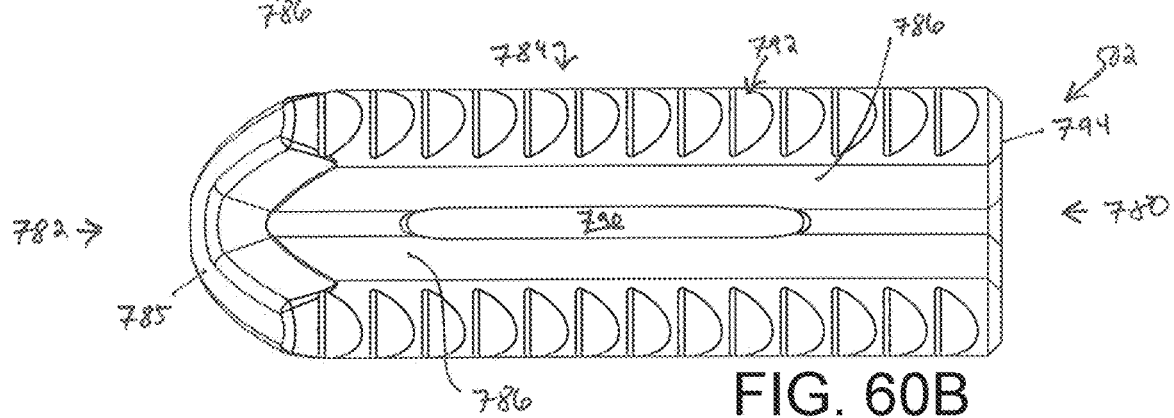
Figure 60C:
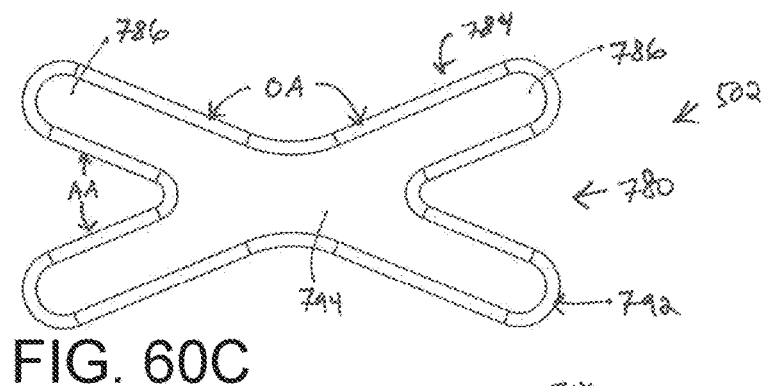
Figure 60D:
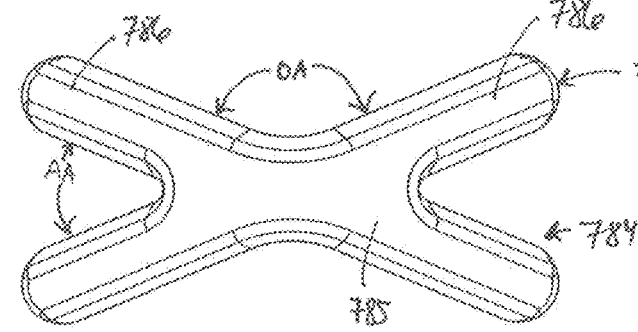
Figure 61A:
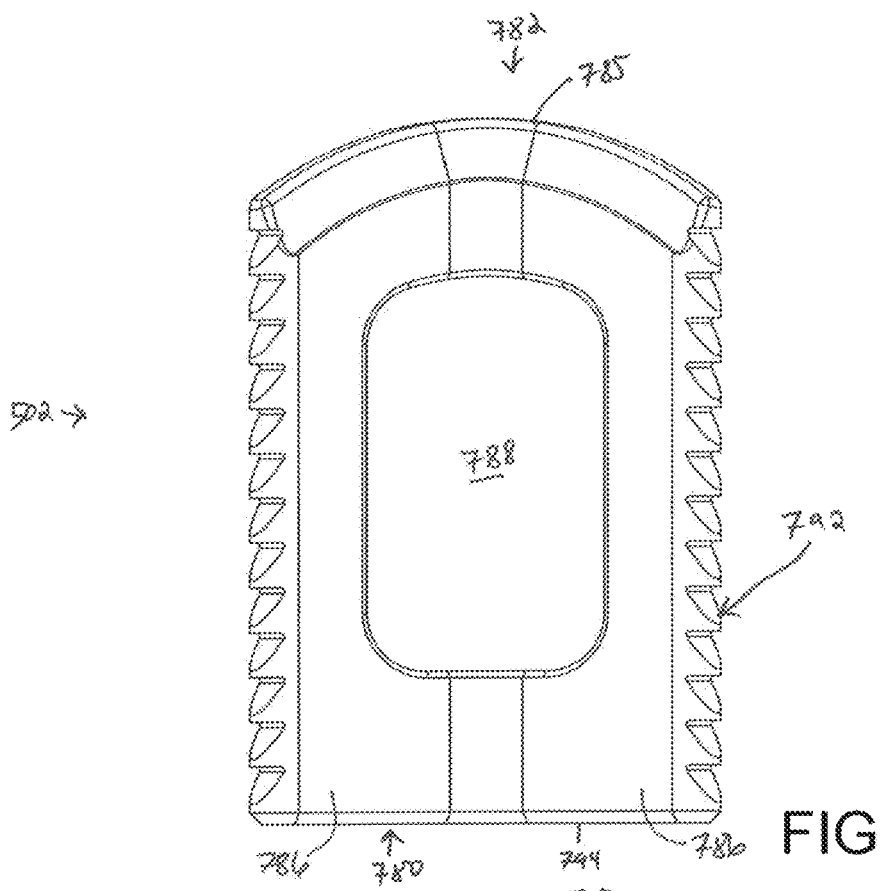
FIGS. 61A-61B are respectively top and bottom views of the joint implant of FIGS. 59A-59B.
Figure 61B:
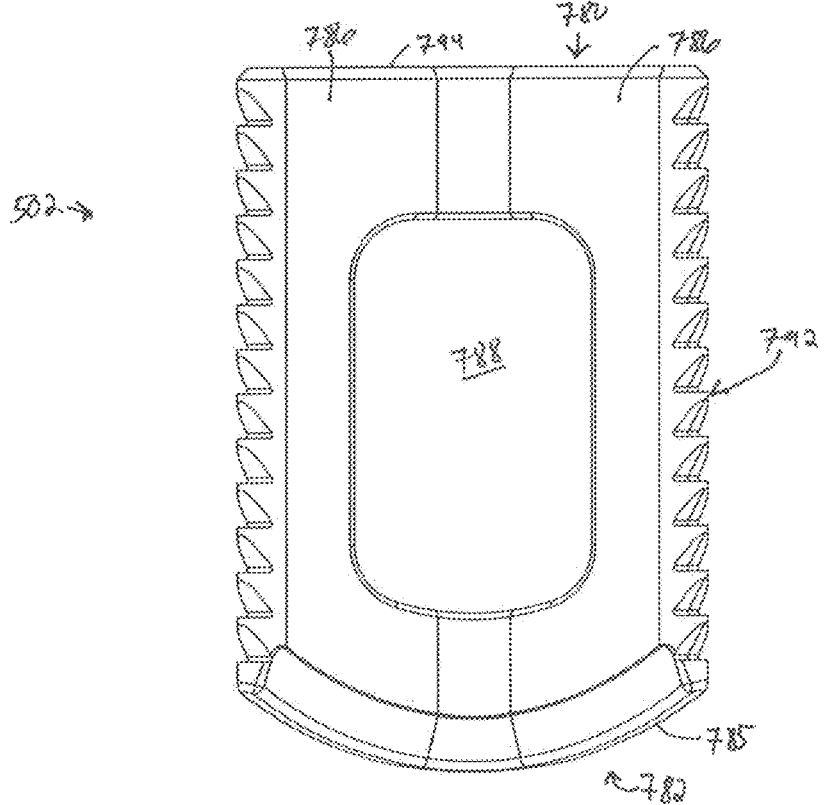

FIGS. 59-61 depict various views of an X-shaped implant 502. In particular, FIGS. 59A-59B are respectively rear isometric, and side isometric views of a joint implant 502. FIGS. 60A-60D are respectively first side, second side, back, and front views of the joint implant 502 of FIGS. 59A-59B. And FIGS. 61A-61B are respectively top and bottom views of the joint implant of FIGS. 59A-59B. As seen in the figures, the X-shaped implant 502 generally includes a proximal end 780, a distal end 782 and an implant body 784 extending between the proximal and distal ends 780, 782. The implant body 784 may include a flattened X-shaped cross section transverse to a length of the implant body 784. That is, the implant body 784 may include a pair of planar members 786 that are coupled to each other at about a midpoint thereof. The pair of planar members 786 are not perpendicular to each other. Instead, the pair of planar members 786 define a pair of acute angles AA and a pair of obtuse angles OA.

The implant body 784 may include openings extending there through. For instance, the implant body 784 may include a first pair of openings 788 and a second pair of openings 790, where the first pair of openings 788 are larger and defined on the pair of planar members 786 that define the obtuse angles OA. The second pair of openings 790 may be smaller than the first pair of openings 788 and defined on the pair of planar members 786 that define the acute angles AA. The first pair of openings 788 can be seen in FIGS. 61A and 61B, and the second pair of openings 790 can be seen in FIGS. 60A and 60B.

The outer edges 792 of the planar members 786 may include ridges, serrations, or other anti-migration elements so as to inhibit migration of the implant 502 after implantation. A proximal face 794 of the implant body 784, at the proximal end 780, may be planar. At an opposite end, a distal edge 785 of the implant body 784, at the distal end 782, may be rounded. That is, a distal edge 785 of the pair of planar members 786 may be rounded. The proximal face 794 of the implant body 784 may include a threaded proximal bore, or other type of retention feature designed to facilitate couple of the implant 502 to an implant arm 504 of a delivery tool. Alternatively, the implant arm 504 may couple to the planar proximal face 794.

Figure 62:
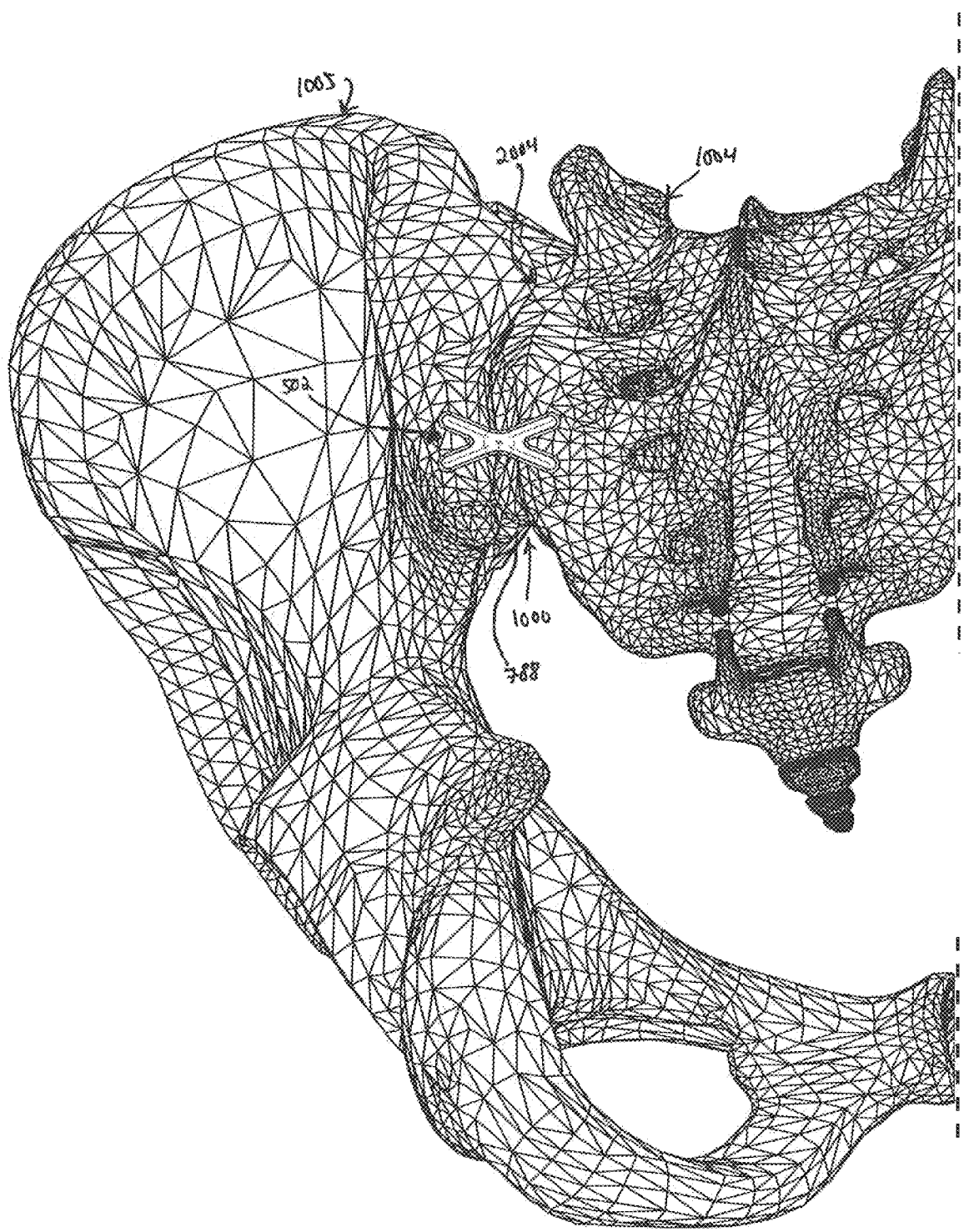
FIG. 62 is a posterior view of the joint implant bridging across the sacroiliac joint.
Figure 63:
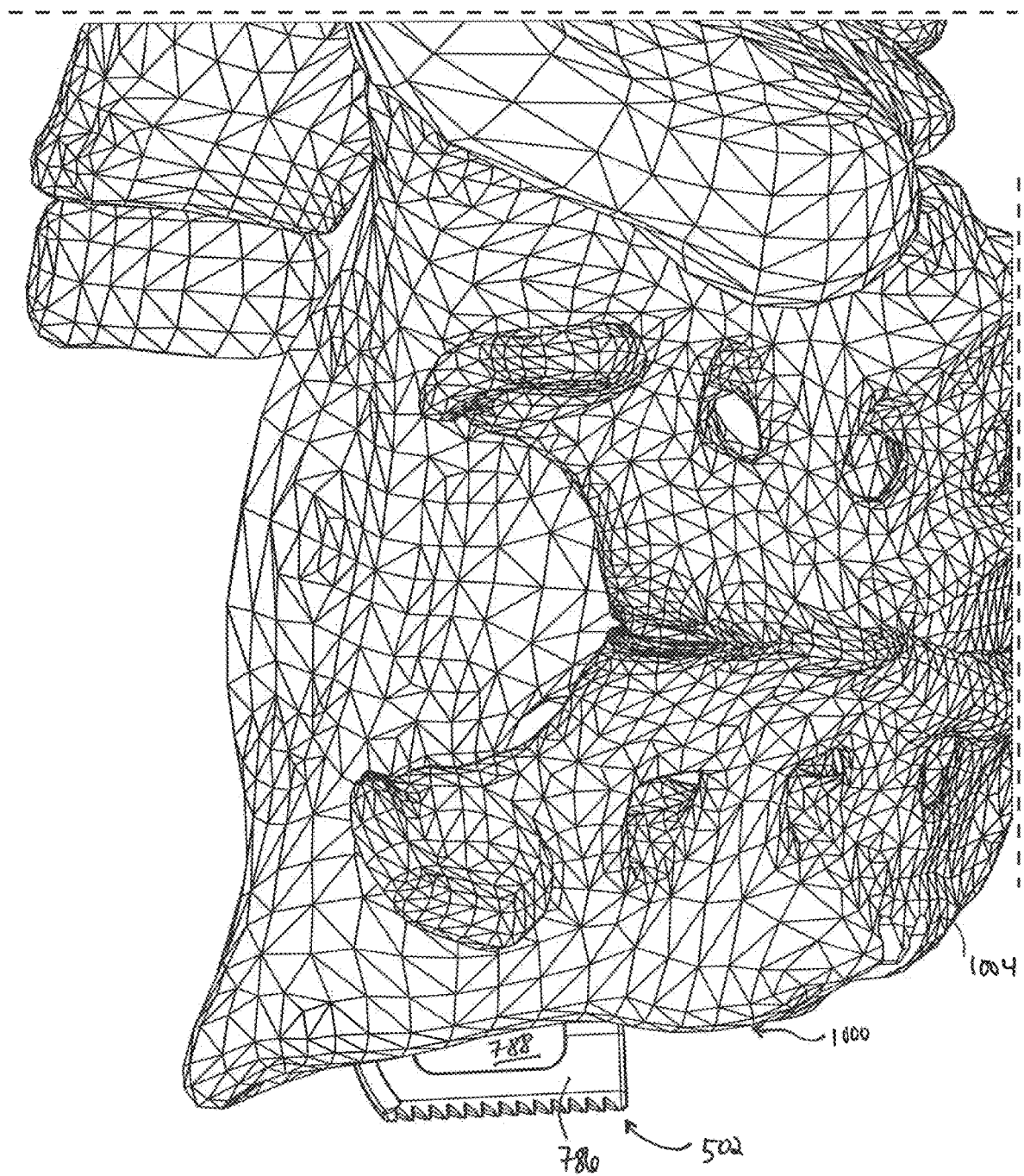
FIG. 63 is a superior view of the joint implant bridging across the sacroiliac joint, where the ilium forming a portion of the sacroiliac joint is removed to show the position of the joint implant.

FIGS. 62-63 depict the joint implant 502 implanted in the sacroiliac joint 1000. In particular, FIG. 62 is a posterior view of the joint implant 502 bridging across the sacroiliac joint 1000. And FIG. 63 is a superior view of the joint implant 502 bridging across the sacroiliac joint 1000, where the ilium 1005 forming a portion of the sacroiliac joint 1000 is removed to show the position of the joint implant 502. As seen in FIG. 62, the joint implant 502 is implanted into the sacroiliac joint 1000 via a posterior access, where the planar members 786 extend or bridge across the joint 1000 and into the sacrum 1004 and the ilium 1005. That is, each of the pair of members 786 extends across the joint 1000 where one end is positioned in the sacrum 1004 and an opposite end 1005 is positioned in the ilium, with no member lying parallel to a joint plane of the joint 1000.

Thus, as seen in FIG. 63, the first pair of openings 788 is oriented vertically or superior-inferior, while the second pair of openings 790 are oriented horizontally or medial-lateral. And as seen in FIG. 62, the joint implant 502 is positioned between the posterior superior iliac spine 2004 and the posterior inferior iliac spine 778 so as to be positioned within the articular region 1044 of the joint 1000. And while FIGS. 62-63 depict the implant 502 positioned in the articular region 1044 of the joint 1000, the implant 502 may alternatively be positioned in the extra-articular region 3007, among other areas of the joint 1000 for implantation.

The joint implant 502 as seen in FIGS. 59-63 may be used with the working cannula 506 and standoff 578 (among other tools such as the anchor arm 508 and implant arm 504, as well as others) as previously described. In such an instance, the inner surface 590 of the standoff 578 and the inner surface 558 of the passageway 556 of the working cannula 506 may be keyed in a corresponding shape of the joint implant 502 in FIGS. 59-63. For example, the inner surfaces 590, 558 of the standoff 578 and working cannula 506 may be keyed to an X-shaped cross-section to permit the joint implant 502 and associated tooling to extend there through. Additionally, other tools described herein may similarly be modified to permit passage through inner surfaces that are keyed to an X-shaped cross-section.

V. Methods of Preparing and Fusing the Sacroiliac Joint

The following section describes methods for preparing and fusing the sacroiliac joint 1000, with reference to FIGS. 64-114, utilizing systems and tools described in previous sections of this application.

Figure 64:
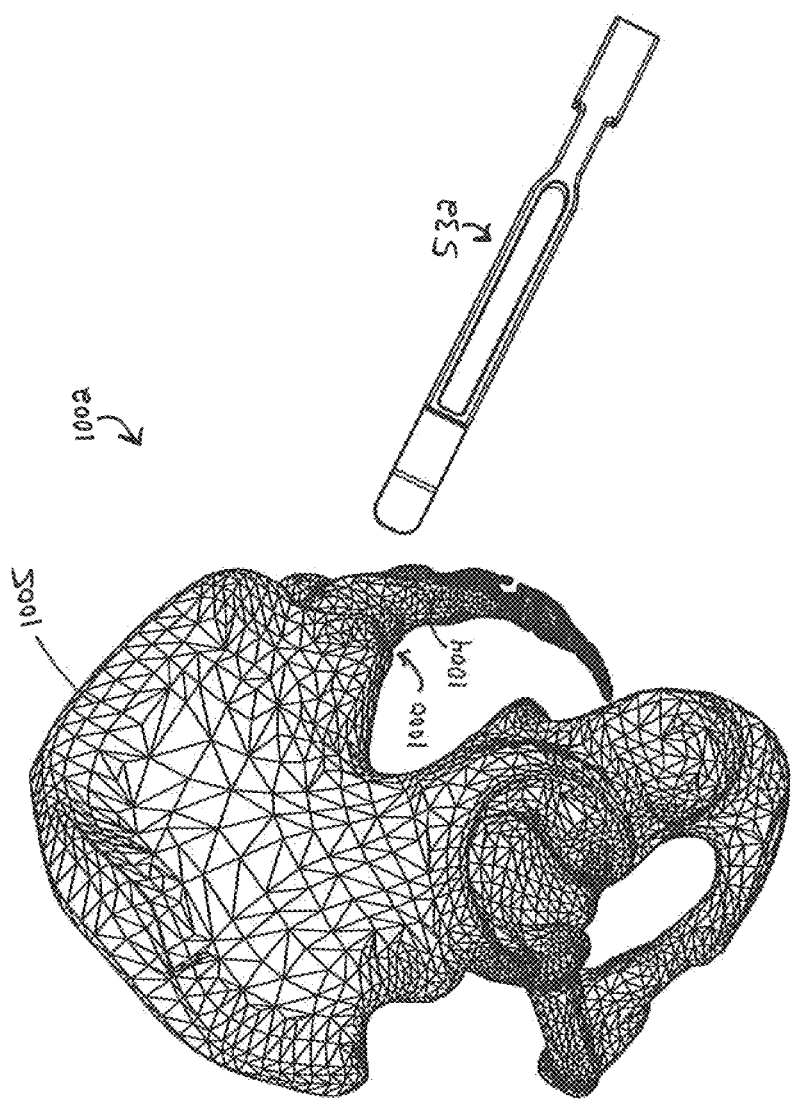
FIG. 64 is a side view of a pelvis with a joint finder positioned proximally thereof.

To begin, reference is made to FIG. 64, which is a side view of a pelvis 1002 with a joint finder 532 positioned proximally thereof. After a patient is anesthetized, and the surgical site is cleaned, a surgeon must locate the joint 1000 in order to prepare the site for a fusion procedure. FIG. 64 as well as many of the other figures in this section show the relevant tools and bones associated with the procedure for clarity. That is, certain steps of the surgical procedure may be omitted herein, but it is understood that other steps may be performed without departing from the scope of the present disclosure.

Figure 65:
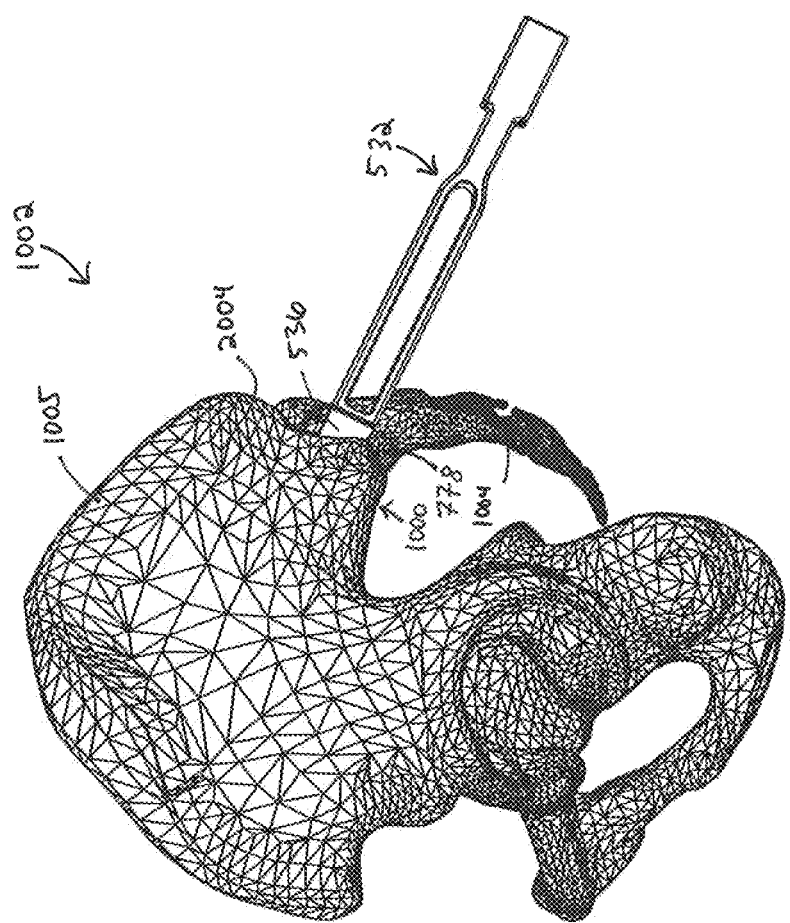
FIG. 65 is a side view of a pelvis with the joint finder positioned in the sacroiliac joint (the steps shown in FIGS. 64-65 are an alternative to the steps shown in FIGS. 66-68, i.e., employing a non-cannulated versus cannulated joint finder).

Accordingly, in FIG. 64, the patient's tissue adjacent the joint 1000 has been opened (via an incision), and the surgeon may use the joint finder 532 to locate the sacroiliac joint 1000 via a posterior access. As seen in FIG. 65, which is a side view of the pelvis 1002, the joint finder 532 may be distally advanced relative to the joint 1000 from the posterior access until the spatulate tip 536 extends into the gap (joint 1000) between the sacrum 1004 and the ilium 1005. This provides the surgeon with the location of the sacroiliac joint 1000 and general angular orientation of it. The joint finder 532 may extend into the articular region 1044 of the joint 1044, which is generally between the posterior superior iliac spine 2004 and the posterior inferior iliac spine 778.

Figure 66:
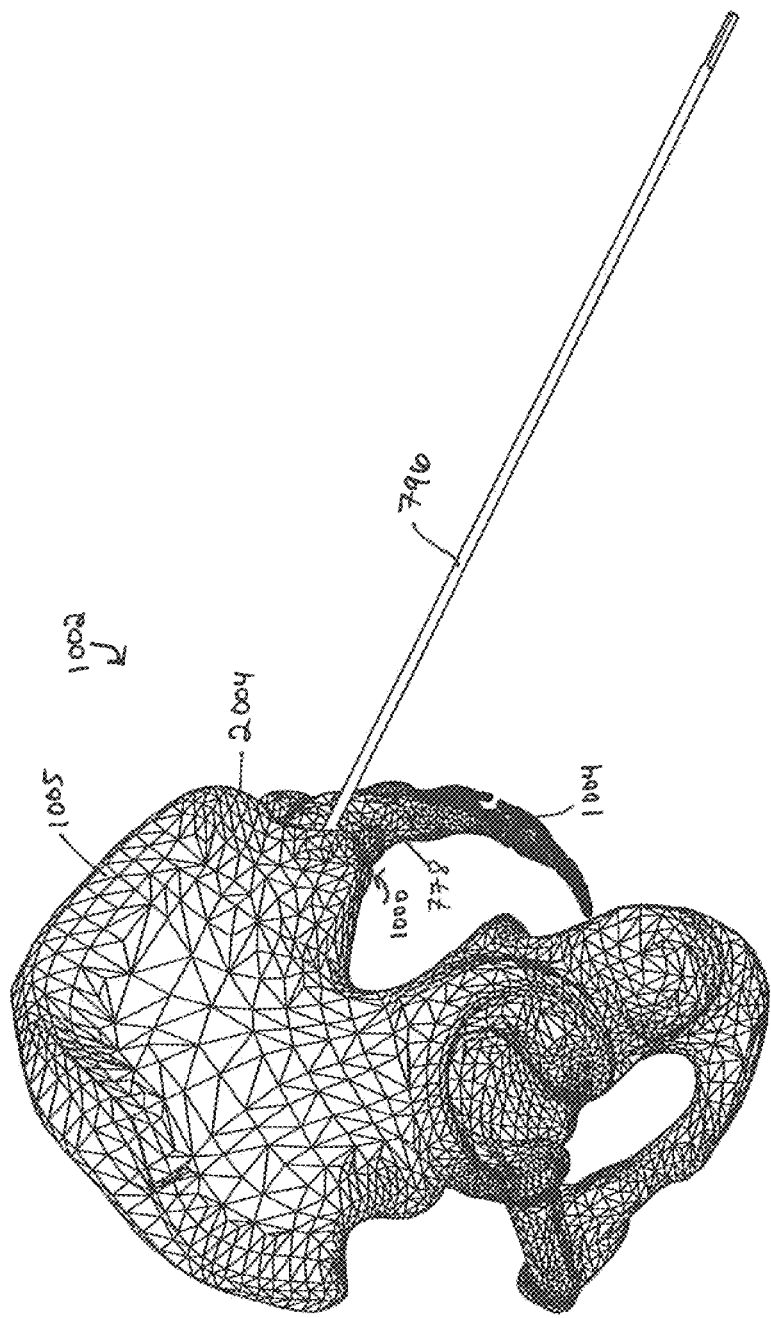
FIG. 66 is a side view of a pelvis with a pin positioned in the sacroiliac joint.

Alternatively, the procedure may begin with a pin and followed by a cannulated joint finder. Upon identification of the location of the joint 1000, and as seen in FIG. 66, the surgeon may advance a pin 796 into the joint 1000 via the posterior access.

Figure 67:
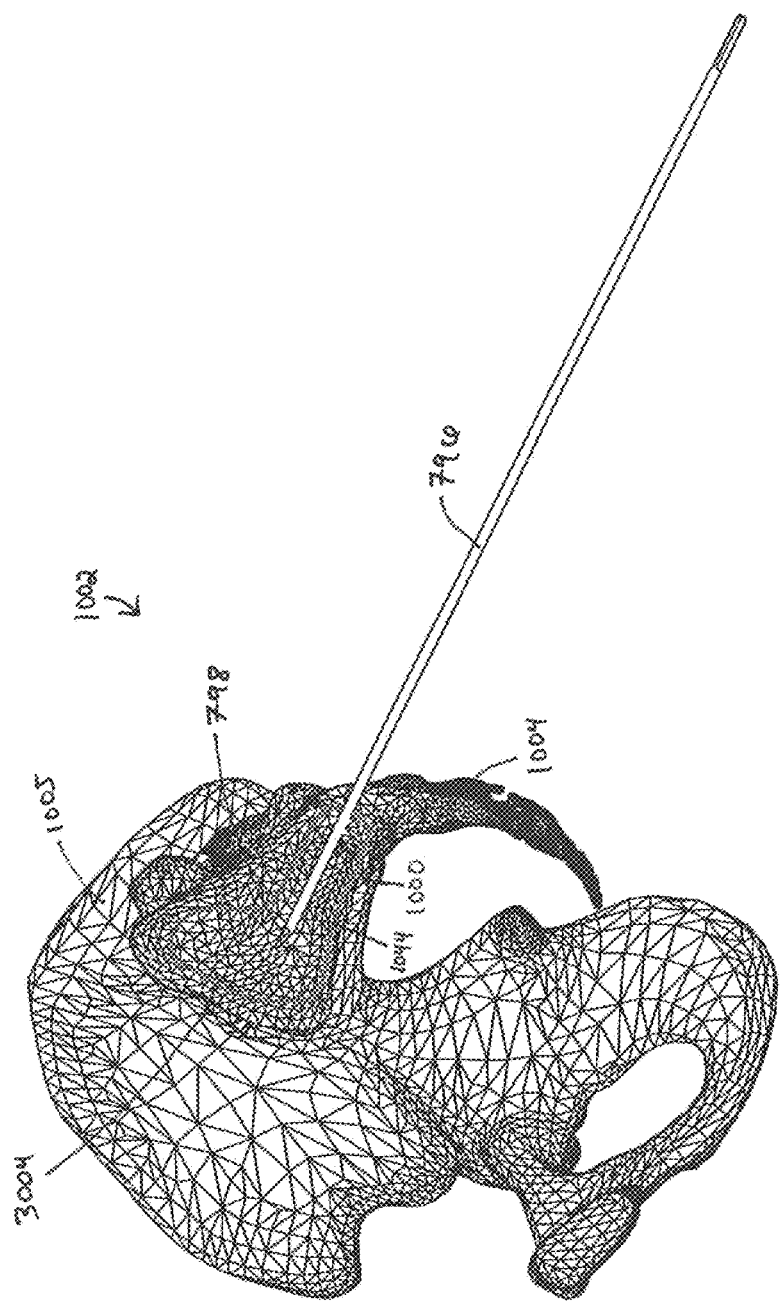
FIG. 67 is a side view of a pelvis with the nearest ilium removed to show the pin in the sacroiliac joint.

FIG. 67 is a side view of a pelvis with the nearest ilium 1005 removed to show the pin 796 in the sacroiliac joint 1000. The articular region 1044 is highlighted in this view to show the position of the pin 796 in the joint 1000. As seen in the figure, the pin 796 is generally positioned in a mid-portion of the joint in a superior-inferior direction, and is generally positioned with the distal tip 798 of the pin 796 posterior to an anterior border segment 3004 of the joint.

FIG. 68 is a side view of the pelvis 1002 with the nearest ilium 1005 removed, and a cannulated joint finder 800 positioned over the pin 796 and in the sacroiliac joint 1000. The cannulated joint finder 800 may include an elongate body 802 with dual spatulate tips 804 at a distal end 806 thereof. A rectangular, block-like handle 808 at a proximal end 810 is coupled to a recessed gripping portion 812 that further couples to the dual spatulate tips 804 that extend to the distal end 806. The handle 808 and the recessed gripping portion 812 may include a longitudinal bore 814 extending there through that opens into a space between the dual spatulate tips 804. The longitudinal bore 814 may receive the pin 796, as seen in FIG. 68, and guide the cannulated joint finder 800 into the articular region 1044 of the joint 1000. The cannulated joint finder 800 may exert a pressure against the joint surfaces of the sacrum 1004 and ilium 1005 with sufficient force to hold the joint distractor in position in the joint 1000.

Figure 69:
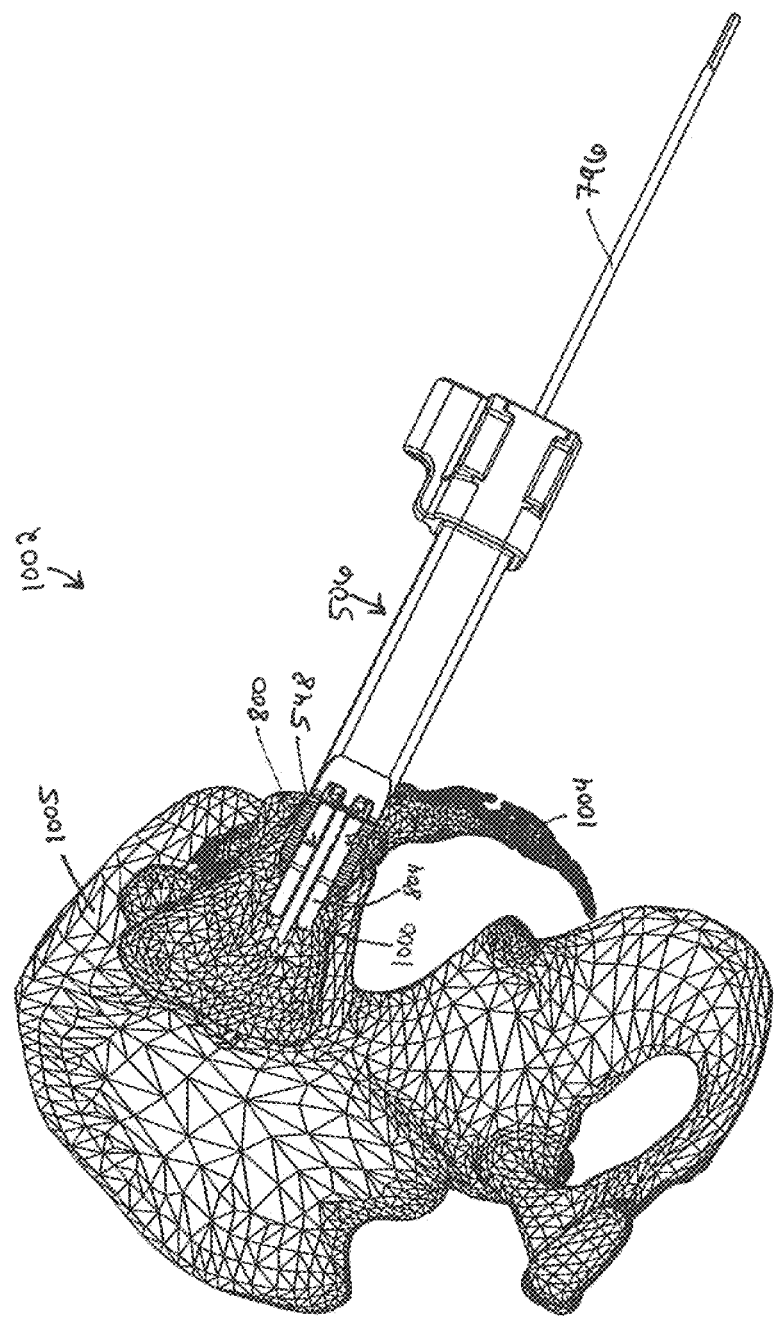
FIG. 69 is a side view of a pelvis with the nearest ilium removed, and a working cannula positioned over the cannulated joint finder and the pin and in the sacroiliac joint.

As seen in FIG. 69, which is a side view of the pelvis 1002 with the nearest ilium 1005 removed, the working cannula 506 may be positioned over the cannulated joint finder 800 and the pin 796 and in the sacroiliac joint 1000. In this position, the pair of prongs 548 extends into the articular region 1044 of the joint 1000, and are positioned superior and inferior to the dual spatulate tips 804 of the joint distractor 800. Alternatively, if not using the pin and cannulated joint finder but using the joint finder as shown in FIGS. 64-65 the working cannula may be position over the joint finder similar to the step shown in FIG. 69.

Figure 70:
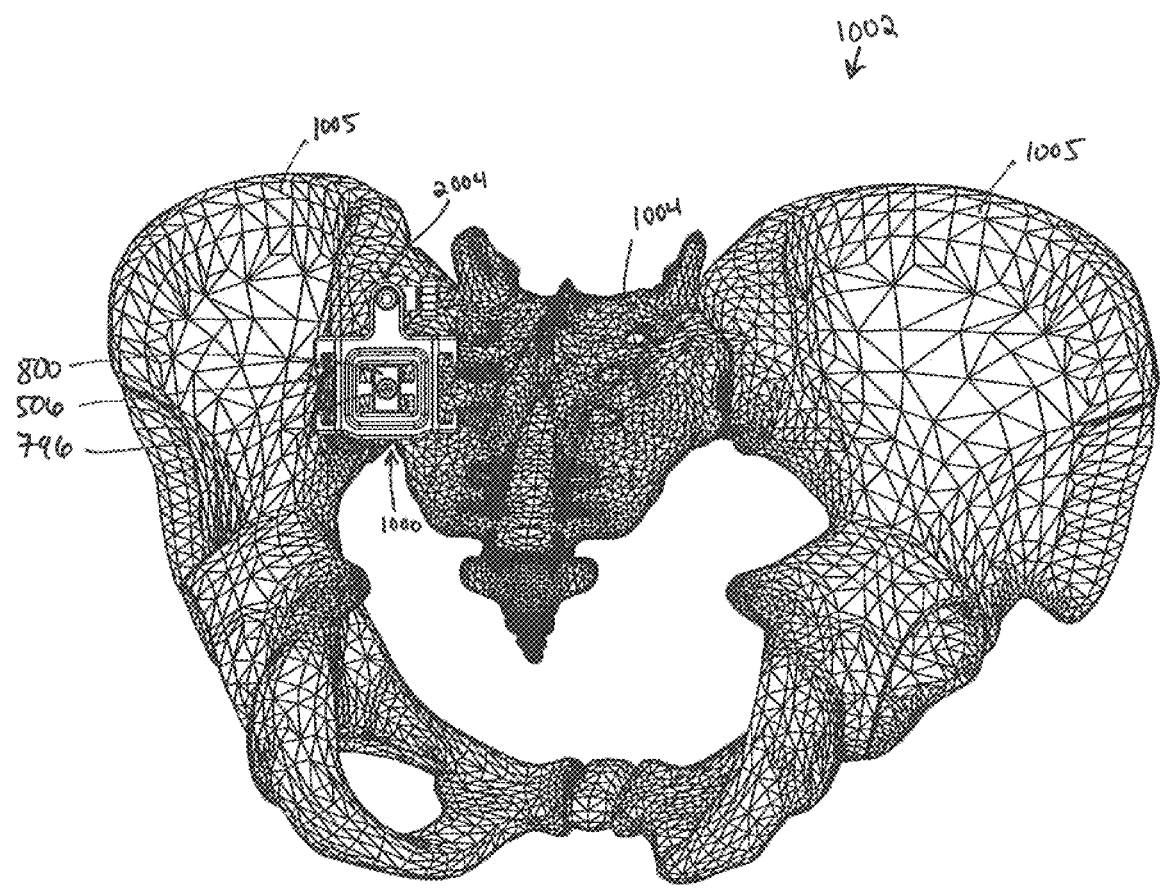
FIG. 70 is a posterior view of the pelvis with the working cannula, cannulated joint finder, and pin positioned in the sacroiliac joint.

FIG. 70 is a posterior view of the pelvis 1002 with the working cannula 506, cannulated joint finder 800, and pin 796 positioned in the sacroiliac joint 1000. It can be seen in this view that pin guide 592 is aligned with the ilium 1005, and in particular the overhang of the posterior superior iliac spine 2004.

Figure 71:
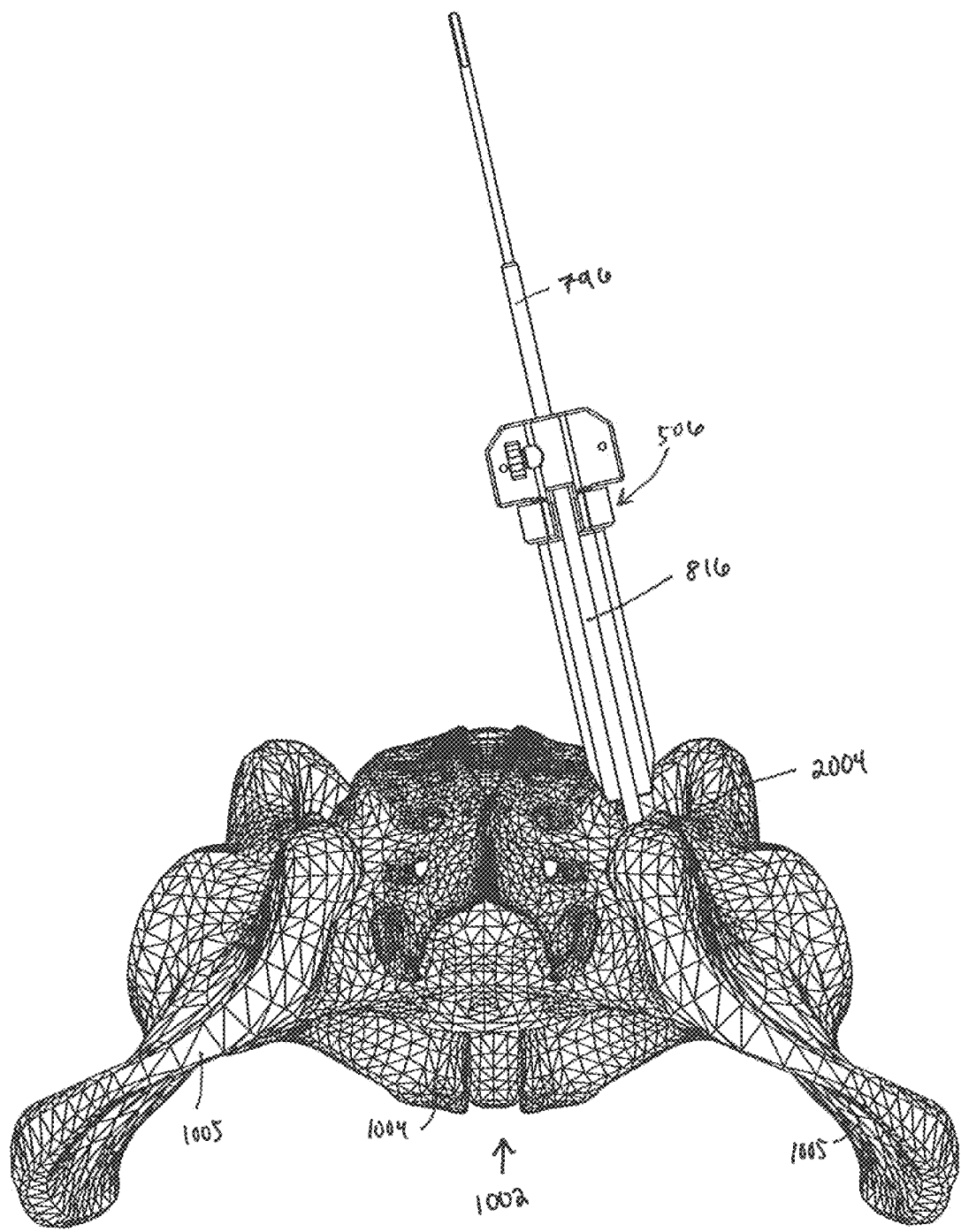
FIG. 71 is a superior view of the pelvis with the working cannula, cannulated joint finder, and pin positioned in the sacroiliac joint and a threaded guidance pin (e.g., a self-drilling and/or self-tapping Schanz screw) inserted though the pin guide at the proximal end of the working cannula and threaded into the area of the ilium near the PSIS and configured and positioned to anchor and stabilize the working cannula in relation to the patient's boney anatomy in lieu of or in addition to attaching the working cannula to the operative table.
Figure 72:
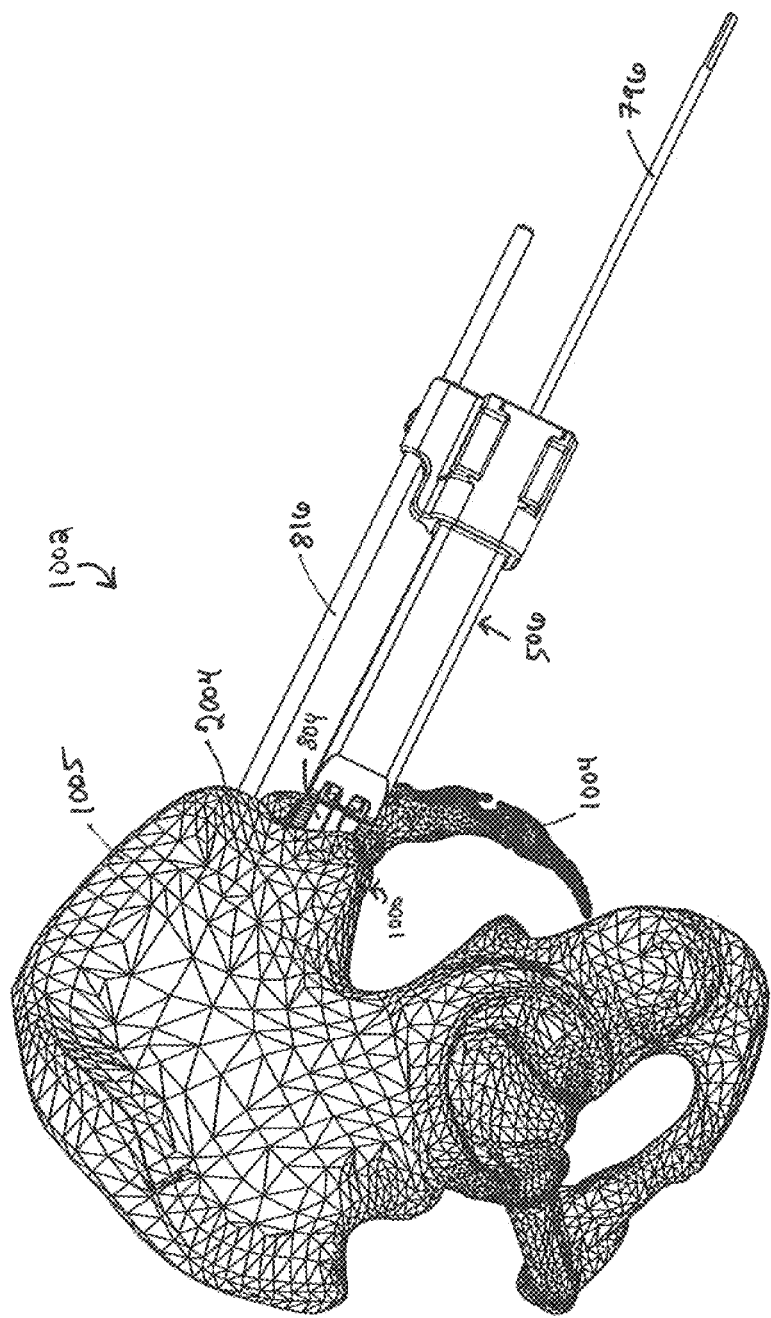
FIG. 72 is a side view of a pelvis with a guidance pin secured to the posterior superior iliac spine of the ilium.

FIGS. 71-72 depict the next step in the procedure, where FIG. 71 is a superior view of the pelvis 1002 with the working cannula 506, cannulated joint finder 800, and a guidance pin 816 positioned in the sacroiliac joint 1000, and where FIG. 72 is a side view of a pelvis 1002 with the guidance pin 816 secured to the overhang of the posterior superior iliac spine 2004 of the ilium 1005.

Figure 73:
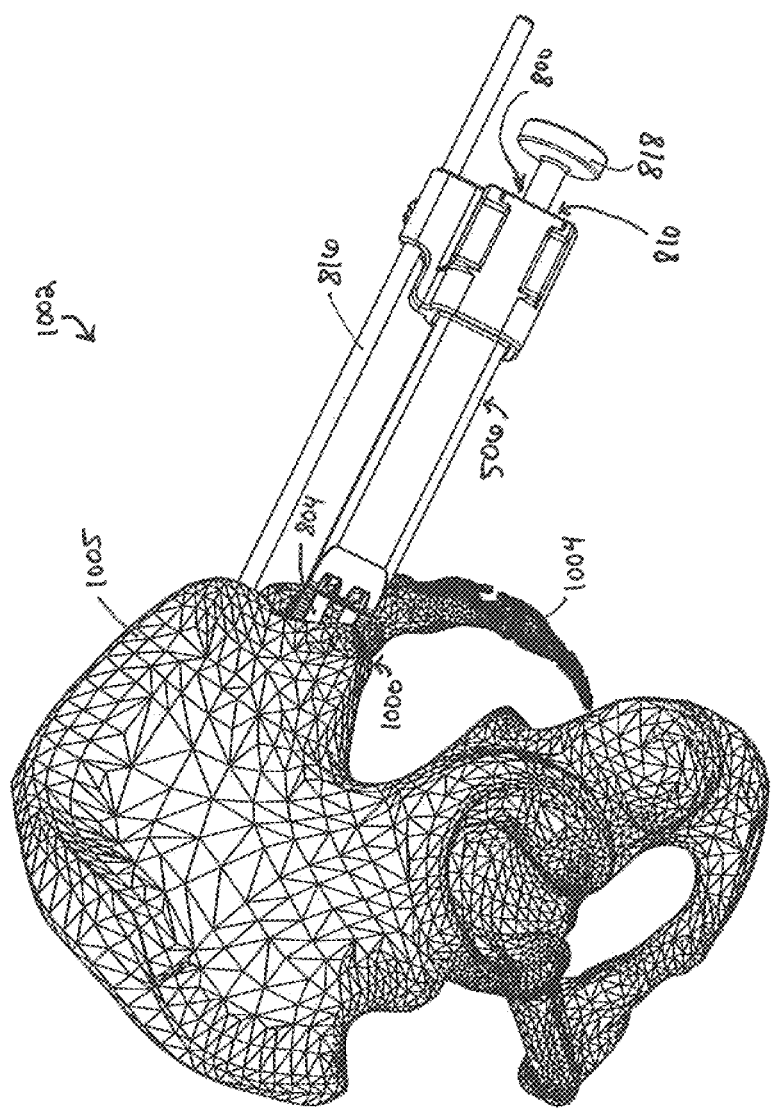
FIG. 73 is a side view of the pelvis with the pin removed from the joint, and a button knob coupled to the proximal end of the cannulated joint finder.
Figure 74:
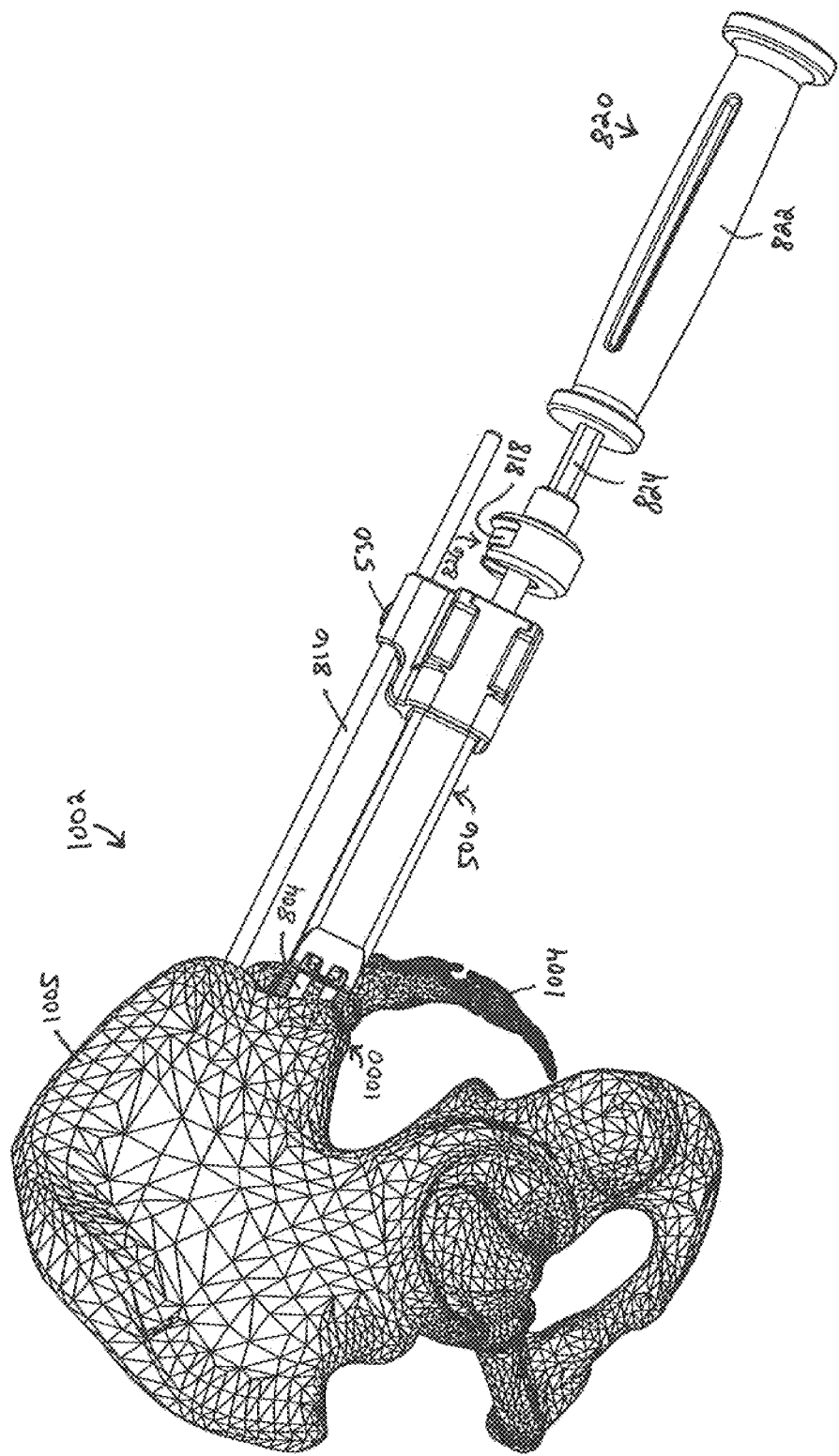
FIG. 74 is a side view of the pelvis with a slide (or slap) hammer assembly coupled to the button knob.

As seen in FIG. 73, which is a side view of the pelvis 1002, the pin 796 positioned within the articular region 1044 of the joint 1000 may be removed, and a button knob 818 may be coupled to the proximal end 810 of the cannulated joint finder 800. The button knob 818 may include a threaded distal end that is threadably engaged with a corresponding threaded portion of the longitudinal bore 814 of the joint distractor 800. A slide (slap) hammer 820 may be coupled with the button knob 818, as seen in FIG. 74. The slide hammer 820 may include an elongate grip 822, a shaft 824 extending distally from the elongate grip 822, and a cylindrical slot 826 for receiving the button knob 818 therein.

Upon coupling the slide hammer 820 to the button knob 818, the elongate grip 822 may be proximally and if required repeatedly retracted so as to remove the cannulated joint finder 800 from the joint 1000, as seen in FIG. 75, which depicts a side view of the pelvis 1002 with the cannulated joint finder 800 removed from within the working cannula 506, which is still in the joint 1000. At this stage of the procedure, the working cannula 506 is held in the joint via the guidance pin 816, which is anchored to the overhang of the posterior superior iliac spine 2004. And the guidance pin 816 may be secured in position relative to the working cannula 506 via a screw lock 530.

Figure 76:
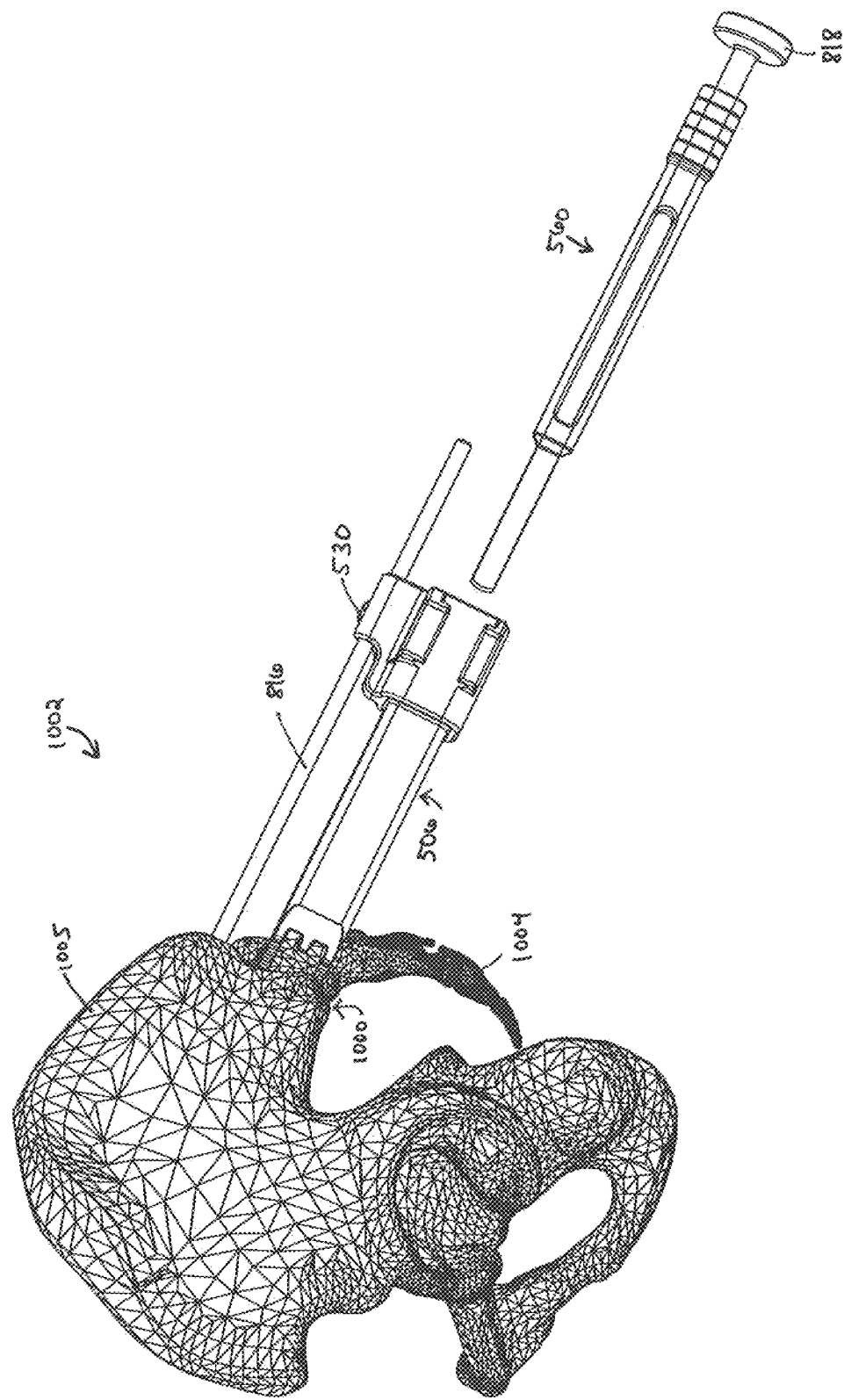
FIG. 76 is a side view of the pelvis with a depth gauge and the working cannula.

Next, as seen in FIG. 76, a depth gauge 560 may be used to determine a suitable depth for preparing the surfaces of the sacrum 1004 and ilium 1005 and for delivering the joint implant 502. FIG. 77 shows a side view of the pelvis 1002 with the nearest ilium 1005 removed, and the depth gauge 560 positioned through the working cannula 560 and in the joint 1000. As seen in the figure, a proximal edge 828 of the working cannula 506 aligns with one of the markers 568 indicating a depth of the elongate tongue 562 within the joint 1000. The surgeon may make note of the depth so that the surfaces of the joint 1000 may be prepared to that depth and so that a correspondingly sizes standoff may be selected to limit various further tools to a precise predetermined depth.

Figure 78:
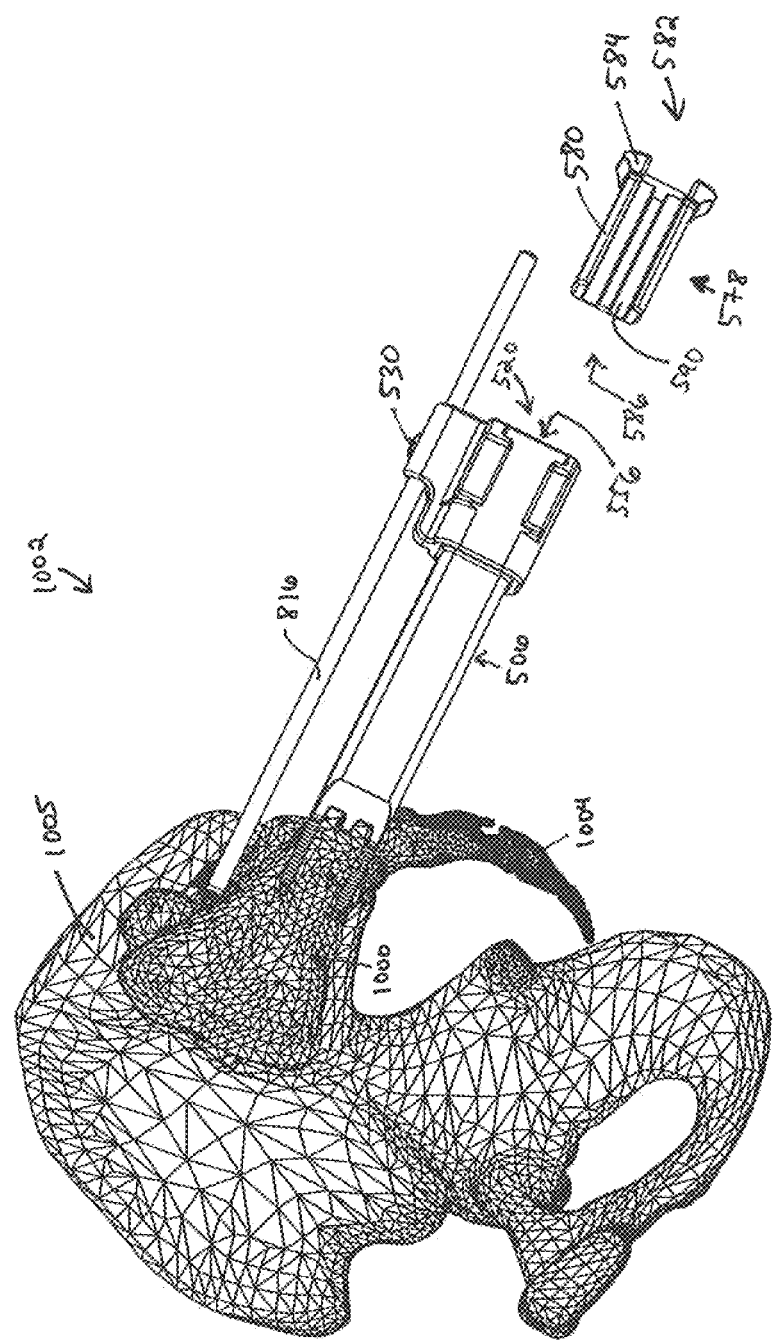
FIG. 78 is a side view of the pelvis with a standoff positioned proximate the working cannula, the standoff size being selected from a set of standoffs corresponding with the measurements obtained from the evaluation with the depth gauge.
Figure 79:
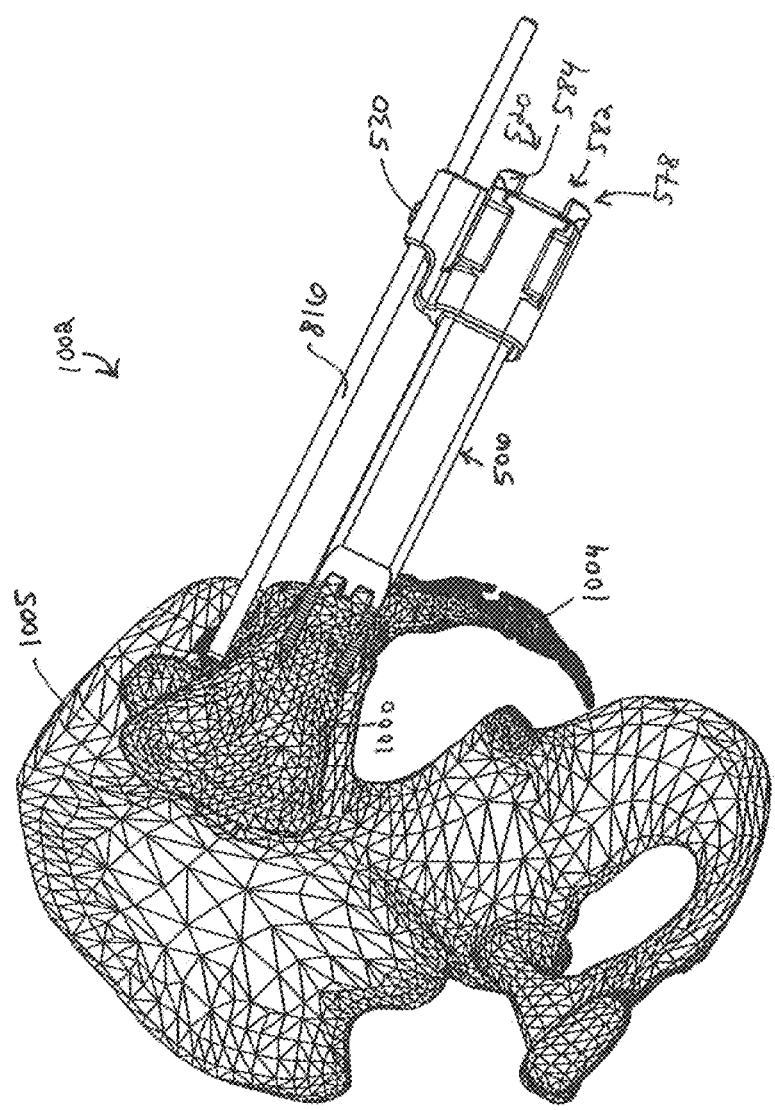
FIG. 79 is a side view of the pelvis with a standoff positioned within the working cannula.

Following the depth measurement, the depth gauge 560 may be removed from the working cannula 506, and a standoff 578 may be positioned within the proximal portion of the passageway 556. FIG. 78 is a side view of the pelvis 1002 with the standoff 578 positioned proximate the working cannula 506, and FIG. 79 is a side view of the pelvis 1002 with the standoff 578 positioned within the working cannula 506. As seen in the figures, the standoff 578 includes a three sided tubular body 580 and a three sided flanged base 584 extending outward from the tubular body 580 at a proximal end 582 of the standoff 578. The tubular body 580 extends to a distal end 586 of the standoff 578. An inner surface 590 of the standoff 578 is keyed in the shape of an I-beam or H-beam so as to match the inner surface 558 of the passageway 556 of the working cannula 506 when the standoff 578 is positioned within the proximal end 520 of the passageway 556 of the working cannula 506.

Figure 80:
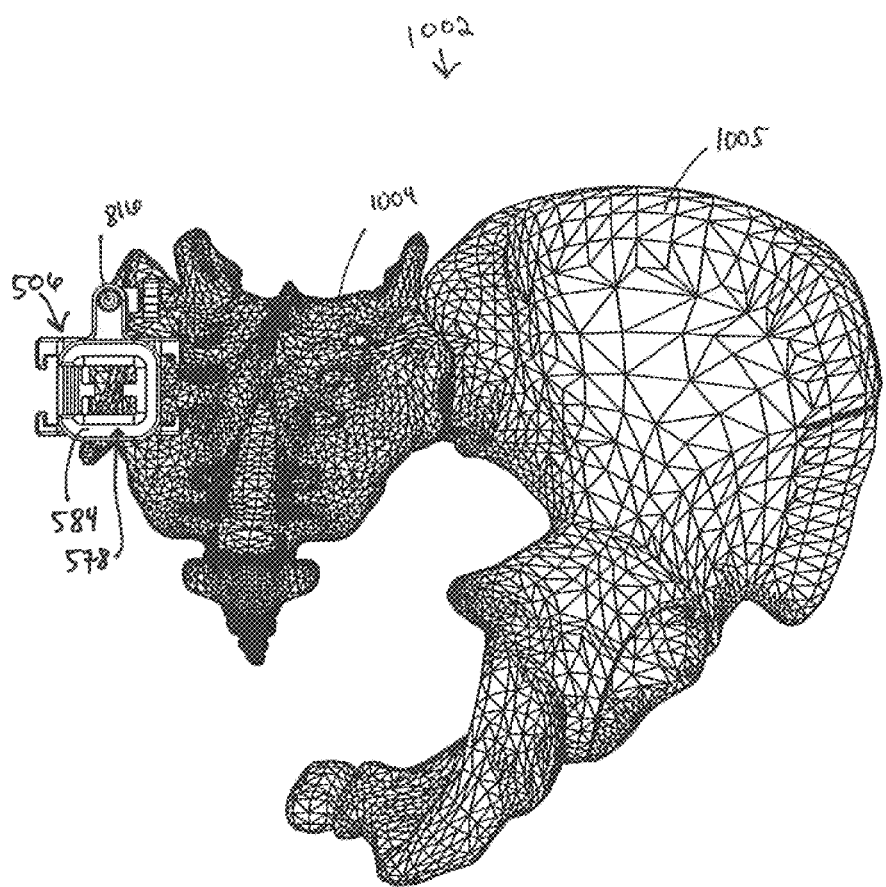
FIG. 80 is a posterior view of the pelvis, the working cannula, the guidance pin and the standoff.

FIG. 80 is a posterior view of the pelvis once the standoff 578 is positioned within the working cannula 506. As seen in the figure, a portion of the sacrum 1004 may be removed to make way for an implant 502 as a portion of the sacrum 1004 is visible through the passageway 556 of the working cannula 506.

Figure 81:
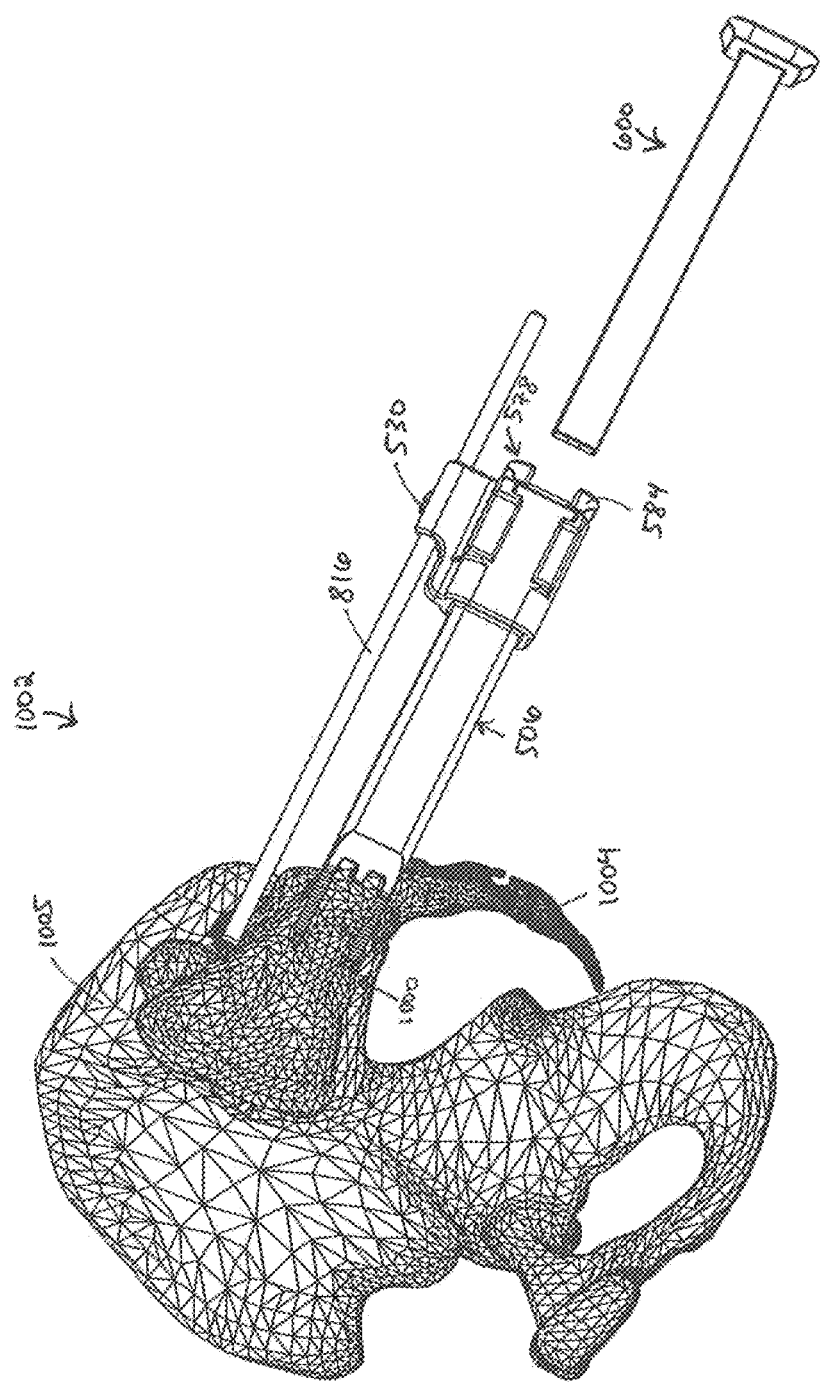
FIG. 81 is a side view of the pelvis with the nearest ilium removed, and a drill guide positioned proximate the working cannula.
Figure 82:
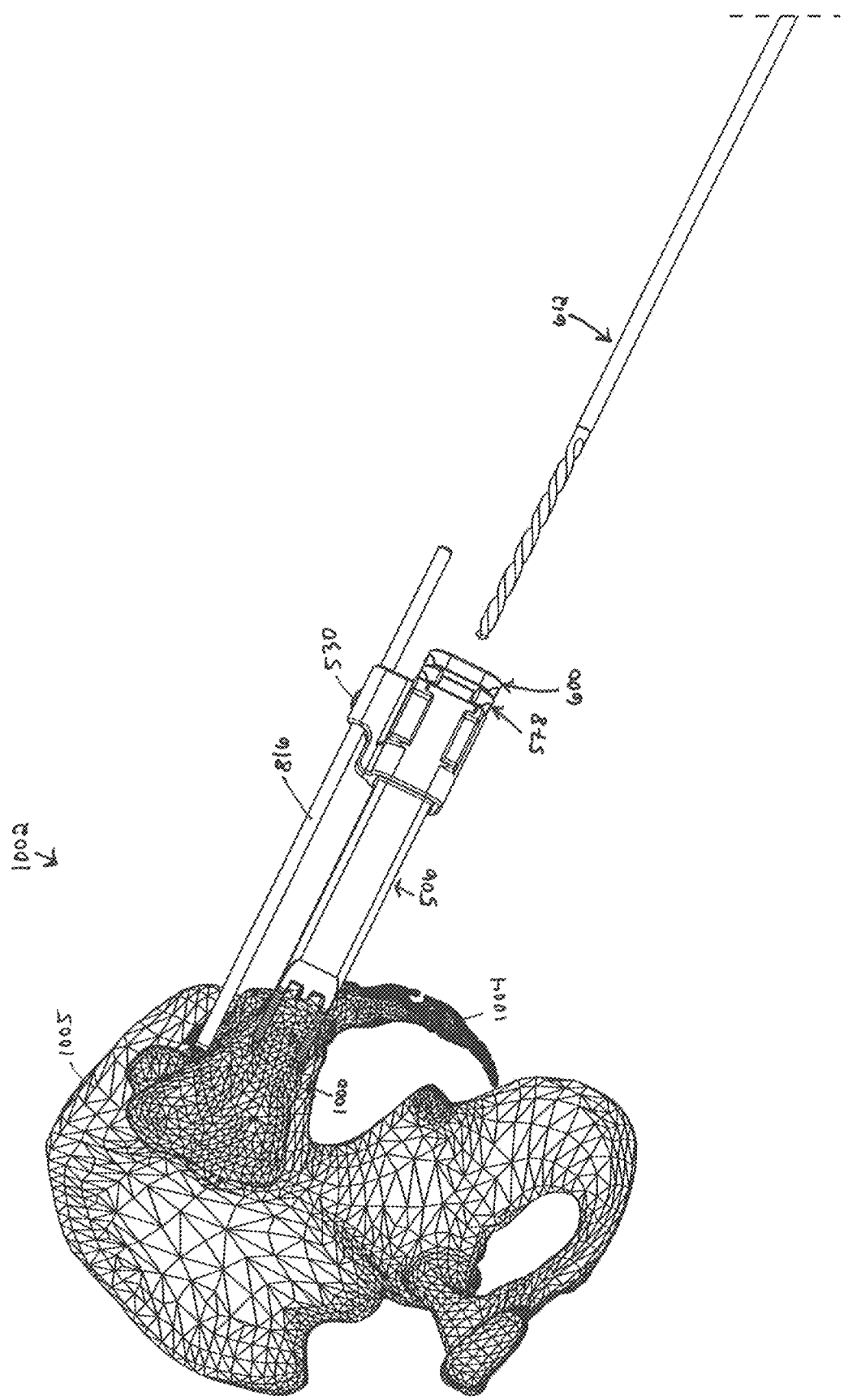
FIG. 82 is a side view of the pelvis with the nearest ilium removed, and a drill bit positioned proximate the working cannula and drill guide positioned therein.
Figure 83:
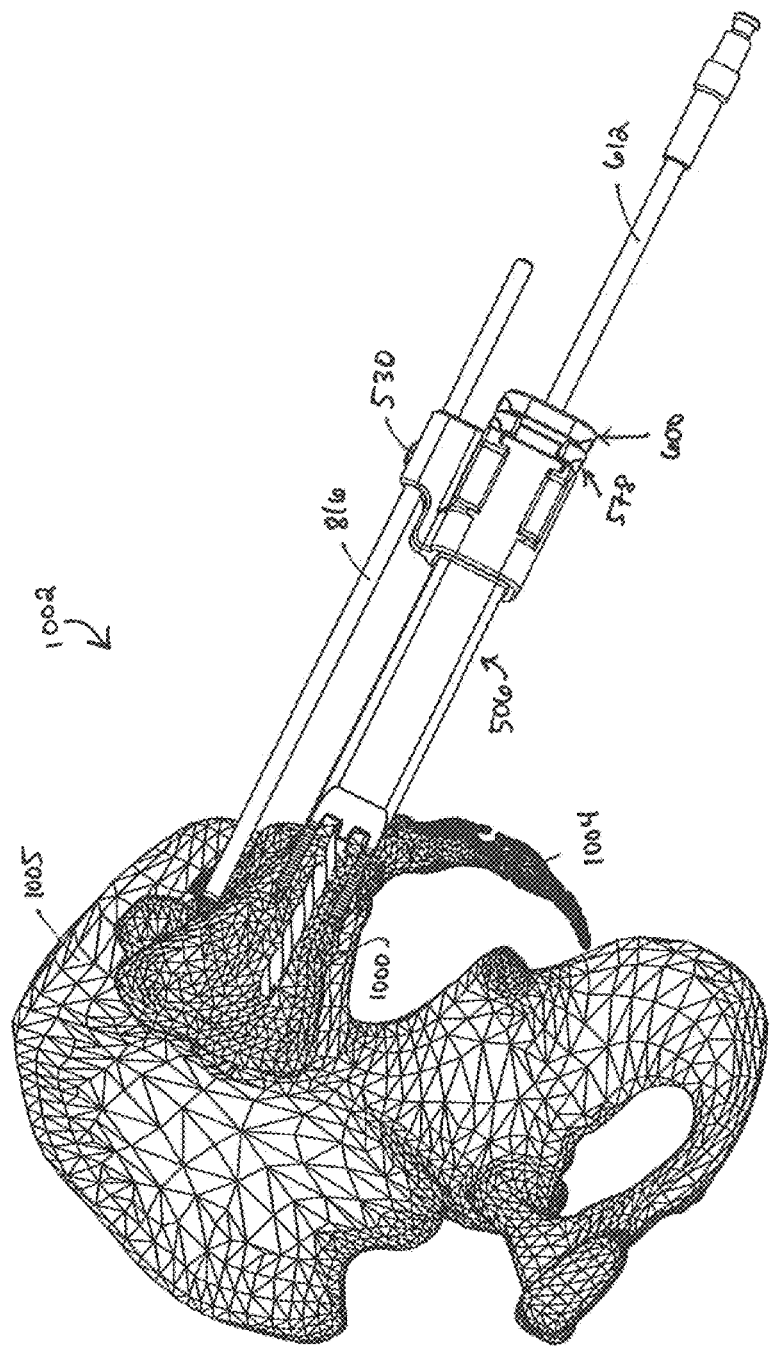
FIG. 83 is a side view of the pelvis with the nearest ilium removed, and a drill extending through a central guide of the drill guide, and into the joint.
Figure 84:
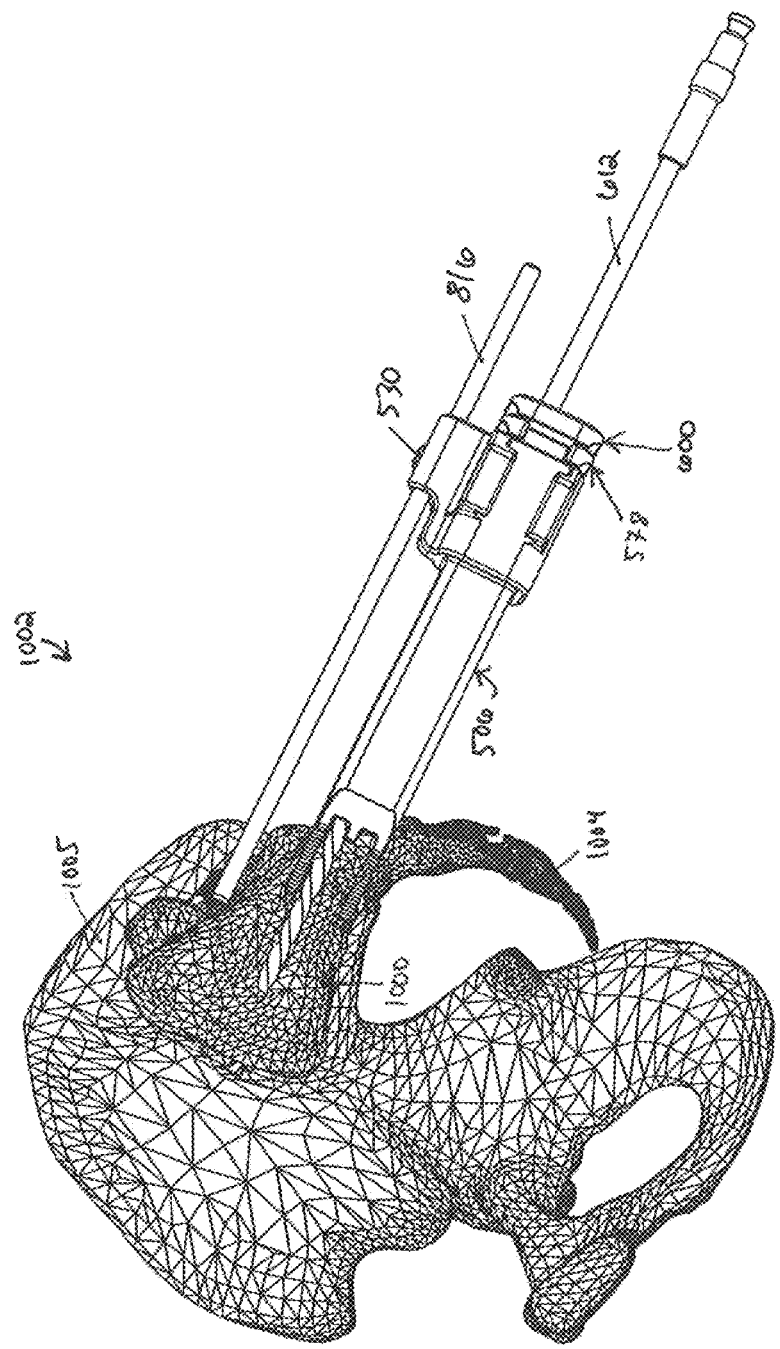
FIG. 84 is a side view of the pelvis with the nearest ilium removed, and a drill extending through a superior guide of the drill guide, and into the joint.

Once the standoff 578 is in position within the working cannula 506, a drill guide insert or drill guide 600 may be inserted into the working cannula 506, and a drill bit 612 may be used to remove portions of the cartilage and bone from the joint 1000, sacrum 1004, and ilium 1005. To that end, FIG. 81 is a side view of the pelvis 1002 with the nearest ilium 1005 removed, and a drill guide 600 positioned proximate the working cannula 506. FIG. 82 is a side view of the pelvis 1002 with the nearest ilium 1005 removed, and a drill bit 612 positioned proximate the working cannula 506 and drill guide 600 positioned therein. As seen in FIG. 83, the drill bit 612 may be guided through a central guide of the drill guide 600, and into the joint 1000 so as to form a central bore. And, as seen in FIG. 84, the drill bit 612 may also be guided through a superior guide of the drill guide 600, and into the joint 1000 so as to form a superior bore in a position superior to the central bore. In certain instances, the central guide and the superior guide may overlap a portion with each other. In certain instances, the central guide and superior guide may not overlap with each other.

Figure 85:
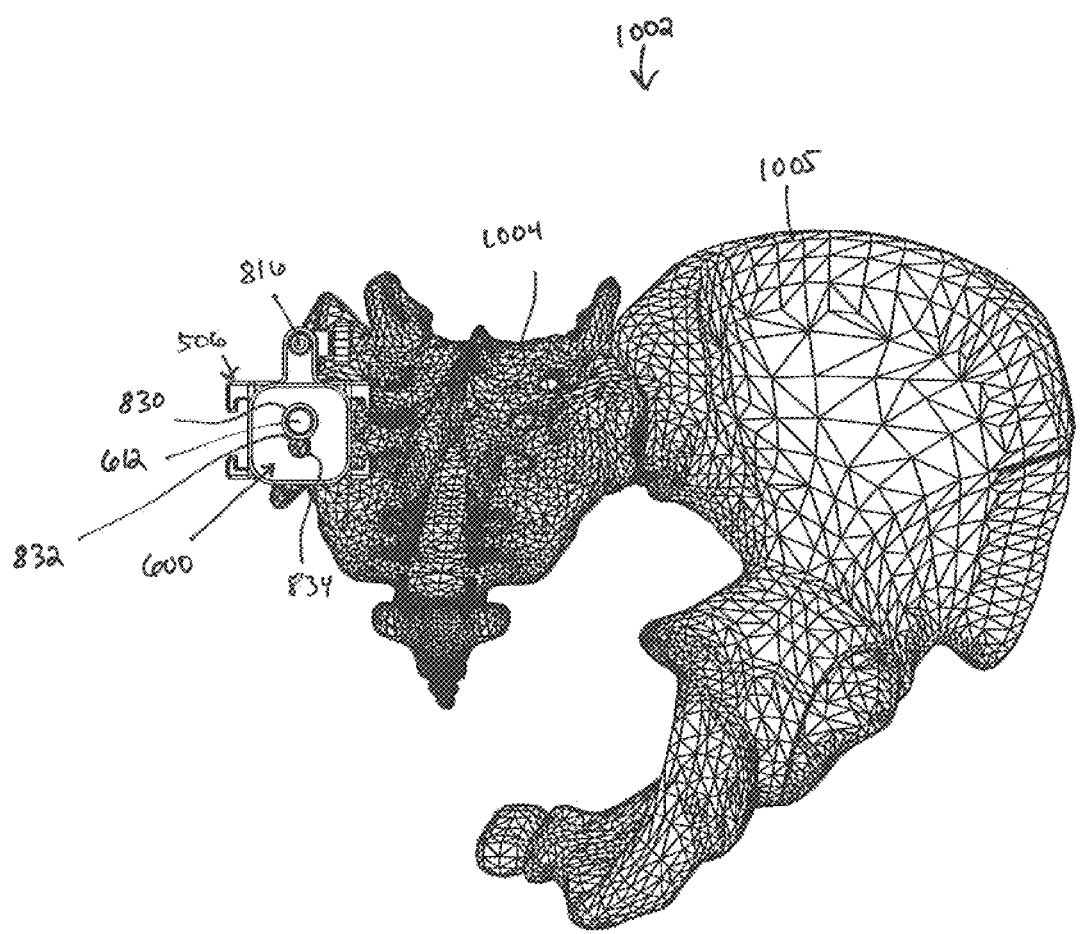
FIG. 85 is a posterior view of the pelvis with the drill positioned in the superior guide of the drill guide, and the working cannula positioned in the joint.
Figure 86:
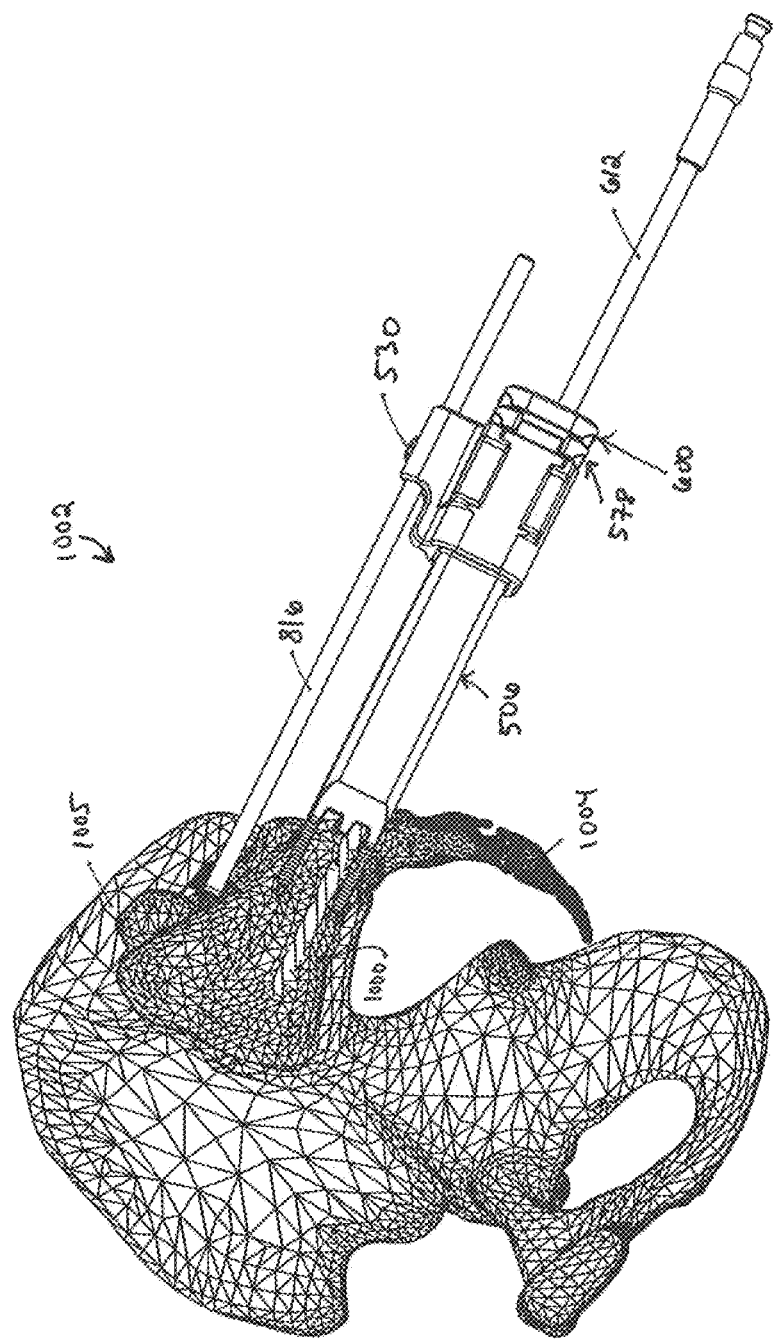
FIG. 86 is a side view of the pelvis with the nearest ilium removed, and a drill extending through an inferior guide of the drill guide, and into the joint.

FIG. 85 is a posterior view of the pelvis 1002 with the drill bit 612 positioned in the superior guide of the drill guide 600. In this instance, the drill guide 600 includes three drill guide holes: a superior guide hole 830; a central guide hole 832; and an inferior guide hole 834. As seen in the figure, a portion of the guide holes 830, 832, 834 overlap (i.e., a portion are coextensive). FIG. 86 shows the drill bit 612 extending through the inferior guide hole 834 of the drill guide 600 so as to remove a portion of the bone and/or cartilage of the joint 1000, sacrum 1004, and ilium 1005.

Figure 87:
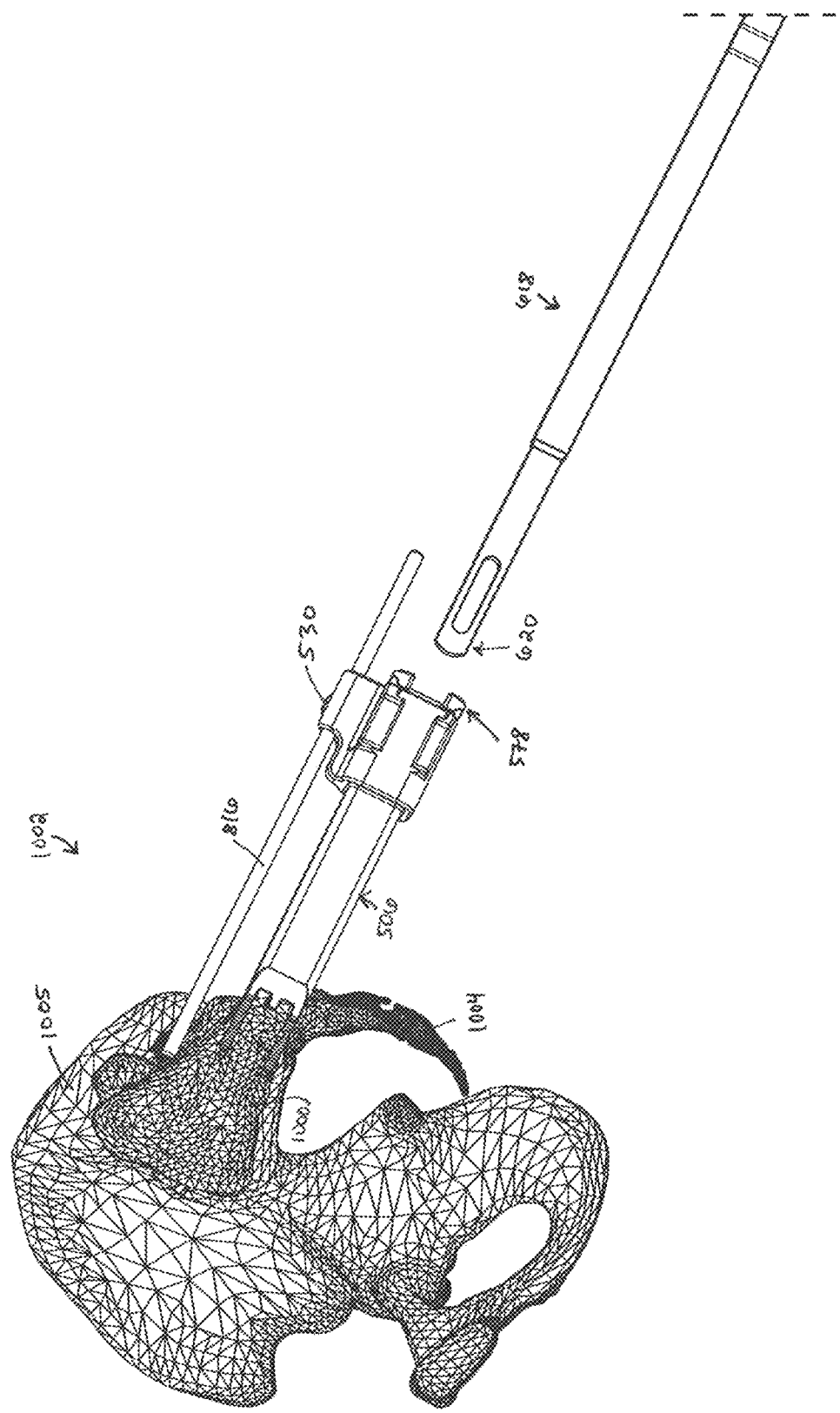
FIG. 87 is a side view of the pelvis with the nearest ilium removed, and a box osteotome positioned proximate the working cannula.
Figure 88:
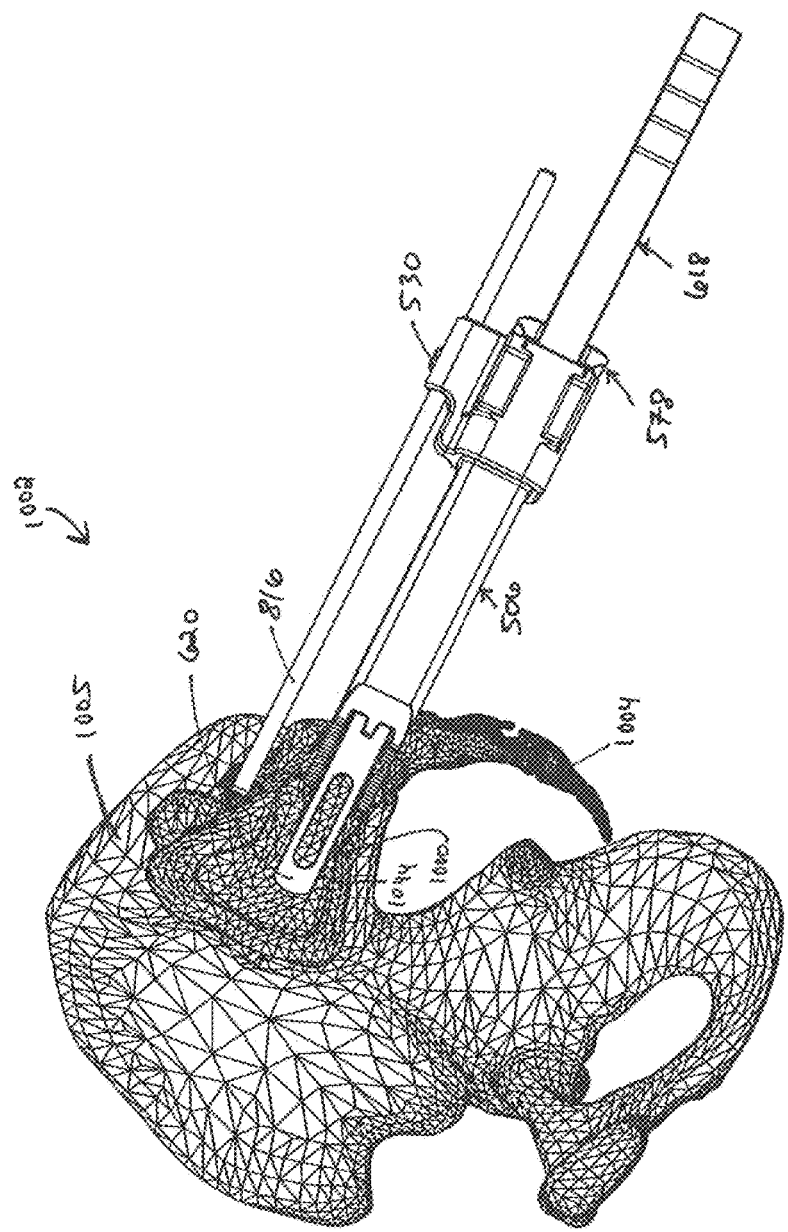
FIG. 88 is a side view of the pelvis with the nearest ilium removed, with the box osteotome extending through the working cannula and into the joint (while the present figure shows an embodiment of the box osteotome without a physical stop and instead with laser markings along the shaft an embodiment such as shown in FIG. 33 may be employed having a physical stop (e.g., configured as a flanged base) and delivered to a maximum depth similar to the step shown in FIG. 91 where the flanged base contacts the proximal end of the standoff).

After utilizing the drill guide 600, a box osteotome 618 (or series of smaller to larger box osteotomes) may be utilized to further prepare the joint surfaces of the sacrum 1004 and ilium 1005, as seen in FIGS. 87-88. FIG. 87 depicts the box osteotome 618 proximate the working cannula 506 and FIG. 88 depicts the box osteotome 618 positioned through the working cannula 506 such that the cutting structure 620 extends into the articular region 1044 of the joint so as to remove a rectangular portion of the joint space formed by the sacrum 1004 and ilium 1005.

Figure 89:
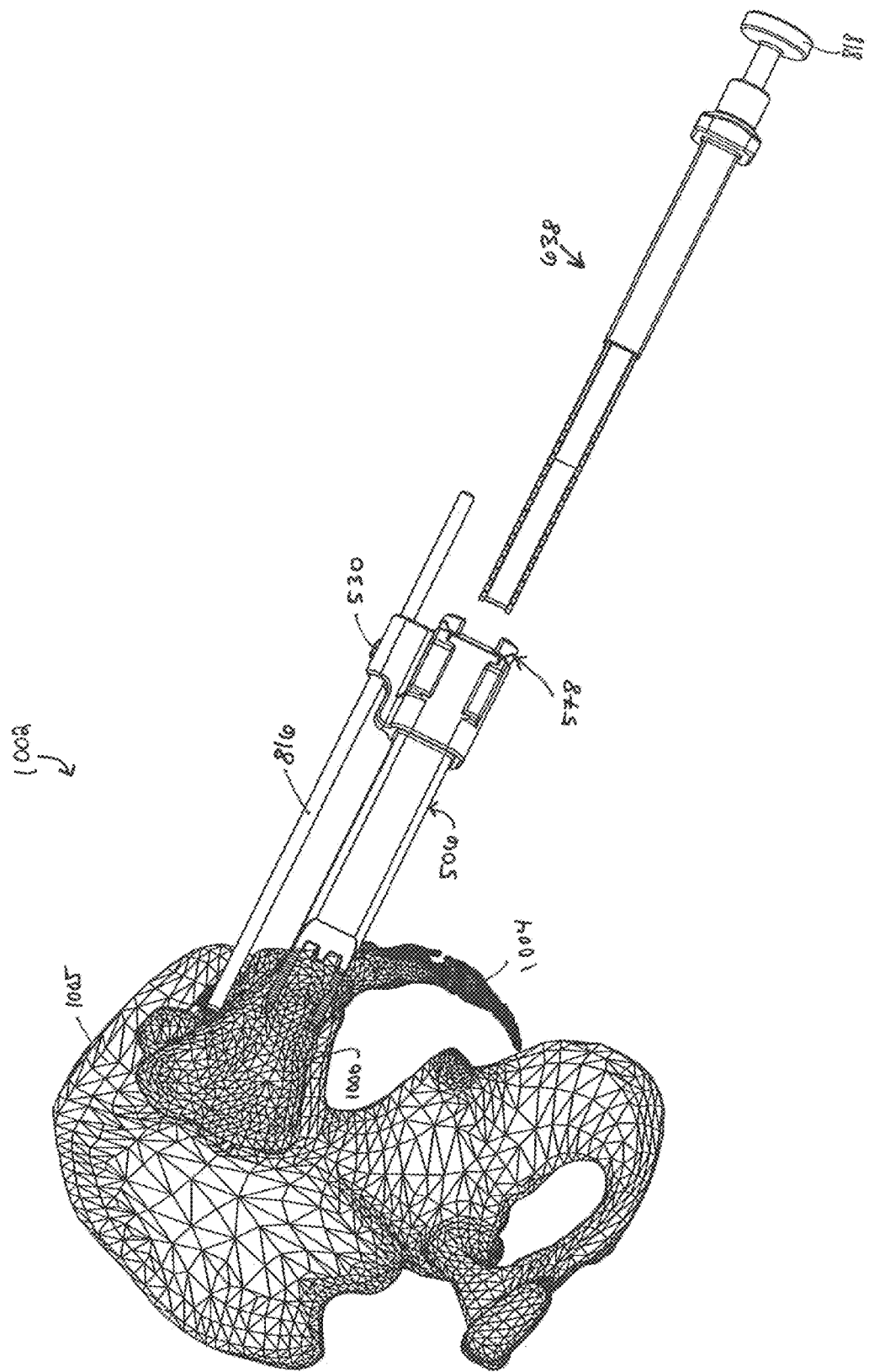
FIG. 89 is a side view of the pelvis with the nearest ilium removed, and a dual saw blade broach positioned proximate the working cannula.
Figure 90:
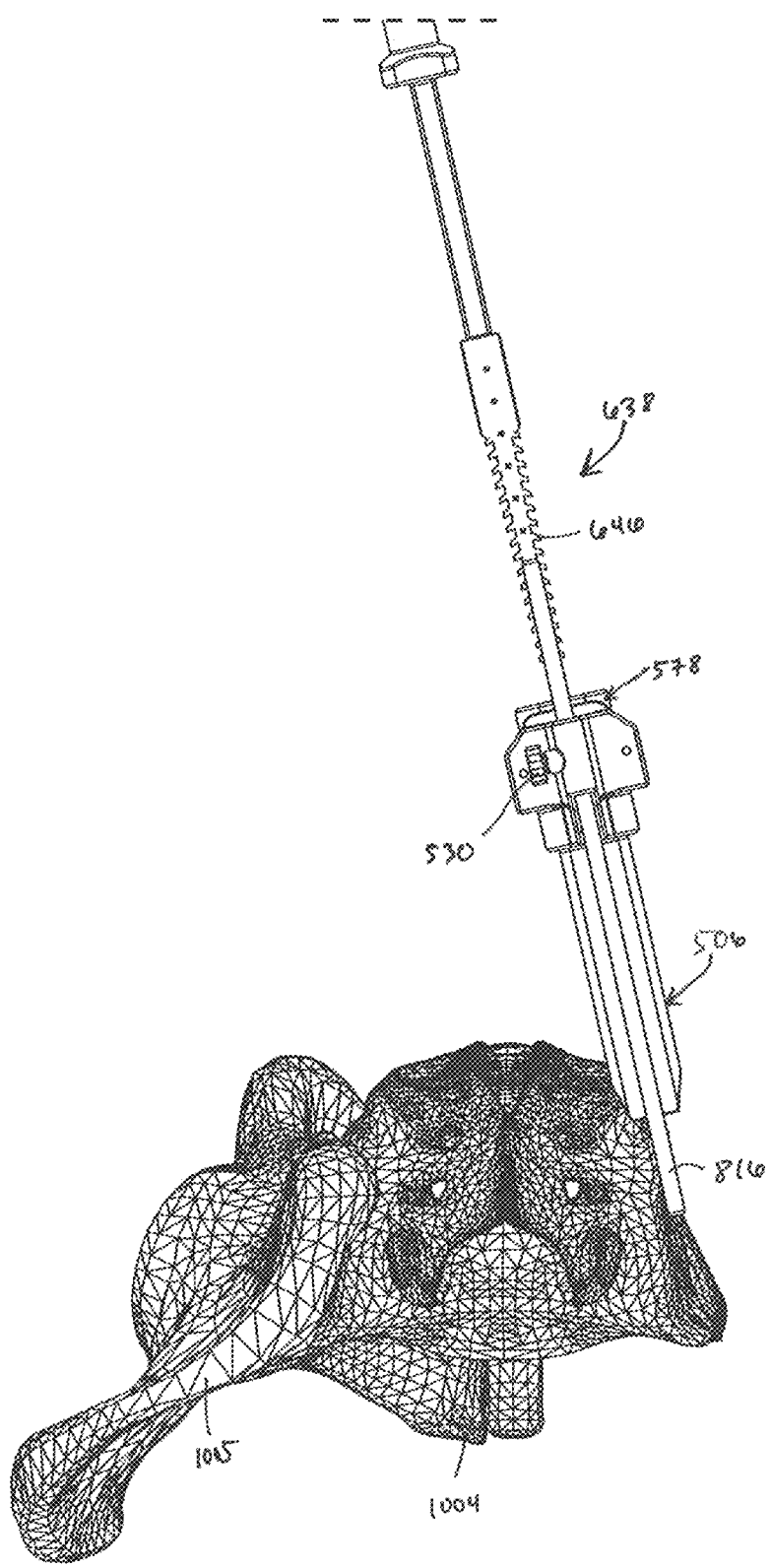
FIG. 90 is a superior view of the dual saw blade broach and the working cannula of FIG. 89.
Figure 91:
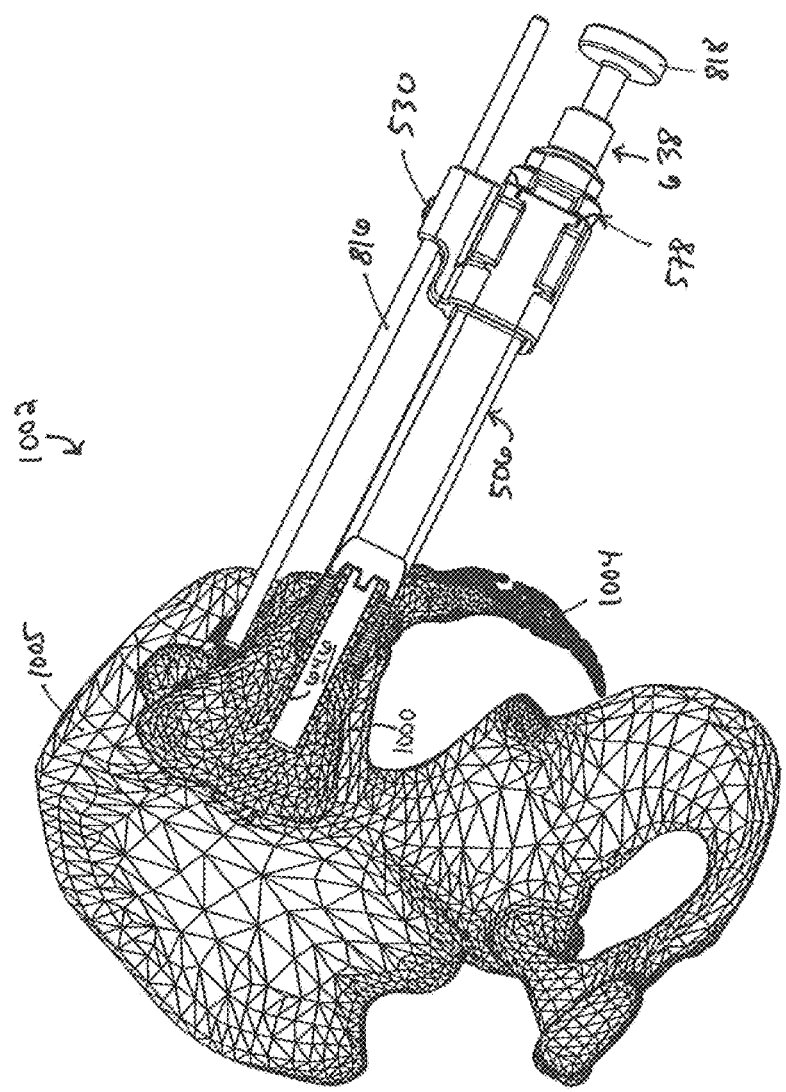
FIG. 91 is a side view of the pelvis with the nearest ilium removed, with the dual saw blade broach positioned through the working cannula and into the joint.

Now that a central portion or plane of the joint 1000 has been prepared, portions of the sacrum and ilium 1004, 1005 may be prepared to receive certain features of the joint implant 502. For instance, FIGS. 89-91 illustrate a dual saw blade broach 638 for use in forming keel-cuts or transverse cuts into the sacrum 1004 and ilium 1005 to receive keels or planar members of a joint implant 502. FIG. 89 depicts the dual saw blade broach 638 positioned proximate the working cannula 506. FIG. 90 is a superior view of the dual saw blade broach 638 showing the serrations along the long edges 646 thereof. And FIG. 91 is a side view of the pelvis 1002 with the nearest ilium removed 1005, with the dual saw blade broach 638 positioned through the working cannula 506 and into the joint 1000 so as to form transverse cuts or channels in the sacrum 1004 and ilium 1004 corresponding to the size and shape of the implant 502 to be implanted subsequently. A series of smaller to larger broaches or chisels may be used.

Figure 92:
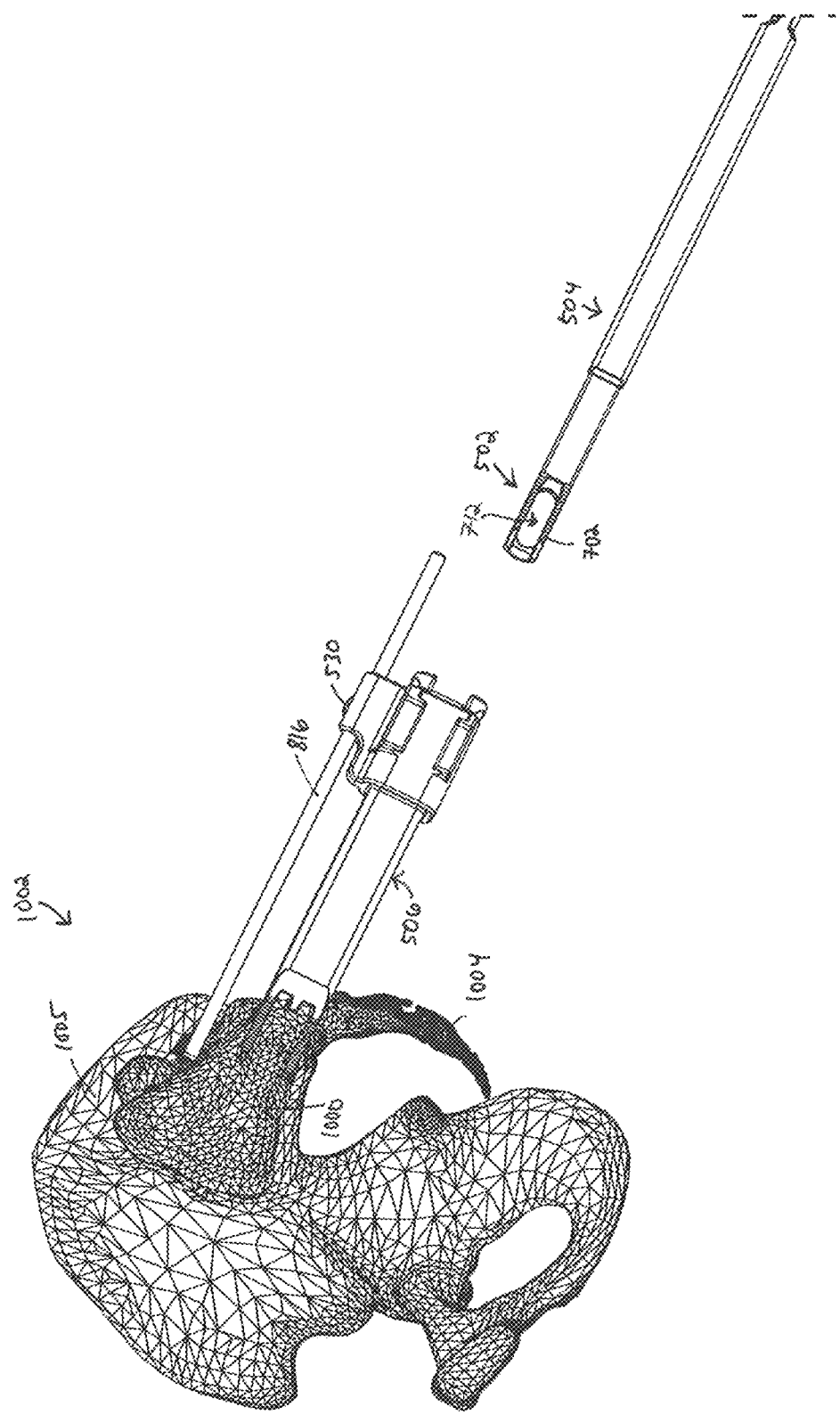
FIG. 92 is a side view of the pelvis with the nearest ilium removed, and a joint implant coupled with an implant arm that is positioned proximate the working cannula.

FIGS. 92-95 depict the implantation of the joint implant 502 in the joint 1000, and, in particular, in the implant receiving space as prepared by the various tools and methods previously described. FIG. 92 is a side view of the pelvis 1002 with the nearest ilium 1005 removed, and a joint implant 502 coupled with an implant arm 504 that is positioned proximate the working cannula. As seen in the figure, the joint implant 502 is oriented with the pair of planar members 702 oriented perpendicular to a plane of the joint 1000, and with the transverse opening 712 extending across the joint 1000 (i.e., perpendicular to a plane of the joint). FIG. 93 is a superior view of the joint implant 502 coupled with the implant arm 504 positioned proximate of the working cannula 506. It can be seen that the trajectory of the implant arm 504 and implant 502 are aligned with a trajectory of the working cannula 506 so the joint implant 502 can pass through the keyed passageway 556 of the working cannula 506.

Figure 94:
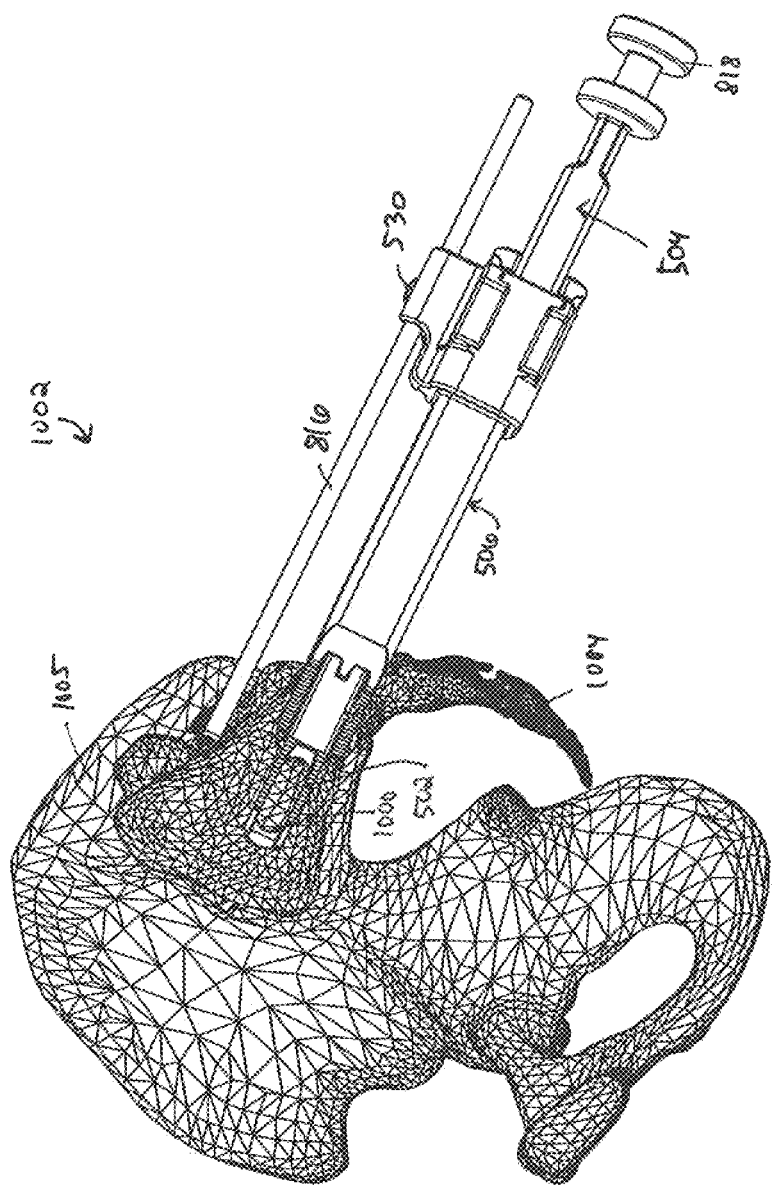
FIG. 94 is a side view of the pelvis with the nearest ilium removed, and the joint implant positioned in the joint, and coupled to the implant arm, which extends through the working cannula (the implant arm may have a physical stop such as a flanged base as similarly shown with the other tools or may have laser marking along the shaft near the proximal end configured and calibrated with a zero marking being a equivalent depth as the joint preparation tools as read from the proximal surface of the standoff and plus or minus various depth measurements, e.g., 5, 10 and 15 mm increments in order to allow the surgeon to select and verify implant positioning to be delivered further distally or proximally to the prepared implant receiving space).
Figure 95:
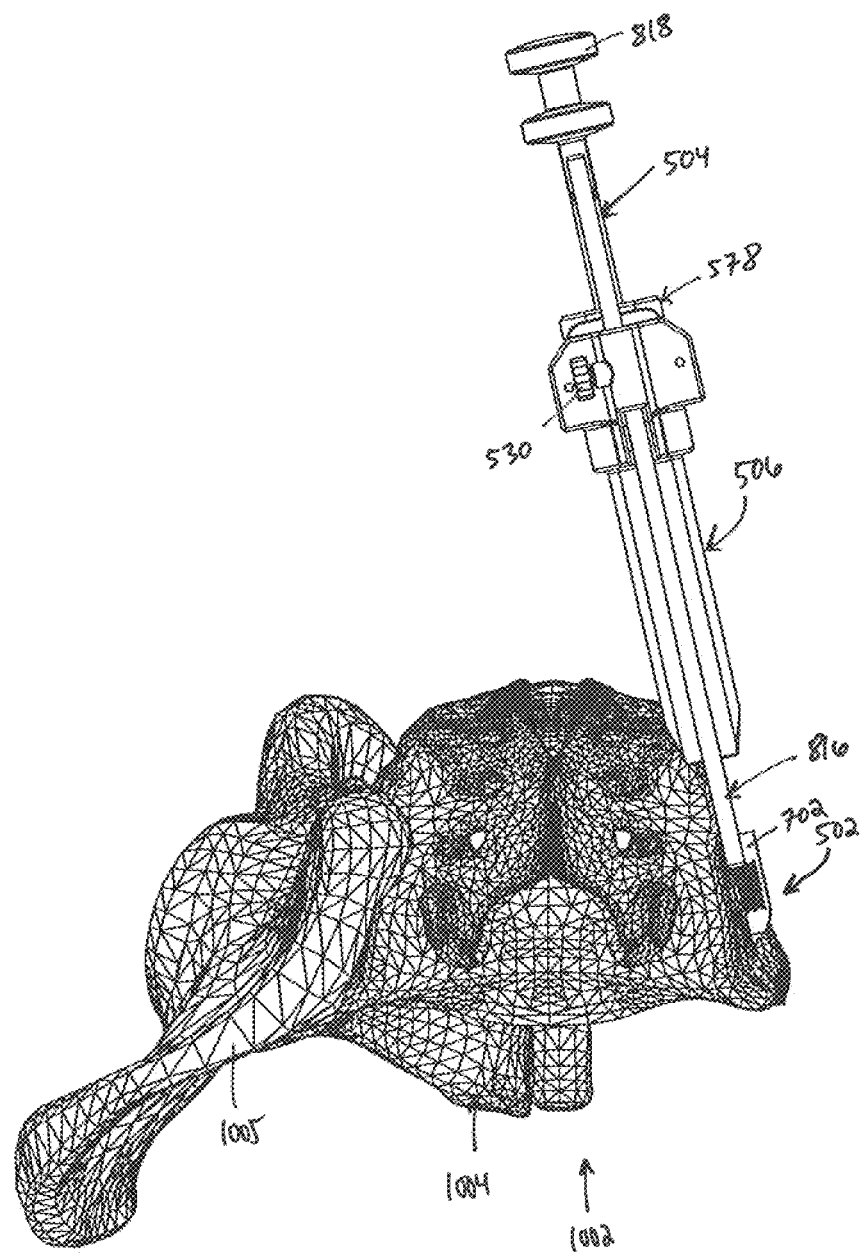
FIG. 95 is a superior view of the joint implant positioned in the joint, and coupled to the implant arm, which extends through the working cannula.

FIG. 94 is a side view of the pelvis 1002 with the nearest ilium 1005 removed, and with the joint implant 502 positioned in the joint 1000. And FIG. 95 is a superior view of the joint implant 502 positioned in the joint 1000. The joint implant 502 is coupled to the implant arm 504, which extends through the working cannula 506. The planar members 702 of the implant 502 are now positioned within the channels formed by the dual saw blade broach 638, and the distal and proximal members 704, 708 are positioned within the plane of the joint 1000 which was prepared and widened by the drill bit 612 and box osteotome 618.

Figure 96:
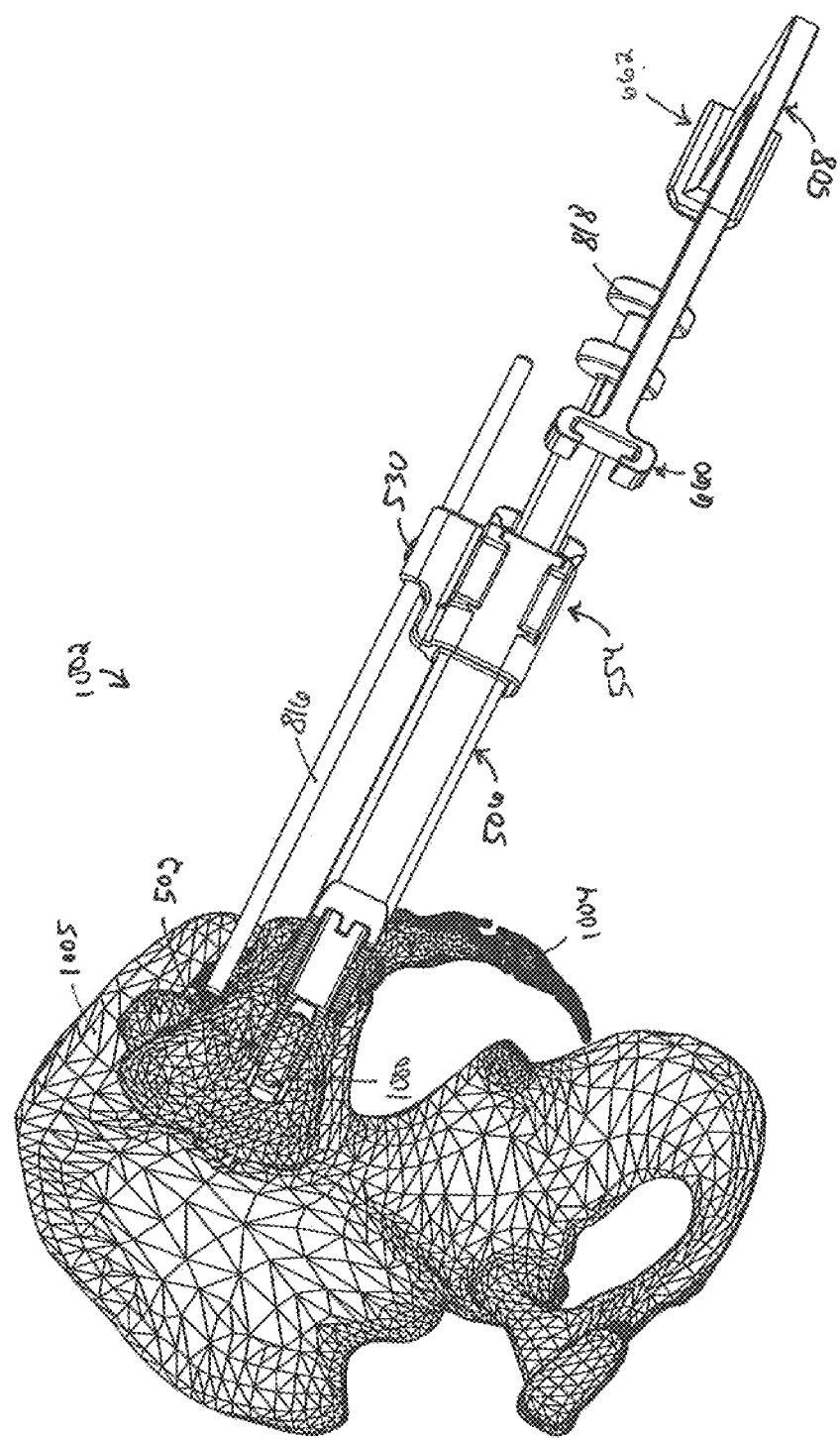
FIG. 96 is a side view of the pelvis with the nearest ilium removed, and an anchor arm positioned proximate the working cannula.
Figure 97:
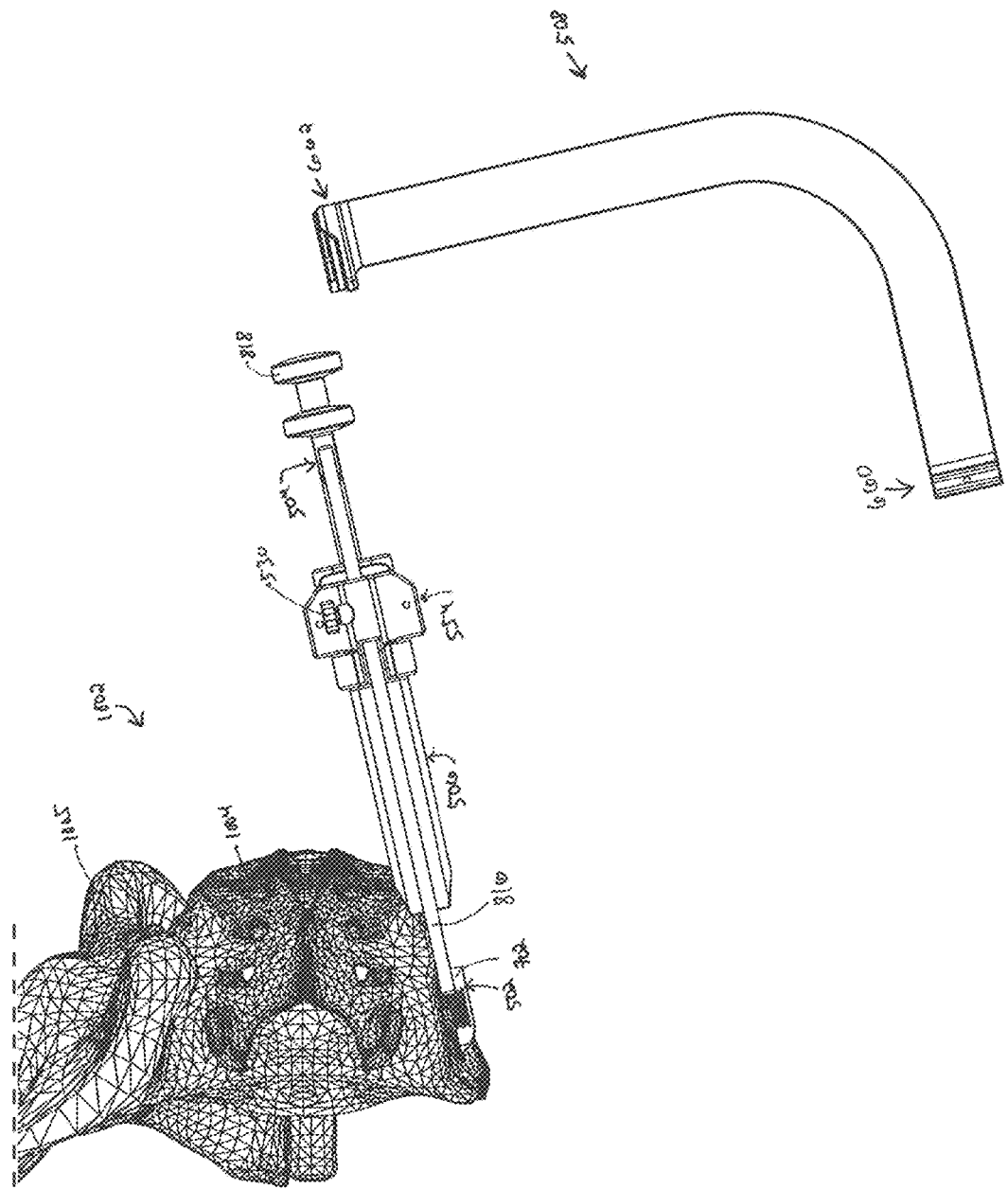
FIG. 97 is a superior view of the anchor arm positioned proximate the working cannula.
Figure 98:
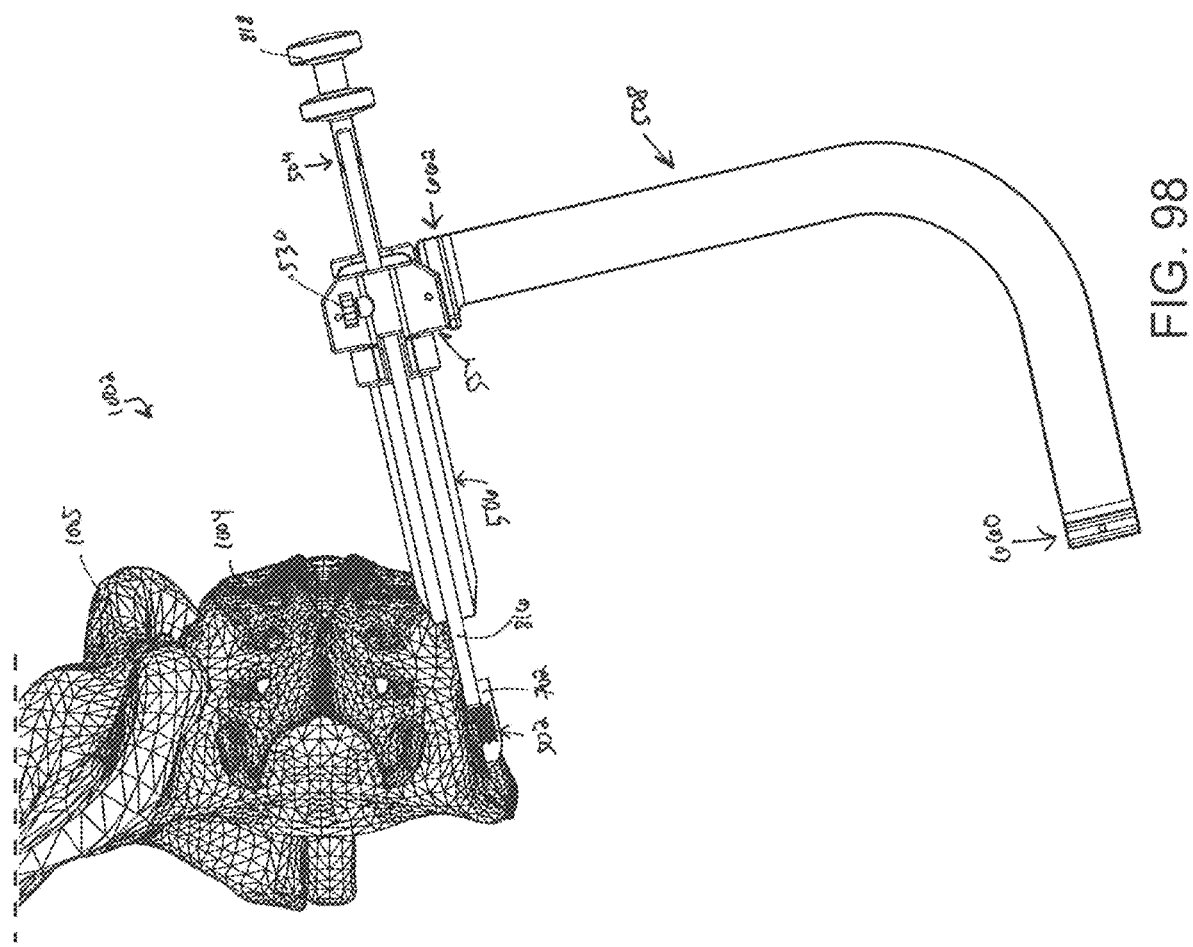
FIG. 98 is a superior view of the anchor arm coupled to the working cannula.
Figure 99:
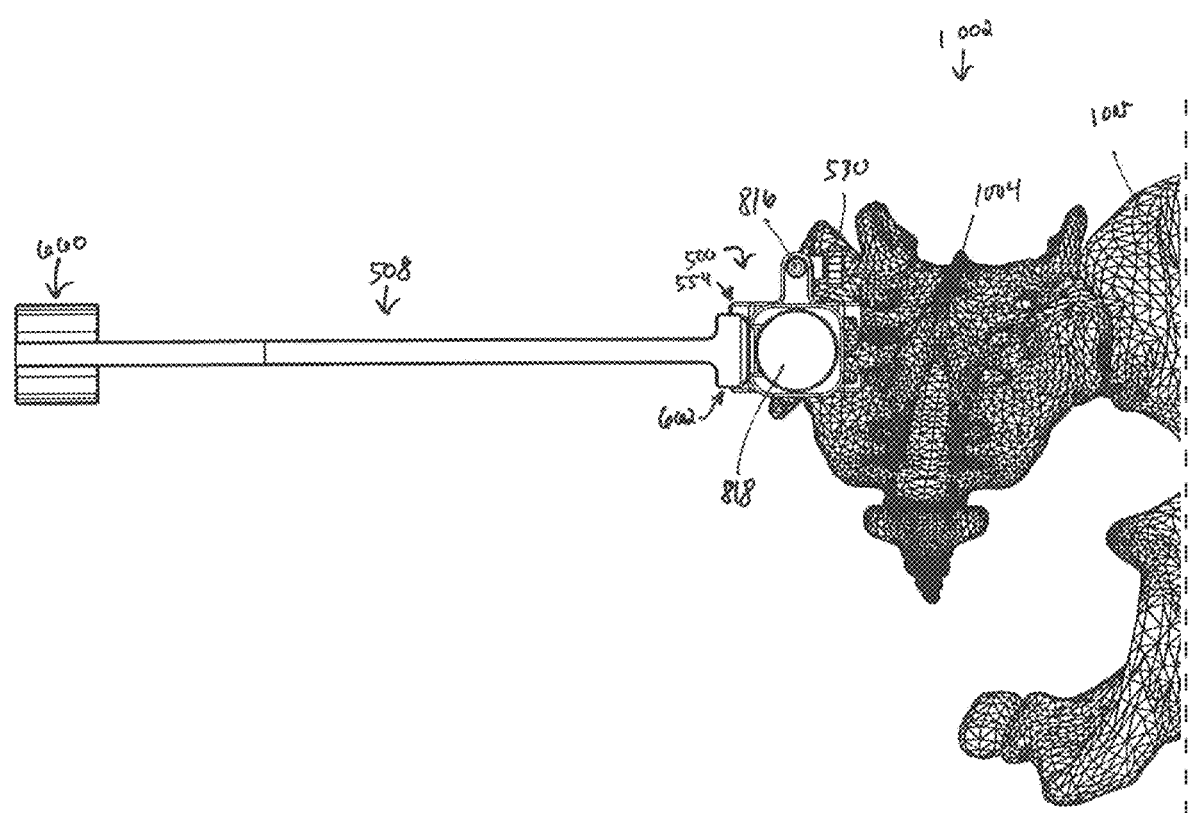
FIG. 99 is a posterior view of the anchor arm coupled to the working cannula.
Figure 100:
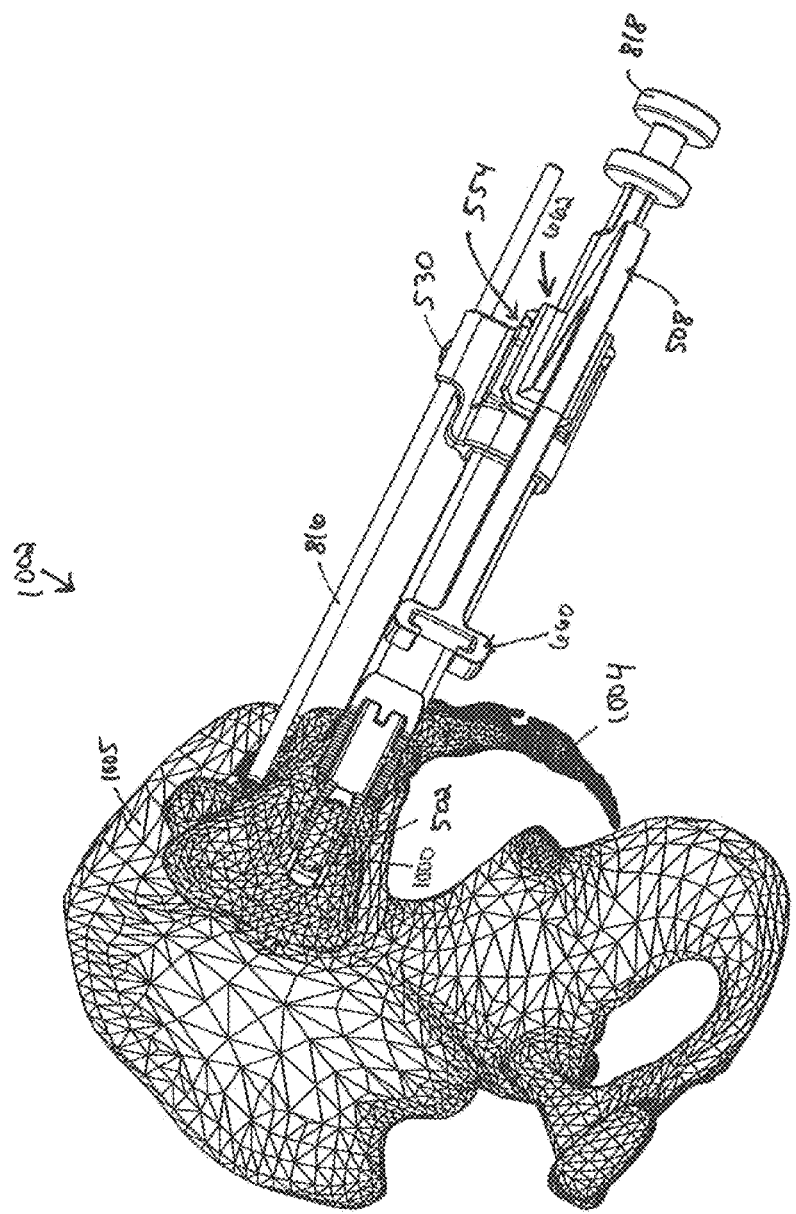
FIG. 100 is a side view of the pelvis with the nearest ilium removed, and the working cannula coupled to the anchor arm.

Upon the joint implant 502 being implanted into the joint 1000, the anchor arm 508 may be coupled to the working cannula, as seen in FIG. 96-100. FIGS. 96-97 show the anchor arm 508 positioned proximate the working cannula 506. And FIGS. 98-100 show the anchor arm 508 coupled with the working cannula 506. In particular, FIGS. 98-100 depict respectively a superior view, posterior view, and a side view of the cannula engagement structure 662 of the anchor arm 508 engaged with the anchor arm engagement structure 554 of the working cannula 506.

In certain aspects, the anchor arm 508 may be locked or otherwise retained to the working cannula 506 via a detent (e.g., ball detent), clamp, peg, screw, switch, latch, cam lock, spring latch, pawl, other fasteners, locking mechanisms or retaining mechanisms.

A benefit of particular configurations of the anchor arm-working arm coupling arrangement is that the joint implant 502 may be positioned in the joint 1000 and with the joint implant still coupled to the implant arm and extending through the working cannula, the anchor arm may be joined therewith unobstructed and due to the rigid connection between the implant receiving space, the implant, the implant arm and the working cannula the alignment and orientation of the working cannula and thereby anchor arm may be maintained throughout the deployment and use of the anchor arm, anchor block, pin etc.

Figure 101:
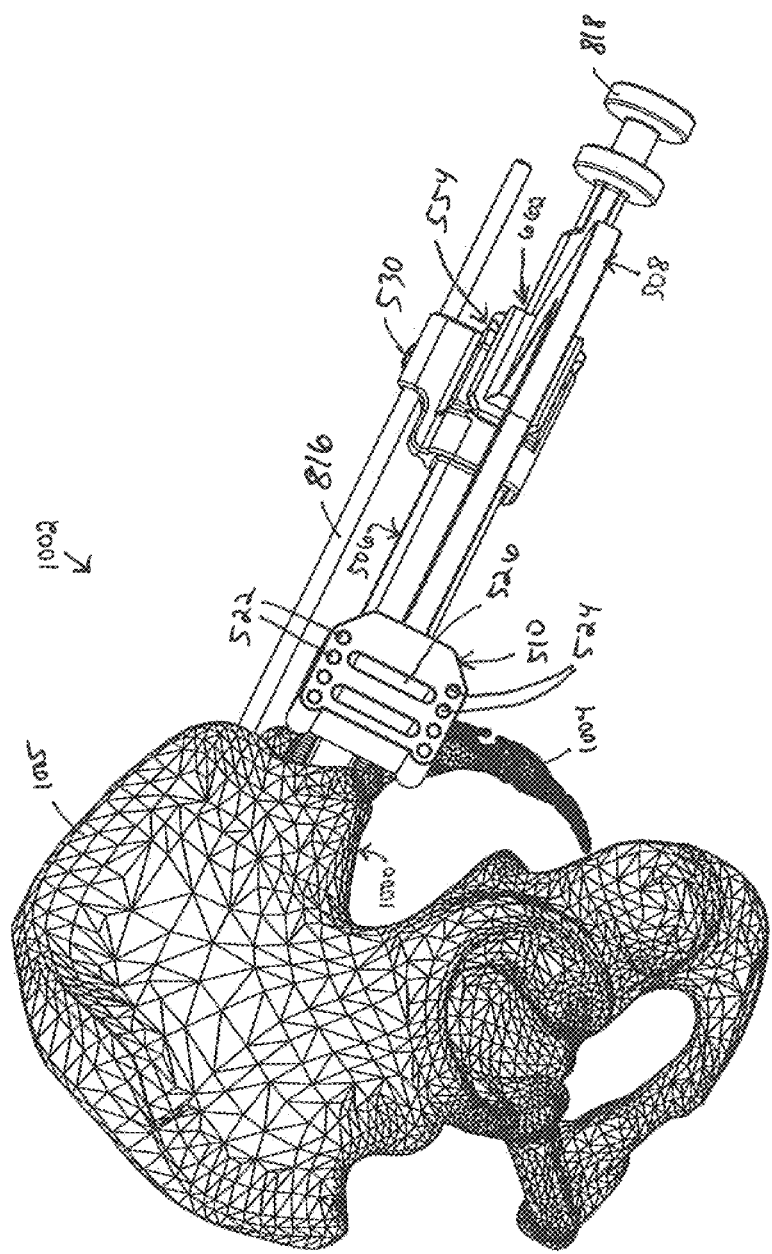
FIG. 101 is a side view of the pelvis with an anchor block coupled to the anchor arm, which is coupled to the working cannula.
Figure 102:
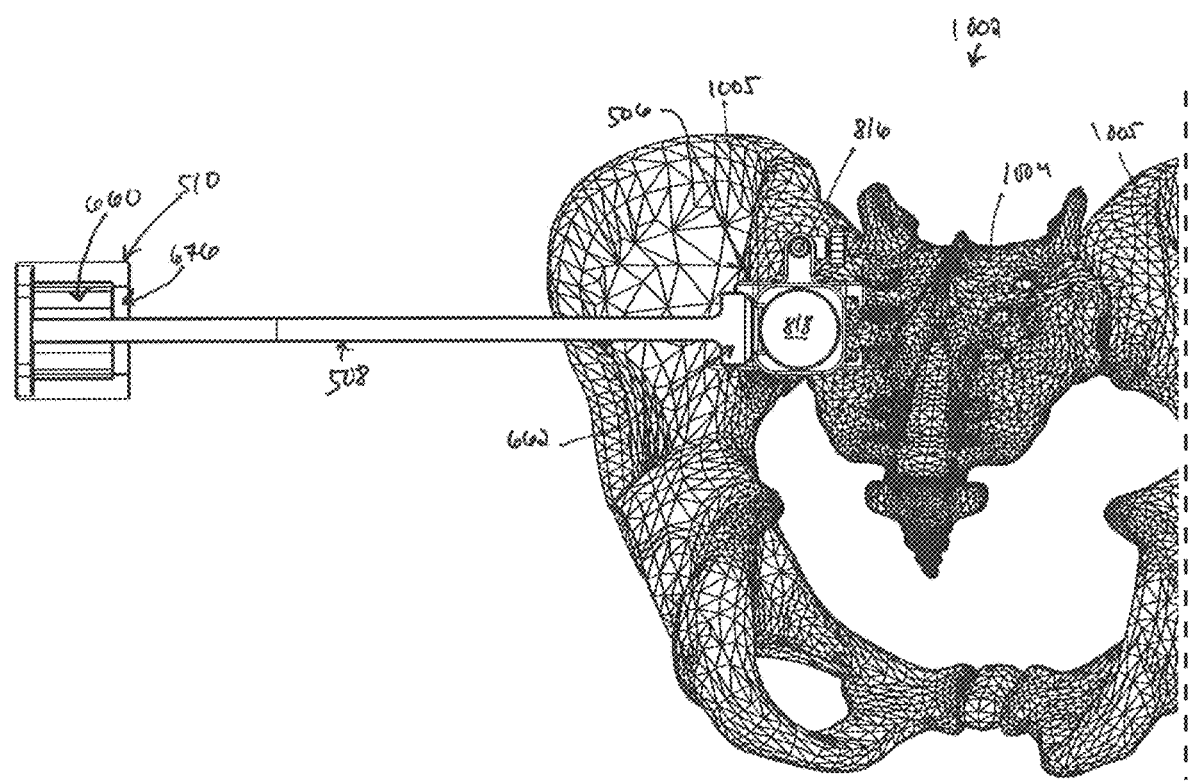
FIG. 102 is a posterior view of the pelvis with the anchor arm coupled to the working cannula, and with the anchor block coupled to the anchor arm.
Figure 103:
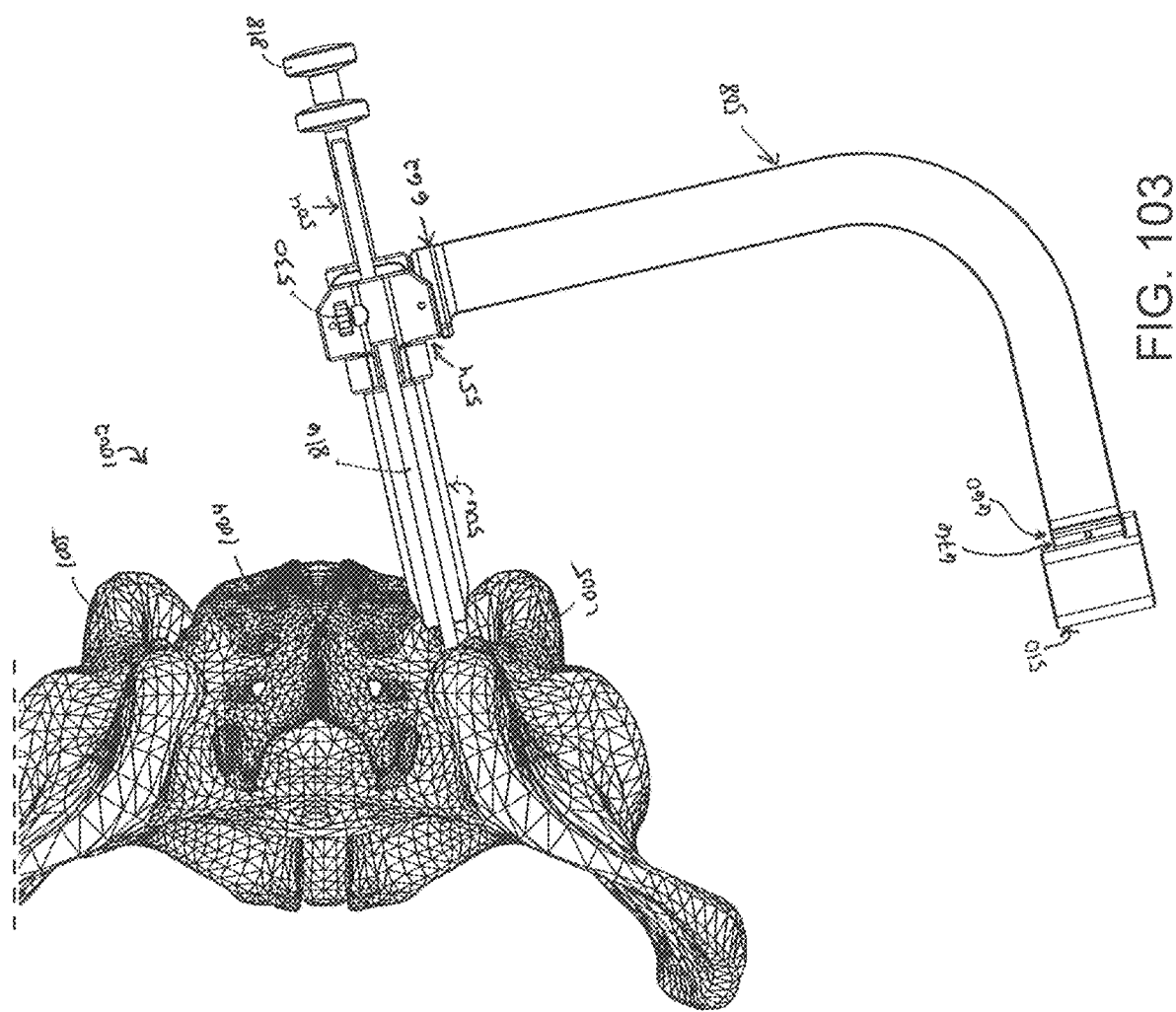
FIG. 103 is a superior view of the pelvis with the anchor arm coupled to the working cannula, and with the anchor block coupled to the anchor arm.

Once the anchor arm 508 is coupled to the working cannula 506, the anchor block 510 may be coupled to the anchor arm 508, as seen in FIGS. 101-103, which depict respectively a side view, a posterior view, and a superior view of the anchor block 510 coupled to the anchor arm 508. The anchor block 510 may include superior guide holes 522, inferior guide holes 524, and superior-inferior slots 526 extending through the anchor block 510. The superior guide holes 522 may guide a pin 512 in a predefined trajectory relative to the joint implant 502 that is superior to the joint implant 502. The inferior guide holes 524 may guide a pin 512 in a predefined trajectory relative to the joint implant 502 that is inferior to the joint implant 502. The anchor block 510 may also include the anchor arm engagement structure 676 that couples to the anchor block engagement structure 660 of the anchor arm 508.

In certain aspects, the anchor block 510 may be locked or otherwise retained to the anchor arm 508 via a detent (e.g., ball detent), clamp, peg, screw, switch, latch, cam lock, spring latch, pawl, other fasteners, locking mechanisms or retaining mechanisms.

Figure 104:
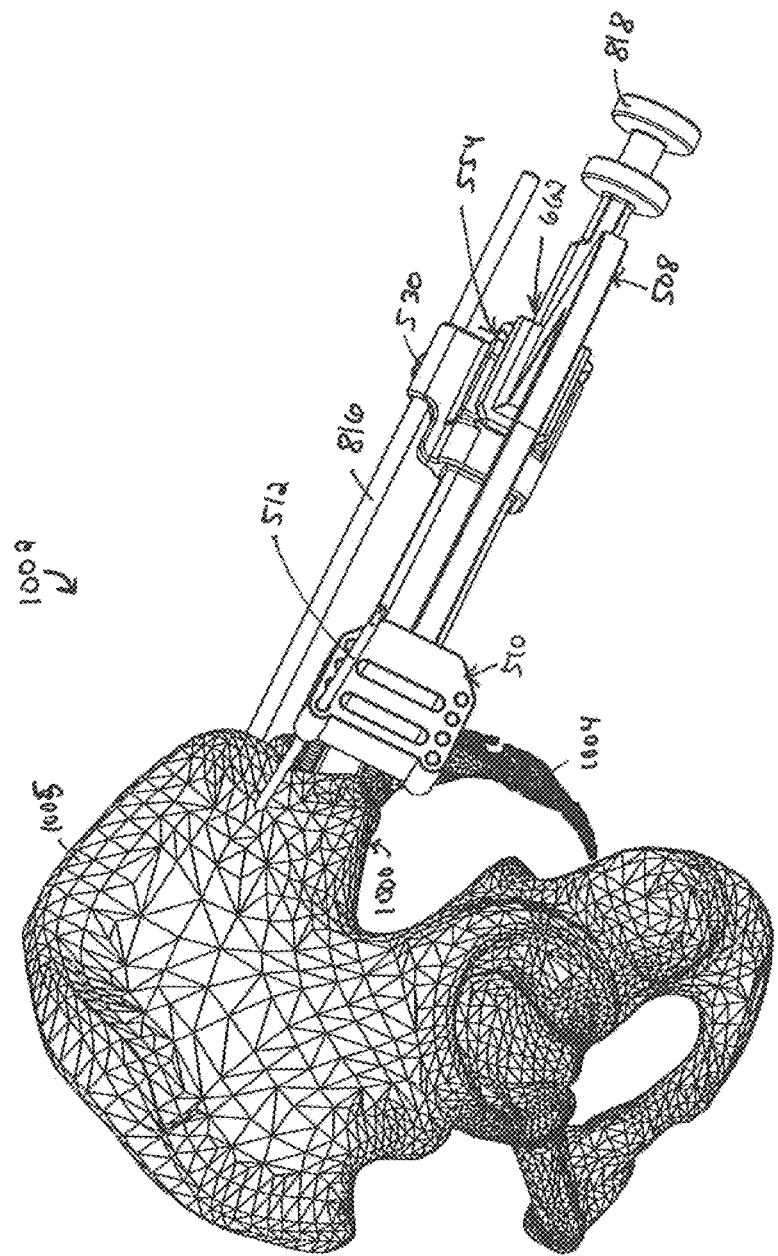
FIG. 104 is a side view of the pelvis with an anchor block coupled to the anchor arm, which is coupled to the working cannula, and a K-wire guided towards the ilium via the anchor block.
Figure 105:
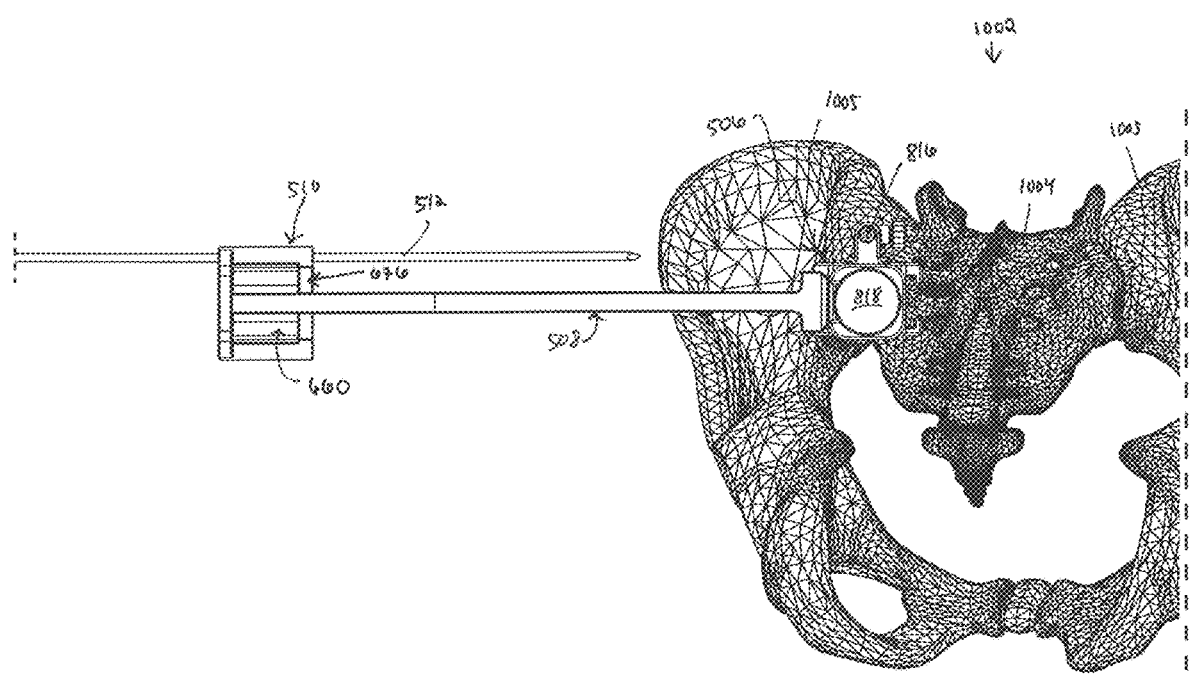
FIG. 105 is a posterior view of the pelvis with an anchor block coupled to the anchor arm, which is coupled to the working cannula, and a K-wire guided towards the ilium via the anchor block.
Figure 106:
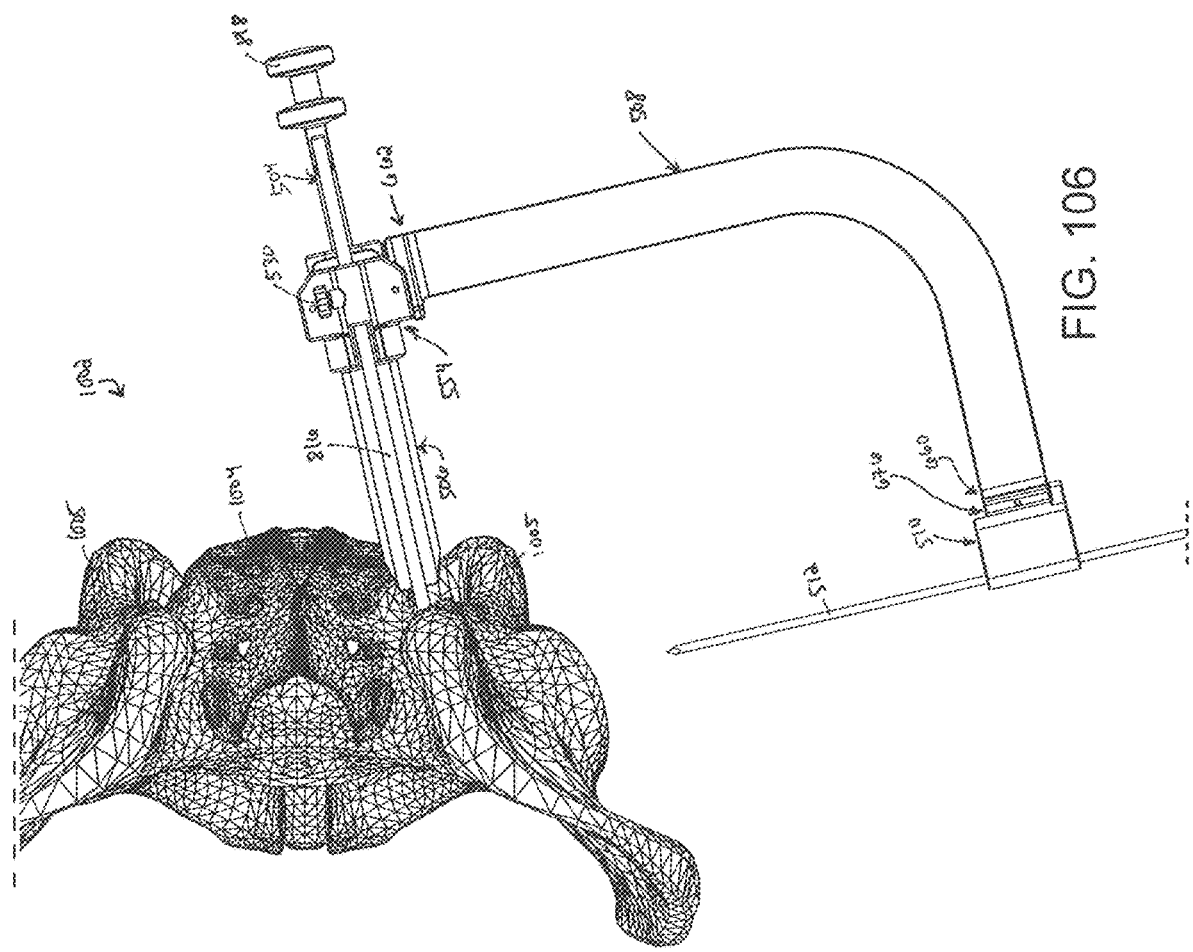
FIG. 106 is a superior view of the pelvis with an anchor block coupled to the anchor arm, which is coupled to the working cannula, and a K-wire guided towards the ilium via the anchor block.

FIGS. 104-106 depict various views of a pin 512 extending through and being guided by one of the superior guide holes 522 of the anchor block 510. More particularly, FIG. 104 is a side view, FIG. 105 is a posterior view, and FIG. 106 is a superior view of the pelvis 1002 with an anchor block 510 coupled to the anchor arm 508, which is coupled to the working cannula 506, and a pin or K-wire 512 guided towards the ilium 1005 via the anchor block 510.

Figure 107:
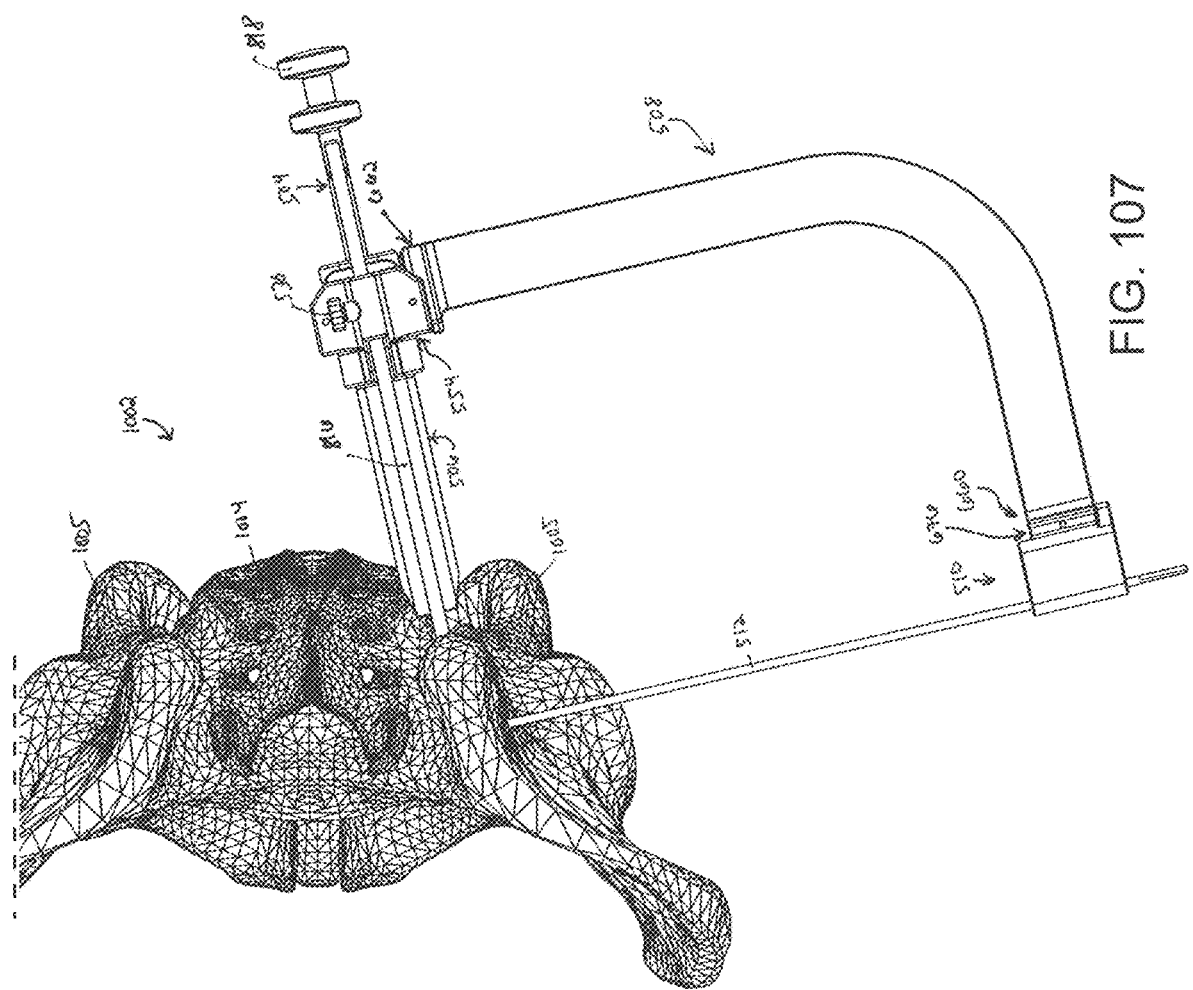
FIG. 107 is a superior view of the pelvis with an anchor block coupled to the anchor arm, which is coupled to the working cannula, and a K-wire extending into the ilium via guidance by the anchor block.
Figure 108:
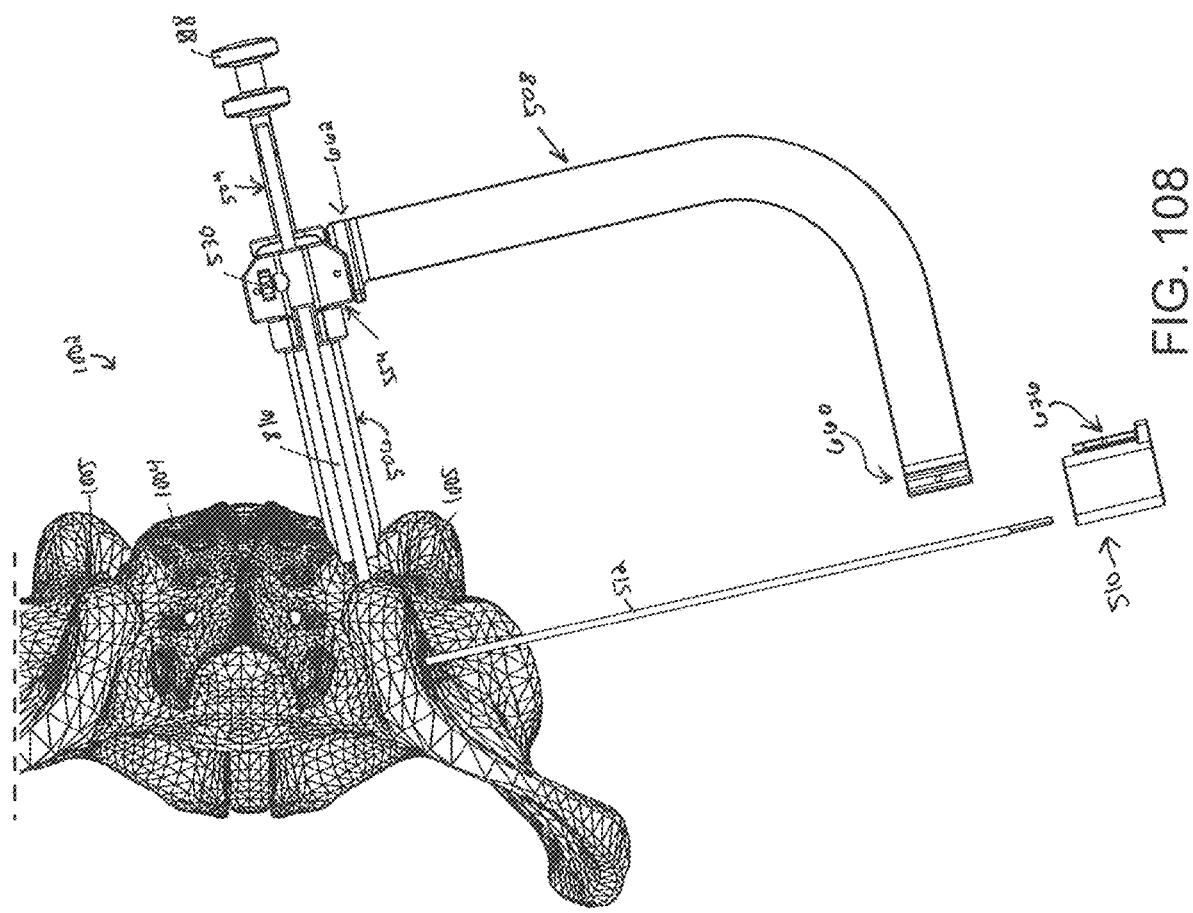
FIG. 108 is a superior view of the pelvis with an anchor block being decoupled from the anchor arm, which is coupled to the working cannula.

FIG. 107 is a superior view of the pelvis 1002 that depicts the pin 512 extending into the ilium 1005 via guidance by the guide block 510 of the anchor arm 508. Upon the pin 512 extending into the ilium 1005 (or further into the sacroiliac joint, or even further into the sacrum), the guide block 510 may be removed from the anchor arm 508, as seen in FIG. 108. More particularly, the guide block 510 may be disengaged or slid away from the pin 512 and anchor arm 508 along a trajectory that is generally parallel to the pin 512. In this way, disengagement of the guide block 510 from the anchor arm 508 limits or eliminates inadvertent bending or displacement of the pin 512.

Additionally, the implant arm 504 may be decoupled from the implant 502 via disengagement of the implant retainer 684 from the proximal bore of the implant (or other feature of the implant that couples the implant arm 504 and implant 502, respectively), and the implant arm 504 may be removed from within the working cannula 506. And, the working cannula 506 and anchor arm 508 (coupled thereto) may be removed from being coupled to the joint area by loosening the screw lock 530 from engagement with the guidance pin 816 extending through the pin guide 592 of the working cannula 506. Upon loosening the screw lock 530, the working cannula 506 may be slidingly removed from engagement with the guidance pin 816, and then the guidance pin 816 may be removed from the overhang of the posterior superior iliac spine 2004. Alternatively, the pin 816 may be removed from the overhang of the posterior superior iliac spine 2004, and from the working cannula 506 prior to the working cannula 506 being removed from the joint 1000.

Figure 109:
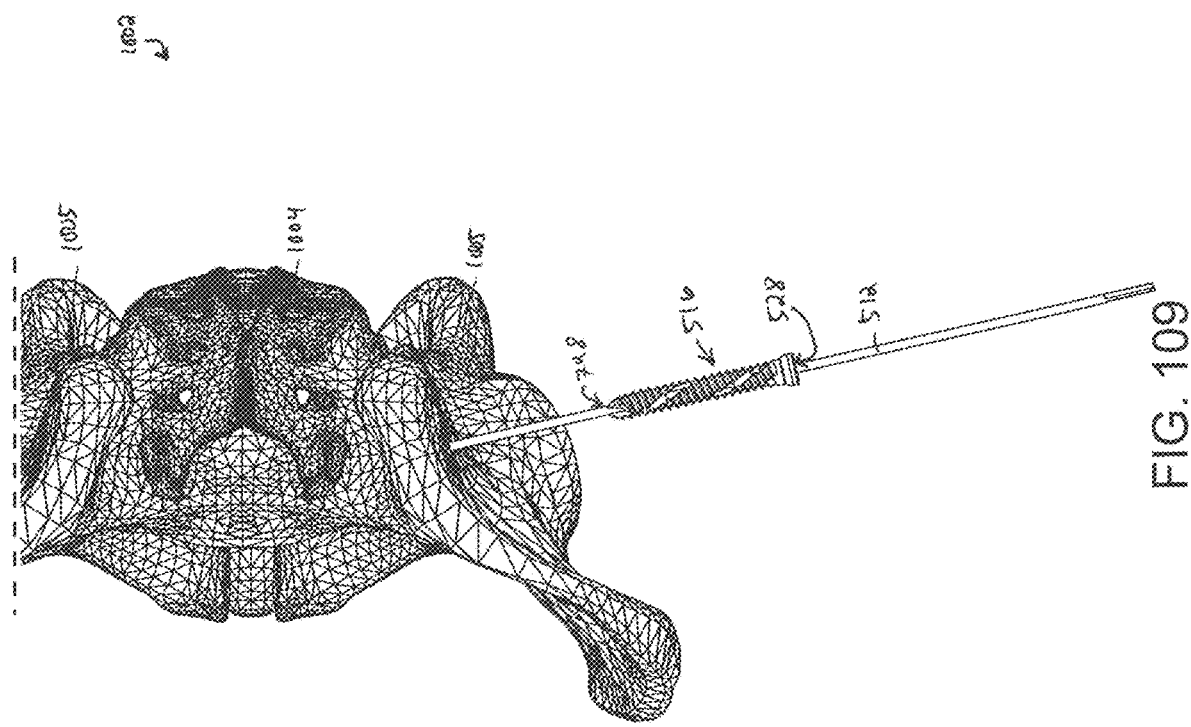
FIG. 109 is a superior view of the pelvis with the K-wire remaining in the pelvis, but with the rest of the tools removed. A bone anchor is guided to the ilium via the K-wire.

With the pin or K-wire 512 positioned in the ilium 1005, a bone anchor 516 may be guided into engagement with the ilium 1005, joint 1000, and sacrum 1004 via the pin 512, as seen in FIG. 109, which is a superior view of the pelvis 1002 with the K-wire 512 remaining in the pelvis 1002, but with the rest of the tools removed. The pin 512 is received within the lumen 528 of the bone anchor 516, and the bone anchor 516 is distally advanced into the bones and joint. As described previously, the bone anchor 516 may include a self-tapping, self-drilling tip 748 to aid in the advancement of the anchor 516 into the bone.

Figure 110:
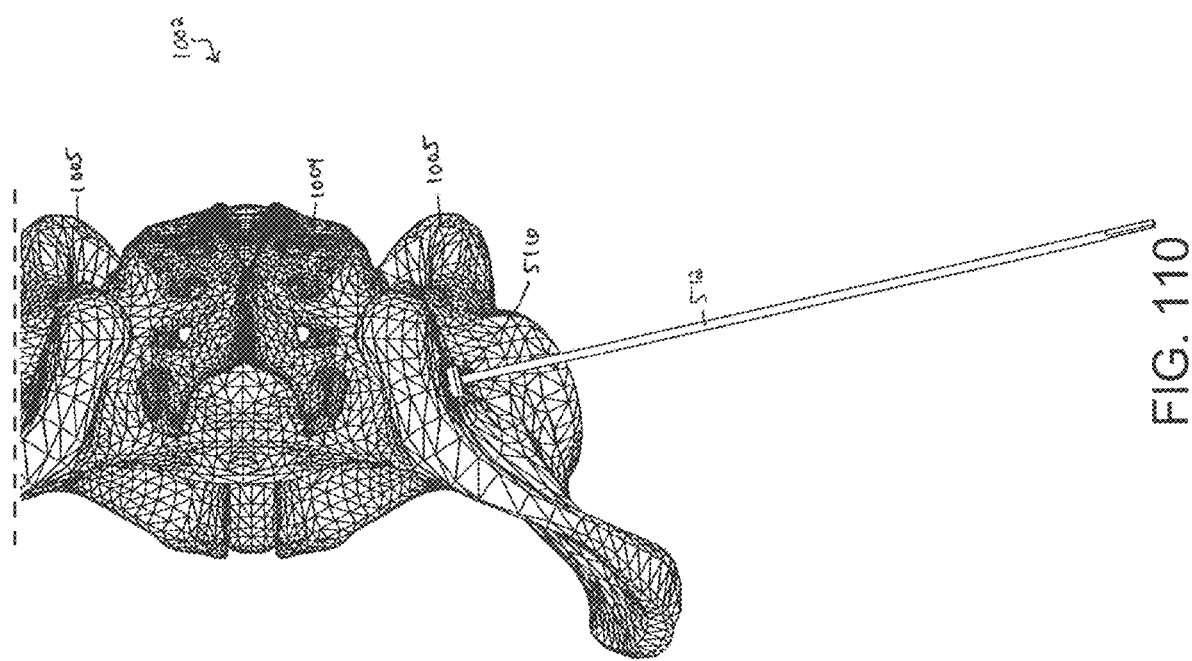
FIG. 110 is a superior view of the pelvis with the bone anchor extending into the ilium, across the joint, and into the sacrum via guidance by the K-wire.
Figure 111:
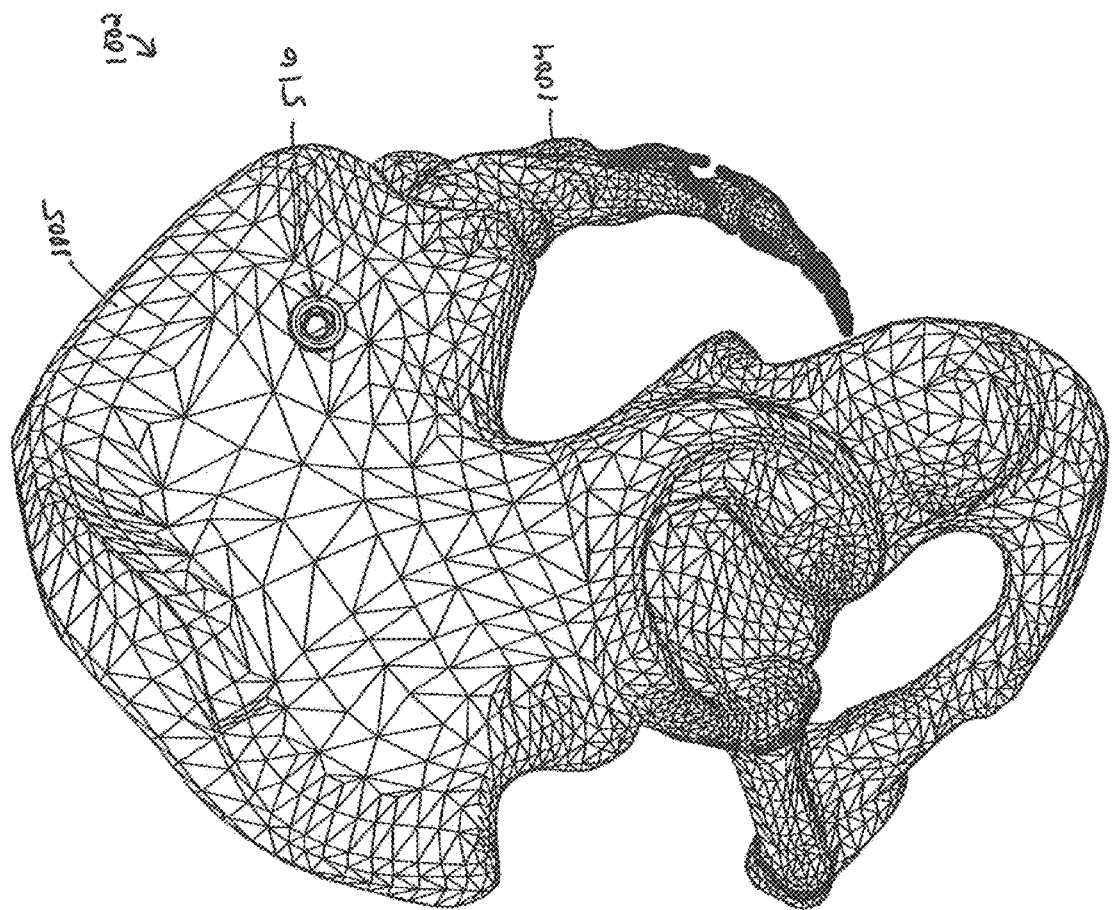
FIG. 111 is a side view of the pelvis with the bone anchor in position, and with the joint implant in the joint (not seen).
Figure 112:
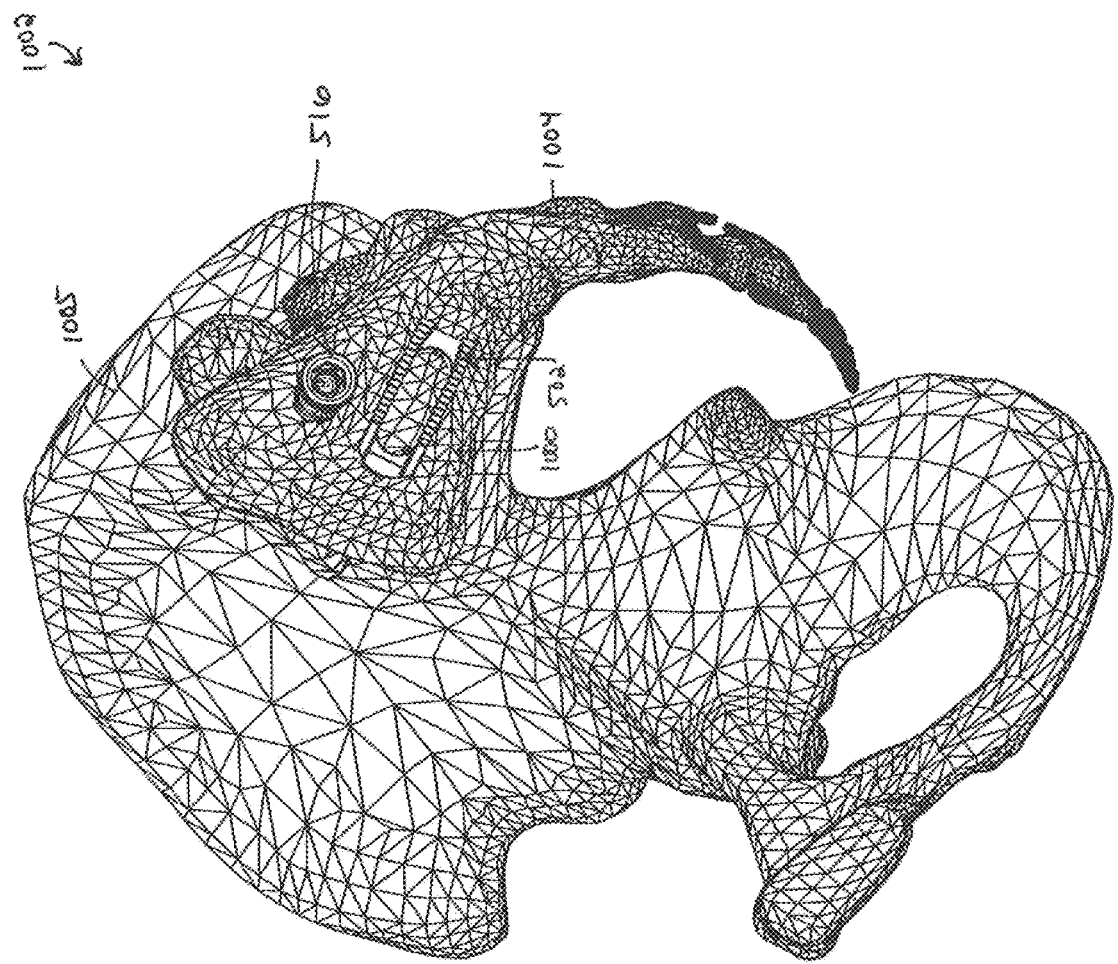
FIG. 112 is a side view of the pelvis with the nearest ilium removed so as to view the joint implant positioned within the joint, and the bone anchor extending across the joint.
Figure 113:
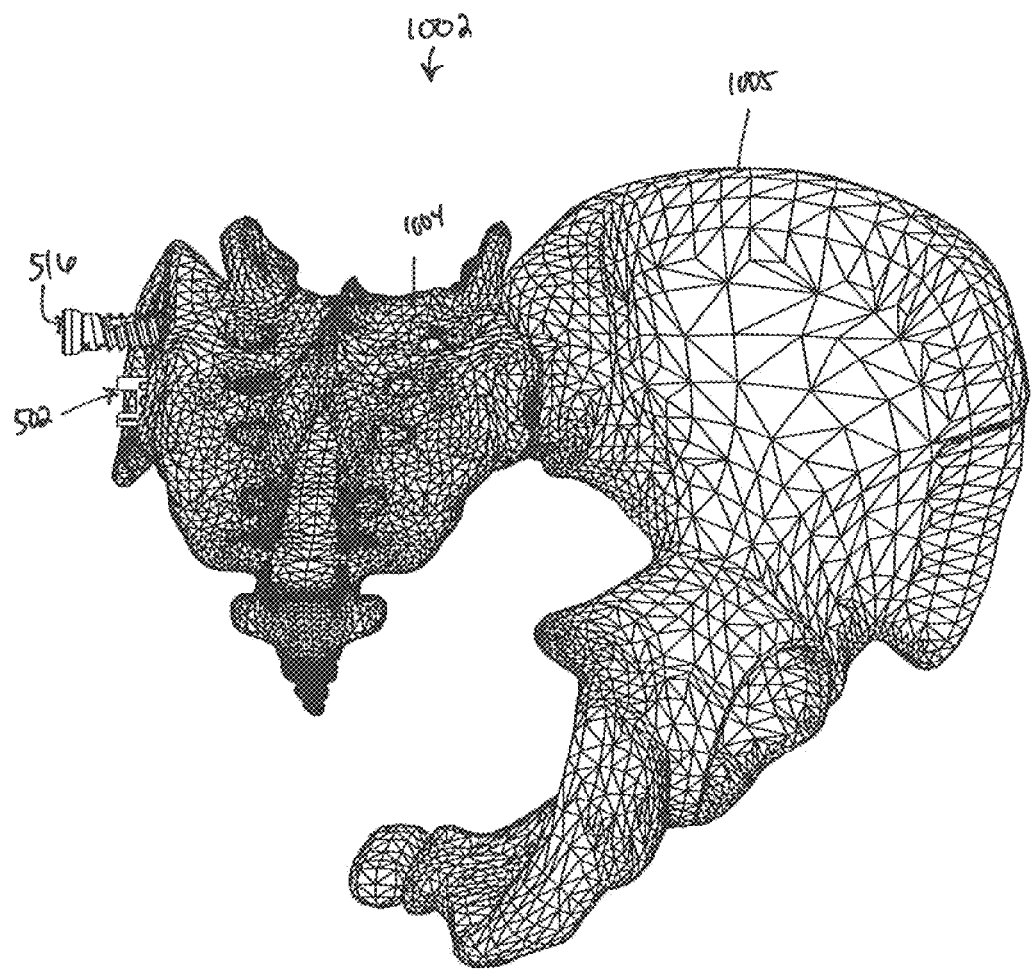
FIG. 113 is a posterior view of the pelvis with the nearest ilium removed so as to view the joint implant positioned within the joint, and the bone anchor extending across the joint.

FIG. 110 depicts the anchor 516 fully delivered into the ilium 1005, joint 1000, and sacrum 1004 via guidance by the pin 512. FIG. 111 depict a side view of the pelvis 1002 with the bone anchor 516 in position and with the pin 512 removed from the lumen 528 of the pin 512. FIGS. 112 and 113 depict the positions of the joint implant 502 and the anchor 516 relative to each other and relative to the joint 1000 is a side view and a posterior view, respectively, of the pelvis 1002 with the nearest ilium 1005 removed.

Figure 114:
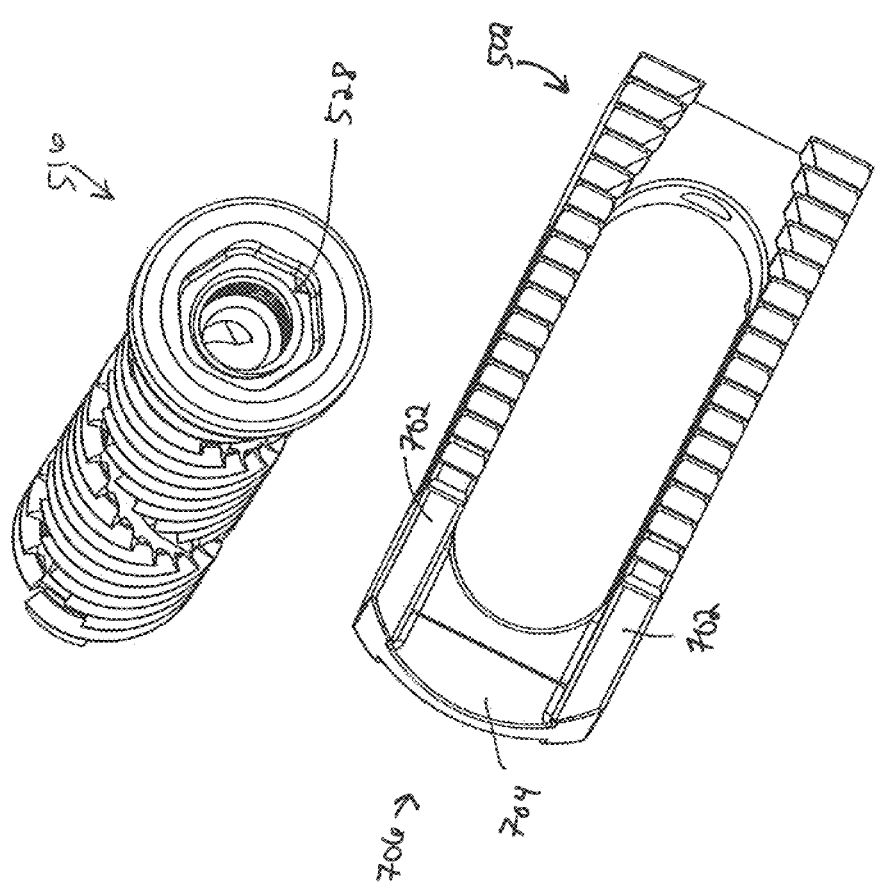
FIG. 114 is an isometric side view of the joint implant and the bone anchor in position adjacent each other in an implanted orientation in the joint.

And FIG. 114 is an isometric side view of the joint implant 502 and the bone anchor 516 in position adjacent each other in an implanted orientation in the joint (not shown). As seen in FIGS. 112-114, the anchor 516 is positioned superiorly to the joint implant 502, and generally in-line with the distal member 704 at the distal end 706. The implanted orientation of the anchor 516 may be dependent on the particular guide hole 522 of the anchor block 510 that the pin 512 was guided by. In this particular instance, the anchor 512 was guided by a most anteriorly positioned guide hole of the superior guide holes 522 of the guide block 510. The other guide holes of the superior guide holes 522 were posterior, meaning the ultimate position of the anchor 516 would be posteriorly positioned to the anchor placement as shown in FIG. 114.

Figure 115:
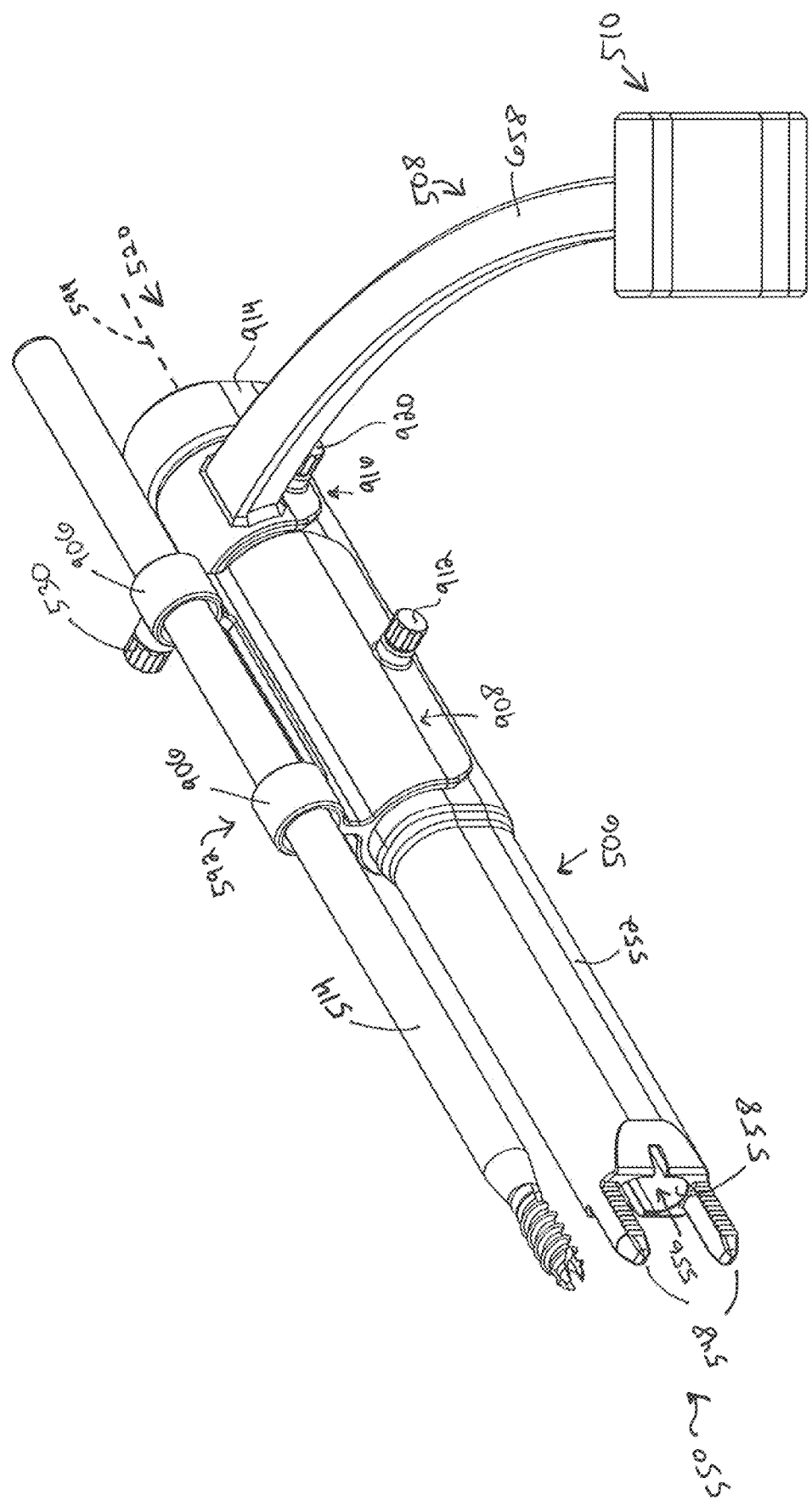
FIG. 115 is a distal isometric view of an exemplary working cannula, an anchor arm, and a pin guide removably coupled together.

VI. Additional or Alternative Tools including the Working Cannula, Anchor Arm, Pin Guide, Joint Finder, and Broach FIGS. 115 and 116 depict, respectively, a distal isometric view of an exemplary working cannula 506, an anchor arm 508, and a pin guide 592 removably coupled together, and a proximal isometric view of the exemplary working cannula 506, the anchor arm 508, and pin guide 592 uncoupled from each other. As seen in the figures, the working cannula 506 may include a pair of prongs, spikes, or projections 548 at a distal end 550 thereof, a tubular body 552 extending proximally from the pair of prongs 548, and a pair of through holes 900, 902 extending transversely through the tubular body 552. A passageway 556 extends through the working cannula 506 from a proximal end 520 to the distal end 550. Within the working cannula 506 is a passageway 556 that extends from the proximal to distal ends 520, 550. An inner surface 558 of the working cannula 506 may be keyed in the shape of a corresponding outer surface of an implant arm (not shown). The tubular body 552 may include indentations 904 for gripping, and a flange 914 just proximal of the indentations 904 at the proximal end 520. The working cannula 506 may include features from the working cannula 506 as previously described.

The pin guide 592 may include a pair of cylindrical eyelets or rings 906 that define a passageway for aligning a guide pin 514 along an axis that is in parallel alignment with a longitudinal axis 594 of passageway 556 of the working cannula 506. The guide pin 514 may be secured in position relative to the working cannula 506 by tightening a screw lock 530. As seen in the figures, the pin guide 592 is positioned on a superior side of the working cannula 506 so as to guide a guide pin into a portion of the ilium (e.g., posterior superior iliac spine) while aligning the longitudinal axis 594 of the passageway 556 of the working cannula 506 with the articular region of the sacroiliac joint.

The pin guide 592 may include a partial sleeve 908 including a cylindrical inner surface 910 and screw locks 912 for coupling the pin guide 592 to the working cannula 506. When the inner surface 910 of the pin guide 592 is positioned over the tubular body 552, the screw locks 912 may be engaged with the distal through holes 900 of the tubular body 552 so as to secure the pin guide 592 to the working cannula 506.

The anchor arm 508 may include a partial sleeve 916 including a cylindrical inner surface 918 and screw locks 920 for securing the anchor arm 508 to the working cannula 506. When the inner surface 918 of the partial sleeve 916 of the anchor arm 508 is positioned over the tubular body 552, the screw locks 920 may be engaged with the proximal through hole 902 so as to secure the anchor arm 508 to the working cannula 506. The anchor arm 508 may include features from the anchor arms 508 as previously described. For example, the anchor arm 508 may include an anchor block 510 opposite the partial sleeve 916 (removable coupled or rigidly coupled to the curvate member 658). The anchor block 510 may include one or more guide holes (not shown) for guiding a pin, which may then be used to guide an anchor, as described in previous embodiments.

With the coupling arrangements of the anchor arm 508 to the working cannula 506, and the pin guide 592 to the working cannula 506, the passageway 556 into the working cannula 506 remains open and unobscured for the passage and/or movement of an implant arm (not shown) therein.

FIGS. 117A-117C depict, respectively, a pair of isometric side views, and a back view of a joint finder 532. The joint finder 532 of FIGS. 117A-117C may include similar features to the joint finders 532 as previously described. In the present instance, the joint finder 532 may include an I-beam or H-beam shaped handle 542 that is integral with the body 534 thereof. As with the embodiment in FIGS. 27A-27D, the joint finder 532 was configured to couple to a round knob at the proximal end 544 via a threaded connection. In the present instance, the handle 542 may be integral with the body 534 and also be keyed to the shape of the inner surface of the working cannula 506 (not shown).

As seen in the figures, the joint finder 532 may include the elongate body 534 with a spatulate tip 536 at a distal end 538 thereof, a transverse opening 540 extending between sides of the body 534, the handle 542 at a proximal end 544, and a recessed gripping portion 546 just distal of the handle 542. The spatulate tip 536 may be used to identify the opening or gap between the sacrum and the ilium. Upon identifying the opening or gap between the sacrum and ilium, the spatulate tip 536 may be advanced into the sacroiliac joint.

FIGS. 118A-118B depict, respectively, an isometric side view and an isometric exploded side view of a broach 638. The dual saw blade broach 638 as seen in the figures may include, a distal body 922 at a distal end 644 thereof that may be manufactured separable from and configured to couple to (via welding or otherwise joined to) an intermediate section 656 of the broach 638.

The distal body 922 may include a pair of saw blades 640 opposite each other and coupled together via an intra-articular member 642. The saw blades 640 may be serrated along the long edges 646, and each saw blade 640 may include a pair of distal tips 648 opposite each other. Opposite the saw blades 640, the distal body 922 may include a proximal base 924 configured to fit within a slot 926 formed by a pair of flattened tines 928 at a distal end 930 of the intermediate section 656. The distal body 922 may be constructed as a single unitary piece. And upon forming, the distal body 922 may be welded or otherwise joined to the intermediate section 656.

The intermediate section 656 may include a rectangular member that extends proximally from the flattened tines 928. The rectangular member may interconnect with a flanged base 650 at a proximal end 652 thereof. A button knob 654 may be coupled with the flanged base 650. In certain instances, the button knob 654 may be integral with the flanged base 650.

The flanged base 650 may be sized and shaped to be prevented from extending beyond the standoff 578 when distally advanced relative to the standoff 578 and working cannula 506. The pair of saw blades 640 are oriented, sized and shaped to fit within the passage defined by the keyed inner surfaces 590, 558 of the standoff 578 and working cannula 506 when the saw blades 640 are oriented horizontally. That is, the intra-articular member 642 may extend vertically between the inner protrusions of the inner surfaces 590, 558 of the standoff 578 and working cannula 506.

The saw blades 640 may match a size and shape of features of a joint implant to be subsequently implanted into the joint. For example, a distance between the pair of saw blades 640 may be the same as a distance between the keels of a joint implant, such as the joint implant shown in FIGS. 23-26. The saw blades 640 may cut a pair of channels into the bones of the sacrum and ilium so as to provide an entry path into the joint for the subsequent delivery of the joint implant. While the dual saw blade broach 638 includes a pair of saw blades 640, the saw blade broach 638 may include a different number and configuration of saw blades 640 to match a particular joint implant.

The foregoing merely illustrates the principles of the embodiments described herein. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the embodiments described herein and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. A system for performing a fusion procedure on a sacroiliac joint defined between a sacrum and an ilium, the system comprising:
    a working cannula comprising a proximal end, a distal end, a tubular body extending between the proximal and distal ends, a cannula passageway defined within the tubular body and having a cannula axis extending there through, a pair of prongs coupled to the tubular body and extending distally there from, an anchor arm engagement structure coupled to the tubular body, and a pin guide coupled to the tubular body and defining a pin passageway having a guidance axis there through that is generally parallel with the cannula axis; and
    an anchor arm including a cannula engagement structure configured to couple to the anchor arm engagement structure of the working cannula, the anchor arm further comprising an elongate member coupled to the cannula engagement structure.

2. The system of claim 1, wherein the pair of prongs lie in a plane that intersects the cannula axis.

3. The system of claim 1, wherein the pair of prongs lie in a plane that intersects the guidance axis.

4. The system of claim 1, wherein the pair of prongs lie in a plane that intersects the cannula axis and the guidance axis.

5. The system of claim 1, wherein the tubular body comprises an inner surface that defines the cannula passageway, the inner surface including a pair of protrusions extending inward from opposite sides of the inner surface.

6. The system of claim 1, wherein the anchor arm further comprises an anchor block engagement structure, and wherein the elongate member is coupled to the anchor block engagement structure.

7. The system of claim 6, further comprising an anchor block including an anchor arm engagement structure configured to couple to the anchor block engagement structure of the anchor arm, the anchor block comprising a plurality of guide holes extending through the anchor block and configured to guide a pin along a trajectory.

8. The system of claim 7, wherein the anchor block further comprises at least one guide slot having an elongated opening extending there through, the at least one guide slot configured to guide a tool along a plurality of trajectories that are limited to those generally within a plane defined by the elongated opening.

9. The system of claim 8, wherein the tool comprises a pin.

10. The system of claim 1, further comprising a standoff comprising a tubular body configured to be positioned within the passageway of the working cannula at the proximal end.

11. The system of claim 10, wherein the standoff further comprises an inner surface including a pair of protrusions extending inward from opposite sides of the inner surface, wherein, when the standoff is positioned within the passageway of the working cannula the pair of protrusions of the standoff and working cannula, respectively, are collinear with each other.

12. The system of claim 1, further comprising an implant arm comprising an implant retainer and an arm member, the implant retainer comprising a shaft having a threaded end configured to couple to a joint implant, the arm member comprising a passageway for receiving the shaft of the implant retainer therein.

13. The system of claim 12, further comprising the joint implant.

14. The system of claim 13, wherein the joint implant comprises an implant body including at least one planar member extending a length between a proximal end and a distal end, and an opening extending through the implant body.

15. The system of claim 14, wherein the implant body defines X-shaped cross-section.

16. The system of claim 14, wherein the joint implant further comprises a flange coupled to the implant body, the flange being generally perpendicular to the implant body, the at least one planar member comprising a first planar member, the opening extending through the first member.

17. The system of claim 1, wherein the inner surface of the tubular body of the working cannula is keyed to a cross-sectional shape of a joint implant to permit passage of the joint implant therethrough.

18. The system of claim 17, further comprising the joint implant.

19. The system of claim 1, wherein the tubular body comprises an inner surface that defines the cannula passageway, the inner surface defining a non-circular perimeter.

20. The system of claim 1, further comprising:
the anchor arm further comprising an anchor block engagement structure, and wherein the elongate member is coupled to the anchor block engagement structure;
an anchor block including an anchor arm engagement structure configured to couple to the anchor block engagement structure of the anchor arm, the anchor block comprising a plurality of guide holes extending through the anchor block and configured to guide a pin along a trajectory; and
an implant arm comprising an implant retainer and an arm member, the implant retainer comprising a shaft having a threaded end configured to couple to a joint implant, the arm member comprising a passageway for receiving the shaft of the implant retainer therein, wherein, movement of the implant arm and the joint implant is independent of movement of the working cannula, the anchor arm, and the anchor block.

21. A method of performing a fusion procedure on a sacroiliac joint defined between a sacrum and an ilium, the sacroiliac joint comprising an articular region, the ilium comprising a posterior superior iliac spine (PSIS) and a posterior inferior iliac spine (PIIS), the method comprising:
inserting a distal tip of a working cannula between the sacrum and the ilium via a posterior access, the distal tip comprising a pair of prongs separated from each other by a distance, the working cannula comprising a tubular body, a cannula passageway extending through the tubular body, a pin guide coupled to the tubular body and defining a pin passageway having a guidance axis there through that is generally parallel with the cannula axis, and an anchor arm engagement structure;
inserting a guide pin into the ilium;
securing the guide pin to the pin guide;
inserting a joint implant through the cannula passageway and at least partially into the articular region of the sacroiliac joint;
coupling a cannula engagement structure of an anchor arm to the anchor arm engagement structure of the working cannula;
coupling an anchor block to the anchor arm, the anchor block comprising a plurality of guide holes extending there through;
inserting a pin through one of the plurality of guide holes and into the ilium along a trajectory defined by the one of the plurality of guide holes; and
guiding a bone anchor into the ilium via guidance by the pin.

22. The method of claim 21, further comprising inserting a distal portion of a cutting tool through the cannula passageway and into the sacroiliac joint so as to prepare the sacrum and the ilium for insertion of the joint implant.

23. The method of claim 22, wherein the cutting tool comprises at least one tool from a group comprising a rasp, a drill bit, a saw blade, and a box osteotome.

24. The method of claim 21, wherein securing the guide pin to the pin guide is via a screw lock of the pin guide.

25. The method of claim 21, wherein the tubular body comprises an inner surface that defines the cannula passageway, the inner surface including a pair of protrusions extending inward from opposite sides of the inner surface.

26. The method of claim 21, further comprising decoupling the anchor block from the anchor arm prior to guiding the bone anchor into the ilium by the pin.

27. The method of claim 21, further comprising decoupling the cannula engagement structure of the anchor arm and the anchor arm engagement structure of the working cannula prior to guiding the bone anchor into the ilium by the pin.

28. The method of claim 21, wherein the guide pin is inserted into the PSIS of the ilium.

29. The method of claim 28, further comprising removing bone material from the PSIS in preparation for inserting the guide pin therein.

30. The method of claim 29, further comprising implanting the bone material into at least one or both of the joint implant and the sacroiliac joint.

31. The method of claim 21, wherein the joint implant is inserted at least partially into the articular region of the sacroiliac joint via a posterior access region defined between the PSIS and the PIIS.

* * * * *